(12) United States Patent
Kwok et al.

(10) Patent No.: US 9,073,918 B2
(45) Date of Patent: Jul. 7, 2015

(54) PYRAZOLO[4,3-B]PYRIDINE-7-AMINE INHIBITORS OF ALK5

(75) Inventors: Lily Kwok, San Diego, CA (US); John David Lawson, Carlsbad, CA (US); Mark Sabat, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 406 days.

(21) Appl. No.: 13/697,421

(22) PCT Filed: May 10, 2011

(86) PCT No.: PCT/US2011/035962
§ 371 (c)(1),
(2), (4) Date: Feb. 12, 2013

(87) PCT Pub. No.: WO2011/146287
PCT Pub. Date: Nov. 24, 2011

(65) Prior Publication Data
US 2013/0324528 A1 Dec. 5, 2013

Related U.S. Application Data

(60) Provisional application No. 61/346,729, filed on May 20, 2010, provisional application No. 61/347,744, filed on May 24, 2010.

(51) Int. Cl.
C07D 471/04 (2006.01)
A61K 31/44 (2006.01)
C07D 401/00 (2006.01)
C07D 513/02 (2006.01)

(52) U.S. Cl.
CPC ..................... C07D 471/04 (2013.01)

(58) Field of Classification Search
USPC ............................ 514/303; 544/328; 546/119
See application file for complete search history.

(56) References Cited

U.S. PATENT DOCUMENTS

| 4,576,952 A | 3/1986 | Hurst et al. |
| 2009/0232828 A1 | 9/2009 | Zhang |

FOREIGN PATENT DOCUMENTS

| EP | 1724268 A1 | 2/2006 |
| WO | WO 2004/013138 A2 | 2/2004 |
| WO | WO 2004/065392 A1 | 8/2004 |
| WO | WO 2006/014325 A2 | 2/2006 |
| WO | WO 2008/005538 A2 | 1/2008 |
| WO | WO 2008/005538 A3 | 1/2008 |
| WO | WO 2009/050183 A2 | 4/2009 |
| WO | WO 2009/133070 A1 | 11/2009 |
| WO | WO 2009/143018 A2 | 11/2009 |
| WO | WO 2009/152083 A1 | 12/2009 |
| WO | WO 2010/036629 A2 | 4/2010 |

*Primary Examiner* — Barbara P Badio
*Assistant Examiner* — Sara E Townsley
(74) *Attorney, Agent, or Firm* — David M. Stemerick

(57) ABSTRACT

The present invention provides ALK5 inhibitors of the formula

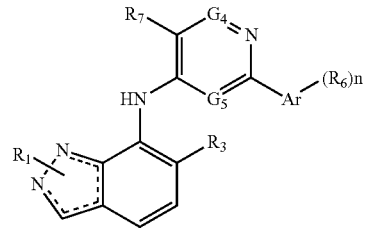

wherein the variables are as defined herein. Also provided are pharmaceutical compositions, methods of making the compounds and intermediates thereof; and methods of using the compounds.

13 Claims, No Drawings

PYRAZOLO[4,3-B]PYRIDINE-7-AMINE INHIBITORS OF ALK5

CROSS-REFERENCE TO RELATED APPLICATIONS

This application is the U.S. National Stage entry under 35 U.S.C. 371(c) of International Application PCT/US2011/035962, which was filed May 10, 2011, which claims the benefit of U.S. Provisional Application No. 61/346,729, filed May 20, 2010, and U.S. Provisional Application No. 61/347,744, filed May 24, 2010 which is herein incorporated by reference.

FIELD OF THE INVENTION

The present invention relates to medicinal chemistry and pharmaceutical science. Provided herein are compounds that inhibit activin-like kinase 5 (ALK5).

BACKGROUND OF THE INVENTION

Transforming growth factors, including TGF-β, play a key role in controlling cellular functions such as proliferation, differentiation, migration, extracellular matrix production, apoptosis, adhesion, and development. Deregulated TGF-β signaling has been identified as a key factor in a number of pathological disorders.

TGF-β and other cyctokines signal through a complex of two structurally and functionally distinct transmembrane receptor serine/threonine kinases, known as type I and type II TGF-β receptors, resulting in activation of TGF-β mediated pathways. The type I TGF-β receptor is also known as activin-like kinase 5 (ALK5). Inhibition of ALK5 antagonizes TGF-β mediated pathways and provides diverse biological effects in clinical applications, including the treatment of cancer, fibrosis, cardiovascular disorders, wound healing, and many others.

Certain inhibitors of ALK5 are disclosed in WO 2004/065392, WO 2009/050183, and WO 2009/133070. The present invention provides inhibitors of ALK5.

SUMMARY OF THE INVENTION

The present invention provides compounds of formula I:

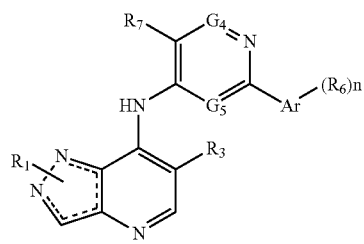

(I)

Wherein
Ar is selected from the group consisting of phenyl, pyridine, and pyrimidine;
$R_1$ is selected from the group consisting of hydrogen, optionally substituted $C_{1-6}$ alkyl, $C_{1-6}$ alkyl$C_{3-6}$ heterocycloalkylamide, optionally substituted $C_{1-8}$ sulfonyl, optionally substituted $C_{5-14}$ aryl, optionally substituted $C_{3-8}$ cycloalkyl, optionally substituted $C_{3-6}$ heterocycloalkyl, optionally substituted $C_{1-10}$ heteroaryl, —C(O)NR$_8$R$_9$, —C(S)NR$_8$R$_9$, —C(O)OR$_{10}$, and —C(O)R$_{11}$;
$R_3$ is selected from the group consisting of hydrogen, halo, and $C_{1-3}$ alkyl;
$G_4$ is selected from the group consisting of N and CR$_4$;
$R_4$ is selected from the group consisting of hydrogen, halo, and $C_{1-3}$ alkyl;
$G_5$ is selected from the group consisting of N and CR$_5$;
$R_5$ is selected from the group consisting of hydrogen, halo, and $C_{1-3}$ alkyl;
each $R_6$ is independently selected from the group consisting of halo, cyano, optionally substituted $C_{1-4}$ alkyl, optionally substituted $C_{2-4}$ alkenyl, optionally substituted $C_{2-4}$ alkynyl, and optionally substituted $C_{1-4}$ alkoxy;
n is 0, 1, 2, or 3;
$R_7$ is selected from the group consisting of hydrogen, halo, cyano, optionally substituted $C_{1-4}$ alkyl, optionally substituted $C_{2-4}$ alkenyl, optionally substituted $C_{2-4}$ alkynyl, and optionally substituted $C_{1-4}$ alkoxy;
$R_8$ is selected from the group consisting of hydrogen, optionally substituted $C_{1-6}$ alkyl, optionally substituted $C_{3-8}$ cycloalkyl, optionally substituted $C_{5-14}$ aryl, optionally substituted $C_{3-6}$ heterocycloalkyl, and optionally substituted $C_{1-10}$ heteroaryl;
$R_9$ is selected from the group consisting of hydrogen and $C_{1-6}$ alkyl;
or $R_5$ and $R_9$ together with the nitrogen to which they are attached form an optionally substituted $C_{3-6}$ heterocycloalkyl;
$R_{10}$ is selected from the group consisting of optionally substituted $C_{1-6}$ alkyl and optionally substituted $C_{3-8}$ cycloalkyl;
$R_{11}$ is selected from the group consisting of hydrogen, optionally substituted $C_{1-6}$ alkyl, optionally substituted $C_{3-8}$ cycloalkyl, optionally substituted $C_{5-14}$ aryl, optionally substituted $C_{3-6}$ heterocycloalkyl, and optionally substituted $C_{1-10}$ heteroaryl;
⚌ is a bond that can be depicted as a single or a double bond;
or a pharmaceutically acceptable salt thereof.

The present invention also provides pharmaceutical compositions, comprising: a compound of formula I and at least one pharmaceutically acceptable excipient.

The compounds of the invention are inhibitors of ALK5 which are useful for the treatment of conditions associated with ALK5, including cancer. Thus, the invention provides methods of treating conditions associated with ALK5, comprising: administering to a patient in need thereof an effective amount of a compound of formula I. Further, the present invention provides for the use of compounds of formula I, including for the manufacture of a medicament, for treating the each particular condition associated with ALK5 described herein.

The present invention also provides processes from making ALK5 inhibitors and intermediates thereof.

DETAILED DESCRIPTION OF THE INVENTION

The term "$C_{2-4}$ alkenyl" refers to a straight or branched alkenyl chain having from two to four carbon atoms and one carbon-carbon double bond, and includes ethylene, propylene, iso-propylene, butylene, iso-butylene, sec-butylene, and the like.

The term "optionally substituted $C_{2-4}$ alkenyl" refers to a $C_{2-4}$ alkenyl optionally having from 1 to 3 substituents independently selected from the group consisting of $C_{1-4}$ alkoxy, $C_{1-9}$ amide, $C_{1-5}$ oxycarbonyl, cyano, $C_{3-8}$ cycloalkyl, halo, hydroxy, optionally substituted $C_{1-10}$ heteroaryl, and optionally substituted phenyl.

The term "$C_{1-3}$ alkyl" refers to a straight or branched alkyl chain having from one to three carbon atoms.

The term "$C_{1-4}$ alkyl" refers to a straight or branched alkyl chain having from one to four carbon atoms.

The term "optionally substituted $C_{1-4}$ alkyl" refers to a $C_{1-4}$ alkyl optionally having from 1 to 5 substituents independently selected from the group consisting of $C_{2-4}$ alkenyl, optionally substituted $C_{1-4}$ alkoxy, $C_{1-4}$ thioalkoxy, $C_{1-9}$ amide, $C_{0-8}$ alkylamino, $C_{1-5}$ oxycarbonyl, cyano, optionally substituted $C_{3-8}$ cycloalkyl, $C_{3-8}$ cycloalkoxy, halo, hydroxy, nitro, oxo, optionally substituted $C_{3-6}$ heterocycloalkyl, optionally substituted $C_{1-10}$ heteroaryl, and optionally substituted phenyl. A particular "optionally substituted $C_{1-4}$ alkyl" is a $C_{1-4}$ alkyl optionally having from 1 to 5 substituents independently selected from the group consisting of $C_{1-4}$ alkoxy, $C_{1-9}$ amide, cyano, $C_{3-8}$ cycloalkyl, halo, hydroxy, $C_{3-6}$ heterocycloalkyl, and optionally substituted phenyl. A more particular "optionally substituted $C_{1-4}$ alkyl" is a $C_{1-4}$ alkyl optionally having from 1 to 5 substituents independently selected from the group consisting of $C_{1-4}$ alkoxy, $C_{1-9}$ amide, $C_{0-8}$ alkylamino, $C_{1-5}$ oxycarbonyl, cyano, $C_{3-8}$ cycloalkyl, halo, hydroxy, $C_{3-6}$ heterocycloalkyl optionally substituted on any ring nitrogen by $C_{1-4}$ alkyl, $C_{1-10}$ heteroaryl, and optionally substituted phenyl. Even more particularly "optionally substituted $C_{1-4}$ alkyl" refers to a $C_{1-4}$ alkyl optionally having from 1 to 5 substituents independently selected from the group consisting of halo, hydroxy, and optionally substituted phenyl.

The term "$C_{1-6}$ alkyl" refers to a straight or branched alkyl chain having from one to six carbon atoms.

The term "optionally substituted $C_{1-6}$ alkyl" refers to a $C_{1-6}$ alkyl optionally having from 1 to 7 substituents independently selected from the group consisting of $C_{0-8}$ alkylamino, $C_{2-4}$ alkenyl, optionally substituted $C_{1-4}$ alkoxy, $C_{1-4}$ thioalkoxy, $C_{1-9}$ amide, $C_{1-5}$ oxycarbonyl, cyano, optionally substituted $C_{3-8}$ cycloalkyl, halo, hydroxy, oxo, optionally substituted $C_{3-6}$ heterocycloalkyl, optionally substituted $C_{1-10}$ heteroaryl, and optionally substituted phenyl. A particular "optionally substituted $C_{1-6}$ alkyl" is a $C_{1-6}$ alkyl optionally having from 1 to 7 substituents independently selected from the group consisting of $C_{1-4}$ alkoxy, $C_{1-9}$ amide, cyano, $C_{3-8}$ cycloalkyl, halo, hydroxy, $C_{3-6}$ heterocycloalkyl, and optionally substituted phenyl. A more particular "optionally substituted $C_{1-6}$ alkyl" is a $C_{1-6}$ alkyl optionally having from 1 to 7 substituents independently selected from the group consisting of $C_{1-4}$ alkoxy, $C_{1-9}$ amide, $C_{0-8}$ alkylamino, $C_{1-5}$ oxycarbonyl, cyano, $C_{3-8}$ cycloalkyl, halo, hydroxy, $C_{3-6}$ heterocycloalkyl optionally substituted on any ring nitrogen by $C_{1-4}$ alkyl, $C_{1-10}$ heteroaryl, and optionally substituted phenyl. Even more particularly "optionally substituted $C_{1-6}$ alkyl" refers to a $C_{1-6}$ alkyl optionally having from 1 to 7 substituents independently selected from the group consisting of $C_{1-9}$ amide, $C_{1-4}$ alkoxy, cyano, $C_{3-8}$ cycloalkyl, halo, hydroxy, $C_{3-6}$ heterocycloalkyl optionally substituted on any ring nitrogen by $C_{1-4}$ alkyl, and optionally substituted phenyl.

The term "$C_{1-8}$ sulfonyl" refers to a sulfonyl linked to a $C_{1-6}$ alkyl group, $C_{3-8}$ cycloalkyl, or an optionally substituted phenyl. A particular "$C_{1-8}$ sulfonyl" refers to a sulfonyl linked to a $C_{1-6}$ alkyl group.

The term "optionally substituted $C_{1-8}$ sulfonyl" refers to a $C_{1-8}$ sulfonyl optionally having from 1 to 7 substituents independently selected from the group consisting of $C_{0-8}$ alkylamino, $C_{2-4}$ alkenyl, optionally substituted $C_{1-4}$ alkoxy, $C_{1-4}$ thioalkoxy, $C_{1-9}$ amide, $C_{1-5}$ oxycarbonyl, cyano, optionally substituted $C_{3-8}$ cycloalkyl, halo, hydroxy, oxo, optionally substituted $C_{3-6}$ heterocycloalkyl, optionally substituted $C_{1-10}$ heteroaryl, and optionally substituted phenyl. A particular "optionally substituted $C_{1-8}$ sulfonyl" is a $C_{1-8}$ sulfonyl optionally having from 1 to 7 substituents independently selected from the group consisting of $C_{1-4}$ alkoxy, cyano, $C_{3-8}$ cycloalkyl, halo, and optionally substituted phenyl.

The term "$C_{1-4}$ alkoxy" refers to a $C_{1-4}$ alkyl attached through an oxygen atom.

The term "optionally substituted $C_{1-4}$ alkoxy" refers to a $C_{1-4}$ alkoxy optionally having from 1 to 6 substituents independently selected from the group consisting of $C_{2-4}$ alkenyl, $C_{1-4}$ alkoxy, $C_{1-9}$ amide, $C_{0-8}$ alkylamino, $C_{1-5}$ oxycarbonyl, cyano, optionally substituted $C_{3-8}$ cycloalkyl, halo, hydroxy, optionally substituted $C_{1-10}$ heteroaryl, and optionally substituted phenyl. A particular "optionally substituted $C_{1-4}$ alkoxy" is a $C_{1-4}$ alkoxy optionally having from 1 to 6 substituents independently selected from the group consisting of $C_{1-4}$ alkoxy, cyano, $C_{3-8}$ cycloalkyl, halo, hydroxy, and optionally substituted phenyl. While it is understood that where the optional substituent is $C_{1-4}$ alkoxy, cyano, halo, or hydroxy then the substituent is generally not alpha to the alkoxy attachment point, the term "optionally substituted $C_{1-4}$ alkoxy" includes stable moieties and specifically includes trifluoromethoxy, difluoromethoxy, and fluoromethoxy.

The term "$C_{2-4}$ alkynyl" refers to a straight or branched alkynyl chain having from two to four carbon atoms and one carbon-carbon triple bond.

The term "optionally substituted $C_{2-4}$ alkynyl" refers to a $C_{2-4}$ alkynyl optionally having from 1 to 3 substituents independently selected from the group consisting of $C_{1-4}$ alkoxy, $C_{1-9}$ amide, $C_{1-5}$ oxycarbonyl, cyano, $C_{3-8}$ cycloalkyl, halo, hydroxy, optionally substituted $C_{1-10}$ heteroaryl, and optionally substituted phenyl.

The term "$C_{1-9}$ amide" refers to an amide group, a —CONRR in which each R is independently selected from the group consisting of hydrogen, $C_{1-4}$ alkyl, $C_{3-8}$ cycloalkyl, and optionally substituted phenyl, for example, —CONH$_2$, —CONHCH$_3$, and —CON(CH$_3$)$_2$. A particular "$C_{1-9}$ amide" refers to an amide having two groups independently selected from the group consisting of hydrogen, $C_{3-8}$ cycloalkyl, and $C_{1-4}$ alkyl.

The term "$C_{1-7}$ amido" refers to a —NHC(O)R group in which R is selected from the group consisting of hydrogen, $C_{1-6}$ alkyl, and optionally substituted phenyl.

The term "$C_{1-5}$ carbamoyl" refers to an O- or N-linked carbamate having a terminal $C_{1-4}$ alkyl.

The term "$C_{1-5}$ ureido" refers to a urea optionally having a $C_{1-4}$ alkyl.

The term "$C_{0-8}$ alkylamino" refers to an amino optionally having one or two $C_{1-4}$ alkyl.

The term "$C_{5-14}$ aryl" refers to a monocyclic and polycyclic unsaturated, conjugated hydrocarbon having aromatic character and having four to fourteen carbon atoms, and includes phenyl, biphenyl, indenyl, cyclopentyldienyl, fluorenyl, and naphthyl. A particular "$C_{5-14}$ aryl" is phenyl.

The term "optionally substituted $C_{5-14}$ aryl" refers to a $C_{5-14}$ aryl optionally having 1 to 5 substituents independently selected from the group consisting of $C_{0-8}$ alkylamino, $C_{1-7}$ amido, $C_{1-9}$ amide, $C_{1-5}$ carbamoyl, $C_{1-6}$ sulfonylamido, $C_{0-6}$ sulfonylamino, $C_{1-5}$ ureido, optionally substituted $C_{1-4}$ alkyl, optionally substituted $C_{1-4}$ alkoxy, cyano, halo, hydroxyl, nitro, $C_{1-5}$ oxycarbonyl, and $C_{1-8}$ sulfonyl. A particular "optionally substituted $C_{5-14}$ aryl" is a $C_{5-14}$ aryl optionally having 1 to 3 substituents independently selected from the group consisting of $C_{1-4}$ alkyl, trifluoromethyl, $C_{1-4}$ alkoxy, trifluoromethoxy, cyano, halo, hydroxyl, and nitro.

The term "$C_{1-5}$ oxycarbonyl" refers to an oxycarbonyl group (—CO$_2$H) and $C_{1-4}$ alkyl ester thereof.

The term "$C_{1-5}$ carbonyloxy" refers to a carbonyloxy group —$O_2CR$) wherein R is selected from the group consisting of hydrogen and $C_{1-4}$ alkyl.

The term "$C_{3-8}$ cycloalkyl" refers to a cycloalkyl ring having from three to eight carbon atoms, and includes cyclopropyl, cyclobutyl, cyclopentyl, cyclohexyl, and the like.

The term "optionally substituted $C_{3-8}$ cycloalkyl" refers to a $C_{3-8}$ cycloalkyl optionally having from 1 to 6 substituents independently selected from the group consisting of optionally substituted $C_{1-4}$ alkyl, $C_{2-4}$ alkenyl, optionally substituted $C_{1-4}$ alkoxy, $C_{1-9}$ amide, $C_{1-7}$ amido, $C_{0-8}$ alkylamino, $C_{1-5}$ oxycarbonyl, cyano, $C_{3-8}$ cycloalkyl, $C_{3-8}$ cycloalkoxy, halo, hydroxy, nitro, oxo, optionally substituted $C_{1-10}$ heteroaryl, and optionally substituted phenyl. A particular "optionally substituted $C_{3-8}$ cycloalkyl" is a $C_{3-8}$ cycloalkyl optionally having from 1 to 6 substituents independently selected from the group consisting of $C_{1-4}$ alkyl, $C_{1-4}$ alkoxy, halo, and hydroxy.

The term "$C_{3-8}$ cycloalkoxy" refers to a $C_{3-8}$ cycloalkyl attached through an oxygen atom.

The terms "halogen" and "halo" refers to a chloro, fluoro, bromo or iodo atom.

The term "$C_{3-6}$ heterocycloalkyl" refers to a 4 to 10 membered monocyclic saturated or partially (but not fully) unsaturated ring having one to four heteroatoms selected from the group consisting of nitrogen, oxygen, and sulfur. It is understood that where sulfur is included that the sulfur may be either —S—, —SO—, and —$SO_2$—. For example, but not limiting, the term includes azetidinyl, pyrrolidinyl, piperidinyl, piperazinyl, morpholinyl, thiomorpholinyl, oxetanyl, dioxolanyl, tetrahydropyranyl, tetrahydrothiopyranyl, dioxidotetrahydrothiopyranyl, tetrahydrofuryl, hexahydropyrimidinyl, tetrahydropyrimidinyl, dihydroimidazolyl, and the like. It is understood that a $C_{3-6}$ heterocycloalkyl can be attached as a substituent through a ring carbon or a ring nitrogen atom. Particular "$C_{3-6}$ heterocycloalkyls" are azetidinyl, pyrrolidinyl, piperidinyl, piperazinyl, morpholinyl, thiomorpholinyl, oxetanyl, dioxidotetrahydrothiopyranyl, and tetrahydropyranyl.

The term "optionally substituted $C_{3-6}$ heterocycloalkyl" refers to a $C_{3-6}$ heterocycloalkyl optionally substituted on the ring carbons with 1 to 4 substituents independently selected from the group consisting of optionally substituted $C_{1-4}$ alkyl, $C_{2-4}$ alkenyl, optionally substituted $C_{1-4}$ alkoxy, $C_{1-9}$ amide, $C_{1-7}$ amido, $C_{0-8}$ alkylamino, $C_{1-5}$ oxycarbonyl, cyano, optionally substituted $C_{3-8}$ cycloalkyl, $C_{3-8}$ cycloalkoxy, halo, hydroxy, nitro, oxo, and optionally substituted phenyl; and optionally having a substituent on each nitrogen independently selected from the group consisting of $C_{1-4}$ alkyl, $C_{2-4}$ alkenyl, $C_{1-9}$ amide (to form a urea), $C_{1-8}$ sulfonyl, $C_{3-8}$ cycloalkyl, optionally substituted $C_{3-6}$ heterocycloalkyl, optionally substituted $C_{1-10}$ heteroaryl, and optionally substituted phenyl. A particular "optionally substituted $C_{3-6}$ heterocycloalkyl" is a $C_{3-6}$ heterocycloalkyl optionally substituted on the ring carbons with 1 to 4 substituents independently selected from the group consisting of $C_{1-4}$ alkyl, $C_{1-4}$ alkoxy, cyano, halo, hydroxy, nitro, oxo; and optionally substituted on each ring nitrogen with a substituent independently selected from the group consisting of $C_{1-4}$ alkyl and $C_{1-8}$ sulfonyl. A more particular "optionally substituted $C_{3-6}$ heterocycloalkyl" is a $C_{3-6}$ heterocycloalkyl optionally substituted on the ring carbons with 1 to 2 substituents independently selected from the group consisting of $C_{1-4}$ alkyl, $C_{1-4}$ alkoxy, cyano, hydroxy, oxo; and optionally substituted on each ring nitrogen independently with a $C_{1-4}$ alkyl.

The term "$C_{1-6}$ alkyl$C_{3-6}$ heterocycloalkylamide" refers to a $C_{1-6}$ alkyl substituted with a $C_{3-6}$ heterocycloalkylamide, for example —CONR'R" where R' and R" are taken together with the nitrogen to which they are attached to form a 4 to 7 membered monocyclic saturated or partially (but not fully) unsaturated ring optionally having one to 2 additional heteroatoms selected from the group consisting of nitrogen, oxygen, and sulfur. It is understood that where sulfur is included that the sulfur may be either —S—, —SO—, and —$SO_2$—. For example, but not limiting, the term includes groups in which R' and R" are taken together to form an azetidine, pyrrolidine, piperidine, piperazine, morpholine, hexahydropyrimidine, tetrahydropyrimidine, and the like. It is understood that the 4 to 7 membered monocyclic saturated or partially (but not fully) unsaturated ring may be optionally substituted in carbon with 1 to 4 substituents independently selected from the group consisting of optionally substituted $C_{1-4}$ alkyl, $C_{2-4}$ alkenyl, optionally substituted $C_{1-4}$ alkoxy, $C_{1-9}$ amide, $C_{1-7}$ amido, $C_{0-8}$ alkylamino, $C_{1-5}$ oxycarbonyl, cyano, optionally substituted $C_{3-8}$ cycloalkyl, $C_{3-8}$ cycloalkoxy, halo, hydroxy, nitro, oxo, and optionally substituted phenyl; and optionally having a substituent on any nitrogen independently selected from the group consisting of $C_{1-4}$ alkyl, $C_{2-4}$ alkenyl, $C_{1-9}$ amide (to form a urea), $C_{1-8}$ sulfonyl, $C_{3-8}$ cycloalkyl, optionally substituted $C_{3-6}$ heterocycloalkyl, optionally substituted $C_{1-10}$ heteroaryl, and optionally substituted phenyl.

The term "$C_{1-10}$ heteroaryl" refers to a five to twelve membered monocyclic or polycyclic unsaturated, conjugated ring(s) having aromatic character and having one to ten carbon atoms and one or more, typically one to four, heteroatoms selected from the group consisting of nitrogen, oxygen, and sulfur. The term "$C_{1-10}$ heteroaryl" particularly includes the benzo forms. For example, but not limiting, the term includes azepinyl, diazepinyl, furyl, thiophenyl, imidazolyl, isothiazolyl, isoxazolyl, oxadiazolyl, oxazolyl, pyrazinyl, pyrazolyl, pyridazinyl, pyridinyl, pyrimidinyl, thiazolyl, thiadiazolyl, triazolyl, tetrazolyl, benzazepinyl, benzodiazepinyl, benzofuryl, benzothiophenyl, benzimidazolyl, imidazopyridinyl, pyrazolopyridinyl, pyrrolopyridinyl, quinazolinyl, thienopyridinyl, indolizinyl, imidazopyridinyl, quinolinyl, isoquinolinyl, indolyl, isoindolyl, benzoxazolyl, benzoxadiazolyl, benzopyrazolyl, benzothiazolyl, and the like. It is understood that a $C_{1-10}$ heteroaryl can be attached as a substituent through a ring carbon or a ring nitrogen atom where such an attachment mode is available, for example for an indolyl, imidazolyl, azepinyl, triazolyl, pyrazinyl, etc.

In particular "$C_{1-10}$ heteroaryl" includes furyl, thiophenyl, imidazolyl, pyrazolyl, pyridazinyl, pyridinyl, and pyrimidinyl.

The term "optionally substituted $C_{1-10}$ heteroaryl" refers to a $C_{1-10}$ heteroaryl optionally having 1 to 5 substituents on carbon independently selected from the group consisting of $C_{1-7}$ amido, $C_{0-8}$ alkylamino, $C_{1-9}$ amide, $C_{1-5}$ carbamoyl, $C_{1-6}$ sulfonylamido, $C_{0-6}$ sulfonylamino, $C_{1-5}$ ureido, optionally substituted $C_{1-4}$ alkyl, optionally substituted $C_{1-4}$ alkoxy, cyano, halo, hydroxyl, oxo, nitro, $C_{1-5}$ oxycarbonyl, and $C_{1-8}$ sulfonyl and optionally having a substituent on each nitrogen independently selected from the group consisting of optionally substituted $C_{1-4}$ alkyl, $C_{1-8}$ sulfonyl, optionally substituted $C_{3-6}$ heterocycloalkyl, and optionally substituted phenyl. A particular "optionally substituted $C_{1-10}$ heteroaryl" is a $C_{1-10}$ heteroaryl optionally having 1 to 5 substituents on carbon independently selected from the group consisting of $C_{1-4}$ alkyl, $C_{1-4}$ alkoxy, cyano, halo, and hydroxyl; and optionally having a substituent on each nitrogen independently selected from the group consisting of $C_{1-4}$ alkyl and $C_{1-8}$ sulfonyl.

The term "oxo" refers to an oxygen atom having a double bond to the carbon to which it is attached to form the carbonyl of a ketone or aldehyde. It is understood that as the term is used herein oxo refers to doubly bonded oxygen attached to the group which has the oxo substituent, as opposed to the oxo group being pendant as a formyl group. For example, an acetyl radical is contemplated as an oxo substituted alkyl group and a pryidone radical is contemplated as oxo substituted $C_{1-10}$ heteroaryl and a piperidinone radical is contemplated as an oxo substituted piperidinyl.

The term "optionally substituted phenyl" refers to a phenyl group optionally having 1 to 5 substituents independently selected from the group consisting of $C_{2-4}$ alkenyl, $C_{1-4}$ alkyl, $C_{1-4}$ alkoxy, $C_{1-9}$ amide, $C_{0-8}$ alkylamino, $C_{1-5}$ oxycarbonyl, cyano, halo, hydrogen, hydroxyl, nitro, $C_{1-8}$ sulfonyl, trifluoromethoxy, and trifluoromethyl. A particular "optionally substituted phenyl" is a phenyl group optionally having 1 to 5 substituents independently selected from the group consisting of $C_{1-4}$ alkyl, $C_{1-4}$ alkoxy, cyano, halo, hydroxyl, nitro, and trifluoromethyl.

The term "$C_{1-6}$ sulfonylamido" refers to a —NHS(O)$_2$—R group wherein R is $C_{1-6}$ alkyl.

The term "$C_{0-6}$ sulfonylamino" refers to a —S(O)$_2$NH—R group wherein R is selected from the group consisting of hydrogen and is $C_{1-6}$ alkyl.

The term "$C_{1-4}$ thioalkoxy" refers to a $C_{1-4}$ alkyl attached through a sulfur atom.

The term "pharmaceutically acceptable salt" refers to salts of pharmaceutically acceptable organic acids and bases and pharmaceutically acceptable inorganic acids and bases. Such salts are well known in the art and include those described in Journal of Pharmaceutical Science, 66, 2-19 (1977). Examples are the hydrochloride salts.

It is understood that, where the terms defined herein mention a number of carbon atoms, that the mentioned number refers to the mentioned group and does not include any carbons that may be present in any optional substituent(s) thereon. It is also understood that "substituted," means that one or more hydrogen atoms of the group substituted are replaced with non-hydrogen atoms or groups, in such a manner that valence requirements are met and that a chemically stable compound results. The term "stable" refers to compounds that are not substantially altered when subjected to conditions to allow for their production. In a non-limiting example, a stable compound or chemically feasible compound is one that is not substantially altered when kept at a temperature of 40° C. or less, in the absence of moisture or other chemically reactive conditions, for about a week.

It is understood that when n is greater than 0, that each $R_6$ is attached at any of the available valencies on Ar.

The skilled artisan will appreciate that certain of the compounds of the present invention exist as isomers. The term "isomer" is understood to include regioisomers, geometric isomers, and stereoisomers. All mixtures of regioisomers and stereoisomers, in any ratio, and specific regiosiomers, geometric isomers, enantiomers, and diastereomers of the compounds of the invention are contemplated by the present invention.

The skilled artisan will appreciate that certain of the compounds of the present invention exist as tautomers. All tautomeric forms the compounds of the invention are contemplated by the present invention.

The terms "compounds of the invention" and "compounds of the present invention" and the like, include the embodiment of formula I and the other embodiments described below including the compounds exemplified herein.

It is understood that $R_1$ is at one of the pyrazolo nitrogens and the other pyrazolo nitrogen is unsubstituted. These embodiments, in addition to particular embodiments including the features ── are depicted at (a) and (b) below.

(a) One embodiment relates to compounds of formula I wherein the compound is

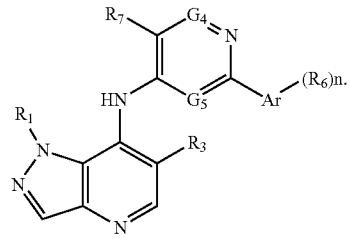

(b) Another embodiment relates to compounds of formula I wherein the compound is

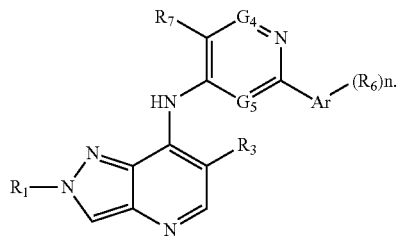

(c) Another embodiment relates to compounds of formula I and embodiments (a) and (b) wherein $G_4$ is $CR_4$ and a more particular embodiment relates to compounds of formula I and embodiments (a) and (b) wherein $G_4$ is $CR_4$ and $R_4$ is selected from the group consisting of hydrogen and methyl.

(d) Another embodiment relates to compounds of formula I and embodiments (a), (b), and (c) wherein $G_5$ is $CR_5$ and a more particular embodiment relates to compounds of formula I and embodiments (a), (b), and (c) wherein $G_5$ is $CR_5$ and $R_5$ is selected from the group consisting of hydrogen and methyl.

(e) Another embodiment relates to compounds of formula I and embodiments (a), (b), and (d) wherein $G_4$ is N.

(f) Another embodiment relates to compounds of formula I and embodiments (a), (b), and (c) wherein $G_5$ is N.

(g) Another embodiment relates to compounds of formula I and embodiments (a), (b), (c), (d), (e), and (f) wherein Ar is phenyl.

(h) Another embodiment relates to compounds of formula I and embodiments (a), (b), (c), (d), (e), and (f) wherein Ar is pyridine.

(i) Another embodiment relates to compounds of formula I and embodiments (a), (b), (c), (d), (e), and (f) wherein Ar is pyrimidine.

(j) Another embodiment relates to compounds of formula I and embodiments (a), (b), (c), (d), (e), (f), (g), (h), and (i) wherein n is 1 to 2 and a more particular embodiment relates to compounds of formula I and embodiments (a), (b), (c), (d), (e), (f), (g), (h), and (i) wherein n is 1 to 2 wherein $R_6$ is selected from the group consisting of halo and methyl, and an even more particular embodiment relates to compounds of formula I and embodiments (a), (b), (c), (d), (e), (f), (g), (h), and (i) wherein n is 2 wherein one of $R_6$ is selected from the group consisting of fluoro and chloro.

(k) Another embodiment relates to compounds of formula I and embodiments (a), (b), (c), (d), (e), (f), (g), (h), (i), and (j) wherein $R_1$ is selected from the group consisting of hydrogen and $C_{1-6}$ alkyl and more particularly $R_1$ is hydrogen and even more particularly $R_1$ is $C_{1-6}$ alkyl.

(l) Another embodiment relates to compounds of formula I and embodiments (a), (b), (c), (d), (e), (f), (g), (h), (i), and (j) wherein $R_1$ is optionally substituted $C_{1-6}$ alkyl.

(m) Another embodiment relates to compounds of formula I and embodiments (a), (b), (c), (d), (e), (f), (g), (h), (i), and (j) wherein $R_1$ is $C_{1-6}$ alkyl optionally substituted with 1 or 2 substituents selected from the group consisting of $C_{1-4}$ alkoxy, $C_{1-9}$ amide, $C_{3-8}$ cycloalkyl, hydroxy, and $C_{3-6}$ heterocycloalkyl.

(n) Another embodiment relates to compounds of formula I and embodiments (a), (b), (c), (d), (e), (f), (g), (h), (i), and (j) wherein $R_1$ is optionally substituted $C_{3-6}$ heterocycloalkyl.

(o) Another embodiment relates to compounds of formula I and embodiments (a), (b), (c), (d), (e), (f), (g), (h), (i), and (j) wherein $R_1$ is $C_{3-6}$ heterocycloalkyl.

(p) Another embodiment relates to compounds of formula I and embodiments (a), (b), (c), (d), (e), (f), (g), (h), (i), and (j) wherein $R_1$ is —C(O)NR$_8$R$_9$ and a particular embodiment relates to compounds of formula I and embodiments (a), (b), (c), (d), (e), (f), (g), (h), (i), and (j) wherein $R_1$ is —C(O)NR$_8$R$_9$ wherein $R_8$ is selected from the group consisting of hydrogen and $C_{1-6}$ alkyl and $R_9$ is selected from the group consisting of hydrogen and $C_{1-6}$ alkyl and an even more particular embodiment relates to compounds of formula I and embodiments (a), (b), (c), (d), (e), (f), (g), (h), (i), and (j) wherein $R_1$ is —C(O)NR$_8$R$_9$ wherein $R_8$ is $C_{1-6}$ alkyl and $R_9$ is hydrogen.

(q) Another embodiment relates to compounds of formula I and embodiments (a), (b), (c), (d), (e), (f), (g), (h), (i), (j), (k), (l), (m), (n), (o), and (p) wherein $R_3$ is hydrogen.

(r) Another embodiment relates to compounds of formula I and embodiments (a), (b), (c), (d), (e), (f), (g), (h), (i), (j), (k), (l), (m), (n), (o), and (p) wherein $R_3$ is halo.

(s) Another embodiment relates to compounds of formula I and embodiments (a), (b), (c), (d), (e), (f), (g), (h), (i), (j), (k), (l), (m), (n), (o), (p), (q), and (r) wherein $R_7$ is selected from the group consisting of hydrogen, halogen, and methyl.

For complete clarity, another embodiment relates to a pharmaceutically acceptable salt of each of the embodiments (a), (b), (c), (d), (e), (f), (g), (h), (i), (j), (k), (l), (m), (n), (o), (p), (q), (r), and (s); formula I; and the compounds exemplified herein.

Again, for complete clarity, another embodiment relates to the isomers of each of the embodiments (a), (b), (c), (d), (e), (f), (g), (h), (i), (j), (k), (l), (m), (n), (o), (p), (q), (r), and (s); formula I; and the compounds exemplified herein.

The compounds of the invention can be prepared by a variety of procedures such as described in Scheme A below. All substituents, unless otherwise indicated, are as previously defined. The products of each step can be recovered by conventional methods including extraction, evaporation, precipitation, chromatography, filtration, trituration, crystallization, and the like. In particular, it is understood that the regioisomers depicted below may be separated by a variety of methods including chromatography and crystallization, and the like.

The procedures may require protection of certain groups, for example hydroxy, amino, or carboxy groups to minimize unwanted reactions. The selection, use, and removal of protecting groups are well known and appreciated as standard practice, for example T. W. Greene and P. G. M. Wuts in Protective Groups in Organic Chemistry (John Wiley and Sons, 1991).

Scheme A

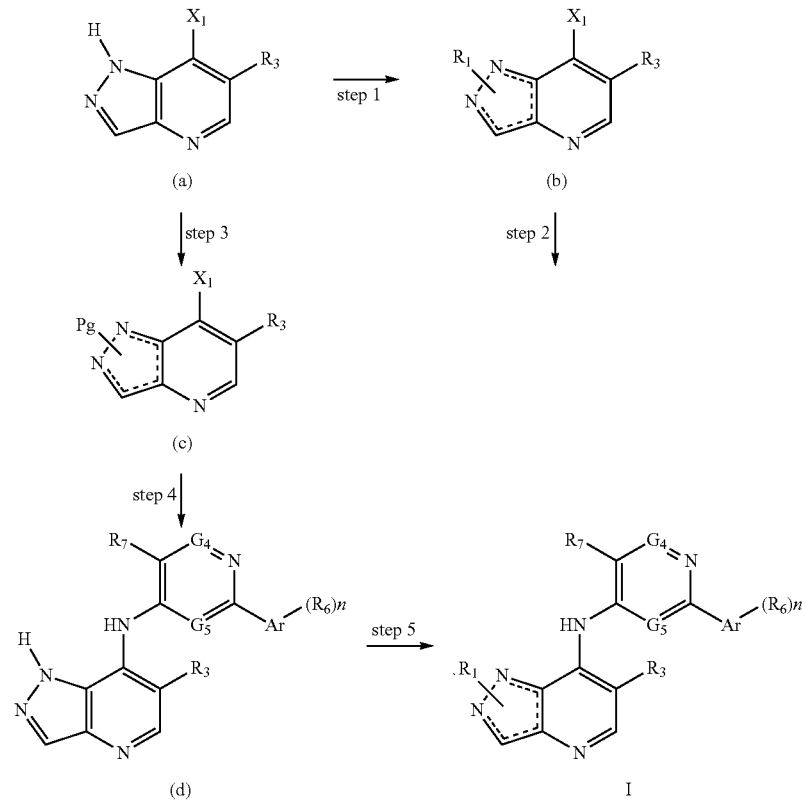

Scheme A, step 1, depicts the reaction of an appropriate compound of formula (a) with an appropriate alkylating reagent to give compounds of formula (b). An appropriate compound of formula (a) is one in which $R_3$ is as desired in the final compound of formula I or gives rise to $R_3$ as desired in the final product of formula I and $X_1$ is a leaving group, including halogens, particularly as bromo and iodo and sulfonates particularly trifluoromethanesulfonate and nosylate. An appropriate alkylating reagent is one of the formula $R_1$—$X_2$ where $R_1$ is as desired in the final compound of formula I or give rise to $R_1$ as desired in the final compound of formula I and $X_2$ is a suitable leaving group, for example a halogen, particularly chloro, bromo, or iodo, or a sulfonate, for example toslylate or nosylate or isocycanates or anhydrides that give rise to $R_1$ as desired in the final compound of formula I.

For example, such a reaction is generally carried out in a solvent, such as DMSO, THF, dimethylformamide, dimethylacetamide, pyridine, acetonitrile, and the like. The reaction is typically carried out with the use of a suitable base, such as alkali metal hydrides, such as sodium hydride; alkali metal alkoxides, such as sodium alkoxides; alkali metal carbonates, such as potassium carbonate, cesium carbonate; alkali metal hydroxides, such as sodium hydroxide and potassium hydroxide, and bases such as lithium diisopropylamide, lithium hexamethyldisilazide, and sodium hexamethyldisilazide, and the like. The reaction is typically carried out at temperatures of from 0° C. to 80° C. and typically requires 1 to 72 hours.

Scheme A, step 2, depicts the reaction of an appropriate compounds of formulas (b) with an appropriate compound of formula (e), shown below to give a compound of formula I or a compound that gives rise to a compound of formula I.

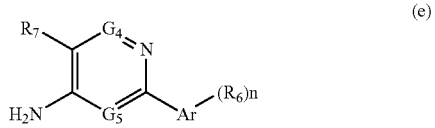

(e)

An appropriate compound of formula (e) is one in which Ar, $G_4$, $G_5$, and n are as desired in the final compound of formula I and $R_6$ and $R_7$ are as desired in the final compound of formula I or give rise to $R_6$ and $R_7$ as desired in the final compound of formula I. Compounds of formula (e) are readily prepared. The amine group can be introduced, if needed, for example from a halogen, a carboxyl group, a nitro group by a variety of methods. A required Ar group can be introduced by various methods, including the Suzuki Stille, Negishi, Ulmann and other organometallic coupling reactions.

For example, such a reaction is generally carried out in a solvent, such as dioxane, THF, dimethylformamide, dimethylacetamide, toluene, xylene, and the like. The reaction may be carried out with the use of a suitable base, such as alkali metal alkoxides, such as sodium alkoxides; alkali metal carbonates, such as potassium carbonate; alkali metal hydroxides, such as sodium hydroxide and potassium hydroxide, and the like. The reaction may be carried out in the presence of a catalyst, such as palladium catalysts. The reaction typically is carried out at temperatures of from 60° C. to 120° C., may be carried out using microwave irradiation, and require about 1 hour to 3 days.

Alternately, Scheme A, step 3, depicts the protection of an appropriate compound of formula (a) to give compounds of formula (c). An appropriate compound of formula (a) is one as discussed above in Scheme A, step 1. The selection, use, and removal of protecting groups are well known and appreciated as standard practice, for example T. W. Greene and P. G. M. Wuts in Protective Groups in Organic Chemistry (John Wiley and Sons, 1991).

Scheme A, step 4, depicts the reaction of an appropriate compounds of formulas (c) with an appropriate compound of formula (e) using the methodology of Scheme A, step 2 discussed above and subsequent deprotection to give a compound of formula (d).

Scheme A, step 5, depicts the reaction of a compound of formula (d) by the methodology for Scheme A, step 1, to give a compound of formula I or a compound that gives rise to a compound of formula I.

It will be recognized by one of ordinary skill in the art that the steps in Scheme A may be varied to provide compounds of formula I. In particular, an appropriate compound of formula (a) can be reacted with an appropriate compound of formula (e) to give directly a compound of formula I in which one of $R_1$ is hydrogen. Also, the order of the steps required to produce the compounds of formula I can be varied in other ways and is dependent upon the particular compound being synthesized, the starting compound, and the relative lability of the substituted moieties.

It is also understood that some compounds of formula I may be elaborated to other compounds of formula I, in additional steps not shown. Such reactions include protection and/or deprotection, hydrolysis, oxidation, reduction, alkylation, amidations, sulfonations, alkynations, alkyenations, and the like. Also, in an optional step, not shown, the compounds of formula I can be converted to a pharmaceutically acceptable salt by methods well known in the art.

The terms used in the examples and preparations below have their ordinary meaning unless indicated otherwise. The examples and preparations below are illustrative only and are not intended to limit the invention in any way. The products of each step can be recovered by conventional methods including extraction, evaporation, precipitation, chromatography, filtration, trituration, crystallization, and the like. In particular, it is understood that particular regioisomers may be separated by a variety of methods including chromatography and crystallization, and the like.

Preparation 1: 7-iodo-1H-pyrazolo[4,3-b]pyridine

Diisopropylamine (50.9 mL, 360 mmol) was added to THF (1600 mL), and the mixture was cooled to 0° C. in an ice bath and then n-butyllithium (137.6 ml, 2.5 M in hexane) was added drop wise at 0° C., and stirred for another 30 minutes. The mixture was then cooled to −78° C., and a solution of 2-cyano-3-fluoropyridine (40 g, 328 mmol) in 300 mL of THF was added. After 25 minutes, a solution of $I_2$ (83.2 g, 328 mmol) in THF (80 mL) was added and the reaction was stirred for 40 minutes at −78° C. The reaction was removed from the cooling bath and quenched with 400 mL sodium thiosulfate solution (10% aq.) followed by water (400 mL). The reaction mixture was diluted with ether (400 mL), and the layers were separated. The organic layer were washed with brine, dried over sodium sulfate, filtered and concentrated to a brown solid. The solid was purified with silica column chromatography eluted with 95:5 hexanes:ethyl acetate to give 3-fluoro-4-iodopicolinonitrile (25.6 g, 31.5% yield) as an off-white solid. $^1$H NMR (400 MHz, DMSO-d6) δ ppm 8.25-8.26 (m, 1H) 8.35 (t, J=5.05 Hz, 1H). MS [M+H] found 249.0.

3-Fluoro-4-iodopicolinonitrile (25.6 g) was dissolved in n-butan-1-ol (250 mL) then hydrazine hydrate (100%, 23.3 mL) was added. The reaction was heated at 105° C. for 2 hours. The reaction mixture was cooled to room temperature, filtered, rinsed with water, and dried for 30 minutes under vacuum to give 7-iodo-1H-pyrazolo[4,3-b]pyridine-3-amine (25 g) as a light yellow solid. $^1$H NMR (400 MHz, DMSO-d6) δ ppm 5.35-5.55 (2H, m) 7.73-7.74 (1H, m) 7.939-7.94 (1H, m). MS [M+H] found 261.0.

To a suspension of 7-iodo-1H-pyrazolo[4,3-b]pyridin-3-amine (23 g) in water (90 mL) and AcOH (75 mL) was added dropwise a solution of sodium nitrite (12.6 g) in water (90 mL) over 30 minutes at 0° C. The mixture was warmed to room temperature and stirred for 24 hours. Then the mixture was cooled to 0° C. again and stirred for another 0.5 hour to give a solid which was collected by filtration and washed with cold water. The solid was suspended in aqueous HI (20 mL 50% HI diluted to 300 mL with water) and dimethoxymethane (600 mL). This mixture was heated to 80° C. for 3 hours, then cooled to room temperature, neutralized with $Na_2CO_3$ solution, and then extracted with ethyl acetate. The organic layer was collected, dried over anhydrous $Na_2SO_4$, filtered, and evaporated under reduced pressure to give a residue. This residue was purified by column chromatography eluting with 1:2 petroleum ether:ethyl acetate to afford the title compound as a light yellow solid (7.8 g). $^1$H-NMR (400 MHz, DMSO-d6) 7.86 (d, J=4.4 Hz, 1H) 8.16 (d, J=4.4 Hz, 1H) 8.46 (s, 1H) 13.67 (s, 1H).

Preparation 2:
2-(5-chloro-2-fluorophenyl)pyridin-4-amine

5-Chloro-2-fluorophenylboronic acid (2.7 g, 15.48 mmol), 2-chloropyridin-4-amine (1.531 g, 11.91 mmol), sodium carbonate (5.96 ml, 11.91 mmol), and bis(triphenylphosphine) palladium chloride (0.836 g, 1.191 mmol) were combined in dioxane (54 mL) and refluxed for 3 hours. The reaction was cooled, the solvent removed in vacuo and the reaction mixture partitioned between brine and EtOAc. The organic layer was separated, dried over $MgSO_4$ filtered and purified using NH silica column chromatography and a gradient of 5-95% EtOAc in hexanes to afford the title compound as a white solid (522 mg; 20%). ESI-MS: m/z 223.1 (M+H).

Preparation 3: 7-iodo-1-(4-methoxybenzyl)-1H-pyrazolo[4,3-b]pyridine and 7-iodo-2-(4-methoxybenzyl)-2H-pyrazolo[4,3-b]pyridine 7-Iodo-1H-pyrazolo[4,3-b]pyridine (100 mg, 0.408 mmol) was combined with sodium hydride (19.59 mg, 0.490 mmol) in DMF (4 mL). The reaction was stirred for 10 minutes and then cooled in an ice bath. 1-(Chloromethyl)-4-methoxybenzene (55.6 µl, 0.408 mmol) was slowly added and the mixture was let stir for 15 minutes, the ice bath was removed and stirring was continued for another 15 minutes, then 20 mL of ice water was added followed by 20 mL of ammonium chloride solution (saturated) and the mixture was extracted with ethyl acetate (5 mL×2). The combined organic layers were dried over sodium sulfate, filtered, and concentrated to get very dark oil. The oil was dissolved in a mixture of ethyl acetate, methanol and dichloromethane and absorbed onto silica gel column which was eluted using 30% ethyl acetate in hexanes to give, after drying for 1 hour under high vacuum, the title compound which was used without further purification. ESI-MS: m/z 366.1 (M+H).

Preparation 4: 2-(5-chloro-2-fluorophenyl)-5-methylpyridin-4-amine

2-Chloro-5-methylpyridin-4-amine (180 mg, 1.262 mmol), 5-chloro-2-fluorophenylboronic acid (220 mg, 1.262 mmol) and Pd(PPh$_3$)$_4$ (365 mg, 0.316 mmol) were combined in dioxane (4 mL) and saturated $K_2CO_3$ solution (2 mL). The mixture was heated at 120° C. for 30 minutes using a microwave. Solvent was removed and the reaction mixture was purified by preparative HPLC eluting with a gradient of 5-40% acetonitrile (containing 0.035% TFA) in water (containing 0.05% TFA) using a Sunfire Prep 5 µm C18, 75×30 mm column to give the title compound as a TFA salt (130 mg, 43.5% yield). ESI-MS: m/z 236.1 (M+H).

Preparation 5:
2-(5-chloro-2,4-difluorophenyl)pyridin-4-amine tert-Butyl 2-bromopyridin-4-ylcarbamate (258 mg, 0.945 mmol), 5-chloro-2,4-difluorophenylboronic acid (236 mg, 1.228 mmol) and bis(triphenylphosphine) palladium chloride (133 mg, 0.189 mmol) were combined in dioxane (5 mL) and saturated $Na_2CO_3$ (0.472 ml, 0.945 mmol). The reaction mixture was heated at 90° C. in an oil bath. After 12 hours, the reaction mixture was cooled, water (10 mL) was added and the reaction mixture was extracted with EtOAc (100 mL, 2×). The organic layers were combined, washed with brine, dried over $Na_2SO_4$, filtered, and concentrated to give a residue. The residue was dissolved in dichloromethane (4 mL) and trifluoroacetic acid was added (4 mL). The reaction was stirred at room temperature for 20 minutes then the solvent was removed on a rotavap and the residue was further dried under high vacuum overnight. This residue was purified by NH column chromatography, eluted with EtOAc in Hexanes (0-100%) to give the title compound (49 mg) as white solid. ESI-MS: m/z 242.0 (M+H).

Preparation 6: 3'-fluoro-6'-methyl-2,2'-bipyridin-4-amine

2-Bromopyridin-4-amine (9 g, 52.0 mmol) and N,N-dimethylpyridin-4-amine (0.636 g, 5.20 mmol) were dissolved in dichloroethane (100 mL) and a solution of phthaloyl dichloride (10.11 ml, 52.0 mmol) in dichloroethylene (20.0 mL) was added dropwise at room temperature. The reaction was stirred for 1 hour and partitioned between saturated bicarbonate and dichloromethane. The organics were separated and dried over Na2SO4, filtered, and evaporated to give a solid. The solid was purified by silica column chromatography in eluting with a gradient of methanol (0-15%) in dichloromethane/to afford product solid which was triturated with methanol and heated briefly to afford the title compound (4.8 g) as an off white solid. 1H NMR (400 MHz, DMSO-d6) ppm 7.69 (dd, J=5.31, 1.77 Hz, 1H) 7.86 (d, J=1.77 Hz, 1H) 7.91-7.98 (m, 2H) 7.99-8.08 (m, 2H) 8.57 (d, J=5.56 Hz, 1H)

Tetrahydrofuran (10 mL) was cooled to −78° C. and tert-Butyllithium (4.56 ml, 6.84 mmol) was added, followed by a solution of 2-bromo-3-fluoro-6-methylpyridine (1 g, 5.26 mmol) in tetrahydrofuran (2.5 mL). The reaction mixture was stirred for 30 minutes then zinc(II)chloride (2.58 g, 18.95 mmol) was added and the reaction was warmed to room temperature over 2 hours. A solution of 2-(2-bromopyridin-4-yl) isoindoline-1,3-dione (9) (1.595 g, 5.26 mmol) and tetrakis(triphenylphosphine)palladium(0) (0.608 g, 0.526 mmol) in THF (10 mL) was added and the reaction was stirred at room temperature over night to give a solid which was collected by filtration to give 2-(3'-fluoro-6'-methyl-2,2'-bipyridin-4-yl)isoindoline-1,3-dione as a white solid (786 mg).

2-(3'-fluoro-6'-methyl-2,2'-bipyridin-4-yl)isoindoline-1, 3-dione (65 mg, 0.195 mmol) was suspended in dichloromethane (3 mL); methylhydrazine (0.205 mL, 3.90 mmol) was added and the mixture was stirred at room temperature over night. The reaction was filtered thru Celite® and the filtrate was concentrated to give the title compound as a clear yellow film which was used without further purification. ESI-MS: m/z 204.1 (M+H).

Preparation 7: 2-(3-chlorophenyl)pyridin-4-amine

2-Chloropyridin-4-amine (200 mg, 1.556 mmol), 3-chlorophenylboronic acid (243 mg, 1.556 mmol) and Pd(PPh$_3$)$_4$ (450 mg, 0.389 mmol) were combined in dioxane (4 mL) and saturated K$_2$CO$_3$ solution (2 mL). The mixture was heated at 120° C. for 30 minutes in a microwave. The solvent was removed to give a residue which was purified by silica column chromatography eluting with a gradient of 0-5% methanol in dichloromethane to give the title compound as light yellow oil (150 mg, 47.1% yield).

Preparation 8: 2-(5-chloro-2-fluorophenyl)-6-methylpyridin-4-amine

Potassium phosphate tribasic (13.84 g, 65.2 mmol), palladium acetate (0.390 g, 1.739 mmol), methyl 2-bromo-6-methylisonicotinate (5 g, 21.73 mmol), 5-chloro-2-fluorophenylboronic acid (5.68 g, 32.6 mmol) and dicyclohexyl(2',6'-diisopropoxybiphenyl-2-yl)phosphine (1.521 g, 3.26 mmol) were combined in toluene (70 mL) and water (14 mL) and heated at 110° C. in an oil bath for 1 hour. The reaction was then cooled and diluted with water (30 mL), filtered through Celite® and the layers were separated. The aqueous layer was extracted with ether and the combined organic layers were dried over sodium sulfate, filtered, and concentrated to give a residue. The residue was dissolved in ethyl acetate/dichloromethane and absorbed onto silica gel before chromatography on silica eluting with 10% ethyl acetate in hexanes to give an off white powder which was dissolved in dichloromethane, dried onto silica gel and further purified by chromatography on silica using a step gradient (0-10% ethyl acetate/hexanes) to give methyl 2-(5-chloro-2-fluorophenyl)-6-methylisonicotinate (1.86 g, 30.6% yield) as an off-white solid. $^1$H NMR (400 MHz, DMSO-d6) δ ppm 2.64-2.68 (3H, m) 3.91-3.95 (3H, m) 7.45 (1H, dd, J=11.12, 8.84 Hz) 7.59 (1H, ddd, J=8.84, 4.29, 2.78 Hz) 7.75-7.81 (1H, m) 8.01 (1H, dd, J=6.57, 2.78 Hz) 8.06 (1H, s). ESI-MS: m/z 280.1 (M+H).

Methyl 2-(5-chloro-2-fluorophenyl)-6-methylisonicotinate (1.86 g, 6.65 mmol) was dissolved in methanol (24 mL) and NaOH (16.6 ml, 33.3 mmol) was added. The reaction was heated at 60° C. for 1.5 hour, cooled to room temperature, acidified (pH~2) with 6N HCl to give a precipitate which was filtered and dried to give 2-(5-chloro-2-fluorophenyl)-6-methylisonicotinic acid (1.17 g) as a off white solid which was used without further purification. ESI-MS: m/z 266.1 (M+H).

2-(5-Chloro-2-fluorophenyl)-6-methylisonicotinic acid (1.1 g, 4.14 mmol), diphenyl phosphorazidate (0.895 ml, 4.14 mmol), triethylamine (0.873 ml, 6.21 mmol), 2-methylpropan-2-ol (0.466 ml, 4.97 mmol) were combined in toluene (12.5 mL) and heated at reflux for 30 minutes, then cooled and concentrated to give a residue. The residue was purified by silica chromatography eluted using a step gradient (0-25% ethyl acetate/hexanes) to give the title compound as an off-white solid. $^1$H NMR (400 MHz, DMSO-d$_6$) δ ppm 1.49 (s, 9H) 2.46 (s, 3H) 7.34-7.42 (m, 2H) 7.49-7.56 (m, 1H) 7.76 (s, 1H) 7.94 (dd, J=6.82, 2.78 Hz, 1H) 9.90 (s, 1H). ESI-MS: m/z 337.2 (M+H).

Preparation 9:
6-(5-chloro-2-fluorophenyl)pyrimidin-4-amine

Bis(triphenylphosphine)palladium chloride (542 mg, 0.772 mmol), tert-butyl 2-bromopyridin-4-ylcarbamate (250 mg, 0.915 mmol), sodium carbonate (0.458 mL, 0.915 mmol), and 5-chloro-2-fluorophenylboronic acid (875 mg, 5.02 mmol) and sodium carbonate (0.458 mL, 0.915 mmol) were combined in dioxane (5 mL) and heated at 100° C. for 4 hours. The reaction mixture was then cooled and evaporated on a rotovap, to afford a yellow solid. The solid was triturated with dichloromethane, filtered, and washed with dichloromethane to give the title compound as a grayish yellow solid (596 mg) ESI-MS: m/z 224.1 (M+H).

Preparation 10:
2-(2-fluoro-5-methylphenyl)pyridin-4-amine

Bis(triphenylphosphine)palladium chloride (0.406 g, 0.578 mmol), tert-butyl 2-bromopyridin-4-ylcarbamate (250 mg, 0.915 mmol), and 2-fluoro-5-methylphenylboronic acid (1.157 g, 7.51 mmol) and sodium carbonate (0.458 ml, 0.915 mmol) were combined in dioxane (10 mL) and heated to reflux for 5 hours. The reaction mixture was cooled, evaporated to remove most of the solvent, and partitioned between brine and EtOAc. The organic layer was separated and dried over Na$_2$SO$_4$, filtered, and concentrate under vacuum to give a residue which was purified by NH silica column chromatography eluting with Hex/EtOAc 1:1 to give a residue which was further purified by repeating the silica column chromatography using the same conditions to give the title compound (986 mg) as clear oil which solidified on standing. ESI-MS: m/z 203.1 (M+H).

Preparation 11: 5,6'-dimethyl-2,2'-bipyridin-4-amine

To a solution of 2-bromo-5-methyl-4-nitropyridine 1-oxide (0.5 g, 2.146 mmol) in acetic acid (10 mL) at 25° C. was added iron (0.479 g, 8.58 mmol). The reaction was heated to 100° C. for 30 minutes, then cooled to room temperature, poured into NaOH (1N, 30 mL), extracted with EtOAc (3×50 mL). The combined organic layers were dried over Na$_2$SO$_4$, filtered, and evaporated to dryness to give 2-bromo-5-methylpyridin-4-amine (213 mg, 53.1% yield) as a brown solid which was used without further purification. ESI-MS: m/z 187.0 (M+H).

Cesium carbonate (331 mg, 1.017 mmol), palladium acetate (5.71 mg, 0.025 mmol), 1,1'-bis(diphenylphosphino)ferrocene (28.5 mg, 0.051 mmol), copper(I)chloride (50.4 mg, 0.509 mmol), 2-bromo-5-methylpyridin-4-amine (200 mg, 1.069 mmol) and 2-(6-methylpyridin-2-yl)-6-phenyl-1,3,6,2-dioxazaborocane (287 mg, 1.017 mmol) were combined in DMF (5 mL) and heated at 105° C. for 2 days. The reaction mixture was then cooled and evaporated on a rotovap to give a residue which was purified by preparative HPLC eluting with a gradient of 5-30% acetonitrile (containing 0.035% TFA) in water (containing 0.05% TFA) using a Sunfire Prep 5 μm C18, 30×75 mm column to afford the title compound as a yellow crystalline solid (44 mg). ESI-MS: m/z 200.2 (M+H).

Preparation 12: 2-(5-chloro-2-fluorophenyl)-5-methylpyrimidin-4-amine trans-Dichlorobis(triphenylphosphine)palladium (II) (1.179 g, 1.680 mmol), 5-chloro-2-fluorophenylboronic acid (6.15 g, 35.3 mmol), 2-chloro-5-methylpyrimidin-4-amine (2.411 g, 16.80 mmol), were combined with 2M Na$_2$CO$_3$ (8.40 ml, 16.80 mmol) in dioxane (79 mL) and then heated at reflux for 1 hour. The reaction mixture was then cooled to room temperature and concentrated on a rotovap to afford a tan solid. The solid was suspended in brine (50 mL) and extracted with EtOAc (20 mL). The organic layer was dried over $Na_2SO_4$, filtered, and concentrated on a rotovap to afford an amber colored oil which was loaded onto silica (12 g) and purified by silica chromatography using a step gradient eluted with (10-75% ethyl acetate/hexanes) to give the title compound. $^1H$ NMR (400 MHz, DMSO-$d_6$) δ ppm 2.03 (3H, d, J=0.76 Hz) 6.85 (2H, br. s.) 7.31 (1H, dd, J=10.61, 8.84 Hz) 7.46-7.55 (1H, m) 7.88 (1H, dd, J=6.57, 3.03 Hz) 8.06 (1H, d, J=0.76 Hz). ESI-MS: m/z 238.1 (M+H).

Preparation 13:
6-fluoro-7-iodo-1H-pyrazolo[4,3-b]pyridine

THF (42 mL) and diisopropylamine (5.6 ml, 39.27 mmol) were combined and cooled at 0° C. then n-butyllithium (17.3 ml, 2.5 M in hexane) was added dropwise at 0° C., and stirred for another 30 minutes. The mixture was then cooled in a dry ice/acetone bath to about −78° C. and a solution of 3,5-difluoropicolinonitrile (5 g, 35.7 mmol) in THF (25 mL) was slowly added. After 30 minutes a solution of $I_2$ (9 g, 35.7 mmol) in THF (35 mL) was added. The reaction was stirred for another 40 minutes at −78° C. in the dry ice/acetone bath, then warmed slightly and quenched with 50 mL sodium thiosulfate solution (10% aq) followed by dilution with water and EtOAc (300 mL). The organic layer was washed with brine, dried over sodium sulfate, filtered, and concentrated to a residue which was purified by silica column chromatography eluting with petroleum ether-ethyl acetate (5:1) to give 3,5-difluoro-4-iodopicolinonitrile as a solid (2 g, 21% yield). $^1H$ NMR (400 MHz, DMSO-d6) δ ppm 8.58 (s, 1H).

3,5-Difluoro-4-iodopicolinonitrile (1.0 g) was combined with butan-1-ol (10 mL) and hydrazine hydrate (100%, 0.82 mL) was added. The reaction was heated at 105° C. and after 2 hours cooled to room temperature, filtered, the filter rinsed with water, and the filtrate was concentrated to give a residue. The residue was washed with water and filtered to give 6-fluoro-7-iodo-1H-pyrazolo[4,3-b]pyridin-3-amine (27) as a solid (290 mg, 28% yield). $^1H$ NMR (400 MHz, DMSO-d6) δ ppm 8.14 (s, 1H) 5.59 (s, 2H). MS [M+H] found 279.0

6-Fluoro-7-iodo-1H-pyrazolo[4,3-b]pyridin-3-amine (250 mg) was combined with water (4 mL) and AcOH (6 mL) was heated to 40° C. until the solution became clear. The reaction mixture was then cooled to 0° C. and a solution of sodium nitrite (137 mg) in water (1 mL) was added dropwise over about 30 minutes. The reaction mixture was then warmed to room temperature, and stirred for 16 hours. The reaction mixture was again cooled to 0° C. and stirred for another 0.5 hour to give a solid which was collected by filtration, and washed with cold water. The solid were suspended in diluted HI (0.25 mL 50% HI diluted with water to 2.75 mL) and dimethoxyethane (6.5 mL) and the reaction mixture was heated to 80° C. for 3 hours, then cooled to room temperature, neutralized with $Na_2CO_3$ solution, and then extracted with ethyl acetate (60 mL). The organic layer was dried over anhydrous $Na_2SO_4$, filtered, and evaporated under reduced pressure to give a residue which was purified by silica gel chromatography eluting with petroleum ether-ethyl acetate (5:1) to afford the title compound (120 mg, 50.6% yield) as a light yellow solid. $^1$H-NMR (400 MHz, DMSO-d6) δ ppm 13.77 (s, 1H) 8.50 (s, 1H) 8.40 (s, 1H). MS [M+H] found 264.0.

Preparation 14:
6-fluoro-7-iodo-1H-pyrazolo[4,3-b]pyridine

6-Fluoro-7-iodo-1H-pyrazolo[4,3-b]pyridin-3-amine (2.0 g, 7.19 mmol) was combined with DMF (15 mL) and cooled to 0° C. before tert-butyl nitrite (1.709 mL, 14.39 mmol) was added. The reaction mixture was then warmed to room temperature and heated at 85° C. for 4 hours. The reaction mixture was cooled to room temperature and HI solution (1.614 g, 7.19 mmol) in water (57%) was added and heated to 85° C. for another 8 hours. The mixture was cooled, concentrated, to give a residue which was purified by preparative HPLC using a Sunfire Prep 5 μm C18, 75×30 mm column eluting with a gradient of 25-45% acetonitrile (containing 10 mM $NH_4HCO_3$) in water (containing 10 mM $NH_4HCO_3$) to give the title compound. (221 mg, 0.840 mmol, 11.68% yield). MS [M+H] found 264.0.

Preparation 15:
7-chloro-6-fluoro-1H-pyrazolo[4,3-b]pyridine

Diisopropylamine (5.60 mL, 39.27 mmol) in THF (40 mL) was cooled to 0° C. and n-BuLi (12.56 mL, 31.4 mmol) was added slowly. After 30 minutes, the reaction was cooled to −78° C. and 3,5-difluoropicolinonitrile (4.0 g, 28.6 mmol) in THF (25 mL) was added and the solution was stirred for 30 minutes. A solution of iodine (10.87 g, 42.8 mmol) in THF (35 mL) was cooled to (−78° C.) and added all at once. After about 30 seconds the reaction was quenched with sodium thiosulfate solution (10 mL) and water (20 mL). The mixture was extracted with EtOAc (2×150 mL) and the combined organics were extracted with brine, dried over $Na_2SO_4$ and concentrated to give a residue which was purified using silica column chromatography eluted with hexanes/EtOAc to give 3,5-difluoro-4-iodopicolinonitrile.

To a solution of 3,5-difluoro-4-iodopicolinonitrile (8.0 g, 30.1 mmol) in EtOH (50 mL) was added 4N HCl in 1,4-dioxane (50 mL, 30.1 mmol) and the mixture was heated at 60° C. for 15 hours. The reaction was cooled to room temperature and evaporated under reduced pressure. The residue was dissolved in EtOAc (100 mL) and washed with saturated $NaHCO_3$ solution (100 mL) and brine. The organics were combined and dried over $Na_2SO_4$ and evaporated. This material was purified on silica gel chromatography eluted with hexane/EtOAc (0-100%) to give ethyl 4-chloro-3,5-difluoropicolinate. MS [M+H] found 222.1.

To a solution of ethyl 4-chloro-3,5-difluoropicolinate (1.5 g, 6.77 mmol) in toluene (25 mL) at −78° C. was added DIBAL (6.77 mL, 6.77 mmol) and the mixture was stirred for 4 hours. Then 3N HCl solution (20 mL) was added slowly and the mixture was allowed to warm to room temperature. After 1 hour, a saturated solution of $NaHCO_3$ was added and the mixture was extracted with $Et_2O$ (2×150 mL). The combined organics were dried over $Na_2SO_4$ and evaporated to give 4-chloro-3,5-difluoropicolinaldehyde (1.15 g, 6.48 mmol, 96% yield) as a yellow liquid which was used in next step without further purification. MS [M+H] found 178.0.

To a solution of 4-chloro-3,5-difluoropicolinaldehyde (533 mg, 3.0 mmol) in n-BuOH (15 mL) was added hydrazine (0.113 mL, 3.60 mmol) and the reaction was heated at 110° C. for 22 hours. The reaction mixture was cooled, concentrated and the residue was dissolved in EtOAc (100 mL) and washed with saturated $Na_2CO_3$ solution, dried over $Na_2SO_4$, and evaporated to give a residue which was purified by silica gel column chromatography eluted with hexanes/EtOAc (0-100%) to give the title compound. MS [M+H] found 172.0.

Preparation 16:
1-cyclopropyl-7-iodo-1H-pyrazolo[4,3-b]pyridine

N-Sodiohexamethyldisilazane (3.40 mL, 2.041 mmol), N,N-dimethylpyridin-4-amine (748 mg, 6.12 mmol), 7-iodo- 2H-pyrazolo[4,3-b]pyridine (500 mg, 2.041 mmol), diacetoxycopper (371 mg, 2.041 mmol) and cyclopropylboronic acid (351 mg, 4.08 mmol) were combined in toluene (15 mL) and sparged with air. The mixture was heated at 95° C. overnight. The mixture was then cooled and poured into saturated NH₄Cl and extracted with EtOAc (2×). The combined organic layers were dried over Na₂SO₄ and concentrated to give a residue which was purified on silica column chromatography eluted with EtOAc/Hexanes (0-97%) using a step gradient and then to 98% EtOAc to give 2-cyclopropyl-7-iodo-2H-pyrazolo[4,3-b]pyridine. The other fractions were further purified on a second silica column chromatography eluted with EtOAc/Hexanes (0-50%) using a step gradient and then to 90% EtOAc to give the title compounds. MS [M+H] found 286.1.

Preparation 17: 7-iodo-1-methyl-1H-pyrazolo[4,3-b]pyridine and 7-iodo-2-methyl-2H-pyrazolo[4,3-b]pyridine A solution of 7-iodo-1H-pyrazolo[4,3-b]pyridine (330 mg, 1.347 mmol) and sodium hydride (64.6 mg, 60% in oil, 1.616 mmol) in THF (2.0 mL) was stirred at 0° C. for 15 minutes. Iodomethane (0.084 mL, 1.347 mmol) was added at 0° C., and the reaction was warmed to room temperature and stirred for 1 hour. The reaction mixture was concentrated in vacuo to give a residue which was purified on column chromatography eluted with 0-60% EtOAc in hexanes to give the title compounds.

Preparation 18: 1-ethyl-7-iodo-1H-pyrazolo[4,3-b]pyridine and 2-ethyl-7-iodo-2H-pyrazolo[4,3-b]pyridine 7-Iodo-2H-pyrazolo[4,3-b]pyridine (426 mg, 1.739 mmol) was dissolved in DMF (5 mL) and cooled to 0° C. NaH (76 mg, 60% in oil, 1.912 mmol) was added and after 5 minutes iodoethane (0.154 mL, 1.912 mmol) was added and the reaction was stirred at room temperature for 1 hour. The reaction was then concentrated to give a residue which was purified by silica chromatography column eluted with a step gradient of ethyl acetate in hexanes (0-80%) to give the title compounds. MS [M+H] found 274.1.

Preparation 19: 7-chloro-6-fluoro-1-methyl-1H-pyrazolo[4,3-b]pyridine and 7-chloro-6-fluoro-2-methyl-2H-pyrazolo[4,3-b]pyridine 7-Chloro-6-fluoro-1H-pyrazolo[4,3-b]pyridine (95 mg, 0.554 mmol) was dissolved in THF (2.0 mL) and cooled to 0° C. NaH (26.6 mg, 60% in oil, 0.664 mmol) was added and the mixture stirred for 15 minutes. Iodomethane (0.035 mL, 0.554 mmol) was added at 0° C. and the reaction was allowed to warm to room temperature for 30 minutes. The reaction mixture was purified with silica column chromatography using 0-80% EtOAc in hexanes as eluent to give the title compounds.

Preparation 20: 7-chloro-6-fluoro-1-ethyl-1H-pyrazolo[4,3-b]pyridine and 7-chloro-6-fluoro-2-ethyl-2H-pyrazolo[4,3-b]pyridine 7-Chloro-6-fluoro-1H-pyrazolo[4,3-b]pyridine (100 mg, 0.699 mmol) was dissolved in THF (2.0 mL) and cooled to 0° C. NaH (28.0 mg, 60% in oil, 0.664 mmol) was added and the mixture stirred for 15 minutes. Iodoethane (0.048 mL, 0.583 mmol) was added at 0° C. and the reaction was allowed to warm to room temperature for 12 hours. The solvent was removed by evaporation to give the title compounds which were used without further purification.

Example 1

N-(2-(5-chloro-2-fluorophenyl)-5-methylpyrimidin-4-yl)-1H-pyrazolo[4,3-b]pyridin-7-amine

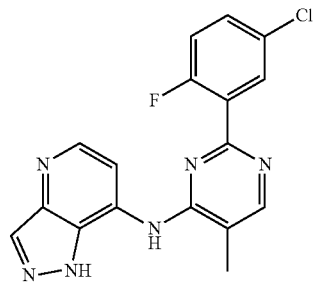 [SMILES: Cc1cnc(-c2cc(Cl)ccc2F)nc1Nc1ccnc2cn[nH]c12]

trans-Dichlorobis(triphenylphosphine)palladium (II) (1.179 g, 1.680 mmol), 5-chloro-2-fluorophenylboronic acid (6.1 g, 35.3 mmol), 2-chloro-5-fluoromethylpyrimidin-4-amine (2.411 g, 16.80 mmol), 2M Na₂CO₃ (8.40 mL, 16.80 mmol) were combined in dioxane (79 mL) and refluxed for 1 hour. The reaction was cooled, concentrated and the solids were suspended in brine (50 mL) and then extracted with EtOAc (20 mL). The layers were separated, the organics were dried over Na₂SO₄, filtered and concentrated to give a residue which was passed through a silica plug (12 g) to give 2-(5-chloro-2-fluorophenyl)-5-methylpyrimidin-4-amine which was without further purification. ¹H NMR (400 MHz, DMSO-d₆) δ ppm 2.03 (3H, d, J=0.76 Hz) 6.85 (2H, br. s.) 7.31 (1H, dd, J=10.61, 8.84 Hz) 7.46-7.55 (1H, m) 7.88 (1H, dd, J=6.57, 3.03 Hz) 8.06 (1H, d, J=0.76 Hz). ESI-MS: m/z 238.1 (M+H).

(R)-BINAP (1.102 g, 1.770 mmol), diacetoxypalladium (0.092 g, 0.411 mmol) and toluene (30 mL) were combined and stirred at 40° C. for 10 minutes. 7-Iodo-2-(4-methoxybenzyl)-2H-pyrazolo[4,3-b]pyridine (1.500 g, 4.11 mmol) suspended in toluene (8 mL), 2-(5-chloro-2-fluorophenyl)-5-methylpyrimidin-4-amine (0.976 g, 4.11 mmol) and sodium 2-methylpropan-2-olate (0.592 g, 6.16 mmol) were added. The mixture was sparged with nitrogen and heated at 100° C. overnight. The reaction was then cooled, MeOH (5 mL) was added and the mixture was concentrated directly onto silica gel and purified by chromatography eluted with EtOAc/hexanes step gradient (35-50%) to give N-(2-(5-chloro-2-fluorophenyl)-5-methylpyrimidin-4-yl)-1-(4-methoxybenzyl)-1H-pyrazolo[4,3-b]pyridin-7-amine and N-(2-(5-chloro-2-fluorophenyl)-5-methylpyrimidin-4-yl)-2-(4-methoxybenzyl)-2H-pyrazolo[4,3-b]pyridin-7-amine. ESI-MS: m/z 475.3 (M+H).

Trifluoroacetic acid (10.53 mL) was added to N-(2-(5-chloro-2-fluorophenyl)-5-methylpyrimidin-4-yl)-1-(4-methoxybenzyl)-1H-pyrazolo[4,3-b]pyridin-7-amine and N-(2-(5-chloro-2-fluorophenyl)-5-methylpyrimidin-4-yl)-2-(4-methoxybenzyl)-2H-pyrazolo[4,3-b]pyridin-7-amine and the reaction was heated at 70° C. for 3 hours. The reaction was cooled and concentrated to a residue which was combined with dichloromethane (25 mL) and then saturated sodium bicarbonate solution (25 mL) to give a solid which was collected by filtration and rinsed with dichloromethane and then water. The solid was then dissolved in EtOAc, washed with water and then saturated sodium bicarbonate solution. The organic layer was dried over Na₂SO₄, and concentrated to a yellow solid which was then dissolved in DMSO (1 mL) and purified via preparative HPLC using a gradient of 25-40% acetonitrile (containing 0.035% TFA) in water (containing 0.05% TFA) to give the title compound as a TFA salt. ¹H NMR (400 MHz, DMSO-d$_6$) δ ppm 2.54 (3H, s) 7.29-7.40 (1H, m) 7.49-7.58 (1H, m) 7.74-7.85 (2H, m) 8.10 (1H, d, J=8.59 Hz) 8.26-8.39 (1H, m) 8.48-8.60 (1H, m) 9.11-9.41 (1H, m) 13.29 (1H, d, J=8.59 Hz). ESI-MS: m/z 355.2 (M+H).

Example 2

7-(2-(5-chloro-2-fluorophenyl)-5-methylpyrimidin-4-ylamino)-N-methyl-1H-pyrazolo[4,3-b]pyridine-1-carboxamide

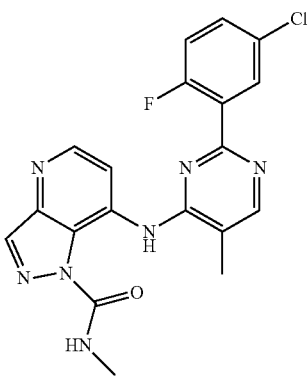 [SMILES: CNC(=O)n1ncc2nccc(Nc3nc(-c4cc(Cl)ccc4F)ncc3C)c21]

N-(2-(5-Chloro-2-fluorophenyl)-5-methylpyrimidin-4-yl)-1H-pyrazolo[4,3-b]pyridin-7-amine (100 mg, 0.282 mmol) was suspended in dry dichloroethane (14 mL) containing pyridine (38.8 μl, 0.479 mmol). Methylcarbamic chloride (27.7 mg, 0.282 mmol) was added and the reaction was heated overnight at 70° C. The mixture was cooled to afford a precipitate which was collected by filtration and dissolved in hot DMSO/DMF before being purified via HPLC using a Sunfire Prep 5 μm C18, 75×30 mm column eluting with a gradient of 40-80% acetonitrile (containing 0.035% TFA) in water (containing 0.05% TFA) to give the title compound as a TFA salt. $^1$H NMR (400 MHz, DMSO-d$_6$) δ ppm 2.54 (3H, s) 2.95 (3H, d, J=4.80 Hz) 7.36 (1H, s) 7.46 (1H, dd, J=10.74, 8.72 Hz) 7.63 (1H, dt, J=7.20, 4.23 Hz) 8.10 (1H, dd, J=6.57, 2.78 Hz) 8.14 (1H, s) 8.46-8.58 (1H, m) 8.65 (1H, s) 8.95-9.10 (1H, m) 12.10 (1H, s). ESI-MS: m/z 412.3 (M+H).

Examples 3 and 4

2-(7-(2-(5-chloro-2-fluorophenyl)-5-methylpyrimidin-4-ylamino)-1H-pyrazolo[4,3-b]pyridin-1-yl)acetamide and 2-(7-(2-(5-chloro-2-fluorophenyl)-5-methylpyrimidin-4-ylamino)-2H-pyrazolo[4,3-b]pyridin-2-yl)acetamide

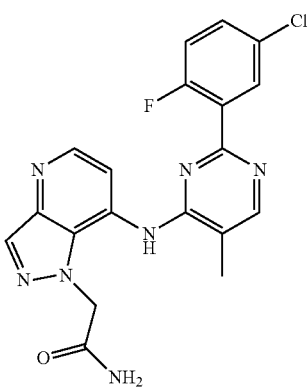

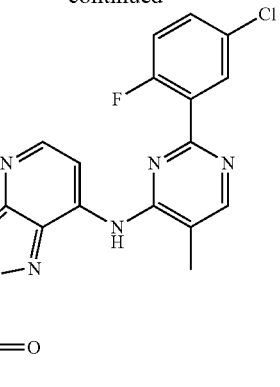

A mixture of N-(2-(5-chloro-2-fluorophenyl)-5-methylpyrimidin-4-yl)-1H-pyrazolo[4,3-b]pyridin-7-amine (160 mg, 0.451 mmol), 2-chloroacetamide (43.0 mg, 0.451 mmol) and Cs$_2$CO$_3$ (294 mg, 0.902 mmol) in DMF (22 mL) was heated in a microwave for 15 minutes at 80° C. The resulting crude material was purified via preparative HPLC using a Sunfire Prep 5 μm C18, 75×30 mm column eluting with a gradient of 20-27% acetonitrile (containing 0.035% TFA) in water (containing 0.05% TFA) to give the title compounds as TFA salts: 2-(7-(2-(5-chloro-2-fluorophenyl)-5-methylpyrimidin-4-ylamino)-1H-pyrazolo[4,3-b]pyridin-1-yl)acetamide $^1$H NMR (400 MHz, DMSO-d$_6$) δ ppm 2.30 (3H, s) 5.21 (2H, s) 7.27-7.40 (1H, m) 7.55 (1H, d, J=8.34 Hz) 7.69 (1H, br. s.) 7.83-7.95 (2H, m) 8.13 (1H, br. s.) 8.32 (1H, s) 8.45-8.55 (2H, m) 9.88 (1H, br. s.). ESI-MS: m/z 412.3 (M+H); 2-(7-(2-(5-chloro-2-fluorophenyl)-5-methylpyrimidin-4-ylamino)-2H-pyrazolo[4,3-b]pyridin-2-yl)acetamide $^1$H NMR (400 MHz, DMSO-d$_6$) δ ppm 2.46 (3H, s) 5.28 (2H, s) 7.46 (3H, dd, J=10.61, 8.84 Hz) 7.59-7.79 (2H, m) 8.07 (1H, dd, J=6.57, 2.78 Hz) 8.23 (1H, d, J=5.81 Hz) 8.48-8.62 (1H, m) 8.74 (2H, d, J=12.13 Hz). ESI-MS: m/z 412.3 (M+H).

Example 5

N-(3'-fluoro-5,6'-dimethyl-2,2'-bipyridin-4-yl)-1-isopropyl-1H-pyrazolo[4,3-b]pyridin-7-amine

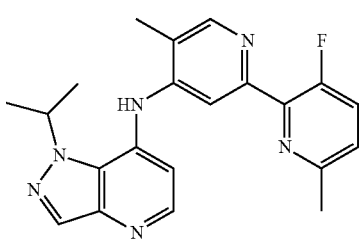 [SMILES: Cc1ccc(F)c(-c2cc(Nc3ccnc4cnn(C(C)C)c34)c(C)cn2)n1]

To a solution of 2-bromo-5-methylpyridine (4 g, 2.3 mmol) in dichloromethane (500 mL) was added m-CPBA (52 g, 304 mmol) at 0° C. The reaction mixture was stirred at room temperature for 20 hours and the then the pH was adjusted to about 9 with a saturated solution of K$_2$CO$_3$. The organic layers were separated and concentrated to give a residue which was purified by flash silica chromatography eluted with petroleum ether/ethyl acetate (1:1) to give 2-bromo-5-methylpyridine 1-oxide (33 g; 75%). $^1$H NMR (CDCL$_3$): δ ppm 8.25 (s, 1H), 8.75 (d, 1H, J=8.4 Hz), 6.95-6.94 (m, 1H), 2.30 (s, 3H).

To a cooled solution (−40 to −45° C.) of 2-bromo-5-methylpyridine 1-oxide (12 g, 63.8 mmol) in dry THF (250 mL) was added a solution of i-PrMgCl.LiCl (127 mL, 165.8 mmol, 1.3M) in THF and the reaction mixture was stirred for 1 hour at −40° C. Dry ZnCl₂ (1 g, 127. mmol) was added and the reaction was warmed to room temperature and stirred for 1 hour. 2-Bromo-3-fluoro-6-methylpyridine (2 g, 127. mmol) and Pd(PPh₃)₄ (5. g, 4.4 mmol) were added and the reaction mixture was refluxed for 20 hours. The mixture was cooled 0° C. and stirred for 1 hour to afford a solid. The solid was collected by filtration and then dissolved in dichloromethane and washed with a saturated solution of ethylenediaminetetraacetic acid and saturated $K_2CO_3$ successively. The organic layers were separated, dried, and concentrated to give a residue which was purified by flash silica chromatography eluted with dichloromethane/MeOH (50:1) to give 2-(3-fluoro-6-methylpyridin-2-yl)-5-methylpyridine 1-oxide (4.3 g; 30.1%). ¹HNMR (CDCL₃): δ ppm 8.22 (s, 1H), 7.47-7.42 (m, 2H), 7.30-7.27 (m, 1H), 7.20-7.28 (m, 1H), 2.61 (s, 3H), 2.38 (s, 3H). MS [M+H] found 219.0.

To a solution of cold $H_2SO_4$ (0-10° C.) (170 mL) was added 2-(3-fluoro-6-methylpyridin-2-yl)-5-methylpyridine 1-oxide (4. g, 19. mmol) followed by portionwise addition of $KNO_3$ (4 g, 39 mmol) and the reaction was heated overnight at 80° C. The reaction mixture was then cooled to room temperature, and poured into ice-water and the pH adjusted to about 8 with a saturated solution of $Na_2CO_3$. The mixture was extracted with dichloromethane, the organic layer dried, and purified by flash silica chromatography eluted with petroleum ether/ethyl acetate (4:1) to give 2-(3-fluoro-6-methylpyridin-2-yl)-5-methyl-4-nitropyridine 1-oxide. (2.9 g; 57.8%). ¹HNMR (CDCL₃): δ ppm 8.37 (s, 1H), 8.27 (s, 1H), 7.50-7.47 (m, 1H), 7.38-7.37 (m, 1H), 2.70 (s, 3H), 2.64 (s, 3H).

To a solution of 2-(3-fluoro-6-methylpyridin-2-yl)-5-methyl-4-nitropyridine 1-oxide (2.7 g, 10.2 mmol) in AcOH (54 mL) was added iron (2.3 g, 40.9 mmol) and the mixture was stirred at 100° C. for 30 minutes, cooled to room temperature, adjusted pH to about 8 with NaOH (1N) and extracted with ethyl acetate. The organic layers were concentrated to give 3'-fluoro-5,6'-dimethyl-2,2'-bipyridin-4-amine. ¹HNMR (CDCL₃) δ ppm 8.32 (s, 1H), 7.43-7.38 (m, 1H), 7.19-7.15 (m, 2H), 4.19 (s, 2H), 2.65 (s, 3H), 2.19 (s, 3H). MS [M+H] found 218.0.

(9,9-Dimethyl-9H-xanthene-4,5-diyl)bis(diphenylphosphine) (1.008 mg, 1.742 μmol), 7-iodo-1-isopropyl-1H-pyrazolo[4,3-b]pyridine (10 mg, 0.035 mmol), Pd₂(dba)₃ (1.595 mg, 1.742 μmol), 3'-fluoro-5,6'-dimethyl-2,2'-bipyridin-4-amine (7.57 mg, 0.035 mmol) and sodium 2-methylpropan-2-olate (10.04 mg, 0.104 mmol) were combined in dioxane (5 mL) and heated at 120° C. for 1 hour. The reaction mixture was then cooled and the crude material was purified by prep-HPLC using a Sunfire Prep 5 μm C18, 75×30 mm column eluting with a gradient of 10-50% acetonitrile (containing 0.035% TFA) in water (containing 0.05% TFA) to give the title compound as a TFA salt. ¹H NMR (400 MHz, METHANOL-d₄) δ ppm 1.51 (d, J=6.57 Hz, 6H) 2.54 (s, 3H) 2.67 (s, 3H) 7.30 (br. s., 1H) 7.54 (dd, J=8.72, 3.66 Hz, 2H) 7.68 (dd, J=11.37, 8.59 Hz, 1H) 8.30 (br. s., 1H) 8.42 (s, 2H). MS [M+H] found 377.3.

Example 6

N-(5,6'-dimethyl-2,2'-bipyridin-4-yl)-1H-pyrazolo[4,3-b]pyridin-7-amine

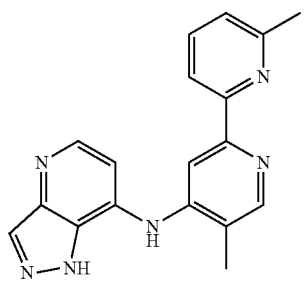 [SMILES: Cc1cccc(-c2cc(Nc3ccnc4cn[nH]c34)c(C)cn2)n1]

(R)-BINAP (0.478 g, 0.767 mmol) and diacetoxypalladium (0.040 g, 0.178 mmol) were combined in toluene (8 mL) and stirred at 40° C. for 10 minutes. 7-Iodo-2-(4-methoxybenzyl)-2H-pyrazolo[4,3-b]pyridine (0.65 g, 1.780 mmol) suspended in toluene (5 mL), 5,6'-dimethyl-2,2'-bipyridin-4-amine (0.355 g, 1.780 mmol) and sodium 2-methylpropan-2-olate (0.257 g, 2.67 mmol) were added. Nitrogen was sparged into the solution for about 2 minutes, and the reaction was heated at 100° C. overnight. The reaction was then cooled to give a solution of N-(5,6'-dimethyl-2,2'-bipyridin-4-yl)-1-(4-methoxybenzyl)-1H-pyrazolo[4,3-b]pyridin-7-amine which was used as is in the next step.

To a solution of N-(5,6'-dimethyl-2,2'-bipyridin-4-yl)-1H-pyrazolo[4,3-b]pyridin-7-amine obtained in the step above was added trifluoroacetic acid (11.4 mL) and the reaction was stirred at 70° C. for 2 hours. The mixture was then concentrated to dryness, re-dissolved in DMF/MeOH (1:1; 8 mL) and filtered and the filtrate purified via HPLC using a Sunfire Prep 5 μm C18, 75×30 mm column eluting with a gradient of 5-25% acetonitrile (containing 0.035% TFA) in water (containing 0.05% TFA) to provide the title compound as a TFA salt. ¹H NMR (400 MHz, DMSO-d₆) δ ppm 2.39 (3H, br. s.) 2.54-2.56 (3H, m) 7.40 (1H, br. s.) 7.84-7.95 (1H, m) 8.10 (1H, s) 8.33-8.82 (4H, m) 10.18 (1H, s) 11.13 (1H, s) 13.55 (1H, s). MS [M+H] found 317.3.

Example 7

(S)-3-(7-(3'-fluoro-5,6'-dimethyl-2,2'-bipyridin-4-ylamino)-2H-pyrazolo[4,3-b]pyridin-2-yl)propane-1,2-diol

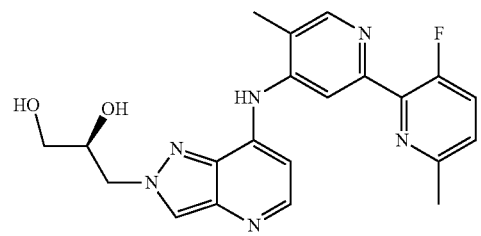 [SMILES: Cc1ccc(F)c(-c2cc(Nc3ccnc4cn(C[C@H](O)CO)nc34)c(C)cn2)n1]

(9,9-Dimethyl-9H-xanthene-4,5-diyl)bis(diphenylphosphine) (7.45 mg, 0.013 mmol), (S)-2-((2,2-dimethyl-1,3-dioxolan-4-yl)methyl)-7-iodo-2H-pyrazolo[4,3-b]pyridine (185 mg, 0.515 mmol), Pd$_2$(dba)$_3$ (11.79 mg, 0.013 mmol), 3'-fluoro-5,6'-dimethyl-2,2'-bipyridin-4-amine (112 mg, 0.515 mmol) and sodium 2-methylpropan-2-olate (149 mg, 1.545 mmol) were combined in dioxane (5 mL) and heated at 120° C. for 1 hour. The mixture was cooled and purified by preparative HPLC using a Sunfire Prep 5 μm C18, 75×30 mm column eluting with a gradient of 5-40% acetonitrile (containing 0.035% TFA) in water (containing 0.05% TFA) to give after evaporation a residue which was dissolved in 1N HCl (2 mL) and stirred at room temperature for 1 hour before being purified by preparative HPLC using a Sunfire Prep 5 μm C18, 75×30 mm column eluting with a gradient of 5-20% acetonitrile (containing 0.035% TFA) in water (containing 0.05% TFA) to give the title compound as a TFA salt. $^1$H NMR (400 MHz, METHANOL-d$_4$) δ ppm 2.57 (s, 3H) 2.64 (s, 3H) 3.40-3.55 (m, 2H) 4.04 (br. s., 1H) 4.51 (dd, J=13.64, 7.83 Hz, 1H) 4.69 (dd, J=13.64, 3.54 Hz, 1H) 7.29 (d, J=6.57 Hz, 1H) 7.55 (dd, J=8.59, 3.54 Hz, 1H) 7.73 (dd, J=11.24, 8.72 Hz, 1H) 8.43 (s, 1H) 8.57 (d, J=6.57 Hz, 1H) 8.67 (s, 1H) 8.76 (s, 1H). MS [M+H] found 409.4.

Example 8

1-(7-(3'-fluoro-5,6'-dimethyl-2,2'-bipyridin-4-ylamino)-2H-pyrazolo[4,3-b]pyridin-2-yl)-2-methyl-propan-2-ol

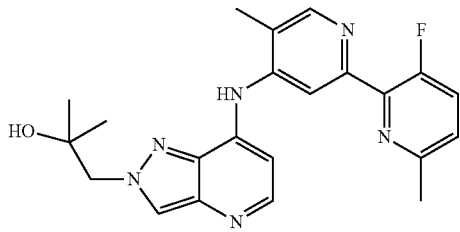 [SMILES: Cc1ccc(F)c(-c2cc(Nc3ccnc4cn(CC(C)(C)O)nc34)c(C)cn2)n1]

7-Iodo-2H-pyrazolo[4,3-b]pyridine (300 mg, 1.224 mmol), 1-chloro-2-methylpropan-2-ol (133 mg, 1.224 mmol) and Cs$_2$CO$_3$ (399 mg, 1.224 mmol) were combined in DMF (5 mL). The mixture was heated at 120° C. for 30 minutes using a microwave. The reaction mixture was then purified by preparative HPLC using a Sunfire Prep 5 μm C18, 75×30 mm column eluting with a gradient of 05-25% acetonitrile (containing 0.035% TFA) in water (containing 0.05% TFA) using basic buffer to afford 1-(7-iodo-2H-pyrazolo[4,3-b]pyridin-2-yl)-2-methylpropan-2-ol (170 mg, 0.536 mmol, 43.8% yield). MS [M+H] found 318.

(9,9-Dimethyl-9H-xanthene-4,5-diyl)bis(diphenylphosphine) (2.281 mg, 3.94 μmol), 1-(7-iodo-2H-pyrazolo[4,3-b]pyridin-2-yl)-2-methylpropan-2-ol (50 mg, 0.158 mmol), Pd$_2$(dba)$_3$ (3.61 mg, 3.94 μmol), 3'-fluoro-5,6'-dimethyl-2,2'-bipyridin-4-amine (34.3 mg, 0.158 mmol) and sodium 2-methylpropan-2-olate (45.5 mg, 0.473 mmol) were combined in dioxane (5 mL) and heated at 120° C. for 1 hour. The solution was cooled, concentrated to give a residue which was purified by preparative HPLC using a Sunfire Prep 5 μm C18, 75×30 mm column eluting with a gradient of 5-40% acetonitrile (containing 0.035% TFA) in water (containing 0.05% TFA) to give the title compound as a TFA salt. $^1$H NMR (400 MHz, METHANOL-d$_4$) δ ppm 1.18 (s, 6H) 2.59 (s, 3H) 2.68 (s, 3H) 4.51 (s, 2H) 7.24 (d, J=6.32 Hz, 1H) 7.57 (dd, J=8.59, 3.54 Hz, 1H) 7.75 (dd, J=11.12, 8.59 Hz, 1H) 8.33 (s, 1H) 8.59 (d, J=6.32 Hz, 1H) 8.65 (s, 1H) 8.78 (s, 1H). MS [M+H] found 407.4.

Example 9

2-(7-(3'-fluoro-5,6'-dimethyl-2,2'-bipyridin-4-ylamino)-2H-pyrazolo[4,3-b]pyridin-2-yl)ethanol

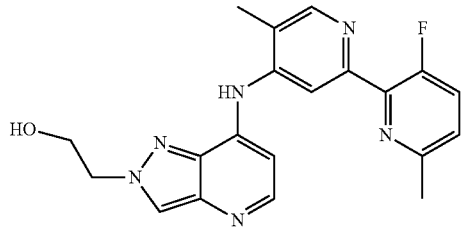 [SMILES: Cc1ccc(F)c(-c2cc(Nc3ccnc4cn(CCO)nc34)c(C)cn2)n1]

7-Iodo-2H-pyrazolo[4,3-b]pyridine (200 mg, 0.816 mmol), 2-(2-bromoethoxy)tetrahydro-2H-pyran (0.123 mL, 0.816 mmol) and Cs$_2$CO$_3$ (266 mg, 0.816 mmol) were combined in DMF (5 mL). The mixture was heated at 120° C. for 30 minutes using a microwave. The crude reaction mixture was purified by preparative HPLC using a Sunfire Prep 5 μm C18, 75×30 mm column eluting with a gradient of 10-50% acetonitrile (containing 0.035% TFA) in water (containing 0.05% TFA) to afford 7-iodo-2-(2-(tetrahydro-2H-pyran-2-yloxy)ethyl)-2H-pyrazolo[4,3-b]pyridine (74 mg, 0.198 mmol, 24.29% yield) and 7-iodo-1-(2-(tetrahydro-2H-pyran-2-yloxy)ethyl)-1H-pyrazolo[4,3-b]pyridine (20 mg, 0.054 mmol, 6.57% yield). MS [M+H] found 374.0.

(9,9-Dimethyl-9H-xanthene-4,5-diyl)bis(diphenylphosphine) (2.98 mg, 5.16 μmol), 7-iodo-2-(2-(tetrahydro-2H-pyran-2-yloxy)ethyl)-2H-pyrazolo[4,3-b]pyridine (77 mg, 0.206 mmol), Pd$_2$(dba)$_3$ (4.72 mg, 5.16 μmol), 3'-fluoro-5,6'-dimethyl-2,2'-bipyridin-4-amine (44.8 mg, 0.206 mmol) and sodium 2-methylpropan-2-olate (59.5 mg, 0.619 mmol) were combined in dioxane (5 mL) and heated at 120° C. for 1 hour. The solution was cooled and concentrated to give a residue which was purified by prep-HPLC using a Sunfire Prep 5 μm C18, 75×30 mm column eluting with a gradient of 5-40% acetonitrile (containing 0.035% TFA) in water (containing 0.05% TFA) and concentrated to a volume of 2 ml. 1N HCl (2 mL) was added and the mixture was stirred at room temperature for 1 hour before being purified by preparative HPLC using a Sunfire Prep 5 μm C18, 75×30 mm column eluting with a gradient of 5-40% acetonitrile (containing 0.035% TFA) in water (containing 0.05% TFA) to give the title compound as a TFA salt. $^1$H NMR (400 MHz, METHANOL-d$_4$) δ ppm 2.54 (s, 3H) 2.62 (s, 3H) 3.88-3.97 (m, 2H) 4.52-4.64 (m, 2H) 7.26 (d, J=6.57 Hz, 1H) 7.52 (dd, J=8.59, 3.54 Hz, 1H) 7.70 (dd, J=11.12, 8.59 Hz, 1H) 8.40 (s, 1H) 8.55 (d, J=6.57 Hz, 1H) 8.67 (s, 1H) 8.74 (s, 1H). MS [M+H] found 379.3.

Example 10

2-(7-(3'-fluoro-5,6'-dimethyl-2,2'-bipyridin-4-ylamino)-1H-pyrazolo[4,3-b]pyridin-1-yl)ethanol

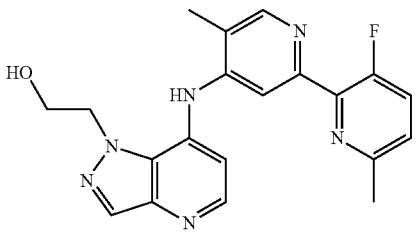 [SMILES: Cc1ccc(F)c(-c2cc(Nc3ccnc4cnn(CCO)c34)c(C)cn2)n1]

(9,9-Dimethyl-9H-xanthene-4,5-diyl)bis(diphenylphosphine) (1.550 mg, 2.68 µmol), 7-iodo-1-(2-(tetrahydro-2H-pyran-2-yloxy)ethyl)-1H-pyrazolo[4,3-b]pyridine (20 mg, 0.054 mmol), Pd₂(dba)₃ (2.454 mg, 2.68 µmol), 3'-fluoro-5,6'-dimethyl-2,2'-bipyridin-4-amine (11.64 mg, 0.054 mmol) and sodium 2-methylpropan-2-olate (15.45 mg, 0.161 mmol) were combined in dioxane (5 mL) and heated at 120° C. for 1 hour. The solution was cooled, concentrated and purified by preparative HPLC using a Sunfire Prep 5 µm C18, 75×30 mm column eluting with a gradient of 10-50% acetonitrile (containing 0.035% TFA) in water (containing 0.05% TFA) to obtain the title compound as a TFA salt. ¹H NMR (400 MHz, METHANOL-d₄) δ ppm 2.60 (s, 3H) 2.69 (s, 3H) 4.04 (t, J=4.67 Hz, 2H) 7.58 (d, J=6.57 Hz, 1H) 7.66 (d, J=4.80 Hz, 1H) 7.71-7.80 (m, 1H) 8.19 (s, 1H) 8.37 (s, 1H) 8.50 (s, 1H) 8.60 (d, J=5.05 Hz, 1H). MS [M+H] found 379.3.

Example 11

N-(3'-fluoro-5,6'-dimethyl-2,2'-bipyridin-4-yl)-1H-pyrazolo[4,3-b]pyridin-7-amine

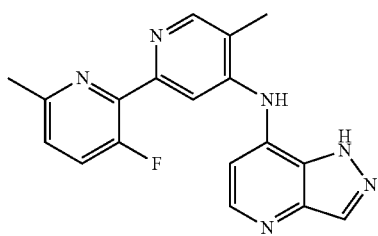 [SMILES: Cc1ccc(F)c(-c2cc(Nc3ccnc4cn[nH]c34)c(C)cn2)n1]

(R)-BINAP (0.735 g, 1.180 mmol), diacetoxypalladium (0.061 g, 0.274 mmol) and toluene (8 mL) were combined and the solution was stirred at 40° C. for 10 minutes. 7-Iodo-2-(4-methoxybenzyl)-2H-pyrazolo[4,3-b]pyridine (1 g, 2.74 mmol) suspended in toluene (8 mL) 3'-fluoro-5,6'-dimethyl-2,2'-bipyridin-4-amine (0.595 g, 2.74 mmol) and sodium 2-methylpropan-2-olate (0.395 g, 4.11 mmol) were added and the flask was sparged with nitrogen for 2 minutes and heated at 100° C. overnight. The reaction mixture was purified by silica column chromatography using a step gradient of EtOAc/hexanes (10-100%) then a step gradient of MeOH in DCM (0-10%) to give N-(3'-fluoro-5,6'-dimethyl-2,2'-bipyridin-4-yl)-1-(4-methoxybenzyl)-1H-pyrazolo[4,3-b]pyridin-7-amine and N-(3'-fluoro-5,6'-dimethyl-2,2'-bipyridin-4-yl)-2-(4-methoxybenzyl)-2H-pyrazolo[4,3-b]pyridin-7-amine. ¹H NMR (400 MHz, DMSO-d₆) δ ppm 1.23 (3H, s) 2.30 (3H, s) 2.45 (3H, s) 5.56 (2H, s) 6.57 (1H, d, J=4.80 Hz) 6.80-6.87 (2H, m) 7.26 (2H, d, J=8.84 Hz) 7.35 (1H, dd, J=8.59, 3.28 Hz) 7.69 (1H, dd, J=10.86, 8.34 Hz) 7.79 (1H, s) 8.21 (1H, d, J=4.80 Hz) 8.48 (1H, s) 8.60 (1H, s) 8.70 (1H, s). MS [M+H] found 455.4.

N-(3'-Fluoro-5,6'-dimethyl-2,2'-bipyridin-4-yl)-1-(4-methoxybenzyl)-1H-pyrazolo[4,3-b]pyridin-7-amine and N-(3'-fluoro-5,6'-dimethyl-2,2'-bipyridin-4-yl)-2-(4-methoxybenzyl)-2H-pyrazolo[4,3-b]pyridin-7-amine and TFA (6.2 mL) were combined and heated at 70° C. for 3 hours. The reaction mixture was cooled, concentrated, and the residue combined with dichloromethane (20 mL). To this mixture was added saturated sodium bicarbonate (20 mL) and the reaction was let stand for 10 minutes to give a solid which was collected by filtration, subsequently dissolved in EtOAc (500 mL), and washed with brine (100 mL). The organic layer was separated, dried over Na₂SO₄ and concentrated to give N-(3'-fluoro-5,6'-dimethyl-2,2'-bipyridin-4-yl)-1H-pyrazolo[4,3-b]pyridin-7-amine (0.15 g, 0.449 mmol, 72.8% yield) as an off-white solid. ¹H NMR (400 MHz, DMSO-d₆) δ ppm 2.38 (3H, s) 2.44 (3H, s) 7.04 (1H, d, J=5.05 Hz) 7.34 (1H, dd, J=8.59, 3.28 Hz) 7.63-7.71 (2H, m) 8.24 (1H, s) 8.34 (1H, d, J=5.05 Hz) 8.43 (1H, s) 8.48 (1H, s) 13.04 (1H, s). MS [M+H] found 335.2.

Example 12

2-(7-(5,6'-dimethyl-2,2'-bipyridin-4-ylamino)-2H-pyrazolo[4,3-b]pyridin-2-yl)acetamide

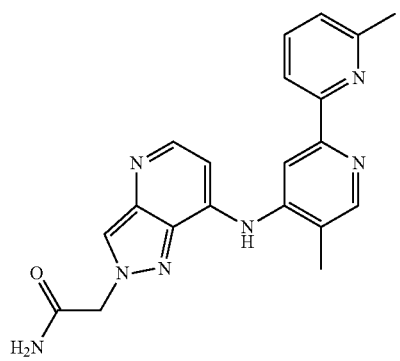 [SMILES: Cc1cccc(-c2cc(Nc3ccnc4cn(CC(N)=O)nc34)c(C)cn2)n1]

N-(5,6'-Dimethyl-2,2'-bipyridin-4-yl)-1H-pyrazolo[4,3-b]pyridin-7-amine (0.05 g, 0.158 mmol), DMF (0.5 mL), Cs₂CO₃ (0.051 g, 0.158 mmol) and 2-chloroacetamide (0.015 g, 0.158 mmol) were combined and heated at 80° C. for 1 hour. The crude material was filtered and purified via preparative HPLC using a Sunfire Prep 5 µm C18, 75×30 mm column eluting with a gradient of 5-30% acetonitrile (containing 0.035% TFA) in water (containing 0.05% TFA) to give the title compound as a TFA salt. ¹H NMR (400 MHz, DMSO-d₆) δ ppm 2.41 (3H, br. s.) 2.60 (3H, s) 5.25 (2H, br. s.) 7.48 (3H, br. s.) 7.90 (3H, d, J=6.06 Hz) 8.43 (2H, s) 8.62 (1H, s) 10.02 (1H, s). MS [M+H] found 374.3.

Examples 13 and 14

2-(7-(3'-fluoro-5,6'-dimethyl-2,2'-bipyridin-4-ylamino)-1H-pyrazolo[4,3-b]pyridin-1-yl)acetamide and 2-(7-(3'-fluoro-5,6'-dimethyl-2,2'-bipyridin-4-ylamino)-2H-pyrazolo[4,3-b]pyridin-2-yl)acetamide

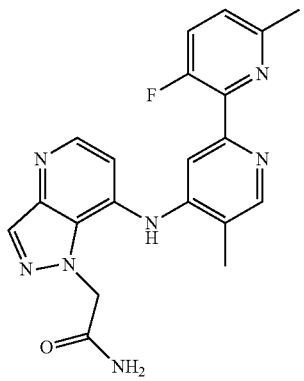

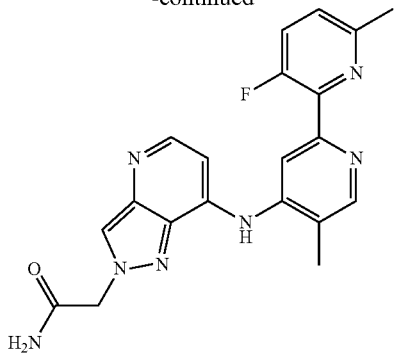

N-(3'-Fluoro-5,6'-dimethyl-2,2'-bipyridin-4-yl)-1H-pyrazolo[4,3-b]pyridin-7-amine (135 mg, 0.404 mmol), DMF (20 mL), Cs$_2$CO$_3$ (132 mg, 0.404 mmol) and 2-chloroacetamide (38.5 mg, 0.404 mmol) were combined and heated in a microwave at 80° C. for 15 minutes and then purified via preparative HPLC using a gradient of 5-30% acetonitrile (containing 0.035% TFA) in water (containing 0.05% TFA) using a Sunfire Prep 5 μm C18, 75×30 mm column to give the title compounds as TFA salts: 2-(7-(3'-fluoro-5,6'-dimethyl-2,2'-bipyridin-4-ylamino)-1H-pyrazolo[4,3-b]pyridin-1-yl)acetamide $^1$H NMR (400 MHz, DMSO-d$_6$) δ ppm 2.33 (3H, s) 5.27 (2H, s) 6.52 (1H, br. s.) 7.36-7.56 (2H, m) 7.76 (2H, dd, J=10.99, 8.46 Hz) 7.95 (1H, s) 8.41 (1H, d, J=6.57 Hz) 8.73 (2H, s) 11.08 (1H, br. s.), MS [M+H] found 392.3, and 2-(7-(3'-fluoro-5,6'-dimethyl-2,2'-bipyridin-4-ylamino)-2H-pyrazolo[4,3-b]pyridin-2-yl)acetamide as yellow foam $^1$H NMR (400 MHz, DMSO-d$_6$) δ ppm 2.43 (3H, br. s.) 2.60 (3H, br. s.) 5.24 (2H, br. s.) 7.23-7.42 (1H, m) 7.47-7.66 (3H, m) 7.87 (2H, br. s.) 8.41-8.56 (2H, m) 8.64 (1H, br. s.) 10.17 (1H, br. s.), MS [M+H] found 392.4.

Example 15

N-(2-(2,5-difluorophenyl)pyridin-4-yl)-1H-pyrazolo[4,3-b]pyridin-7-amine

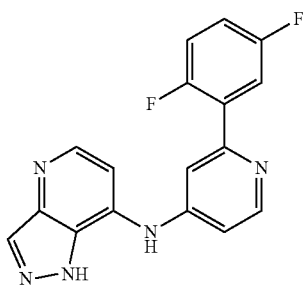 [SMILES: Fc1ccc(F)c(-c2cc(Nc3ccnc4cn[nH]c34)ccn2)c1]

7-Iodo-1H-pyrazolo[4,3-b]pyridine (1.5 g, 6.12 mmol) was dissolved in dry DMF (51.0 mL), cooled to 0° C. and NaH (0.245 g, 60% in oil, 6.12 mmol) was added. After 15 minutes and (2-(chloromethoxy)ethyl)trimethylsilane (1.080 mL, 6.12 mmol) was added and the mixture was warmed to room temperature over 2 hours then poured into ice water (350 mL) to give a solid which was filtered off. The filtrate was combined with dichloromethane and evaporated onto silica gel. Silica gel chromatography eluted with 0-5% MeOH in DCM gave 7-iodo-1-((2-(trimethylsilyl)ethoxy)methyl)-1H-pyrazolo[4,3-b]pyridine.

(R)-BINAP (0.85 g 1.371 mmol), diacetoxypalladium (0.071 g, 0.318 mmol) and toluene (8 mL) were combined and warmed at 40° C. for 10 minutes under nitrogen. 7-Iodo-1-((2-(trimethylsilyl)ethoxy)methyl)-1H-pyrazolo[4,3-b]pyridine (1.19 g, 3.18 mmol), 2-(2,5-difluorophenyl)pyridin-4-amine (0.656 g, 3.18 mmol) and sodium 2-methylpropan-2-olate (0.459 g, 4.77 mmol) suspended in toluene (8 mL) were added and the mixture was sparged with nitrogen (2 minutes) and then heated at 100° C. for overnight. The reaction mixture was cooled, concentrated onto silica and purified by column chromatography eluting with 0-5% MeOH in DCM gradient to give N-(2-(2,5-difluorophenyl)pyridin-4-yl)-1-((2-(trimethylsilyl)ethoxy)methyl)-1H-pyrazolo[4,3-b]pyridin-7-amine and N-(2-(2,5-difluorophenyl)pyridin-4-yl)-2-((2-(trimethylsilyl)ethoxy)methyl)-2H-pyrazolo[4,3-b]pyridin-7-amine. MS [M+H] found 454.4.

A mixture of N-(2-(2,5-difluorophenyl)pyridin-4-yl)-1-((2-(trimethylsilyl)ethoxy)methyl)-1H-pyrazolo[4,3-b]pyridin-7-amine and N-(2-(2,5-difluorophenyl)pyridin-4-yl)-2-((2-(trimethylsilyl)ethoxy)methyl)-2H-pyrazolo[4,3-b]pyridin-7-amine (1.2 g, 3.2 mmol) were combined with trifluoroacetic acid (1.1 mL) and stirred at 70° C. for 15 minutes. Anisole (20 μL) was then added and the mixture was further heated at 70° C. The reaction mixture was then purified via preparative HPLC using a gradient of 10-30% acetonitrile (containing 0.035% TFA) in water (containing 0.05% TFA) using a Sunfire Prep 5 μm C18, 75×30 mm column to give the title compound as a TFA salt. $^1$H NMR (400 MHz, DMSO-d$_6$) δ ppm 7.39-7.52 (m, 4H) 7.79 (br. s., 2H) 7.95 (s, 1H) 8.57 (d, J=6.32 Hz, 2H) 8.76 (br. s., 2H). MS [M+H] found 324.2.

Example 16

N-(2-(5-chloro-2-fluorophenyl)-5-methylpyridin-4-yl)-6-fluoro-2-(2-methoxyethyl)-2H-pyrazolo[4,3-b]pyridin-7-amine

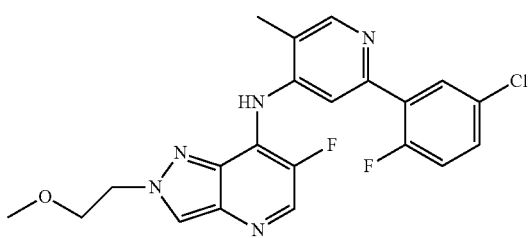 [SMILES: COCCn1cc2ncc(F)c(Nc3cc(-c4cc(Cl)ccc4F)ncc3C)c2n1]

6-Fluoro-7-iodo-1H-pyrazolo[4,3-b]pyridine (150 mg, 0.570 mmol) was dissolved in DMF (5 mL) and sodium hydride (34.2 mg, 0.855 mmol) was added slowly, followed by 1-bromo-2-methoxyethane (0.080 ml, 0.855 mmol). After 90 minutes, the reaction was quenched with crushed ice and the reaction mixture was purified by preparative HPLC eluting with 20/80 (v/v) water/acetonitrile in 10 mmol NH$_4$HCO$_3$ in water on a Phenomenex Gemini Prep 5 μm C18, 75×30 mm column) to give 6-fluoro-7-iodo-2-(2-methoxyethyl)-2H-pyrazolo[4,3-b]pyridine (52 mg, 28.4% yield) as white solid. MS [M+H] found 322.1

6-Fluoro-7-iodo-1-(2-methoxyethyl)-1H-pyrazolo[4,3-b]pyridine (45 mg, 0.140 mmol) were combined in dioxane (4 mL) and the following was added sequentially (9,9-dimethyl-9H-xanthene-4,5-diyl)bis(diphenylphosphine) (20.27 mg, 0.035 mmol), Tris(dibenzylideneacetone)dipalladium(0) (32.1 mg, 0.035 mmol), sodium tert-butoxide (40.4 mg, 0.420 mmol) and 2-(5-chloro-2-fluorophenyl)-5-methylpyridin-4-amine (7) (33.2 mg, 0.140 mmol). The reaction vessel was sealed and heated at 110° C. for an hour. The mixture was then cooled, evaporated to dryness, the residue was dissolved in DMF and purified by preparative HPLC (eluting with gradient of 20-45% ACN (containing 0.035% TFA) in water (containing 0.05% TFA) using a Sunfire Prep 5 μm C18, 75×30 mm column) to give the title compound (30 mg, 49.8% yield) as a TFA salt. $^1$H NMR (400 MHz, DMSO-$d_6$) δ ppm 2.44 (s, 3H) 3.12 (s, 3H) 3.59-3.81 (m, 2H) 4.57 (t, J=5.18 Hz, 2H) 7.09 (s, 1H) 7.42 (dd, J=10.11, 9.09 Hz, 1H) 7.55-7.70 (m, 1H) 7.77 (dd, J=6.44, 2.65 Hz, 1H) 8.53 (s, 1H) 8.67 (br. s., 1H) 8.80 (s, 1H) 9.70 (br. s., 1H). MS [M+H] found 430.3.

Example 17

N-(2-(5-chloro-2-fluorophenyl)pyridin-4-yl)-1H-pyrazolo[4,3-b]pyridin-7-amine

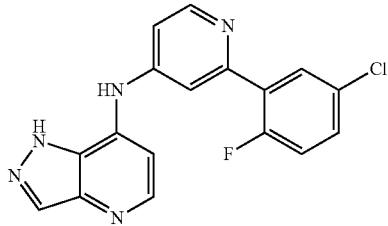 [SMILES: Fc1ccc(Cl)cc1-c1cc(Nc2ccnc3cn[nH]c23)ccn1]

Into a 5 mL oven-dried microwave vial was added (R)-BINAP (159 mg, 0.255 mmol) and diacetoxypalladium (13.28 mg, 0.059 mmol). Toluene (2 mL) was added and the solution was stirred at 40° C. for 10 min. Then 7-iodo-2-(4-methoxybenzyl)-2H-pyrazolo[4,3-b]pyridine (216 mg, 0.592 mmol) in 2 mL of toluene was added, followed by 2-(5-chloro-2-fluorophenyl)pyridin-4-amine (132 mg, 0.592 mmol) and sodium 2-methylpropan-2-olate (85 mg, 0.887 mmol). Nitrogen was sparged into the solution for about 2 minutes, and the reaction was heated in a 100° C. oil bath over night. The reaction mixture was cooled and purified using silica column chromatography (0-5 methanol/dichloromethane) to give a residue. The residue was further purified by silica column chromatography (1:1 Ethyl acetate/hexanes) gave 100 mg of N-(2-(5-chloro-2-fluorophenyl)pyridin-4-yl)-2-(4-methoxybenzyl)-2H-pyrazolo[4,3-b]pyridin-7-amine. MS [M+H] found 460.3.

To a vial containing N-(2-(5-chloro-2-fluorophenyl)pyridin-4-yl)-2-(4-methoxybenzyl)-2H-pyrazolo[4,3-b]pyridin-7-amine was added 5 mL of neat TFA and the mixture was heated at 70° C. for 3 hours. Cooled to room temperature and concentrated to dryness. The residue was purified by preparative HPLC eluting with a gradient of 10-30% acetonitrile (containing 0.035% TFA) in water (containing 0.05% TFA) using a Sunfire Prep 5 μm C18, 75×30 mm column conditions to give, after drying in vacuo, the title compound as a TFA salt as an off-white solid. $^1$HNMR (400 MHz, DMSO-$d_6$) δ ppm 7.31-7.60 (4H, m) 7.62 (1H, ddd, J=8.78, 4.11, 2.78 Hz) 7.86 (1H, br. s.) 8.01 (1H, dd, J=6.69, 2.65 Hz) 8.56 (2H, d, J=6.32 Hz) 8.75 (1H, d, J=5.81 Hz) 11.12 (1H, br. s.), MS [M+H] found 340.2.

Example 18 and 19

N-(2-(5-chloro-2-fluorophenyl)pyridin-4-yl)-1-propyl-1H-pyrazolo[4,3-b]pyridin-7-amine and N-(2-(5-chloro-2-fluorophenyl)pyridin-4-yl)-2-propyl-2H-pyrazolo[4,3-b]pyridin-7-amine

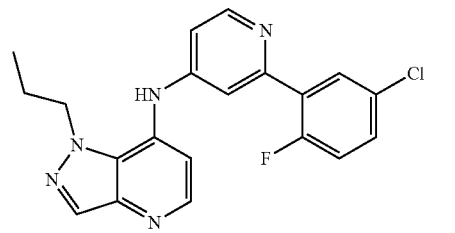

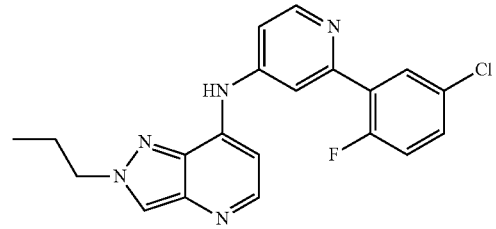

A mixture of 7-iodo-1H-pyrazolo[4,3-b]pyridine (50 mg, 0.204 mmol), 1-chloropropane (0.018 mL, 0.204 mmol), tetrabutylammonium iodide (75 mg, 0.204 mmol) and cesium carbonate (199 mg, 0.612 mmol) in DMF (1.0 mL) was heated in a microwave for 15 minutes at 80° C. Additional 1-chloropropane (0.018 mL, 0.204 mmol), tetrabutylammonium iodide (75 mg, 0.204 mmol) and cesium carbonate 65 mg were added and microwave heating was continued at 80° C. for 30 min. Poured into 10 mL water then extracted with ethyl acetate, dried over sodium sulfate and concentrated to a dark film which was carried forward to next step as is. MS [M+H] found 288.1.

A mixture of sodium 2-methylpropan-2-olate (48.7 mg, 0.507 mmol), 7-iodo-1-propyl-1H-pyrazolo[4,3-b]pyridine (52 mg, 0.181 mmol), 2-(5-chloro-2-fluorophenyl)pyridin-4-amine (40.3 mg, 0.181 mmol), Pd(OAc)$_2$ (4.07 mg, 0.018 mmol), and 2,2'-bis(diphenylphosphino)-1,1'-binaphthyl (48.6 mg, 0.078 mmol) in dioxane (2012 μl) was heated in a microwave for 1 hour at 110° C. The reaction was filtered, concentrated and reconstituted in DMF and purified by preparative HPLC eluting with a gradient of 10-30% acetonitrile (containing 0.035% TFA) in water (containing 0.05% TFA) using a Sunfire Prep 5 μm C18, 75×30 mm column to afford title compounds as TFA salts. N-(2-(5-chloro-2-fluorophenyl)pyridin-4-yl)-1-propyl-1H-pyrazolo[4,3-b]pyridin-7-amine: $^1$H NMR (400 MHz, DMSO-$d_6$) δ ppm 0.68 (3H, t, J=7.45 Hz) 1.62-1.75 (2H, m) 4.47 (4H, br. s.) 7.07-7.17 (1H, m) 7.36-7.51 (2H, m) 7.65 (1H, br. s.) 7.93 (1H, dd, J=6.44, 2.65 Hz) 8.38 (1H, s) 8.43-8.60 (2H, m), MS [M+H] found 382.3; and N-(2-(5-chloro-2-fluorophenyl)pyridin-4-yl)-2-propyl-2H-pyrazolo[4,3-b]pyridin-7-amine: $^1$H NMR (400 MHz, DMSO-$d_6$) δ ppm 0.88 (3H, t, J=7.45 Hz) 1.87-2.06 (2H, m) 4.53 (3H, t, J=6.69 Hz) 7.18-7.27 (1H, m) 7.40-7.52 (1H, m) 7.53-7.70 (2H, m) 7.97 (1H, s) 8.02 (1H, dd, J=6.82, 3.03 Hz) 8.51 (1H, d, J=6.82 Hz) 8.74 (1H, br. s.) 8.80 (1H, s), MS [M+H] found 382.3.

Example 20

N-(2-(5-chloro-2-fluorophenyl)pyridin-4-yl)-1-isopropyl-1H-pyrazolo[4,3-b]pyridin-7-amine

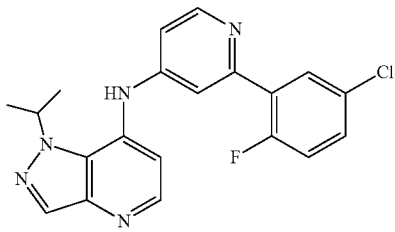 [SMILES: CC(C)n1ncc2nccc(Nc3ccnc(-c4cc(Cl)ccc4F)c3)c21]

7-Iodo-2H-pyrazolo[4,3-b]pyridine (50 mg, 0.204 mmol), 2-iodopropane (0.024 ml, 0.245 mmol) and sodium hydride (9.79 mg, 0.408 mmol) were combined in DMF (5 mL) and the mixture was stirred at room temperature for 1 hour, then purified by preparative HPLC using a Sunfire Prep 5 μm C18, 75×30 mm column eluting with a gradient of 20-70% acetonitrile (containing 0.035% TFA) in water (containing 0.05% TFA) to afford 7-iodo-1-isopropyl-1H-pyrazolo[4,3-b]pyridine as a TFA salt (111 mg, 18.78% yield). MS [M+H] found 288.1.

7-iodo-1-isopropyl-1H-pyrazolo[4,3-b]pyridine (11 mg, 0.038 mmol), Tris(dibenzylideneacetone)dipalladium(0) (0.877 mg, 0.958 μmol), (9,9-dimethyl-9H-xanthene-4,5-diyl)bis(diphenylphosphine) (5.54 mg, 9.58 μmol), 2-(5-chloro-2-fluorophenyl)pyridin-4-amine (8.53 mg, 0.038 mmol) and sodium 2-methylpropan-2-olate (11.05 mg, 0.115 mmol) were combined in dioxane (5 mL). The mixture was heated at 140° C. for 1 hour. The reaction was cooled and the crude material was purified by preparative HPLC using a Sunfire Prep 5 μm C18, 75×30 mm column eluting with a gradient of 10-40% acetonitrile (containing 0.035% TFA) in water (containing 0.05% TFA) to afford the title compound as a TFA salt (3.3 mg, 22.56% yield). $^1$H NMR (400 MHz, METHANOL-d4) δ ppm 1.50 (d, J=6.57 Hz, 6H) 5.13 (m, 1H) 7.20 (dd, J=6.82, 2.53 Hz, 1H) 7.35-7.46 (m, 3H) 7.66 (ddd, J=8.97, 4.42, 2.78 Hz, 1H) 7.81 (dd, J=6.32, 2.78 Hz, 1H) 8.32 (s, 1H) 8.40 (d, J=6.82 Hz, 1H) 8.54 (d, J=5.30 Hz, 1H). MS [M+H] found 382.3.

Example 21

N-(2-(5-chloro-2-fluorophenyl)pyridin-4-yl)-1-(tetrahydro-2H-pyran-4-yl)-1H-pyrazolo[4,3-b]pyridin-7-amine

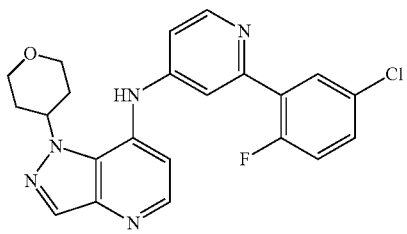 [SMILES: Fc1ccc(Cl)cc1-c1cc(Nc2ccnc3cnn(C4CCOCC4)c23)ccn1]

7-Iodo-2H-pyrazolo[4,3-b]pyridine (50 mg, 0.204 mmol), 4-iodotetrahydro-2H-pyran (43.3 mg, 0.204 mmol) and sodium hydride (9.79 mg, 0.408 mmol) were combined in DMF (5 mL). The mixture was stirred at room temperature for 1 hour and then purified by preparative HPLC using a Sunfire Prep 5 μm C18, 75×30 mm column eluting with a gradient of 20-70% acetonitrile (containing 0.035% TFA) in water (containing 0.05% TFA) to afford 7-iodo-1-(tetrahydro-2H-pyran-4-yl)-1H-pyrazolo[4,3-b]pyridine as a TFA salt (22 mg, 32.8% yield). MS [M+H] found 330.1.

7-Iodo-1-(tetrahydro-2H-pyran-4-yl)-1H-pyrazolo[4,3-b]pyridine (22 mg, 0.067 mmol), Tris(dibenzylideneacetone)dipalladium(0) (1.530 mg, 1.671 μmol), (9,9-dimethyl-9H-xanthene-4,5-diyl)bis(diphenylphosphine) (9.67 mg, 0.017 mmol), 2-(5-chloro-2-fluorophenyl)pyridin-4-amine (14.88 mg, 0.067 mmol) and sodium 2-methylpropan-2-olate (19.27 mg, 0.201 mmol) were mixed in dioxane (5 ml). The mixture was heated at 140° C. for 1 hour. The reaction mixture was then cooled and purified by preparative HPLC using a Sunfire Prep 5 μm C18, 75×30 mm column eluting with a gradient of 10-40% acetonitrile (containing 0.035% TFA) in water (containing 0.05% TFA) to afford the title compound as a TFA salt (2.6 mg, 6.13 μmol, 9.18% yield). $^1$H NMR (400 MHz, METHANOL-d4) δ ppm 1.83-1.92 (m, 2H) 2.27 (m, 2H) 3.44 (m, 2H) 4.00 (m 2H) 5.00 (m, 1H) 7.27 (dd, J=6.95, 2.40 Hz, 1H) 7.37 (dd, J=10.11, 8.84 Hz, 1H) 7.47 (d, J=1.77 Hz, 1H) 7.52 (d, J=5.31 Hz, 1H) 7.64 (ddd, J=8.91, 4.36, 2.65 Hz, 1H) 7.78 (dd, J=6.32, 2.53 Hz, 1H) 8.33 (s, 1H) 8.41 (d, J=6.82 Hz, 1H) 8.56 (d, J=5.30 Hz, 1H). MS [M+H] found 424.3.

Example 22

N-(2-(5-chloro-2-fluorophenyl)pyridin-4-yl)-1-(4-methoxybenzyl)-1H-pyrazolo[4,3-b]pyridin-7-amine and N-(2-(5-chloro-2-fluorophenyl)pyridin-4-yl)-2-(4-methoxybenzyl)-2H-pyrazolo[4,3-b]pyridin-7-amine

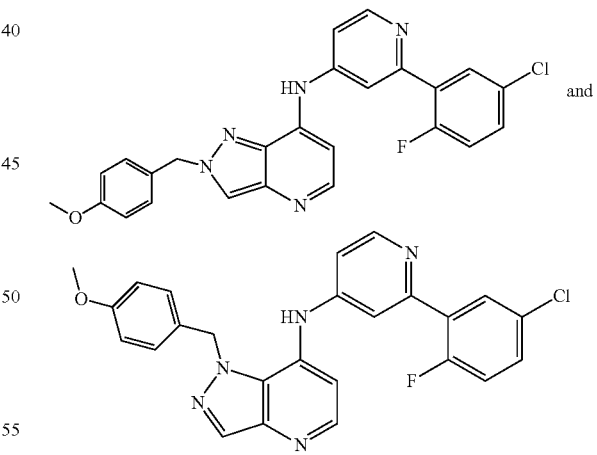

7-Iodo-1H-pyrazolo[4,3-b]pyridine (1 g, 4.08 mmol) and sodium hydride (0.196 g, 4.90 mmol) were combined in dry DMF (41 ml). The reaction mixture was stirred for 10 minutes and chilled to 0° C. 1-(Chloromethyl)-4-methoxybenzene (0.584 ml, 4.29 mmol) was added. And the mixture was stirred for 15 minutes at 0° C. and then for 30 minutes at room temperature. The crude reaction mixture was diluted with ice water (200 mL) and saturated ammonium chloride solution (50 mL) and extracted with ethyl acetate (50 mL×2). The organics were combined, dried over sodium sulfate and concentrated to give dark oil. The crude material was purified on a silica gel column chromatography (30% Ethyl acetate in hexanes) to give the p-methoxybenzyl protected product as a mixture of isomers (1:1) which was dried under vacuum for 1 hour and used immediately in the next step. MS [M+H] found 366.1.

Example 23 and 24

N-(2-(5-chloro-2-fluorophenyl)pyridin-4-yl)-2-((tetrahydro-2H-pyran-4-yl)methyl)-2H-pyrazolo[4,3-b]pyridin-7-amine and N-(2-(5-chloro-2-fluorophenyl)pyridin-4-yl)-1-((tetrahydro-2H-pyran-4-yl)methyl)-1H-pyrazolo[4,3-b]pyridin-7-amine

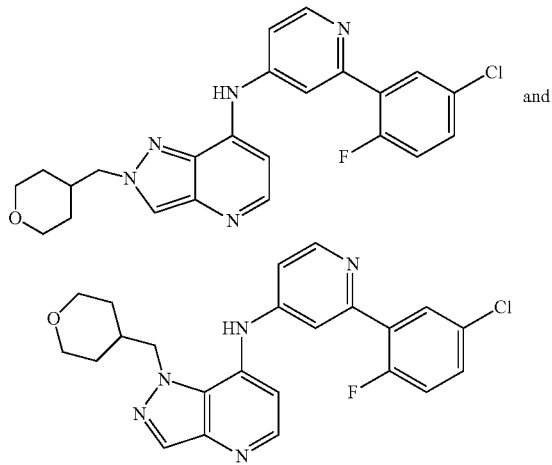

and

7-Iodo-1H-pyrazolo[4,3-b]pyridine (1 g, 4.08 mmol) and sodium hydride (0.196 g, 4.90 mmol) were combined in dry DMF (41 ml). The reaction mixture was stirred for 10 minutes and chilled to 0° C. 1-(Chloromethyl)-4-methoxybenzene (0.584 ml, 4.29 mmol) was added and the mixture was stirred for 15 minutes at 0° C. and then for 30 minutes at room temperature. The crude reaction mixture was diluted with ice water (200 mL) and saturated ammonium chloride solution (50 mL) and extracted with ethyl acetate (50 mL×2). The organics were combined, dried over sodium sulfate and concentrated to give dark oil. The crude material was purified on a silica gel column chromatography (30% Ethyl acetate in hexanes) to give the p-methoxybenzyl protected product as a mixture of isomers (1:1) which was dried under vacuum for 1 hour and used immediately in the next step. MS [M+H] found 366.1.

(R)-BINAP (0.808 g, 1.298 mmol), diacetoxypalladium (0.068 g, 0.301 mmol) and Toluene (10 mL) was added to a round bottom flask and the solution was stirred at 40° C. for 10 minutes. This mixture was removed from heat and a suspension of 7-iodo-2-(4-methoxybenzyl)-2H-pyrazolo[4,3-b]pyridine (1.1 g, 3.01 mmol), 2-(5-chloro-2-fluorophenyl)pyridin-4-amine (0.671 g, 3.01 mmol) and sodium 2-methylpropan-2-olate (0.434 g, 4.52 mmol) in toluene (11 mL) was added. The reaction mixture was sparged with nitrogen and heated at 100° C. overnight. The reaction mixture was cooled to room temperature, concentrated in-vacuo and purified on a silica gel column chromatography (Ethyl acetate/hexanes 1:1) to give as a mixture N-(2-(5-chloro-2-fluorophenyl)pyridin-4-yl)-2-(4-methoxybenzyl)-2H-pyrazolo[4,3-b]pyridin-7-amine and N-(2-(5-chloro-2-fluorophenyl) pyridin-4-yl)-1-(4-methoxybenzyl)-1H-pyrazolo[4,3-b]pyridin-7-amine as a yellow foam; MS [M+H] found 460.3.

To the mixture from the previous step was added TFA (8 mL) and the mixture was stirred at 70° C. for 2.5 hours. The reaction was cooled to room temperature, concentrated under vacuum, and the residue was taken up in dichloromethane (20 mL) to which was added saturated sodium bicarbonate solution (10 mL). The resulting solids were filtered, dissolved in Ethyl acetate and washed with water (5 mL) of then washed again with saturated sodium bicarbonate solution (10 mL), dried over sodium sulfate, concentrated, and dried under high vacuum to give N-(2-(5-chloro-2-fluorophenyl)pyridin-4-yl)-1H-pyrazolo[4,3-b]pyridin-7-amine (0.386 g, 1.136 mmol, 70.5% yield) as a yellow powder. ¹H NMR (400 MHz, DMSO-d₆) δ ppm 7.11-7.22 (1H, m) 7.27 (1H, d, J=5.05 Hz) 7.42 (1H, dd, J=10.86, 8.84 Hz) 7.51-7.62 (2H, m) 8.02 (1H, dd, J=6.57, 2.78 Hz) 8.26 (1H, d, J=1.26 Hz) 8.38 (1H, d, J=5.05 Hz) 8.53 (1H, d, J=5.56 Hz) 9.39 (1H, s) 12.96 (1H, s). MS [M+H] found 340.2.

A mixture of N-(2-(5-chloro-2-fluorophenyl)pyridin-4-yl)-1H-pyrazolo[4,3-b]pyridin-7-amine (50 mg, 0.147 mmol), 4-(bromomethyl)tetrahydro-2H-pyran (26.9 μl, 0.147 mmol) and cesium carbonate (96 mg, 0.294 mmol) in DMF (736 μl) was heated in a microwave for 15 minutes at 80° C. The mixture was filtered and purified by preparative HPLC eluting with a gradient of 15-25% acetonitrile (containing 0.035% TFA) in water (containing 0.05% TFA) using a Sunfire Prep 5 μm C18, 75×30 mm to give the title compounds as TFA salts. N-(2-(5-chloro-2-fluorophenyl)pyridin-4-yl)-2-((tetrahydro-2H-pyran-4-yl)methyl)-2H-pyrazolo[4,3-b]pyridin-7-amine. ¹H NMR (400 MHz, DMSO-d₆) δ ppm 1.16 (5H, br. s.) 1.88 (1H, br. s.) 3.00 (2H, br. s.) 3.69 (2H, d, J=11.62 Hz) 4.41 (2H, br. s.) 7.20 (1H, s) 7.40-7.56 (3H, m) 7.70 (1H, s) 7.86-7.96 (1H, m) 8.42 (1H, br. s.) 8.50 (1H, d, J=6.32 Hz) 8.59 (1H, br. s.). MS [M+H] found 438.3.

N-(2-(5-chloro-2-fluorophenyl)pyridin-4-yl)-1-((tetrahydro-2H-pyran-4-yl)methyl)-1H-pyrazolo[4,3-b]pyridin-7-amine. ¹H NMR (400 MHz, DMSO-d₆) δ ppm 1.25-1.48 (4H, m) 2.20-2.30 (1H, m) 3.16-3.31 (2H, m) 3.76-3.91 (2H, m) 4.47 (2H, d, J=7.33 Hz) 7.25 (1H, d, J=6.57 Hz) 7.46 (1H, dd, J=10.86, 8.84 Hz) 7.57-7.66 (2H, m) 7.97 (1H, s) 8.01 (1H, dd, J=6.57, 2.78 Hz) 8.54 (1H, d, J=6.57 Hz) 8.76 (1H, d, J=5.56 Hz) 8.81 (1H, s) 11.37 (1H, s). MS [M+H] found 438.4

Example 25

N-(2-(5-chloro-2-fluorophenyl)pyridin-4-yl)-2-((tetrahydrofuran-2-yl)methyl)-2H-pyrazolo[4,3-b]pyridin-7-amine

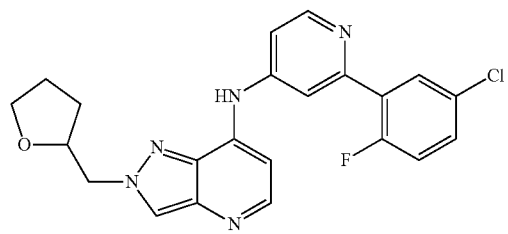 [SMILES: Fc1ccc(Cl)cc1-c1cc(Nc2ccnc3cn(CC4CCCO4)nc23)ccn1]

7-Iodo-1H-pyrazolo[4,3-b]pyridine (50 mg, 0.204 mmol), 2-(bromomethyl)tetrahydrofuran (33.7 mg, 0.204 mmol) and cesium carbonate (133 mg, 0.408 mmol) in DMF (1.0 mL) were heated in a microwave 80° C. for 15 minutes. The reaction was cooled, poured into water (10 mL) and extract with ethyl acetate (5 mL). The organics were dried over sodium sulfate, filtered and concentrated to provide 7-iodo-2-((tetrahydrofuran-2-yl)methyl)-2H-pyrazolo[4,3-b]pyridine (43 mg) which was used as is without further purification. MS [M+H] found 330.1.

Sodium 2-methylpropan-2-olate (35.2 mg, 0.366 mmol), 7-iodo-1-((tetrahydrofuran-2-yl)methyl)-1H-pyrazolo[4,3-b]pyridine (43 mg, 0.131 mmol), 2-(5-chloro-2-fluorophenyl)pyridin-4-amine (29.1 mg, 0.131 mmol), Pd(OAc)2 (2.93 mg, 0.013 mmol), and 2,2'-bis(diphenylphosphino)-1,1'-binaphthyl (35.1 mg, 0.056 mmol) were combined in dioxane (1452 µl) and heated in a microwave for 2 hours at 110° C., then cooled and purified by preparative HPLC using a Sunfire Prep 5 µm C18, 75×30 mm column eluting with a gradient of 10-35% acetonitrile (containing 0.035% TFA) in water (containing 0.05% TFA) to give the title compound as a TFA salt. $^1$H NMR (400 MHz, DMSO-d6) δ ppm 1.64-1.75 (1H, m) 1.85 (2H, quin, J=7.07 Hz) 1.97-2.07 (1H, m) 3.63-3.71 (1H, m) 3.76-3.84 (1H, m) 4.38 (2H, dt, J=11.37, 6.95 Hz) 4.54-4.69 (3H, m) 7.26 (1H, d, J=6.57 Hz) 7.46 (1H, dd, J=10.86, 8.84 Hz) 7.58-7.65 (1H, m) 7.98 (1H, s) 8.02 (1H, dd, J=6.57, 2.78 Hz) 8.54 (1H, d, J=6.32 Hz) 8.73-8.83 (1H, m) 11.32 (1H, s). MS [M+H] 424.3

Example 26 and 27

N-(2-(5-chloro-2-fluorophenyl)pyridin-4-yl)-1-(piperidin-4-ylmethyl)-1H-pyrazolo[4,3-b]pyridin-7-amine and N-(2-(5-chloro-2-fluorophenyl)pyridin-4-yl)-2-(piperidin-4-ylmethyl)-2H-pyrazolo[4,3-b]pyridin-7-amine

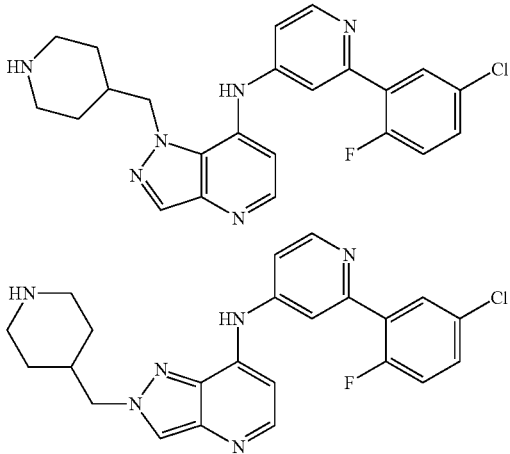

A solution of 7-iodo-1H-pyrazolo[4,3-b]pyridine (76 mg, 0.310 mmol) in DMF (4 ml) was cooled in an ice bath. Sodium hydride (16.13 mg, 0.403 mmol) was added and the reaction was stirred for 5 minutes. 4-Bromomethyl-piperidine-1-carboxylic acid tert-butyl ester (104 mg, 0.372 mmol) was added and the reaction was warmed to room temperature and then to 65° C. for 20 minutes. The reaction was then cooled, quenched with water and saturated NH$_4$Cl solution and extracted with EtOAc. The organic layer were separated, dried over Na$_2$SO$_4$, filtered, and concentrated in vacuo to give tert-butyl 4-((7-iodo-2H-pyrazolo[4,3-b]pyridin-2-yl)methyl)piperidine-1-carboxylate which was used in the next step without further purification.

tert-Butyl 4-((7-iodo-2H-pyrazolo[4,3-b]pyridin-2-yl)methyl)piperidine-1-carboxylate, 2,2'-bis(diphenylphosphino)-1,1'-binaphthyl, sodium 2-methylpropan-2-olate, palladium (II)acetate, and 2-(5-chloro-2-fluorophenyl)pyridin-4-amine were combined in dioxane (5 ml) and heated at 110° C. overnight. The reaction was cooled, concentrated and TFA/dichloromethane (1/1) was added. The solvent was evaporated in vacuo to give a residue. The residue was purified by preparative HPLC using a Sunfire Prep 5 µm C18, 75×30 mm column eluting with a gradient of 1-45% acetonitrile (containing 0.035% TFA) in water (containing 0.05% TFA) to afford N-(2-(5-chloro-2-fluorophenyl)pyridin-4-yl)-1-(piperidin-4-ylmethyl)-1H-pyrazolo[4,3-b]pyridin-7-amine as a TFA salt (15 mg, 11%). $^1$H NMR (400 MHz, METHANOL-d4) δ ppm 1.38-1.58 (m, 2H) 1.70 (d, J=12.88 Hz, 2H) 2.18-2.31 (m, 1H) 2.71-2.97 (m, 2H) 4.54 (d, J=6.82 Hz, 2H) 7.25 (dd, J=6.95, 2.40 Hz, 1H) 7.39 (t, J=9.60 Hz, 1H) 7.45-7.53 (m, 2H) 7.60-7.73 (m, 1H) 7.80 (dd, J=6.32, 2.53 Hz, 1H) 8.32 (s, 1H) 8.41 (d, J=6.82 Hz, 1H) 8.58 (br. s., 1H).). MS [M+H] found 437.4. Some fractions were concentrated and again purified by preparative HPLC eluting with a gradient of 10-25% acetonitrile (containing 0.035% TFA) in water (containing 0.05% TFA) using a Sunfire Prep 5 µm C18, 75×30 mm column to give N-(2-(5-chloro-2-fluorophenyl)pyridin-4-yl)-2-(piperidin-4-ylmethyl)-2H-pyrazolo[4,3-b]pyridin-7-amine as a TFA salt (20 mg, 15%). $^1$H NMR (400 MHz, METHANOL-d4) δ ppm 1.48-1.72 (m, 2H) 1.78-2.01 (m, 2H) 2.46 (qd, J=7.49, 4.29 Hz, 2H) 2.85-3.07 (m, 2H) 3.36-3.51 (m, 2H) 4.58 (d, J=7.07 Hz, 2H) 7.25-7.37 (m, 2H) 7.55 (ddd, J=8.84, 4.29, 2.78 Hz, 1H) 7.62 (dd, J=5.68, 2.15 Hz, 1H) 7.87-8.01 (m, 2H) 8.47 (br. s., 1H) 8.65 (s, 1H) 8.75 (d, J=5.81 Hz, 1H). MS [M+H] found 437.4.

Example 28

4-((7-(2-(5-chloro-2-fluorophenyl)pyridin-4-ylamino)-2H-pyrazolo[4,3-b]pyridin-2-yl)methyl)-N-ethylpiperidine-1-carboxamide

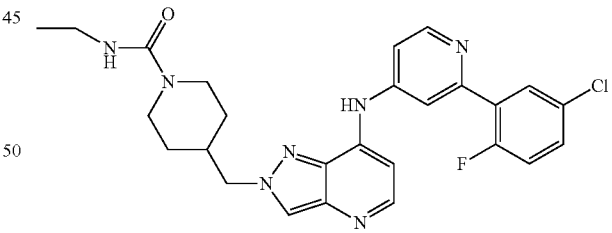

N-(2-(5-Chloro-2-fluorophenyl)pyridin-4-yl)-2-(piperidin-4-ylmethyl)-2H-pyrazolo[4,3-b]pyridin-7-amine (20 mg, 0.046 mmol) and N,N-diisopropylethylamine (7.97 µl, 0.046 mmol) were combined in dichloromethane (1.5 mL) followed by ethyl isocyanate (3.62 µl, 0.046 mmol). The reaction was then stirred at room temperature over night. The solvent was then evaporated to give a residue which was partitioned between EtOAc and 1N NaOH. The organic layer was washed with water and then brine, dried over Na$_2$SO$_4$, filtered, concentrated, and evaporated in-vacuo to give the title compound as a light yellow solid. MS [M+H] found 507.0.

Example 29

7-(2-(5-chloro-2-fluorophenyl)pyridin-4-ylamino)-
N-ethyl-1H-pyrazolo[4,3-b]pyridine-1-carboxamide

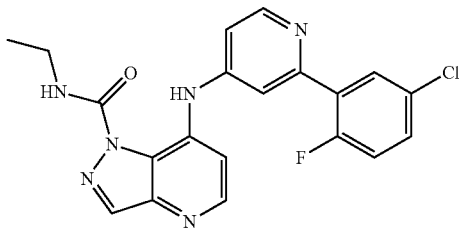 [SMILES: CCNC(=O)n1ncc2nccc(Nc3ccnc(-c4cc(Cl)ccc4F)c3)c21]

N-(2-(5-Chloro-2-fluorophenyl)pyridin-4-yl)-1H-pyrazolo[4,3-b]pyridin-7-amine (50 mg, 0.147 mmol) was suspended in dry acetonitrile (1472 µl). Isocyanatoethane (11.56 µl, 0.147 mmol) was added by syringe. The reaction was stirred at room temperature for 6 hours, then placed in heating block set at 82° C. for 1.5 hours and then stirred at room temperature over the weekend. The reaction mixture was then evaporated to give a residue which was dissolved in DMSO/methanol and filtered. The filtrate was purified by preparative HPLC using a Sunfire Prep 5 µm C18, 75×30 mm column eluting with a gradient of 25-45% acetonitrile (containing 0.035% TFA) in water (containing 0.05% TFA) to afford title compound as a TFA salt. $^1$H NMR (400 MHz, DMSO-d6) δ ppm 1.14-1.23 (m, 3H) 3.35-3.46 (m, 2H) 7.47-7.56 (m, 2H) 7.59-7.71 (m, 2H) 7.76 (s, 1H) 7.99 (dd, J=6.57, 2.53 Hz, 1H) 8.57 (d, J=5.31 Hz, 1H) 8.65 (d, J=6.32 Hz, 1H) 8.70 (s, 1H) 9.19 (t, J=5.81 Hz, 1H) 11.87 (s, 1H). MP 256° C. MS [M+H] found 411.3.

Example 30

7-(2-(5-chloro-2-fluorophenyl)pyridin-4-ylamino)-
1H-pyrazolo[4,3-b]pyridine-1-carboxamide

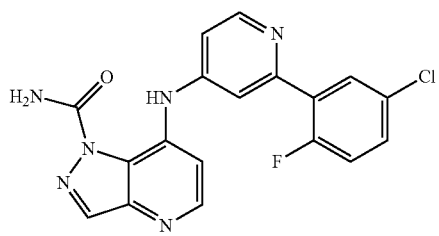 [SMILES: NC(=O)n1ncc2nccc(Nc3ccnc(-c4cc(Cl)ccc4F)c3)c21]

N-(2-(5-Chloro-2-fluorophenyl)pyridin-4-yl)-1H-pyrazolo[4,3-b]pyridin-7-amine (50 mg, 0.147 mmol) was suspended in dioxane (1472 µl). Isocyanatotrimethylsilane (19.92 µl, 0.147 mmol) was added by syringe and the reaction mixture was stirred at room temperature for 1 hour. The reaction mixture was then heated to 110° C. for 4 hours and then at 65° C. over night. Reaction was then cooled to give a solid which was collected by filtration, dissolved in warm DMF (2 mL) and DMSO (0.5 mL) and purified by preparative HPLC using a Sunfire Prep 5 µm C18, 75×30 mm column eluting with a gradient of 25-45% acetonitrile (containing 0.035% TFA) in water (containing 0.05% TFA) to give the title compound (contaminated with N-(2-(5-chloro-2-fluorophenyl)pyridin-4-yl)-1H-pyrazolo[4,3-b]pyridin-7-amine) as a TFA salt. $^1$H NMR (400 MHz, DMSO-d$_6$) δ ppm 7.44-7.54 (m, 2H) 7.59-7.68 (m, 2H) 7.72 (s, 1H) 7.98-8.06 (m, 1H) 8.43 (s, 1H) 8.49-8.60 (m, 1H) 8.62-8.68 (m, 1H) 11.86 (s, 1H). MS [M+H] found 383.1.

Example 31

2-(7-(2-(5-chloro-2-fluorophenyl)pyridin-4-ylamino)-1H-pyrazolo[4,3-b]pyridin-1-yl)-N-methylacetamide

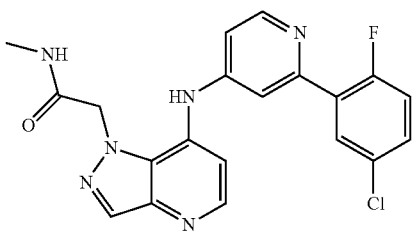 [SMILES: CNC(=O)Cn1ncc2nccc(Nc3ccnc(-c4cc(Cl)ccc4F)c3)c21]

N-(2-(5-Chloro-2-fluorophenyl)pyridin-4-yl)-1H-pyrazolo[4,3-b]pyridin-7-amine (50 mg, 0.147 mmol), 2-bromo-N-methylacetamide (22.37 mg, 0.147 mmol) and cesium carbonate (96 mg, 0.294 mmol) were combined in DMF (736 µl) and heated in a microwave for 15 minutes at 80° C. The reaction mixture was cooled, filtered, and purified by preparative HPLC using a Sunfire Prep 5 µm C18, 75×30 mm column eluting with a gradient of 15-20% acetonitrile (containing 0.035% TFA) in water (containing 0.05% TFA) to give the title compound as a TFA salt. $^1$H NMR (400 MHz, DMSO-d6) δ ppm 2.41 (3H, d, J=4.55 Hz) 5.24 (2H, s) 7.00-7.25 (1H, m) 7.34 (1H, s) 7.44-7.60 (2H, m) 7.68-7.84 (1H, m) 7.87-8.02 (1H, m) 8.25 (1H, br. s.) 8.42 (1H, s) 8.51 (1H, d, J=6.57 Hz) 8.60 (1H, d, J=5.05 Hz) 10.94 (1H, br. s.). MS [M+H] found 411.3.

Example 32

7-(2-(5-chloro-2-fluorophenyl)pyridin-4-ylamino)-
N-methyl-1H-pyrazolo[4,3-b]pyridine-1-carboxamide

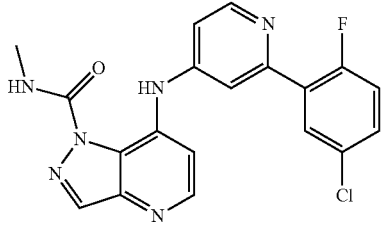 [SMILES: CNC(=O)n1ncc2nccc(Nc3ccnc(-c4cc(Cl)ccc4F)c3)c21]

N-(2-(5-Chloro-2-fluorophenyl)pyridin-4-yl)-1H-pyrazolo[4,3-b]pyridin-7-amine (30 mg, 0.088 mmol), methylcarbamic chloride (9.07 mg, 0.088 mmol) and pyridine (12.14 µl, 0.150 mmol) were combined in dichloroethylene (441 µl) was heated at 60° C. over night. Then pyridine (12.14 µl, 0.150 mmol) and methylcarbamic chloride (9.07 mg, 0.088 mmol) was added and heating was continued at 60° C. for 1 hour more. The reaction was then concentrated to a residue which was suspended in DMSO/methanol (1:1; 2 mL) and filtered and the filtrate purified by preparative HPLC using a Phenomenex Gemini C18, 5 μm, ID30×75 mm column eluting with a gradient of 25-35% (containing 0.035% TFA) in water (containing 0.05% TFA) to give the title compound as a TFA salt. ¹H NMR (400 MHz, DMSO-d6) δ ppm 2.06-2.11 (3H, m) 7.48-7.55 (2H, m) 7.63-7.72 (2H, m) 7.77 (1H, s) 8.00 (1H, dd, J=6.57, 2.78 Hz) 8.57 (1H, d, J=5.56 Hz) 8.66 (1H, d, J=6.06 Hz) 8.71 (1H, s) 9.11 (1H, d, J=4.80 Hz) 11.88 (1H, s). MP 256° C. MS [M+H] found 397.3

Example 33 and 34

N-(2-(5-chloro-2-fluorophenyl)pyridin-4-yl)-1-(3-methoxypropyl)-1H-pyrazolo[4,3-b]pyridin-7-amine and N-(2-(5-chloro-2-fluorophenyl)pyridin-4-yl)-2-(3-methoxypropyl)-2H-pyrazolo[4,3-b]pyridin-7-amine

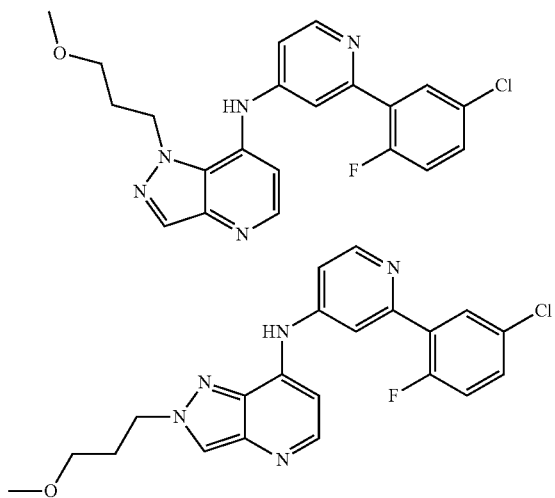

Sodium 2-methylpropan-2-olate (39.0 mg, 0.406 mmol), 7-iodo-1-(3-methoxypropyl)-1H-pyrazolo[4,3-b]pyridine (46 mg, 0.145 mmol), 2-(5-chloro-2-fluorophenyl)pyridin-4-amine (32.3 mg, 0.145 mmol), Pd(OAc)₂ (3.26 mg, 0.015 mmol), and 2,2'-bis(diphenylphosphino)-1,1'-binaphthyl (38.9 mg, 0.063 mmol) were combined in dioxane (1612 μl) was heated in a microwave for 1 hour at 110° C. The reaction mixture was then cooled, filtered and concentrated to give a residue which was dissolved in DMF and purified by preparative HPLC using a Sunfire Prep 5 μm C18, 75×30 mm column eluting with a gradient of 15-35% acetonitrile (containing 0.035% TFA) in water (containing 0.05% TFA) to give the title compounds as TFA salts. N-(2-(5-chloro-2-fluorophenyl)pyridin-4-yl)-2-(3-methoxypropyl)-2H-pyrazolo[4,3-b]pyridin-7-amine ¹H NMR (400 MHz, DMSO-d6) δ ppm 1.86-1.95 (2H, m) 2.73 (1H, s) 2.89 (1H, s) 3.06 (3H, s) 3.15 (2H, t, J=6.44 Hz) 4.51-4.63 (1H, m) 7.04-7.19 (1H, m) 7.37-7.52 (3H, m) 7.93 (2H, dd, J=6.69, 2.65 Hz) 8.38 (1H, s) 8.46-8.51 (1H, m) 8.50-8.56 (1H, m). MS [M+H] found 412.3.

N-(2-(5-chloro-2-fluorophenyl)pyridin-4-yl)-1-(3-methoxypropyl)-1H-pyrazolo[4,3-b]pyridin-7-amine ¹H NMR (400 MHz, DMSO-d6) δ ppm 2.21 (2H, dt, J=13.39, 6.44 Hz) 3.24 (3H, s) 3.36 (2H, d, J=6.06 Hz) 4.62 (2H, t, J=7.07 Hz) 7.18-7.29 (1H, m) 7.45 (1H, dd, J=10.86, 8.84 Hz) 7.55-7.63 (2H, m) 7.97 (1H, s) 8.02 (1H, dd, J=6.57, 2.78 Hz) 8.51 (1H, d, J=6.32 Hz) 8.75 (1H, d, J=5.56 Hz) 8.80 (1H, s) 11.05-11.32 (1H, m). MS [M+H] 412.3.

Example 35

N-(2-(5-chloro-2-fluorophenyl)pyridin-4-yl)-2-(2-methoxyethyl)-2H-pyrazolo[4,3-b]pyridin-7-amine and N-(2-(5-chloro-2-fluorophenyl)pyridin-4-yl)-1-(2-methoxyethyl)-2H-pyrazolo[4,3-b]pyridin-7-amine

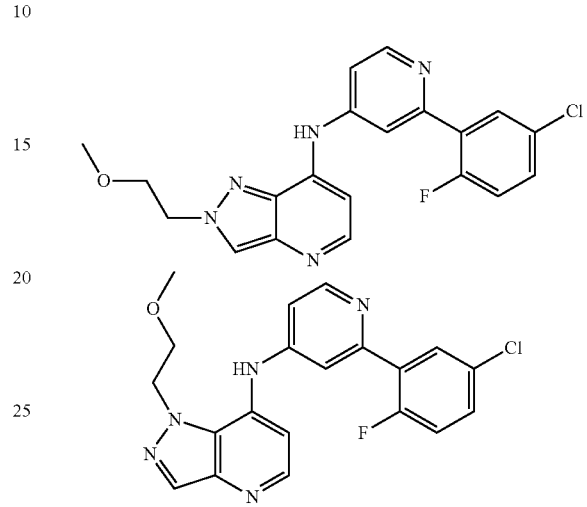

7-Bromo-1-(2-methoxyethyl)-1H-pyrazolo[4,3-b]pyridine (50 mg, 0.195 mmol), 7-bromo-2-(2-methoxyethyl)-2H-pyrazolo[4,3-b]pyridine (0.00 μmol), sodium 2-methylpropan-2-olate (52.5 mg, 0.547 mmol), 2-(5-chloro-2-fluorophenyl)pyridin-4-amine (43.5 mg, 0.195 mmol), diacetoxypalladium (4.38 mg, 0.020 mmol), and 2,2'-bis(diphenylphosphino)-1,1'-binaphthyl (52.4 mg, 0.084 mmol) were combined in dioxane (2.0 mL) and heated in a microwave for 1 hour at 110° C. The reaction mixture was then cooled, and concentrated to give a residue which was dissolved in DMSO (2.0 mL), filtered, and purified via preparative HPLC using a Phenomenex Gemini C18, 5 μm, ID30×75 mm eluting with a gradient of 10-40% acetonitrile (containing 0.035% TFA) in water (containing 0.05% TFA) to give the title compounds as a 3:1 mixture of N-(2-(5-chloro-2-fluorophenyl)pyridin-4-yl)-1-(2-methoxyethyl)-2H-pyrazolo[4,3-b]pyridin-7-amine and N-(2-(5-chloro-2-fluorophenyl)pyridin-4-yl)-2-(2-methoxyethyl)-2H-pyrazolo[4,3-b]pyridin-7-amine (as judged by NMR) as TFA salts. MS [M+H] found 398.3

Example 36 and 37

N-(2-(5-chloro-2-fluorophenyl)pyridin-4-yl)-1-(cyclopropylmethyl)-1H-pyrazolo[4,3-b]pyridin-7-amine and N-(2-(5-chloro-2-fluorophenyl)pyridin-4-yl)-2-(cyclopropylmethyl)-2H-pyrazolo[4,3-b]pyridin-7-amine

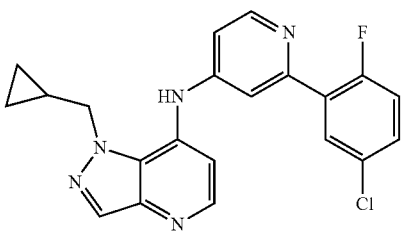

43

-continued

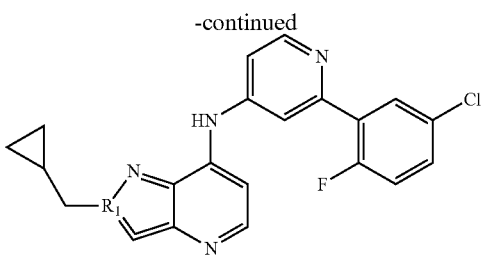

7-Iodo-1H-pyrazolo[4,3-b]pyridine (50 mg, 0.204 mmol), bromomethylcyclopropane (27.5 mg, 0.204 mmol) and cesium carbonate (133 mg, 0.408 mmol) in DMF (1.0 mL) were heated in a microwave at 80° C. for 15 minutes. Additional bromomethylcyclopropane (27.5 mg, 0.204 mmol) was then added and the reaction was further heated in a microwave at 80° C. for 30 minutes. The reaction was cooled and poured into water (10 mL) and extracted with ethyl acetate (5 mL). The organic layer was dried over sodium sulfate, filtered and concentrated in vacuo to give 1-(cyclopropylmethyl)-7-iodo-1H-pyrazolo[4,3-b]pyridine and 2-(cyclopropylmethyl)-7-iodo-2H-pyrazolo[4,3-b]pyridine as a mixture (60/40); MS [M+H] found 300.1.

Sodium 2-methylpropan-2-olate (35.4 g, 368 mmol), a mixture of 1-(cyclopropylmethyl)-7-iodo-1H-pyrazolo[4,3-b]pyridine and 2-(cyclopropylmethyl)-7-iodo-2H-pyrazolo[4,3-b]pyridine (39.3, 131 mmol), 2-(5-chloro-2-fluorophenyl)pyridin-4-amine (29.3 g, 131 mmol), Pd(OAc)$_2$ (2.95 g, 13.14 mmol), and 2,2'-bis(diphenylphosphino)-1,1'-binaphthyl (35.3 g, 56.6 mmol) were combined in dioxane (1460 mL) was heated in a microwave for 1 hour at 110° C. and then over night at 80° C. in an oil bath. The reaction mixture was then cooled and concentrated to give a residue which was dissolved in DMF and purified by preparative HPLC using a Sunfire Prep 5 μm C18, 75×30 mm column eluting with a gradient of 15-35% acetonitrile (containing 0.035% TFA) in water (containing 0.05% TFA) to give the title compounds as TFA salts. N-(2-(5-chloro-2-fluorophenyl)pyridin-4-yl)-1-(cyclopropylmethyl)-1H-pyrazolo[4,3-b]pyridin-7-amine: $^1$H NMR (400 MHz, DMSO-d6) δ ppm 0.20-0.40 (4H, m) 4.41 (1H, br. s.) 4.58 (1H, br. s.) 4.76-4.88 (2H, m) 5.60 (1H, d, J=5.31 Hz) 7.07-7.22 (1H, m) 7.34-7.55 (2H, m) 7.67 (1H, d, J=8.34 Hz) 7.91-8.00 (1H, m) 8.38 (1H, br. s.) 8.42-8.70 (2H, m). MS [M+H] found 394.3.

N-(2-(5-chloro-2-fluorophenyl)pyridin-4-yl)-2-(cyclopropylmethyl)-2H-pyrazolo[4,3-b]pyridin-7-amine: $^1$H NMR (400 MHz, DMSO-d6) δ ppm 0.46-0.70 (4H, m) 4.44 (1H, d, J=7.33 Hz) 4.65 (1H, t, J=6.95 Hz) 5.01-5.12 (1H, m) 5.25-5.37 (1H, m) 5.82 (1H, ddt, J=17.18, 10.36, 6.69, 6.69 Hz) 7.24 (1H, dt, J=6.57, 2.65 Hz) 7.41-7.51 (1H, m) 7.58-7.66 (1H, m) 7.93-8.06 (2H, m) 8.50-8.57 (1H, m) 8.76 (1H, d, J=5.81 Hz) 8.79-8.88 (1H, m). MS [M+H] found 394.3.

Example 38

2-(7-(2-(5-chloro-2-fluorophenyl)pyridin-4-ylamino)-1H-pyrazolo[4,3-b]pyridin-1-yl)-N,N-dimethylacetamide

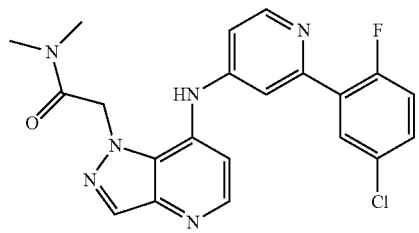 [SMILES: CN(C)C(=O)Cn1ncc2nccc(Nc3ccnc(-c4cc(Cl)ccc4F)c3)c21]

44

N-(2-(5-Chloro-2-fluorophenyl)pyridin-4-yl)-1H-pyrazolo[4,3-b]pyridin-7-amine (42 mg, 0.124 mmol), 2-chloro-N,N-dimethylacetamide (12.71 μl, 0.124 mmol) and K$_2$CO$_3$ (17.08 mg, 0.124 mmol) were combined in DMF (618 μl) and heated in a microwave at 80° C. for 15 minutes, then cooled and purified by preparative HPLC using a Sunfire Prep 5 μm C18, 75×30 mm column eluting with a gradient of 10-20% acetonitrile (containing 0.035% TFA) in water (containing 0.05% TFA) to give the title compound as a TFA salt. $^1$H NMR (400 MHz, DMSO-d6) δ ppm 2.44 (3H, s) 5.59 (2H, s) 6.80-7.11 (1H, m) 7.23 (1H, br. s.) 7.45 (1H, br. s.) 7.53 (1H, t, J=9.47 Hz) 7.69-7.81 (1H, m) 7.87 (1H, dd, J=6.32, 2.53 Hz) 8.35-8.51 (1H, m) 8.53-8.68 (1H, m) 10.48-10.72 (1H, m) 10.60 (1H, br. s.). MP 293° C. MS [M+H] found 425.3.

Example 39

7-(2-(5-chloro-2-fluorophenyl)pyridin-4-ylamino)-N,N-dimethyl-1H-pyrazolo[4,3-b]pyridine-1-carboxamide

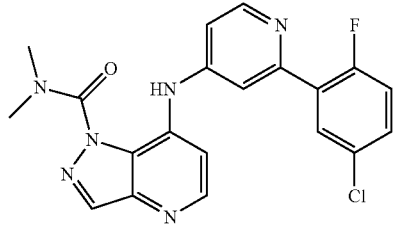 [SMILES: CN(C)C(=O)n1ncc2nccc(Nc3ccnc(-c4cc(Cl)ccc4F)c3)c21]

To N-(2-(5-chloro-2-fluorophenyl)pyridin-4-yl)-1H-pyrazolo[4,3-b]pyridin-7-amine (75 mg, 0.221 mmol), pyridine (30.4 μl, 0.375 mmol) in dichloroethylene (1104 μl) was added dimethylcarbamic chloride (23.74 mg, 0.221 mmol). The reaction mixture was heated at 60° C. over night in a sealed tube, then cooled and purified by preparative HPLC using a Sunfire Prep 5 μm C18, 75×30 mm column eluting with a gradient of 20-30% acetonitrile (containing 0.035% TFA) in water (containing 0.05% TFA) to give the title compound as a TFA salts. $^1$H NMR (400 MHz, DMSO-d6) δ ppm 2.96 (3H, br. s.) 3.13 (3H, br. s.) 7.26 (1H, dd, J=6.44, 2.40 Hz) 7.47-7.56 (2H, m) 7.59 (1H, d, J=5.31 Hz) 7.65-7.76 (1H, m) 7.93 (1H, dd, J=6.44, 2.65 Hz) 8.54 (1H, d, J=6.57 Hz) 8.64-8.72 (2H, m). MS [M+H] found 411.3.

Example 40 and 41

1-(2-(7-(2-(5-chloro-2-fluorophenyl)pyridin-4-ylamino)-2H-pyrazolo[4,3-b]pyridin-2-yl)ethyl)imidazolidin-2-one and 1-(2-(7-(2-(5-chloro-2-fluorophenyl)pyridin-4-ylamino)-1H-pyrazolo[4,3-b]pyridin-1-yl)ethyl)imidazolidin-2-one

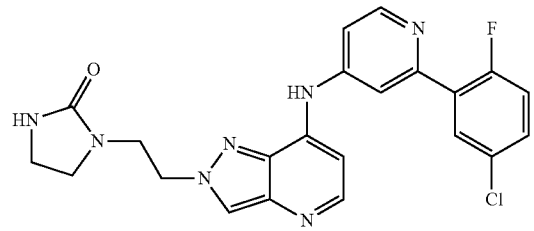

-continued

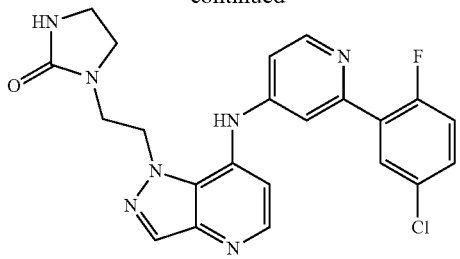

N-(2-(5-Chloro-2-fluorophenyl)pyridin-4-yl)-1H-pyrazolo[4,3-b]pyridin-7-amine (50 mg, 0.147 mmol), 1-(2-chloroethyl)imidazolidin-2-one (21.87 mg, 0.147 mmol), tetrabutylammonium iodide (54.4 mg, 0.147 mmol), cesium carbonate (96 mg, 0.294 mmol) were combined in DMF (1.0 mL) and heated in microwave at 80° C. for 15 minutes. Additional 1-(2-chloroethyl)imidazolidin-2-one (21.87 mg, 0.147 mmol), cesium carbonate (96 mg, 0.294 mmol) and tetrabutylammonium iodide (54.4 mg, 0.147 mmol) were added and heated in a microwave at 80° C. for 1 hour, then the reaction was cooled and purified by preparative HPLC using a Sunfire Prep 5 μm C18, 75×30 mm column eluting with a gradient of 15-20% acetonitrile (containing 0.035% TFA) in water (containing 0.05% TFA) to give the title compounds as TFA salts. 1-(2-(7-(2-(5-chloro-2-fluorophenyl)pyridin-4-ylamino)-1H-pyrazolo[4,3-b]pyridin-1-yl)ethyl)imidazolidin-2-one: $^1$H NMR (400 MHz, DMSO-d6) δ ppm 2.07 (1H, s) 3.01-3.19 (4H, m) 3.36 (3H, br. s.) 4.66 (3H, br. s.) 6.20 (1H, br. s.) 7.21 (1H, s) 7.40-7.59 (2H, m) 7.69 (1H, br. s.) 7.89-7.98 (1H, m) 8.41 (1H, s) 8.44-8.62 (1H, m). MS [M+H] found 452.3.
1-(2-(7-(2-(5-chloro-2-fluorophenyl)pyridin-4-ylamino)-2H-pyrazolo[4,3-b]pyridin-2-yl)ethyl)imidazolidin-2-one: $^1$H NMR (400 MHz, DMSO-d6) δ ppm 2.05-2.12 (1H, m) 3.12-3.22 (3H, m) 3.29-3.37 (2H, m) 3.66 (2H, t, J=6.06 Hz) 4.69 (2H, t, J=6.06 Hz) 6.21-6.57 (1H, m) 7.27 (1H, d, J=6.57 Hz) 7.47 (1H, dd, J=10.86, 8.84 Hz) 7.58-7.66 (1H, m) 7.97-8.06 (1H, m) 8.53-8.57 (1H, m) 8.77 (1H, d, J=5.56 Hz) 8.85 (1H, s) 11.30-11.60 (1H, m). MS [M+H] found 452.3.

Example 42

2-(7-(2-(5-chloro-2-fluorophenyl)pyridin-4-ylamino)-1H-pyrazolo[4,3-b]pyridin-1-yl)-1-morpholinoethanone

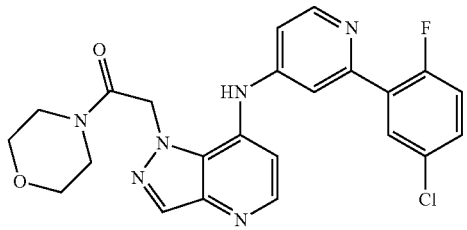 [SMILES: O=C(Cn1ncc2nccc(Nc3ccnc(-c4cc(Cl)ccc4F)c3)c21)N1CCOCC1]

N-(2-(5-Chloro-2-fluorophenyl)pyridin-4-yl)-1H-pyrazolo[4,3-b]pyridin-7-amine (50 mg, 0.147 mmol), 2-chloro-1-morpholinoethanone (19.15 μl, 0.147 mmol) and $K_2CO_3$ (20.34 mg, 0.147 mmol) were combined in DMF (736 μl) and heated in a microwave for 15 minutes at 80° C., then cooled and purified by preparative HPLC using a Sunfire Prep 5 μm C18, 75×30 mm column eluting with a gradient of 15-18% acetonitrile (containing 0.035% TFA) in water (containing 0.05% TFA) to give the title compound as a TFA salt. $^1$H NMR (400 MHz, DMSO-d6) δ ppm 3.04 (2H, br. s.) 3.30 (2H, t, J=4.67 Hz) 3.47 (2H, d, J=4.55 Hz) 3.58 (2H, d, J=4.80 Hz) 5.67 (2H, s) 7.13 (1H, d, J=5.31 Hz) 7.26 (1H, br. s.) 7.44-7.52 (1H, m) 7.52-7.64 (1H, m) 7.76 (1H, ddd, J=8.91, 4.36, 2.65 Hz) 7.87 (1H, dd, J=6.32, 2.78 Hz) 7.94-8.01 (1H, m) 8.43 (1H, s) 8.51 (1H, s) 8.58-8.68 (1H, m). MS [M+H] found 467.3.

Example 43 and 44

2-(7-(2-(5-chloro-2-fluorophenyl)pyridin-4-ylamino)-2H-pyrazolo[4,3-b]pyridin-2-yl)acetamide and 2-(7-(2-(5-chloro-2-fluorophenyl)pyridin-4-ylamino)-1H-pyrazolo[4,3-b]pyridin-1-yl)acetamide

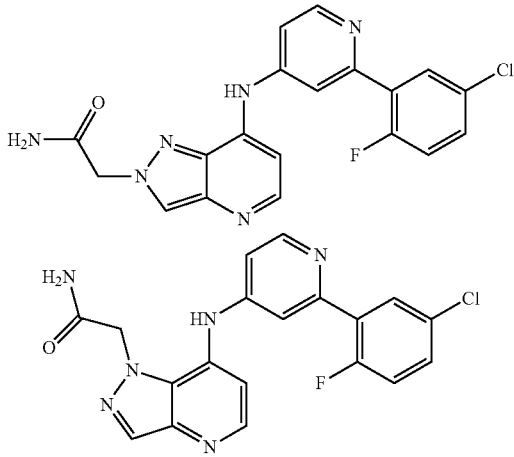

N-(2-(5-Chloro-2-fluorophenyl)pyridin-4-yl)-1H-pyrazolo[4,3-b]pyridin-7-amine (40 mg, 0.118 mmol), 2-chloroacetamide (11.01 mg, 0.118 mmol) and cesium carbonate (57.5 mg, 0.177 mmol) were combined in DMF (1.5 mL) and heated in a microwave for 15 minutes at 80° C. The reaction mixture was then cooled, filtered, and purified by preparative HPLC using a Sunfire Prep 5 μm C18, 75×30 mm column eluting with a gradient of 15-20% acetonitrile (containing 0.035% TFA) in water (containing 0.05% TFA) to give the title compounds as TFA salts. 2-(7-(2-(5-chloro-2-fluorophenyl)pyridin-4-ylamino)-2H-pyrazolo[4,3-b]pyridin-2-yl)acetamide $^1$H NMR (400 MHz, DMSO-d6) δ ppm 5.24 (2H, s) 7.15-7.24 (1H, m) 7.28-7.39 (2H, m) 7.45-7.59 (2H, m) 7.68-7.79 (2H, m) 7.86-7.93 (1H, m) 8.42 (1H, s) 8.48-8.54 (1H, m) 8.56-8.63 (1H, m) 10.62-11.09 (1H, m). MS [M+H] found 397.3.
2-(7-(2-(5-chloro-2-fluorophenyl)pyridin-4-ylamino)-1H-pyrazolo[4,3-b]pyridin-1-yl)acetamide. $^1$H NMR (400 MHz, DMSO-d6) δ ppm 5.30 (2H, s) 7.29 (1H, d, J=6.57 Hz) 7.43-7.56 (2H, m) 7.58-7.67 (2H, m) 7.79 (1H, s) 7.96-8.09 (2H, m) 8.57 (1H, d, J=6.57 Hz) 8.72-8.84 (2H, m) 11.38 (1H, s). MP 131-132° C. MS [M+H] found 397.3.

Example 45

2-(7-(2-(5-chloro-2-fluorophenyl)pyridin-4-ylamino)-2H-pyrazolo[4,3-b]pyridin-2-yl)propanamide

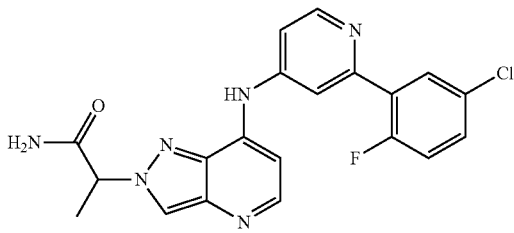 [SMILES: CC(C(N)=O)n1cc2nccc(Nc3ccnc(-c4cc(Cl)ccc4F)c3)c2n1]

N-(2-(5-Chloro-2-fluorophenyl)pyridin-4-yl)-1H-pyrazolo[4,3-b]pyridin-7-amine (60 mg, 0.177 mmol), 2-bromopropanamide (26.8 mg, 0.177 mmol) and cesium carbonate (115 mg, 0.353 mmol) were combined in DMF (1 mL) and heated in a microwave for 15 minutes at 80° C. The reaction mixture was then cooled, filtered and purified by preparative HPLC using a Sunfire Prep 5 μm C18, 75×30 mm column eluting with a gradient of 18-25% acetonitrile (containing 0.035% TFA) in water (containing 0.05% TFA) to give the title compound as a TFA salt. $^1$H NMR (400 MHz, DMSO-d6) δ ppm 1.67-1.85 (3H, m) 5.45-5.71 (1H, m) 7.13 (1H, d, J=6.06 Hz) 7.21 (1H, br. s.) 7.32 (1H, br. s.) 7.39-7.59 (3H, m) 7.69-7.77 (1H, m) 7.90 (1H, dd, J=6.44, 2.65 Hz) 8.43 (1H, br. s.) 8.49 (1H, d, J=6.57 Hz) 8.59 (1H, br. s.) 10.85 (1H, br. s.). MS [M+H] found 411.3.

Example 46

(R)-3-(7-(2-(5-chloro-2-fluorophenyl)pyridin-4-ylamino)-2H-pyrazolo[4,3-b]pyridin-2-yl)propane-1,2-diol

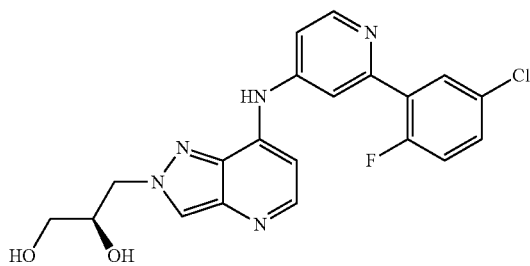 [SMILES: OC[C@H](O)Cn1cc2nccc(Nc3ccnc(-c4cc(Cl)ccc4F)c3)c2n1]

7-Iodo-1H-pyrazolo[4,3-b]pyridine (50 mg, 0.204 mmol), (R)-4-(chloromethyl)-2,2-dimethyl-1,3-dioxolane (30.7 mg, 0.204 mmol), and cesium carbonate (133 mg, 0.408 mmol) in DMF (1.0 mL) was heated in a microwave at 80° C. for 15 minutes. Additional (R)-4-(chloromethyl)-2,2-dimethyl-1,3-dioxolane (61.4 mg, 0.204 mmol) and cesium carbonate (67 mg) was added the reaction was heated in microwave at 80° C. for 2 hour. Additional (R)-4-(chloromethyl)-2,2-dimethyl-1,3-dioxolane (30.7 mg, 0.204 mmol), tetrabutylammonium iodide (301 mg, 0.816 mmol) and cesium carbonate (133 mg, 0.408 mmol) was added and the reaction was heated in microwave at 80° C. for 60 minutes, then the reaction was transferred to an oil bath and heating was continued overnight at 75° C. The reaction was cooled and poured into water (10 mL) and extracted with ethyl acetate (5 mL). The organic layer were dried over sodium sulfate, filtered, and concentrated to give (S)-1-((2,2-dimethyl-1,3-dioxolan-4-yl)methyl)-7-iodo-1H-pyrazolo[4,3-b]pyridine MS [M+H] found 360.2.

A mixture of sodium 2-methylpropan-2-olate (37.5 mg, 0.390 mmol), (S)-1-((2,2-dimethyl-1,3-dioxolan-4-yl)methyl)-7-iodo-1H-pyrazolo[4,3-b]pyridine (50 mg, 0.139 mmol), 2-(5-chloro-2-fluorophenyl)pyridin-4-amine (31.0 mg, 0.139 mmol), palladium(II) acetate (3.13 mg, 0.014 mmol), and 2,2'-bis(diphenylphosphino)-1,1'-binaphthyl (37.4 mg, 0.060 mmol) in dioxane (1547 μL) was heated in a microwave at 110° C. for 1 hour. The crude reaction mixture was filtered, concentrated under vacuum, reconstituted in a DMF, and purified using preparative HPLC using a Sunfire Prep 5 μm C18, 75×30 mm column eluted using a gradient of 15-35% acetonitrile (containing 0.035% TFA in water (containing 0.05% TFA) to give (R)-3-(7-(2-(5-chloro-2-fluorophenyl)pyridin-4-ylamino)-2H-pyrazolo[4,3-b]pyridin-2-yl)propane-1,2-diol as a TFA salt. MS [M+H] found 454.3.

(R)-3-(7-(2-(5-chloro-2-fluorophenyl)pyridin-4-ylamino)-2H-pyrazolo[4,3-b]pyridin-2-yl)propane-1,2-diol as a TFA salt was dissolved in 600 ml a 1:1 mix of THF and water then added 5 μL of TFA and stir for 2 hours at room temperature, then concentrate to obtain a residue. The residue in was dissolved in DMSO and purified by preparative HPLC using a Sunfire Prep 5 μm C18, 75×30 mm column eluting with a gradient of 10-30% acetonitrile (containing 0.035% TFA) in water (containing 0.05% TFA) to give the title compound as its TFA salt. $^1$H NMR (400 MHz, DMSO-d6) δ ppm 3.38-3.43 (2H, m) 3.99-4.07 (1H, m) 4.41-4.52 (2H, m) 4.70 (2H, dd, J=13.52, 3.41 Hz) 7.26 (1H, d, J=6.57 Hz) 7.45 (1H, dd, J=10.86, 8.84 Hz) 7.57-7.64 (2H, m) 7.98 (1H, s) 8.02 (1H, dd, J=6.57, 2.78 Hz) 8.53 (1H, d, J=6.57 Hz) 8.72 (1H, s) 8.73-8.81 (1H, m) 11.35 (1H, s). MS [M+H] found 414.3.

Example 47

(S)-3-(7-(2-(5-chloro-2-fluorophenyl)pyridin-4-ylamino)-2H-pyrazolo[4,3-b]pyridin-2-yl)propane-1,2-diol

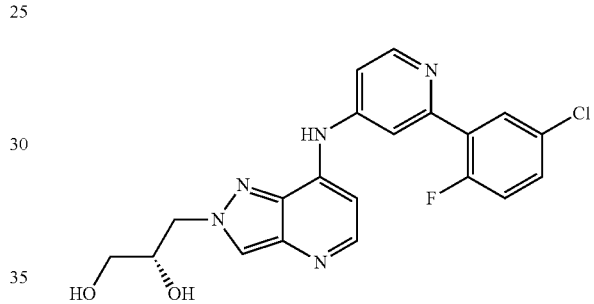

7-Iodo-1H-pyrazolo[4,3-b]pyridine (50 mg, 0.204 mmol), (S)-4-(chloromethyl)-2,2-dimethyl-1,3-dioxolane (30.7 mg, 0.204 mmol), and cesium carbonate (133 mg, 0.408 mmol) in DMF (1.0 mL) were heated in a microwave at 80° C. for 15 minutes. Additional (S)-4-(chloromethyl)-2,2-dimethyl-1,3-dioxolane (30.7 mg, 0.204 mmol) and heat in microwave for 1 hour at 80° C. Additional (S)-4-(chloromethyl)-2,2-dimethyl-1,3-dioxolane (61.4 mg, 0.204 mmol) and cesium carbonate (67 mg) was added the reaction was heated in microwave at 80° C. for 2 hour. Then tetrabutylammonium iodide (75 mg, 0.204 mmol), (S)-4-(chloromethyl)-2,2-dimethyl-1,3-dioxolane (30.7 mg, 0.204 mmol) and cesium carbonate (65 mg) were added and the reaction mixture was heated in microwave at 80° C. for 15 minutes followed by yet another addition of tetrabutylammonium iodide (230 mg), (S)-4-(chloromethyl)-2,2-dimethyl-1,3-dioxolane (30.7 mg, 0.204 mmol) and cesium carbonate (65 mg) and the mixture was heated at 70° C. (oil bath) for 48 hours. The reaction was then cooled, poured into water (10 ml) and extracted with ethyl acetate (5 mL). The organic layer was separated, dried over sodium sulfate, filtered. and concentrated under vacuum to give (R)-1-((2,2-dimethyl-1,3-dioxolan-4-yl)methyl)-7-iodo-1H-pyrazolo[4,3-b]pyridine. MS [M+H] found 360.2.

A mixture of sodium 2-methylpropan-2-olate (37.5 mg, 0.390 mmol), (R)-1-((2,2-dimethyl-1,3-dioxolan-4-yl)methyl)-7-iodo-1H-pyrazolo[4,3-b]pyridine (50 mg, 0.139 mmol), 2-(5-chloro-2-fluorophenyl)pyridin-4-amine (31.0 mg, 0.139 mmol), palladium(II) acetate (3.13 mg, 0.014 mmol), and 2,2'-bis(diphenylphosphino)-1,1'-binaphthyl (37.4 mg, 0.060 mmol) in dioxane (1547 μl) were heated in a microwave at 110° C. for 1 hour. The reaction mixture was filtered, concentrated, and then dissolved in DMF before being purified by preparative HPLC using a Sunfire Prep 5 μm C18, 75×30 mm column eluted using a gradient of 15-35% acetonitrile (containing 0.035% TFA in water (containing 0.05% TFA) to give (S)-3-(7-(2-(5-chloro-2-fluorophenyl) pyridin-4-ylamino)-2H-pyrazolo[4,3-b]pyridin-2-yl)propane-1,2-diol as a TFA salt. MS [M+H] found 454.4.

(S)-3-(7-(2-(5-Chloro-2-fluorophenyl)pyridin-4-ylamino)-2H-pyrazolo[4,3-b]pyridin-2-yl)propane-1,2-diol TFA salt was dissolved in 600 ml a 1:1 mix of THF and water then added 5 μL of TFA and the reaction mixture was stirred for 2 hours at room temperature before being concentrated to give a residue. The residue was dissolved in DMSO and purified by preparative HPLC using a Sunfire Prep 5 μm C18, 75×30 mm column eluting with a gradient of 10-25% acetonitrile (containing 0.035% TFA) in water (containing 0.05% TFA) to give the title compound as a TFA salt. $^1$H NMR (400 MHz, DMSO-d6) δ ppm 3.38-3.55 (2H, m) 3.98-4.08 (1H, m) 4.39-4.52 (2H, m) 4.66-4.76 (2H, m) 7.26 (1H, d, J=6.57 Hz) 7.46 (1H, dd, J=10.74, 8.72 Hz) 7.57-7.66 (2H, m) 7.96-8.00 (1H, m) 8.02 (1H, dd, J=6.57, 2.78 Hz) 8.49-8.58 (1H, m) 8.72 (1H, s) 8.73-8.82 (1H, m) 11.34 (1H, s). MS [M+H] found 414.3.

Example 48

N-(2-(3-chlorophenyl)pyridin-4-yl)-2-methyl-2H-pyrazolo[4,3-b]pyridin-7-amine

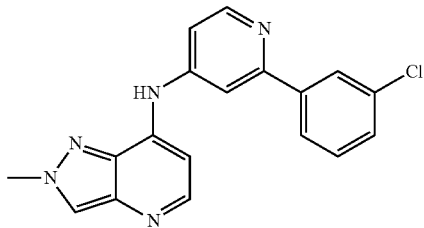 [SMILES: Cn1cc2nccc(Nc3ccnc(-c4cccc(Cl)c4)c3)c2n1]

To a solution of 2-methylpyridin-4-amine (10.2 g, 94 mmol) and nitric acid (56.5 ml, 1273 mmol) in water (75 mL) was added a solution of sodium nitrite (9.44 g, 137 mmol) in water (38 mL) at 0° C. with vigorous stirring over 25 minutes. The reaction was then stirred at 0° C. for 30 minutes and stored in refrigerator set at −17° C. overnight. The reaction mixture was filtered and the solids dried under vacuum to give 2-methylpyridin-4-ol (6.5 g, 59.6 mmol, 63.2% yield) as beige solid. $^1$H NMR (400 MHz, DMSO-d$_6$) δ ppm 2.53-2.60 (m, 3H) 7.01-7.17 (m, 2H) 8.36-8.49 (m, 1H). MS [M+H] found 110.1.

To a solution of fuming nitric acid (14.51 mL, 345 mmol), and sulfuric acid (14.45 ml, 271 mmol) was added 2-methylpyridin-4-ol (6.5 g, 59.6 mmol) portion wise at 25° C. and then stirred in oil bat set at 130° C. for 2 hours. The reaction was cooled to room temperature, poured over ice and the pH was adjusted to ~7 using sodium carbonate. The mixture was cooled and a yellow precipitate formed which was then filtered and dried under vacuum for 2 hours in a rotovap set at 60° C. The solids were then slurried in methanol (100 mL) and sonicated 2×. The suspension was filtered and the solids discarded and the filtrate was concentrated under vacuum to give 2-methyl-3-nitropyridin-4-ol. $^1$H NMR (400 MHz, DMSO-d$_6$) δ ppm 2.28 (3H, br. s.) 6.18-6.42 (1H, m) 7.71 (1H, d, J=7.58 Hz) 12.09 (1H, br. s.); MS [M+H] found 155.0.

A mixture of 2-methyl-3-nitropyridin-4-ol (2 g, 12.98 mmol) and phosphorus oxybromide (24.93 g, 87 mmol) was melted at 140° C. in a pressure vessel over 3 hours. The reaction mixture was cooled, poured into chloroform (100 mL) and ice water (100 mL). The layers were separated and the organic layer was washed with water (2×25 mL), saturated sodium bicarbonate (2×75 mL), dried over magnesium sulfate, filtered, and concentrated to give an oil. The oil was treated with a mixture of dichloromethane and chloroform (50 mL, 3:1) to give a solid which was filtered and dried under vacuum. The filtrate was reduced in volume by 50% under vacuum, loaded on a silica column and eluted with 2% methanol in dichloromethane to give additional product which was concentrated and combined with the initial batch to give 4-bromo-2-methyl-3-nitropyridine (1.4 g, 6.45 mmol, 49.7% yield); MS [M+H] found 217.0. $^1$H NMR (400 MHz, DMSO-d$_6$) δ ppm 2.53 (s, 3H) 7.88 (dd, J=5.31, 0.51 Hz, 1H) 8.52-8.59 (m, 1H).

4-Bromo-2-methyl-3-nitropyridine (1.2 g, 5.53 mmol) was dissolved in HCl (2.189 ml, 26.3 mmol), tin(II)chloride dihydrate (4.99 g, 22.12 mmol) was added and stirred at 40° C. for 1 hour. The reaction mixture was made basic with 30% NaOH (18 mL), extracted with EtOAc, dried over sodium sulfate and concentrated under vacuum to give a yellow oil. The oil was further dried under high vacuum for 4 hours to give 4-bromo-2-methylpyridin-3-amine (1 g, 5.35 mmol, 97% yield) which was stored at −17° C. until use and was used without further purification. $^1$H NMR (400 MHz, DMSO-d$_6$) δ ppm 2.26-2.42 (3H, m) 5.05-5.34 (2H, m) 7.17-7.32 (1H, m) 7.46-7.64 (1H, m). MS [M+H] found 187.0.

4-Bromo-2-methylpyridin-3-amine (1 g, 5.35 mmol) was combined with acetic anhydride (2.125 mL, 22.5 mmol), DMAP (69 mg) and heated at 60° C. overnight. The reaction was then cooled, diluted with dichloromethane and then washed with saturated sodium bicarbonate (6 mL). The organic layer was dried over magnesium sulfate and concentrated under vacuum to afford an oil. The oil was purified on silica column chromatography eluted with 98:2 chloroform/methanol to give the desired product N-acetyl-N-(4-bromo-2-methylpyridin-3-yl)acetamide (1 g) (containing 5% starting material by NMR) which was used without further purification. $^1$H NMR (400 MHz, DMSO-d$_6$) δ ppm 2.21-2.27 (m, 6H) 2.36-2.41 (m, 3H) 7.69-7.82 (m, 1H) 8.30-8.42 (m, 1H). MS [M+H] found 271.0.

To a solution of N-acetyl-N-(4-bromo-2-methylpyridin-3-yl)acetamide (0.95 g, 3.50 mmol) in methanol (14.02 mL) was added 1M NaOH (0.876 ml, 0.876 mmol) and the reaction was stirred at room temperature for 30 minutes. The reaction mixture was neutralized with 1N HCl (400 uL) and then concentrated under vacuum to give a residue that was purified on silica column chromatography eluting with (chloroform:methanol, 97:3) Concentration of the product fractions gave N-(4-bromo-2-methylpyridin-3-yl)acetamide (0.7 g, 3.06 mmol, 87% yield) as a white solid. $^1$H NMR (400 MHz, DMSO-d$_6$) δ ppm 2.04-2.10 (m, 3H) 2.39 (s, 3H) 7.49-7.60 (m, 1H) 8.12-8.26 (m, 1H) 9.65-9.83 (m, 1H). MS [M+H] found 229.1.

To a solution of N-(4-bromo-2-methylpyridin-3-yl)acetamide (0.6 g, 2.62 mmol) in toluene (26.2 ml) was added potassium acetate (0.308 g, 3.14 mmol) and acetic anhydride (0.743 ml, 7.86 mmol). The mixture was stirred for 15 minutes and isopentyl nitrite (0.806 ml, 6.02 mmol) was added and the reaction was heated at 85° C. for 4 hours. The reaction was cooled and partitioned between ethyl acetate (75 mL) and water (75 mL). The organic layer was separated, dried over MgSO₄, and concentrated to a brown oil. The oil was purified on silica column chromatography eluted with methanol:dichloromethane (3:97). Concentration of product fractions afforded 7-bromo-1H-pyrazolo[4,3-b]pyridine (90 mg, 0.454 mmol, 17.35% yield) as an amber solid. ¹H NMR (400 MHz, DMSO-d₆) δ ppm 7.71 (1H, d, J=4.80 Hz) 8.32-8.40 (1H, m) 8.40-8.51 (1H, m) 13.89 (1H, br. s.). MS [M+H] found 197.9.

A solution of 7-bromo-1H-pyrazolo[4,3-b]pyridine (100 mg, 0.505 mmol) and sodium hydride (24.24 mg, 0.606 mmol) in THF (2.0 mL) was stirred at 0° C. for 15 minutes. Iodomethane (71.7 mg, 0.505 mmol) was added, and the reaction was warmed to room temperature for 1 hour. The reaction was quenched with water, extracted with EtOAc, dried over MgSO₄, and evaporated to dryness to give 7-bromo-2-methyl-2H-pyrazolo[4,3-b]pyridine which was used without further purification.

7-Bromo-2-methyl-2H-pyrazolo[4,3-b]pyridine sodium 2-methylpropan-2-olate (63.5 mg, 0.660 mmol), 2-(3-chlorophenyl)pyridin-4-amine (48.3 mg, 0.236 mmol), palladium (II) acetate (5.29 mg, 0.024 mmol), and (R)-BINAP (63.3 mg, 0.102 mmol) were combined in dioxane (2.0 mL) and heated in a microwave 110° C. for 1 hour. The reaction mixture was cooled and purified via preparative mass trigger LCMS using a Phenomenex Gemini C18, 5 μm, ID30×75 mm eluting with a gradient of 10-25% acetonitrile (containing 0.035% TFA) in water (containing 0.05% TFA) to give the title compound as a TFA salt. ¹H NMR (400 MHz, DMSO-d6) δ ppm 4.33 (s, 3H) 7.29 (d, J=6.57 Hz, 1H) 7.53-7.60 (m, 3H) 7.98-8.09 (m, 1H) 8.12 (s, 2H) 8.52 (d, J=6.82 Hz, 1H) 8.72 (d, J=5.56 Hz, 1H) 8.79 (s, 1H) 11.27 (br. s., 1H). MS [M+H] found 336.2.

Example 49

N-(2-(5-chloro-2-fluorophenyl)-5-methylpyridin-4-yl)-1H-pyrazolo[4,3-b]pyridin-7-amine

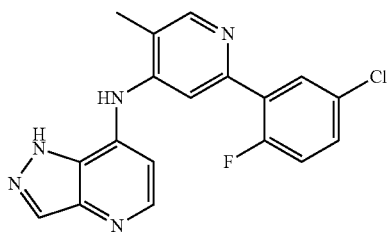 [SMILES: Cc1cnc(-c2cc(Cl)ccc2F)cc1Nc1ccnc2cn[nH]c12]

7-Iodo-1H-pyrazolo[4,3-b]pyridine (0.75 g, 3.06 mmol) and sodium hydride were combined in DMF (30.6 mL) (0.147 g, 3.67 mmol) and stirred for 10 minutes then cooled to 0° C. 1-(Chloromethyl)-4-methoxybenzene (0.438 ml, 3.21 mmol) was added and the reaction was stirred at 0° C. for 15 minutes and then warmed to room temperature over 2 hours. Ice water (200 mL) and saturated ammonium chloride solution (50 mL) was added and the mixture was extracted with ethyl acetate (75 mL×2). The organics were combined, dried over sodium sulfate, and concentrated to dark oil. The oil was dissolved in a mixture of ethyl acetate, methanol and dichloromethane and loaded onto a silica chromatography column which was eluted using 40% ethyl acetate in hexanes to give 7-iodo-1-(4-methoxybenzyl)-1H-pyrazolo[4,3-b]pyridine and 7-iodo-2-(4-methoxybenzyl)-2H-pyrazolo[4,3-b]pyridine as a dark yellow film (1 g) which was used immediately. MS [M+H] found 366.2.

(R)-BINAP (0.735 g, 1.180 mmol), diacetoxypalladium (0.061 g, 0.274 mmol) and toluene (8 mL) were combined and stirred at 40° C. for 10 minutes. The reaction was removed from heat and 2-(5-chloro-2-fluorophenyl)-5-methylpyridin-4-amine (0.648 g, 2.74 mmol) and sodium 2-methylpropan-2-olate (0.395 g, 4.11 mmol) were added along with the material from the previous step (1 g, 2.74 mmol) suspended in toluene (12 mL). The reaction mixture was then sparged with nitrogen and heated at 100° C. over night. The reaction mixture was cooled to room temperature and purified on silica column chromatography eluting with a step gradient of Hexanes/EtOAc (0-50% over 85 minutes) to afford N-(2-(5-chloro-2-fluorophenyl)-5-methylpyridin-4-yl)-1-(4-methoxybenzyl)-1H-pyrazolo[4,3-b]pyridin-7-amine and N-(2-(5-chloro-2-fluorophenyl)-5-methylpyridin-4-yl)-2-(4-methoxybenzyl)-2H-pyrazolo[4,3-b]pyridin-7-amine (0.6 g, 46%) as a 30:70 mixture. MS [M+H] found 474.3.

To the flask containing N-(2-(5-chloro-2-fluorophenyl)-5-methylpyridin-4-yl)-1-(4-methoxybenzyl)-1H-pyrazolo[4,3-b]pyridin-7-amine and N-(2-(5-chloro-2-fluorophenyl)-5-methylpyridin-4-yl)-2-(4-methoxybenzyl)-2H-pyrazolo[4,3-b]pyridin-7-amine (0.561, 1.184) was added TFA (5.9 mL) and the mixture was stirred at 70° C. for 3 hours. The reaction was cooled to room temperature and concentrated under vacuum to a dark amber residue. To this residue was combined with dichloromethane (25 mL) and saturated sodium carbonate solution (25 mL) resulting in a precipitate which was filtered, rinsed with dichloromethane and water and dissolved in EtOAc, then extracted with water and saturated sodium bicarbonate The organic layer was separated, dried over sodium sulfate, and concentrated to give a yellow solid that was purified by preparative HPLC using a Sunfire Prep 5 μm C18, 75×30 mm column eluting with a gradient of 18-25% acetonitrile (containing 0.035% TFA) in water (containing 0.05% TFA) to give the title compound as a TFA salt. ¹H NMR (400 MHz, DMSO-d6) δ ppm 2.30-2.40 (m, 3H) 7.42 (dd, J=10.86, 8.84 Hz, 1H) 7.53-7.67 (m, 1H) 7.79 (br. s., 1H) 7.94-8.04 (m, 1H) 8.46 (d, J=5.81 Hz, 1H) 8.76 (s, 1H). MS [M+H] found 354.2.

Example 50 and 51

2-(7-(2-(5-chloro-2-fluorophenyl)-5-methylpyridin-4-ylamino)-2H-pyrazolo[4,3-b]pyridin-2-yl)acetamide and 2-(7-(2-(5-chloro-2-fluorophenyl)-5-methylpyridin-4-ylamino)-1H-pyrazolo[4,3-b]pyridin-1-yl)acetamide

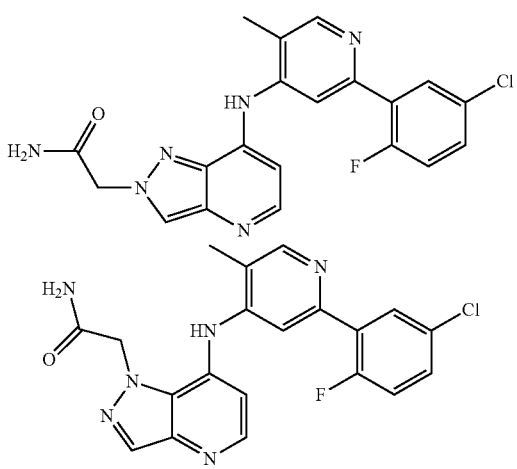

N-(2-(5-Chloro-2-fluorophenyl)-5-methylpyridin-4-yl)-1H-pyrazolo[4,3-b]pyridin-7-amine (50 mg, 0.141 mmol), 2-chloroacetamide (13.22 mg, 0.141 mmol) and cesium carbonate (92 mg, 0.283 mmol) were combined in DMF (707 μl) and heated in a microwave for 15 minutes at 80° C. The reaction mixture is cooled, filtered, and purified by preparative HPLC using a Sunfire Prep 5 μm C18, 75×30 mm column eluting with a gradient of 18-25% acetonitrile (containing 0.035% TFA) in water (containing 0.05% TFA) to give the title compounds as TFA salts.

2-(7-(2-(5-chloro-2-fluorophenyl)-5-methylpyridin-4-ylamino)-2H-pyrazolo[4,3-b]pyridin-2-yl)acetamide $^1$H NMR (400 MHz, DMSO-d6) δ ppm 2.31-2.42 (3H, m) 5.28 (2H, s) 7.29 (1H, br. s.) 7.36-7.52 (2H, m) 7.58 (1H, d, J=11.62 Hz) 7.67 (1H, br. s.) 7.82-8.05 (2H, m) 8.41 (1H, d, J=6.82 Hz) 8.57 (1H, br. s.) 8.70-8.81 (1H, m) 10.12 (1H, br. s.). MS [M+H] found 411.3.

2-(7-(2-(5-chloro-2-fluorophenyl)-5-methylpyridin-4-ylamino)-1H-pyrazolo[4,3-b]pyridin-1-yl)acetamide 2-(7-(2-(5-chloro-2-fluorophenyl)-5-methylpyridin-4-ylamino)-1H-pyrazolo[4,3-b]pyridin-1-yl)acetamide $^1$H NMR (400 MHz, DMSO-d6) δ ppm 2.32 (s, 3H) 5.28 (s, 2H) 6.52 (d, J=6.57 Hz, 1H) 7.42 (dd, J=10.86, 8.84 Hz, 1H) 7.51 (s, 1H) 7.55-7.61 (m, 1H) 7.79 (s, 1H) 7.86 (s, 1H) 8.01 (dd, J=6.57, 2.78 Hz, 1H) 8.41 (d, J=6.82 Hz, 1H) 8.73 (s, 1H) 8.78 (s, 1H) 11.11 (s, 1H). MS [M+H] found 411.3.

Example 52

7-(2-(5-chloro-2-fluorophenyl)-5-methylpyridin-4-ylamino)-N-methyl-1H-pyrazolo[4,3-b]pyridine-1-carboxamide

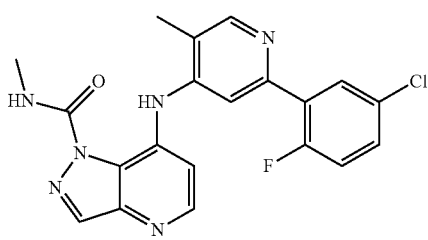 [SMILES: CNC(=O)n1ncc2nccc(Nc3cc(-c4cc(Cl)ccc4F)ncc3C)c21]

N-(2-(5-Chloro-2-fluorophenyl)-5-methylpyridin-4-yl)-1H-pyrazolo[4,3-b]pyridin-7-amine (150 mg, 0.424 mmol), pyridine (58.3 μl, 0.721 mmol) were combined dichloroethylene (2120 μl) and then methylcarbamic chloride (41.7 mg, 0.424 mmol) was added. The reaction vessel was sealed and heated at 70° C. overnight. The reaction mixture was then cooled and purified by preparative HPLC using a Sunfire Prep 5 μm C18, 75×30 mm column eluting with a gradient of 25-35% acetonitrile (containing 0.035% TFA) in water (containing 0.05% TFA) to give the title compound as a TFA salt. $^1$H NMR (400 MHz, DMSO-d6) δ ppm 2.43 (3H, s) 2.93 (3H, d, J=4.55 Hz) 7.40-7.51 (2H, m) 7.55-7.64 (1H, m) 7.94 (1H, s) 7.99 (1H, dd, J=6.82, 2.78 Hz) 8.48 (1H, d, J=5.56 Hz) 8.61 (1H, s) 8.66 (1H, s) 9.06 (1H, d, J=4.29 Hz) 11.36 (1H, br. s.). MP 135° C. MS [M+H] found 411.3.

Example 53

7-(2-(5-chloro-2-fluorophenyl)-5-methylpyridin-4-ylamino)-N-ethyl-1H-pyrazolo[4,3-b]pyridine-1-carboxamide

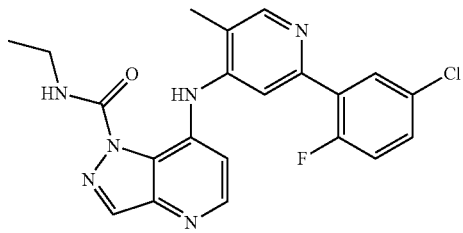 [SMILES: CCNC(=O)n1ncc2nccc(Nc3cc(-c4cc(Cl)ccc4F)ncc3C)c21]

N-(2-(5-Chloro-2-fluorophenyl)-5-methylpyridin-4-yl)-1H-pyrazolo[4,3-b]pyridin-7-amine (50 mg, 0.141 mmol) was suspended in acetonitrile (1413 μl) and isocyanatoethane (11.10 μl, 0.141 mmol) was added by syringe. The reaction was heated at 70° C. for 2 hours, then cooled and concentrated to give a residue which was dissolved in DMSO/methanol and purified by preparative HPLC using a Sunfire Prep 5 μm C18, 75×30 mm column eluting with a gradient of 30-45% acetonitrile (containing 0.035% TFA) in water (containing 0.05% TFA) to give the title compound as a TFA salt. $^1$H NMR (400 MHz, DMSO-d6) δ ppm 1.20 (t, J=7.07 Hz, 3H) 2.43 (s, 3H) 3.37-3.46 (m, 2H) 7.40-7.51 (m, 2H) 7.59 (s, 1H) 7.93 (s, 1H) 7.98 (dd, J=6.57, 2.78 Hz, 1H) 8.48 (d, J=5.56 Hz, 1H) 8.61 (s, 1H) 8.66 (s, 1H) 9.14-9.21 (m, 1H) 11.38 (s, 1H). MS [M+H] found 425.3.

Example 54

7-(2-(5-chloro-2-fluorophenyl)-5-methylpyridin-4-ylamino)-N-isopropyl-1H-pyrazolo[4,3-b]pyridine-1-carboxamide

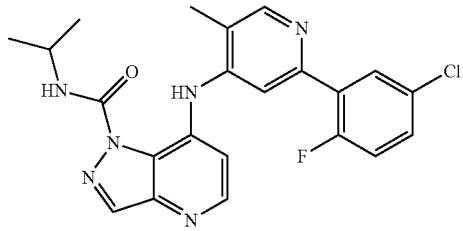 [SMILES: Cc1cnc(-c2cc(Cl)ccc2F)cc1Nc1ccnc2cnn(C(=O)NC(C)C)c12]

N-(2-(5-Chloro-2-fluorophenyl)-5-methylpyridin-4-yl)-1H-pyrazolo[4,3-b]pyridin-7-amine (50 mg, 0.141 mmol) was combined with acetonitrile (1413 μl) and then 2-isocyanatopropane (13.86 μl, 0.141 mmol) was added by syringe. The reaction was heated at 70° C. for 2 hours, then cooled and concentrated to give a residue which was dissolved in DMSO/methanol and purified by preparative HPLC using a Sunfire Prep 5 μm C18, 75×30 mm column eluting with a gradient of 18-25% acetonitrile (containing 0.035% TFA) in water (containing 0.05% TFA) to give the title compound as a TFA salt. $^1$H NMR (400 MHz, DMSO-d6) δ ppm 1.27 (d, J=6.82 Hz, 6H) 2.46 (s, 3H) 4.06-4.19 (m, 1H) 7.48 (dd, J=10.61, 8.84

Hz, 1H) 7.56 (d, J=5.56 Hz, 1H) 7.66 (ddd, J=8.84, 4.29, 2.78 Hz, 1H) 7.94 (s, 1H) 7.97 (dd, J=6.57, 2.78 Hz, 1H) 8.55 (d, J=5.56 Hz, 1H) 8.66 (s, 1H) 8.70 (s, 1H) 9.00 (d, J=8.08 Hz, 1H) 11.52-11.67 (m, 1H). MP 292° C. MS [M+H] found 439.4.

Example 55

2-(7-(2-(5-chloro-2-fluorophenyl)-5-methylpyridin-4-ylamino)-2H-pyrazolo[4,3-b]pyridin-2-yl)-2-methylpropanamide

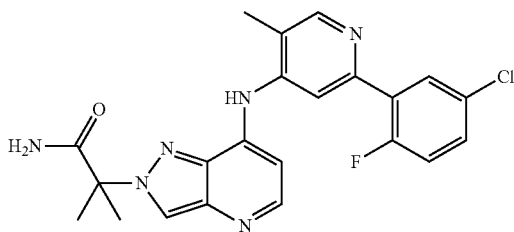 [SMILES: Cc1cnc(-c2cc(Cl)ccc2F)cc1Nc1ccnc2cn(C(C)(C)C(N)=O)nc12]

N-(2-(5-Chloro-2-fluorophenyl)-5-methylpyridin-4-yl)-1H-pyrazolo[4,3-b]pyridin-7-amine (31 mg, 0.088 mmol), 2-bromo-2-methylpropanamide (14.55 mg, 0.088 mmol) and cesium carbonate (42.8 mg, 0.131 mmol) were combined in DMF (1 mL) and heated in a microwave for 45 minutes at 80° C. Then the reaction mixture was heated in an oil bath at 50° C. over night. Then more 2-bromo-2-methylpropanamide (14.55 mg, 0.088 mmol) was added and the reaction mixture was heated in a microwave for 30 minutes at 80° C. Then the reaction was heated in an oil bath to 70° C. for 4 hours. The reaction mixture was then cooled, diluted with methanol, filtered, and purified by preparative HPLC using a Sunfire Prep 5 μm C18, 75×30 mm column eluting with a gradient of 20-30% acetonitrile (containing 0.035% TFA) in water (containing 0.05% TFA) to give the title compound as a TFA salt. ¹H NMR (400 MHz, DMSO-d6) δ ppm 1.92 (s, 6H) 2.27-2.32 (m, 3H) 6.51 (d, J=6.82 Hz, 1H) 7.13-7.28 (m, 1H) 7.30 (s, 1H) 7.39-7.47 (m, 1H) 7.55-7.61 (m, 1H) 7.85 (s, 1H) 8.02 (dd, J=6.82, 2.78 Hz, 1H) 8.39 (d, J=6.57 Hz, 1H) 8.75 (s, 1H) 8.78 (s, 1H) 11.00 (br. s., 1H). MS [M+H] found 439.4.

Example 56

N-(2-(5-chloro-2-fluorophenyl)-5-methylpyridin-4-yl)-2-(ethylsulfonyl)-2H-pyrazolo[4,3-b]pyridin-7-amine

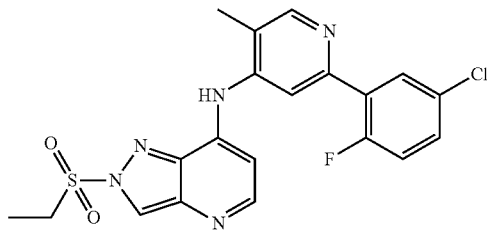 [SMILES: CCS(=O)(=O)n1cc2nccc(Nc3cc(-c4cc(Cl)ccc4F)ncc3C)c2n1]

N-(2-(5-Chloro-2-fluorophenyl)-5-methylpyridin-4-yl)-1H-pyrazolo[4,3-b]pyridin-7-amine (30 mg, 0.085 mmol) and sodium hydride (3.39 mg, 0.085 mmol) were combined in DMF (424 μl). and stirred for 10 minutes then cooled in an ice bath. Ethanesulfonyl chloride (8.08 μl, 0.085 mmol) was slowly added and the reaction was stirred in the ice bath for 30 minutes before quenching with water. The mixture was then warmed to room temperature and a minimal amount of methanol was added. The mixture was filtered and purified by preparative HPLC using a Sunfire Prep 5 μm C18, 75×30 mm column eluting with a gradient of 30-45% acetonitrile (containing 0.035% TFA) in water (containing 0.05% TFA) to afford the title compound as a TFA salt. ¹H NMR (400 MHz, DMSO-d6) δ ppm 1.01-1.11 (3H, m) 2.38-2.42 (3H, m) 3.80 (2H, q, J=7.24 Hz) 7.36-7.52 (1H, m) 7.61 (3H, br. s.) 7.85-7.97 (1H, m) 8.58 (1H, s) 8.67 (1H, br. s.) 8.94 (1H, s) 9.24 (1H, s). MS [M+H] found 446.3.

Example 57

N-(2-(5-chloro-2-fluorophenyl)-6-methylpyridin-4-yl)-1H-pyrazolo[4,3-b]pyridin-7-amine

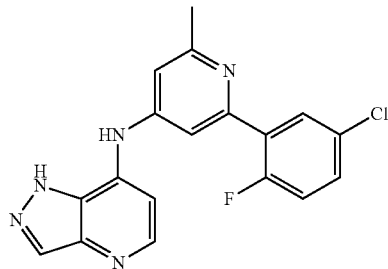 [SMILES: Cc1cc(Nc2ccnc3cn[nH]c23)cc(-c2cc(Cl)ccc2F)n1]

7-Iodo-1H-pyrazolo[4,3-b]pyridine (0.77 g, 3.14 mmol) and sodium hydride (0.151 g, 3.77 mmol) were combined in DMF (31.4 ml) and stirred for 10 minutes and cooled to 0° C. 1-(Chloromethyl)-4-methoxybenzene (0.449 ml, 3.30 mmol) was added and the reaction was allowed to stir at room temperature for 1 hour. The reaction mixture was poured into ice water (200 mL) containing saturated ammonium chloride (50 mL) and extracted with ethyl acetate (2×50 mL). The organics were separated and dried over sodium sulfate, filtered, and absorbed onto silica gel. Column chromatography with hexanes/ethyl acetate (0-50%) gave the products 7-iodo-1-(4-methoxybenzyl)-1H-pyrazolo[4,3-b]pyridine and 7-iodo-2-(4-methoxybenzyl)-2H-pyrazolo[4,3-b]pyridine as a 6:4 mixture of isomers (0.9 g, 78%). MS [M+H] found 366.1.

(R)-BINAP (0.632 g, 1.015 mmol), diacetoxypalladium (0.053 g, 0.236 mmol) and toluene (10 mL) were combined and heated at 40° C. for 10 minutes. The reaction was removed from heat and 7-iodo-1-(4-methoxybenzyl)-1H-pyrazolo[4,3-b]pyridine and 7-iodo-2-(4-methoxybenzyl)-2H-pyrazolo[4,3-b]pyridine as a 6:4 mixture of isomers (0.86 g, 2.355 mmol) suspended in toluene (15 mL), 2-(5-chloro-2-fluorophenyl)-6-methylpyridin-4-amine (0.557 g, 2.355 mmol), and sodium 2-methylpropan-2-olate (0.339 g, 3.53 mmol) were added. The reaction was sparged with nitrogen and heated at 100° C. over night. The reaction was cooled to room temperature and methanol (5 mL) was added. This solution was absorbed onto silica gel and chromatographed on silica gel eluting with a step gradient of ethyl acetate: hexanes (35-100%) to afford N-(2-(5-chloro-2-fluorophenyl)-6-methylpyridin-4-yl)-2-(4-methoxybenzyl)-2H-pyrazolo[4,3-b]pyridin-7-amine and N-(2-(5-chloro-2-fluorophenyl)-6-methylpyridin-4-yl)-1-(4-methoxybenzyl)-1H-pyrazolo[4,3-b]pyridin-7-amine as an orange foam (0.89 g, 79%). MS [M+H] found 474.4.

To N-(2-(5-chloro-2-fluorophenyl)-6-methylpyridin-4-yl)-2-(4-methoxybenzyl)-2H-pyrazolo[4,3-b]pyridin-7-amine and N-(2-(5-chloro-2-fluorophenyl)-6-methylpyridin-4-yl)-1-(4-methoxybenzyl)-1H-pyrazolo[4,3-b]pyridin-7-amine (0.89 g, 1.88 mmole) was added TFA (9.38 mL) and the mixture was stirred at 70° C. for 4 hours. The reaction was cooled to room temperature and concentrated to a dark amber residue. The residue was combined with dichloromethane (25 mL) followed by a saturated solution of Na₂CO₃ (25 mL) to give a solid. The solid was filtered, rinsed with dichloromethane and then water and then dissolved in ethyl acetate (600 mL), extracted with water and then saturated Na₂CO₃. The organic layer was separated, dried over sodium sulfate, and concentrated to give the title compound as a light yellow solid (0.46 g, 69%). A portion of this material (0.04 g) was purified with preparative using a Sunfire Prep 5 μm C18, 75×30 mm column HPLC eluting with a gradient of 15-25% acetonitrile (containing 0.035% TFA) in water (containing 0.05% TFA) to provide the title compound as a TFA salt. $^1$H NMR (400 MHz, DMSO-d6) δ ppm 2.62 (s, 3H) 7.45-7.53 (m, 2H) 7.64 (br. s., 2H) 8.00 (d, J=4.04 Hz, 2H) 8.56 (d, J=6.06 Hz, 2H). MS [M+H] found 354.2.

Example 58

7-(2-(5-chloro-2-fluorophenyl)-6-methylpyridin-4-ylamino)-N-methyl-1H-pyrazolo[4,3-b]pyridine-1-carboxamide

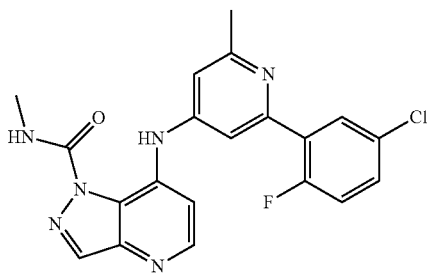 [SMILES: CNC(=O)n1ncc2nccc(Nc3cc(C)nc(-c4cc(Cl)ccc4F)c3)c21]

N-(2-(5-Chloro-2-fluorophenyl)-6-methylpyridin-4-yl)-1H-pyrazolo[4,3-b]pyridin-7-amine (150 mg, 0.424 mmol), pyridine (58.3 μl, 0.721 mmol) were combined in dichloroethylene (2120 μl) in a dried vessel and then methylcarbamic chloride (41.7 mg, 0.424 mmol) was added and the reaction was heated at 70° C. for 1 h and then at 60° C. over night. The reaction mixture was cooled to give a solid which was collected by filtration, dissolved in a warm mixture of ethanol and DMSO (1:1; about 5 mL) and purified via preparative mass trigger LCMS using a Sunfire Prep 5 μm C18, 75×30 mm column eluted with a gradient of 25-35% acetonitrile (containing 0.035% TFA) in water (containing 0.05% TFA) to give the title compound as a TFA salt. $^1$H NMR (400 MHz, DMSO-d6) δ ppm 2.58-2.68 (3H, m) 2.87-2.96 (3H, m) 7.44-7.58 (2H, m) 7.62 (0H, s) 7.67-7.78 (2H, m) 7.98 (1H, dd, J=6.32, 2.78 Hz) 8.60 (1H, d, J=5.56 Hz) 8.66-8.76 (1H, m) 9.08 (1H, d, J=4.55 Hz) 11.94 (1H, s). MP 248° C. MS [M+H] found 411.3.

Example 59

7-(2-(5-chloro-2-fluorophenyl)-6-methylpyridin-4-ylamino)-N-ethyl-1H-pyrazolo[4,3-b]pyridine-1-carboxamide

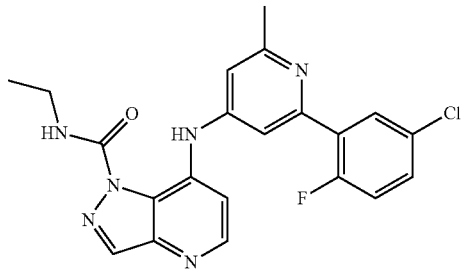 [SMILES: CCNC(=O)n1ncc2nccc(Nc3cc(C)nc(-c4cc(Cl)ccc4F)c3)c21]

N-(2-(5-Chloro-2-fluorophenyl)-6-methylpyridin-4-yl)-1H-pyrazolo[4,3-b]pyridin-7-amine (46 mg, 0.130 mmol) was combined with acetonitrile (1300 μl) and then isocyanatoethane (10.21 μl, 0.130 mmol) was added by syringe. The reaction was stirred at 70° C. for 3 hours, then cooled and concentrated to give a residue which was dissolved in DMSO and purified via preparative mass trigger LCMS using a gradient of 30-40% acetonitrile (containing 0.035% TFA) in water (containing 0.05% TFA) using a Sunfire Prep 5 μm C18, 75×30 mm column to give the TFA salt of the title compound as a yellow solid. $^1$H NMR (400 MHz, DMSO-d6) δ ppm 1.10-1.25 (3H, m) 2.59-2.69 (3H, m) 3.34-3.47 (2H, m) 7.46-7.57 (2H, m) 7.61 (1H, s) 7.65-7.80 (2H, m) 7.98 (1H, dd, J=6.57, 2.78 Hz) 8.60 (1H, d, J=5.31 Hz) 8.71 (1H, s) 9.18 (1H, t, J=5.81 Hz) 11.89 (1H, s). MP 245° C. MS [M+H] found 425.3.

Example 60A and 60B 2-(7-(2-(5-chloro-2-fluorophenyl)-6-methylpyridin-4-ylamino)-1H-pyrazolo[4,3-b]pyridin-1-yl)acetamide and 2-(7-(2-(5-chloro-2-fluorophenyl)-6-methylpyridin-4-ylamino)-2H-pyrazolo[4,3-b]pyridin-2-yl)acetamide

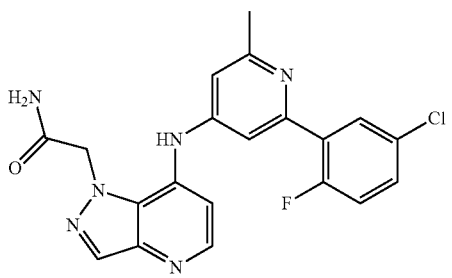

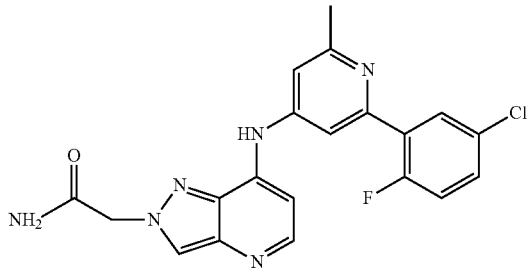

N-(2-(5-Chloro-2-fluorophenyl)-6-methylpyridin-4-yl)-1H-pyrazolo[4,3-b]pyridin-7-amine (103.5 mg, 0.293 mmol), 2-chloroacetamide (27.4 mg, 0.293 mmol) and cesium carbonate (143 mg, 0.439 mmol) were combined in DMF (1463 μl) and heated in a microwave for 45 minutes at 80° C. The reaction was then cooled, filtered, and purified by preparative HPLC eluting with a gradient of 15-15% acetonitrile (containing 0.035% TFA) in water (containing 0.05% TFA) using a Sunfire Prep 5 μm C18, 75×30 mm column to give the title compounds as a 7:3 mixture (judged by NMR) as TFA salts. MS [M+H] found 411.3.

Example 61

N-(2-(5-chloro-2-fluorophenyl)-6-methylpyridin-4-yl)-2-(ethylsulfonyl)-2H-pyrazolo[4,3-b]pyridin-7-amine

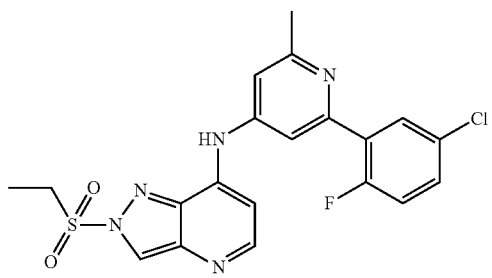 [SMILES: CCS(=O)(=O)n1cc2nccc(Nc3cc(C)nc(-c4cc(Cl)ccc4F)c3)c2n1]

N-(2-(5-Chloro-2-fluorophenyl)-6-methylpyridin-4-yl)-1H-pyrazolo[4,3-b]pyridin-7-amine (100 mg, 0.283 mmol) and sodium hydride (11.31 mg, 0.283 mmol) were combined in DMF (1413 μl). After stirring for 10 minutes the reaction mixture was cooled in an ice bath. Ethanesulfonyl chloride (26.9 μl, 0.283 mmol) was slowly added and the mixture was stirred in the ice bath for 30 minutes and then warmed to room temperature. Methanol (0.5 mL) was added and the reaction mixture was filtered and the filtrate was purified by preparative HPLC eluting with a gradient of 25-28% acetonitrile (containing 0.035% TFA) in water (containing 0.05% TFA) using a Sunfire Prep 5 μm C18, 75×30 mm column conditions to give the title compound as a TFA salt. $^1$H NMR (400 MHz, DMSO-d6) δ ppm 0.94-1.12 (m, 3H) 2.57 (s, 3H) 3.71 (q, J=7.33 Hz, 2H) 7.02-7.17 (m, 1H) 7.17-7.47 (m, 1H) 7.47-7.65 (m, 1H) 7.69-7.81 (m, 2H) 7.81-8.01 (m, 1H) 8.79-8.89 (m, 1H) 8.98 (s, 1H). MS [M+H] found 446.3

Example 62

7-(2-(5-chloro-2,4-difluorophenyl)pyridin-4-ylamino)-N-ethyl-1H-pyrazolo[4,3-b]pyridine-1-carboxamide

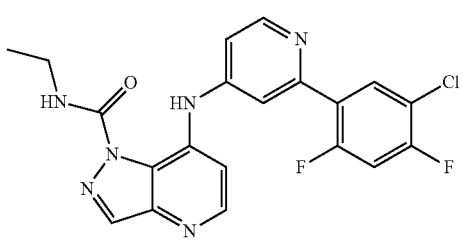 [SMILES: CCNC(=O)n1ncc2nccc(Nc3ccnc(-c4cc(Cl)c(F)cc4F)c3)c21]

The title compound was prepared by methodology similar to Example 14 except using 2-(5-chloro-2,4-difluorophenyl)pyridin-4-amine. $^1$H NMR (400 MHz, CHLOROFORM-d) δ ppm 1.27 (t, J=7.33 Hz, 3H) 3.42-3.55 (m, 2H) 6.96 (dd, J=10.61, 8.59 Hz, 1H) 7.15 (dd, J=5.56, 2.02 Hz, 1H) 7.32 (d, J=5.31 Hz, 1H) 7.49 (br. s., 1H) 7.62 (s, 1H) 8.07 (t, J=8.21 Hz, 1H) 8.18 (s, 1H) 8.38 (d, J=5.31 Hz, 1H) 8.52 (d, J=5.56 Hz, 1H) 11.27 (s, 1H). MS [M+H] found 428.0.

Example 63

7-(2-(5-chloro-2,4-difluorophenyl)pyridin-4-ylamino)-N-methyl-1H-pyrazolo[4,3-b]pyridine-1-carboxamide

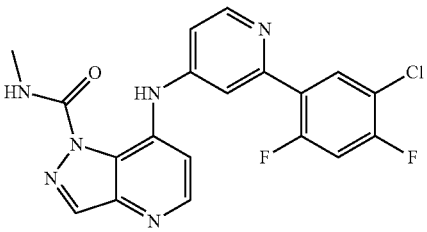 [SMILES: CNC(=O)n1ncc2nccc(Nc3ccnc(-c4cc(Cl)c(F)cc4F)c3)c21]

The title compound as a TFA salt was prepared by methodology similar to Example 23 and 24 except using 2-(5-chloro-2,4-difluorophenyl)pyridin-4-amine. MS [M+H] found 415.3.

Example 64

N-(3'-fluoro-6'-methyl-2,2'-bipyridin-4-yl)-2H-pyrazolo[4,3-b]pyridin-7-amine

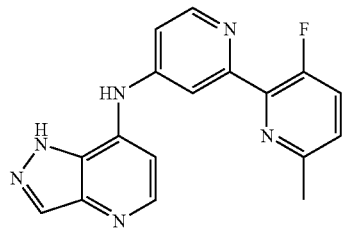 [SMILES: Cc1ccc(F)c(-c2cc(Nc3ccnc4cn[nH]c34)ccn2)n1]

7-Iodo-2H-pyrazolo[4,3-b]pyridine (1 g, 4.08 mmol) and sodium hydride (0.196 g, 8.16 mmol) were combined in DMF (15 mL) at room temperature. The mixture was stirred at room temperature for 10 minutes and 1-(chloromethyl)-4-methoxybenzene (0.554 ml, 4.08 mmol) was added. The mixture was stirred at room temperature for 1 hour the quenched with ice water and purified by preparative HPLC using a Phenomenex Gemini Prep 5 μm C18, 75×30 mm column eluting with a gradient of 20-90% 10 mmol NH$_4$HCO$_3$ in 20/80 (v/v) water/acetonitrile in 10 mmol NH$_4$HCO$_3$ in water to give the 7-iodo-2-(4-methoxybenzyl)-2H-pyrazolo[4,3-b]pyridine (300 mg, 20.1% yield) as a white powder. MS [M+H] found 366.1.

7-Iodo-2-(4-methoxybenzyl)-2H-pyrazolo[4,3-b]pyridine (198 mg, 0.541 mmol), Tris(dibenzylideneacetone)dipalladium(0) (12.39 mg, 0.014 mmol), (9,9-dimethyl-9H-xanthene-4,5-diyl)bis(diphenylphosphine) (78 mg, 0.135 mmol), 3'-fluoro-6'-methyl-2,2'-bipyridin-4-amine (110 mg, 0.541 mmol) and sodium 2-methylpropan-2-olate (156 mg, 1.624 mmol) were combined in dioxane (5 mL). The mixture was heated at 120° C. for 2 hours then cooled and purified by preparative HPLC using a Sunfire Prep 5 μm C18, 75×30 mm column eluting with a gradient of 10-50% acetonitrile (containing 0.035% TFA) in water (containing 0.05% TFA) to afford N-(3'-fluoro-6'-methyl-2,2'-bipyridin-4-yl)-2-(4-methoxybenzyl)-2H-pyrazolo[4,3-b]pyridin-7-amine (120 mg, 50.3% yield) as a yellow solid. MS [M+H] found 441.4.

N-(3'-Fluoro-6'-methyl-2,2'-bipyridin-4-yl)-2-(4-methoxybenzyl)-2H-pyrazolo[4,3-b]pyridin-7-amine (120 mg, 0.272 mmol) was dissolved in TFA (5 mL) and heated at 70° C. for 3 hours. The reaction mixture was then cooled and evaporated under vacuum to give a residue which was triturated with ether to give the title compound as a TFA salt (80 mg, 92% yield). MS [M+H] found 321.3.

Example 65 and 66

N-(3'-fluoro-6'-methyl-2,2'-bipyridin-4-yl)-1-methyl-1H-pyrazolo[4,3-b]pyridin-7-amine and N-(3'-fluoro-6'-methyl-2,2'-bipyridin-4-yl)-2-methyl-2H-pyrazolo[4,3-b]pyridin-7-amine

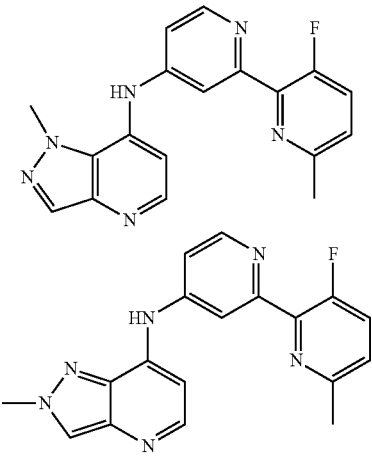

7-Iodo-2H-pyrazolo[4,3-b]pyridine (100 mg, 0.408 mmol), iodomethane (0.025 ml, 0.408 mmol) and cesium carbonate (266 mg, 0.816 mmol) were combined in DMF (5 mL). The mixture was stirred at room temperature for 1 hour then purified by preparative HPLC eluting with a gradient of 20-70% 10 mmol NH₄HCO₃ in 20/80 (v/v) water/acetonitrile in 10 mmol NH₄HCO₃ in water using a Phenomenex Gemini Prep 5 μm C18, 75×30 mm column to give 7-iodo-2-methyl-2H-pyrazolo[4,3-b]pyridine (15 mg, 14.19% yield) and 7-iodo-1-methyl-1H-pyrazolo[4,3-b]pyridine (30 mg, 28.4% yield). MS [M+H] found 260.0. 7-Iodo-2-methyl-2H-pyrazolo[4,3-b]pyridine (15 mg, 0.058 mmol), Tris(dibenzylideneacetone)dipalladium(0) (1.326 mg, 1.448 μmol), (9,9-dimethyl-9H-xanthene-4,5-diyl)bis(diphenylphosphine) (8.38 mg, 0.014 mmol), 3'-fluoro-6'-methyl-2,2'-bipyridin-4-amine (11.77 mg, 0.058 mmol) and sodium 2-methylpropan-2-olate (16.69 mg, 0.174 mmol) were combined in dioxane (5 mL). The mixture was heated at 120° C. for 2 hours and then purified by preparative HPLC eluting with a gradient of 5-40% acetonitrile (containing 0.035% TFA) in water (containing 0.05% TFA) using a Sunfire Prep 5 μm C18, 75×30 mm column to afford the title compound as a TFA salt.

N-(3'-fluoro-6'-methyl-2,2'-bipyridin-4-yl)-2-methyl-2H-pyrazolo[4,3-b]pyridin-7-amine as a TFA salt (13 mg, 67.1% yield). ¹H NMR (400 MHz, METHANOL-d4) δ ppm 2.71 (s, 3H) 4.41 (s, 3H) 7.60-7.66 (m, 2H) 7.84 (dd, J=11.24, 8.72 Hz, 1H) 7.95 (dd, J=6.69, 2.40 Hz, 1H) 8.53 (d, J=2.27 Hz, 1H) 8.68 (d, J=6.32 Hz, 1H) 8.72-8.76 (m, 2H). MS [M+H] found 335.3.

7-Iodo-1-methyl-1H-pyrazolo[4,3-b]pyridine (30 mg, 0.116 mmol), Tris(dibenzylideneacetone)dipalladium(0) (2.65 mg, 2.90 μmol), (9,9-dimethyl-9H-xanthene-4,5-diyl)bis(diphenylphosphine) (16.75 mg, 0.029 mmol), 3'-fluoro-6'-methyl-2,2'-bipyridin-4-amine (23.53 mg, 0.116 mmol) and sodium 2-methylpropan-2-olate (33.4 mg, 0.347 mmol) were combined in dioxane (5 mL). The mixture was heated at 120° C. for 2 hours then was cooled and purified by preparative HPLC eluting with a gradient of 5-40% acetonitrile (containing 0.035% TFA) in water (containing 0.05% TFA) using a Sunfire Prep 5 μm C18, 75×30 mm column to afford the title compound as a TFA salt.

N-(3'-fluoro-6'-methyl-2,2'-bipyridin-4-yl)-1-methyl-1H-pyrazolo[4,3-b]pyridin-7-amine as a TFA salt (19.2 mg, 49.6% yield). ¹H NMR (400 MHz, METHANOL-d4) δ ppm 2.69 (s, 3H) 4.25 (s, 3H) 7.30 (dd, J=7.07, 2.53 Hz, 1H) 7.55-7.64 (m, 2H) 7.80 (dd, J=11.49, 8.72 Hz, 1H) 8.01 (d, J=2.53 Hz, 1H) 8.32 (s, 1H) 8.45 (d, J=7.07 Hz, 1H) 8.64 (d, J=5.05 Hz, 1H). MP 127-128° C. MS [M+H] found 335.3.

Example 67 and 68

N-(3'-fluoro-6'-methyl-2,2'-bipyridin-4-yl)-1-isopropyl-1H-pyrazolo[4,3-b]pyridin-7-amine and N-(3'-fluoro-6'-methyl-2,2'-bipyridin-4-yl)-2-isopropyl-2H-pyrazolo[4,3-b]pyridin-7-amine

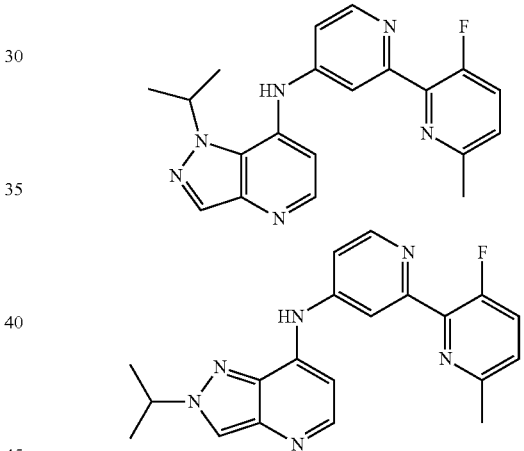

7-Iodo-2H-pyrazolo[4,3-b]pyridine (100 mg, 0.408 mmol), 2-iodopropane (0.049 ml, 0.490 mmol) and sodium hydride (19.59 mg, 0.816 mmol) were combined in DMF (5 mL). The mixture was stirred at room temperature for 1 hour then quenched by the addition of ice. The reaction mixture was purified by preparative HPLC eluting with a gradient of 20-90% 10 mmol NH₄HCO₃ in 20/80 (v/v) water/acetonitrile in 10 mmol NH₄HCO₃ in water using a Phenomenex Gemini Prep 5 μm C18, 75×30 mm column to give 7-iodo-2-isopropyl-2H-pyrazolo[4,3-b]pyridine (35 mg, 29.9% yield) and 7-iodo-1-isopropyl-1H-pyrazolo[4,3-b]pyridine (25 mg, 0.34% yield). MS [M+H] found 288.1.

7-Iodo-1-isopropyl-1H-pyrazolo[4,3-b]pyridine (24 mg, 0.084 mmol), Tris(dibenzylideneacetone)dipalladium(0) (2.82 mg, 3.08 μmol), (9,9-dimethyl-9H-xanthene-4,5-diyl)bis(diphenylphosphine) (17.80 mg, 0.031 mmol), 3'-fluoro-6'-methyl-2,2'-bipyridin-4-amine (25 mg, 0.123 mmol) and sodium 2-methylpropan-2-olate (35.5 mg, 0.369 mmol) were combined in dioxane (5 mL). The mixture was heated at 120° C. for 2 hours, then cooled and purified by preparative HPLC using a Phenomenex Gemini Prep 5 μm C18, 75×30 mm column eluting with a gradient of 20-50% 10 mmol NH₄HCO₃ in 20/80 (v/v) water/acetonitrile in 10 mmol NH₄HCO₃ in water to afford N-(3'-fluoro-6'-methyl-2,2'-bipyridin-4-yl)-1-isopropyl-1H-pyrazolo[4,3-b]pyridin-7-amine (7 mg, 15.70% yield). ¹H NMR (400 MHz, METHANOL-d₄) δ ppm 1.48 (s, 6H) 2.61 (s, 3H) 5.08-5.21 (m, 1H) 7.03 (dd, J=5.81, 2.02 Hz, 1H) 7.36-7.47 (m, 2H) 7.49 (s, 1H) 7.62-7.71 (m, 1H) 8.30 (s, 1H) 8.42 (d, J=6.06 Hz, 1H) 8.51 (d, J=4.80 Hz, 1H). MS [M+H] found 363.4.

7-Iodo-2-isopropyl-2H-pyrazolo[4,3-b]pyridine (10 mg, 0.035 mmol), Tris(dibenzylideneacetone)dipalladium(0) (0.797 mg, 0.871 μmol), (9,9-dimethyl-9H-xanthene-4,5-diyl)bis(diphenylphosphine) (5.04 mg, 8.71 μmol), 3'-fluoro-6'-methyl-2,2'-bipyridin-4-amine (7.08 mg, 0.035 mmol) and sodium 2-methylpropan-2-olate (10.04 mg, 0.104 mmol) were combined in dioxane (5 mL). The mixture was heated at 120° C. for 2 hours, then cooled and purified by preparative HPLC using a Sunfire Prep 5 μm C18, 75×30 mm column eluting with a gradient of 10-50% acetonitrile (containing 0.035% TFA) in water (containing 0.05% TFA) to afford N-(3'-fluoro-6'-methyl-2,2'-bipyridin-4-yl)-2-isopropyl-2H-pyrazolo[4,3-b]pyridin-7-amine as a TFA salt (6.6 mg, 52.3% yield). ¹H NMR (400 MHz, METHANOL-d₄) δ ppm 1.72 (d, J=6.82 Hz, 6H) 2.72 (s, 3H) 4.99-5.14 (m, 1H) 7.58 (d, J=6.06 Hz, 1H) 7.63 (dd, J=8.59, 3.54 Hz, 1H) 7.83 (dd, J=11.24, 8.72 Hz, 1H) 7.91 (dd, J=6.57, 2.53 Hz, 1H) 8.48 (d, J=2.53 Hz, 1H) 8.66 (d, J=6.06 Hz, 1H) 8.73 (d, J=6.82 Hz, 1H) 8.76 (s, 1H). MS [M+H] found 363.4.

Example 69

(S)-3-(7-(3'-fluoro-6'-methyl-2,2'-bipyridin-4-ylamino)-2H-pyrazolo[4,3-b]pyridin-2-yl)propane-1,2-diol

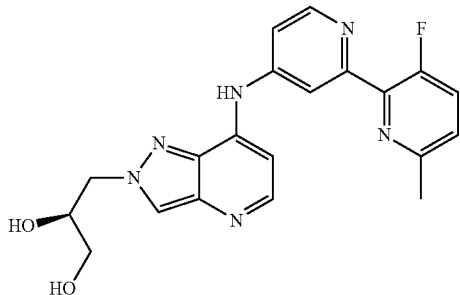 [SMILES: Cc1ccc(F)c(-c2cc(Nc3ccnc4cn(C[C@H](O)CO)nc34)ccn2)n1]

7-Iodo-2H-pyrazolo[4,3-b]pyridine (100 mg, 0.408 mmol), (R)-4-(chloromethyl)-2,2-dimethyl-1,3-dioxolane (0.056 ml, 0.408 mmol) and cesium carbonate (266 mg, 0.816 mmol) were combined in DMF (5 mL) at room temperature. The mixture was heated at 120° C. for 1 hour, then cooled and purified by preparative HPLC using a Phenomenex Gemini Prep 5 μm C18, 75×30 mm column eluting with a gradient of 20-70% 10 mmol NH₄HCO₃ in 20/80 (v/v) water/acetonitrile in 10 mmol NH₄HCO₃ in water to give (S)-2-((2,2-dimethyl-1,3-dioxolan-4-yl)methyl)-7-iodo-2H-pyrazolo[4,3-b]pyridine (51 mg, 34.8% yield). MP 85-87° C. MS [M+H] found 360.1.

(S)-2-((2,2-Dimethyl-1,3-dioxolan-4-yl)methyl)-7-iodo-2H-pyrazolo[4,3-b]pyridine (51 mg, 0.142 mmol), Tris(dibenzylideneacetone)dipalladium(0) (3.25 mg, 3.55 μmol), (9,9-dimethyl-9H-xanthene-4,5-diyl)bis(diphenylphosphine) (20.54 mg, 0.035 mmol), 3'-fluoro-6'-methyl-2,2'-bipyridin-4-amine (28.9 mg, 0.142 mmol) and sodium 2-methylpropan-2-olate (40.9 mg, 0.426 mmol) were combined in dioxane (5 mL). The mixture was heated at 120° C. for 2 hours, then cooled and purified by preparative HPLC using a Phenomenex Gemini Prep 5 μm C18, 75×30 mm column eluting with a gradient of 5-40% acetonitrile (containing 0.035% TFA) in water (containing 0.05% TFA) to give (S)-1-((2,2-dimethyl-1,3-dioxolan-4-yl)methyl)-N-(3'-fluoro-6'-methyl-2,2'-bipyridin-4-yl)-1H-pyrazolo[4,3-b]pyridin-7-amine which was combined with methanol (5 mL) and 1N HCl (2 mL) and stirred at room temperature for 30 minutes before evaporation to afford the title compound (12.5 mg, 22.32% yield) as a HCl salt. ¹H NMR (400 MHz, METHANOL-d4) δ ppm 2.57 (s, 3H) 3.41 (m, 1H) 3.49 (m, 1H) 3.97-4.10 (m, 1H) 4.51 (m, 1H) 4.69 (m, 1H) 7.51 (dd, J=8.59, 3.54 Hz, 1H) 7.64 (d, J=6.32 Hz, 1H) 7.71 (dd, J=11.24, 8.72 Hz, 1H) 8.01 (d, J=5.05 Hz, 1H) 8.53 (s, 1H) 8.63 (d, J=6.32 Hz, 1H) 8.66-8.71 (m, 2H). MP 182-184° C. MS [M+H] found 395.3.

Example 70

1-(7-(3'-fluoro-6'-methyl-2,2'-bipyridin-4-ylamino)-1H-pyrazolo[4,3-b]pyridin-1-yl)-2-methylpropan-2-ol

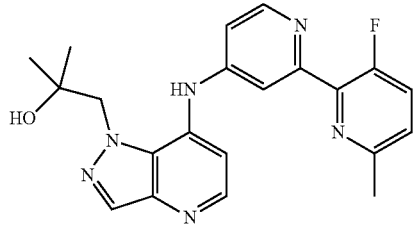 [SMILES: Cc1ccc(F)c(-c2cc(Nc3ccnc4cnn(CC(C)(C)O)c34)ccn2)n1]

N-(3'-Fluoro-6'-methyl-2,2'-bipyridin-4-yl)-2H-pyrazolo[4,3-b]pyridin-7-amine (40 mg, 0.125 mmol), 2,2-dimethyloxirane (9.00 mg, 0.125 mmol) and cesium carbonate (81 mg, 0.250 mmol) were combined in DMF (5 mL). The mixture was heated at 120° C. for 30 minutes, then cooled and purified by preparative HPLC using a Sunfire Prep 5 μm C18, 75×30 mm column eluting with a gradient of 5-40% acetonitrile (containing 0.035% TFA) in water (containing 0.05% TFA) to afford the title compound as a TFA salt (4.5 mg, 9.18% yield). ¹H NMR (400 MHz, MeOD) δ ppm 1.37 (s, 6H) 2.72 (s, 3H) 4.70 (s, 2H) 7.58-7.68 (m, 2H) 7.78 (d, J=5.31 Hz, 1H) 7.84 (dd, J=11.37, 8.59 Hz, 1H) 8.16 (d, J=2.02 Hz, 1H) 8.38 (s, 1H) 8.58 (d, J=6.82 Hz, 1H) 8.65 (d, J=5.31 Hz, 1H). MP 135-136° C. MS [M+H] found 393.4.

Example 71 and 72

2-(7-(3'-fluoro-6'-methyl-2,2'-bipyridin-4-ylamino)-1H-pyrazolo[4,3-b]pyridin-1-yl)ethanol and 2-(7-(3'-fluoro-6'-methyl-2,2'-bipyridin-4-ylamino)-2H-pyrazolo[4,3-b]pyridin-2-yl)ethanol

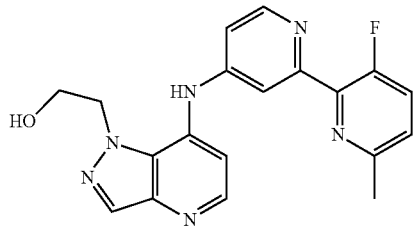

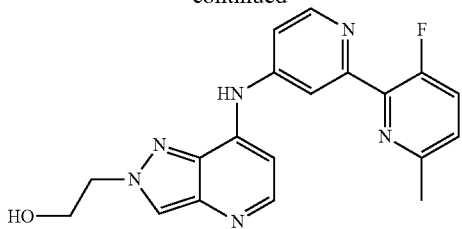

N-(3'-Fluoro-6'-methyl-2,2'-bipyridin-4-yl)-2H-pyrazolo[4,3-b]pyridin-7-amine (21 mg, 0.066 mmol), 2-bromoethanol (8.19 mg, 0.066 mmol) and cesium carbonate (42.7 mg, 0.131 mmol) were combined in DMF (5 mL). The mixture was heated at 120° C. for 30 minutes, then cooled and purified by preparative HPLC using a Phenomenex Gemini Prep 5 μm C18, 75×30 mm column eluting with a gradient of 20-70% 10 mmol $NH_4HCO_3$ in 20/80 (v/v) water/acetonitrile in 10 mmol $NH_4HCO_3$ in water to afford 2-(7-(3'-fluoro-6'-methyl-2,2'-bipyridin-4-ylamino)-2H-pyrazolo[4,3-b]pyridin-2-yl)ethanol (2.1 mg, 8.79% yield). 2-(7-(3'-Fluoro-6'-methyl-2,2'-bipyridin-4-ylamino)-1H-pyrazolo[4,3-b]pyridin-1-yl)ethanol containing fractions were concentrated and subsequently purified by preparative HPLC using a Sunfire Prep 5 μm C18, 75×30 mm column eluting with a gradient of 5-40% acetonitrile (containing 0.035% TFA) in water (containing 0.05% TFA) to afford the title compound as TFA salts.

2-(7-(3'-fluoro-6'-methyl-2,2'-bipyridin-4-ylamino)-2H-pyrazolo[4,3-b]pyridin-2-yl)ethanol: $^1$H NMR (400 MHz, MeOD) δ ppm 2.63 (s, 3H) 4.09 (t, J=5.31 Hz, 2H) 4.62 (t, J=5.31 Hz, 2H) 7.29 (d, J=5.05 Hz, 1H) 7.43 (dd, J=8.72, 3.41 Hz, 1H) 7.49-7.55 (m, 1H) 7.67 (dd, J=10.36, 8.59 Hz, 1H) 7.89 (s, 1H) 8.36 (d, J=5.30 Hz, 1H) 8.43 (s, 1H) 8.56 (d, J=5.81 Hz, 1H). MS [M+H] found 365.3.

2-(7-(3'-fluoro-6'-methyl-2,2'-bipyridin-4-ylamino)-1H-pyrazolo[4,3-b]pyridin-1-yl)ethanol: $^1$H NMR (400 MHz, METHANOL-$d_4$) δ ppm 2.72 (s, 3H) 4.05 (t, J=5.31 Hz, 2H) 4.84 (t, J=5.31 Hz, 2H) 7.53 (dd, J=6.82, 2.53 Hz, 1H) 7.64 (dd, J=8.46, 3.66 Hz, 1H) 7.72 (d, J=5.31 Hz, 1H) 7.83 (dd, J=11.37, 8.84 Hz, 1H) 8.13 (d, J=2.27 Hz, 1H) 8.39 (s, 1H) 8.54 (d, J=7.07 Hz, 1H) 8.64 (d, J=5.31 Hz, 1H). MS [M+H] found 365.3.

Example 73

N-(3'-fluoro-6'-methyl-2,2'-bipyridin-4-yl)-1-(2-methoxyethyl)-1H-pyrazolo[4,3-b]pyridin-7-amine

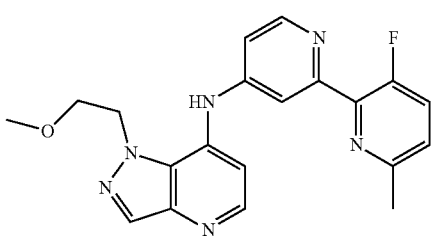 [SMILES: COCCn1ncc2nccc(Nc3ccnc(-c4nc(C)ccc4F)c3)c21]

7-Iodo-2H-pyrazolo[4,3-b]pyridine (100 mg, 0.408 mmol), 1-bromo-2-methoxyethane (56.7 mg, 0.408 mmol) and cesium carbonate (266 mg, 0.816 mmol) were combined in DMF (5 mL). The mixture was heated at 120° C. for 1 hour, then cooled and purified by preparative HPLC using a Phenomenex Gemini Prep 5 μm C18, 75×30 mm column eluting with a gradient of 20-70% 10 mmol $NH_4HCO_3$ in 20/80 (v/v) water/acetonitrile in 10 mmol $NH_4HCO_3$ in water to give 7-iodo-2-(2-methoxyethyl)-2H-pyrazolo[4,3-b]pyridine (30 mg, 24.25% yield) and 7-iodo-1-(2-methoxyethyl)-1H-pyrazolo[4,3-b]pyridine (30 mg, 24.25% yield). MS [M+H] found 304.1.

7-Iodo-1-(2-methoxyethyl)-1H-pyrazolo[4,3-b]pyridine (22 mg, 0.073 mmol), Tris(dibenzylideneacetone)dipalladium(0) (1.662 mg, 1.815 μmol), (9,9-dimethyl-9H-xanthene-4,5-diyl)bis(diphenylphosphine) (10.50 mg, 0.018 mmol), 3'-fluoro-6'-methyl-2,2'-bipyridin-4-amine (14.75 mg, 0.073 mmol) and sodium 2-methylpropan-2-olate (20.93 mg, 0.218 mmol) were combined in dioxane (5 mL). The mixture was heated at 120° C. for 1 hour, then cooled and purified by preparative HPLC using a Sunfire Prep 5 μm C18, 75×30 mm column eluting with a gradient of 5-40% acetonitrile (containing 0.035% TFA) in water (containing 0.05% TFA) to afford the title compound as a TFA salt (6 mg, 21.85% yield). $^1$H NMR (400 MHz, METHANOL-$d_4$) δ ppm 2.71 (s, 3H) 3.29 (s, 3H) 3.81-3.84 (m, 2H) 4.81-4.85 (m, 2H) 7.39 (dd, J=6.82, 2.53 Hz, 1H) 7.60-7.65 (m, 2H) 7.83 (dd, J=11.49, 8.72 Hz, 1H) 8.02 (d, J=2.53 Hz, 1H) 8.38 (s, 1H) 8.49 (d, J=7.07 Hz, 1H) 8.63 (d, J=5.05 Hz, 1H). MS [M+H] found 379.3.

Example 74

7-(3'-fluoro-6'-methyl-2,2'-bipyridin-4-ylamino)-N-methyl-1H-pyrazolo[4,3-b]pyridine-1-carboxamide

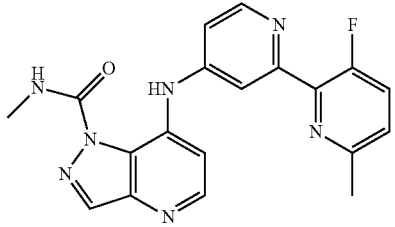 [SMILES: CNC(=O)n1ncc2nccc(Nc3ccnc(-c4nc(C)ccc4F)c3)c21]

N-(3'-Fluoro-6'-methyl-2,2'-bipyridin-4-yl)-2H-pyrazolo[4,3-b]pyridin-7-amine (20 mg, 0.062 mmol), methylcarbamic chloride (5.84 mg, 0.062 mmol) and pyridine (5.93 mg, 0.075 mmol) were combined in dichloromethane (5 mL). The mixture was heated at 70° C. for 30 minutes, then cooled and purified by preparative HPLC using a Sunfire Prep 5 μm C18, 75×30 mm column eluting with a gradient of 20-50% acetonitrile (containing 0.035% TFA) in water (containing 0.05% TFA) to afford the title compound as a TFA salt (2.2 mg, 9.34% yield). $^1$H NMR (400 MHz, METHANOL-d4) δ ppm 2.72 (s, 3H) 3.10 (s, 3H) 7.65 (dd, J=8.72, 3.66 Hz, 1H) 7.79-7.84 (m, 1H) 7.85-7.90 (m, 2H) 8.00 (s, 1H) 8.33 (d, J=2.53 Hz, 1H) 8.52 (s, 1H) 8.61 (d, J=6.82 Hz, 1H) 8.70 (d, J=5.56 Hz, 1H). MS [M+H] found 378.3.

Example 75

7-(2-(2-fluoro-5-methylphenyl)pyridin-4-ylamino)-N-methyl-1H-pyrazolo[4,3-b]pyridine-1-carboxamide

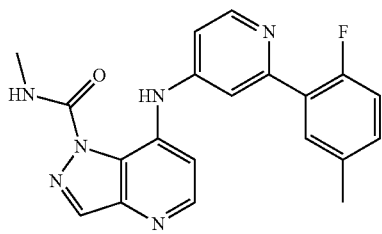 [SMILES: CNC(=O)n1ncc2nccc(Nc3ccnc(-c4cc(C)ccc4F)c3)c21]

N-(2-(2-Fluoro-5-methylphenyl)pyridin-4-yl)-1H-pyrazolo[4,3-b]pyridin-7-amine (42 mg, 0.132 mmol), pyridine (18.08 μl, 0.224 mmol) were combined in dichloroethylene (658 μl) and then methylcarbamic chloride (13.52 mg, 0.132 mmol) was added and the reaction was heated at 60° C. Additional methylcarbamic chloride (80 mg) and pyridine (100 uL) were added and heating continued at 60° C. overnight. The reaction mixture was then cooled, concentrated, and purified by preparative HPLC using a Sunfire Prep 5 μm C18, 75×30 mm column eluting with a gradient of 5-95% acetonitrile (containing 0.035% TFA) in water (containing 0.05% TFA) to give the title compound as a TFA salt. $^1$H NMR (DMSO-d6) δ: 11.86 (s, 1H), 9.06 (d, J=4.5 Hz, 1H), 8.71 (s, 1H), 8.60 (t, J=6.1 Hz, 2H), 7.61-7.78 (m, 3H), 7.52 (dd, J=6.3, 2.0 Hz, 1H), 7.28-7.47 (m, 2H), 2.93 (d, J=4.5 Hz, 3H), 2.38 (s, 3H); ESI-MS: 376.0 m/z (M+H).

Example 76 and 77

N-(2-(2-fluoro-5-methylphenyl)pyridin-4-yl)-1-(piperidin-4-yl)-1H-pyrazolo[4,3-b]pyridin-7-amine and N-(2-(2-fluoro-5-methylphenyl)pyridin-4-yl)-2-(piperidin-4-yl)-2H-pyrazolo[4,3-b]pyridin-7-amine

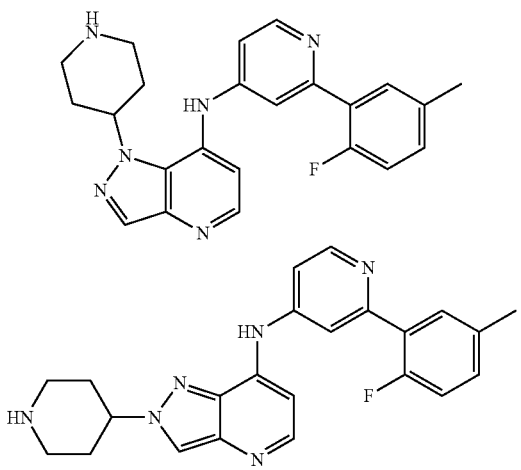

Sodium hydride (55.2 mg, 1.379 mmol) was added to a solution of 7-iodo-1H-pyrazolo[4,3-b]pyridine (260 mg, 1.061 mmol) in DMF (1.5 mL) at 0° C., and the reaction was stirred for 5 minutes. tert-Butyl 4-bromopiperidine-1-carboxylate (364 mg, 1.379 mmol) was added and the reaction was warmed to room temperature and then heated at 65° C. for 2 hours. The reaction was cooled, quenched with water, and concentrated in vacuo. The residue was partitioned between saturated NH$_4$Cl solution and EtOAc. The organic layer was separated, dried over Na$_2$SO$_4$, and concentrated in vacuo to afford a residue. The residue was purified with silica column chromatography eluted with hexanes/ethyl acetate step gradient (0-100% EtOAc over 45 minutes), to afford tert-butyl 4-(7-iodo-2H-pyrazolo[4,3-b]pyridin-2-yl)piperidine-1-carboxylate (57 mg, 13%). The fractions containing tert-butyl 4-(7-iodo-1H-pyrazolo[4,3-b]pyridin-1-yl)piperidine-1-carboxylate were chromatographed again under the same conditions to give tert-butyl 4-(7-iodo-1H-pyrazolo[4,3-b]pyridin-1-yl)piperidine-1-carboxylate (60 mg, 13%). MS [M+H] found 429.2 tert-Butyl 4-(7-iodo-1H-pyrazolo[4,3-b]pyridin-1-yl)piperidine-1-carboxylate (57.0 mg, 0.067 mmol), 2,2'-bis(diphenylphosphino)-1,1'-binaphthyl (41.4 mg, 0.067 mmol), 2-(2-fluoro-5-methylphenyl)pyridin-4-amine (40.4 mg, 0.200 mmol) and t-butoxide (17.91 mg, 0.186 mmol) were dissolved in dioxane (3 mL) and sparged with N$_2$. Palladium(II) acetate (29.9 mg, 0.133 mmol) and 2,2'-bis(diphenylphosphino)-1,1'-binaphthyl (41.4 mg, 0.067 mmol) were added next and the mixture was heated at 120° C. for 2 hours. The reaction was cooled to room temperature and diluted with methanol. This mixture was filtered and the filtrate was purified by preparative HPLC using a Sunfire Prep 5 μm C18, 75×30 mm column eluting with a gradient of 15-40% acetonitrile (containing 0.035% TFA) in water (containing 0.05% TFA) to give N-(2-(2-fluoro-5-methylphenyl)pyridin-4-yl)-1-(piperidin-4-yl)-1H-pyrazolo[4,3-b]pyridin-7-amine (17 mg, 32%)

A solution of 2-(2-fluoro-5-methylphenyl)pyridin-4-amine (42.5 mg, 0.210 mmol), tert-butyl 4-(7-iodo-2H-pyrazolo[4,3-b]pyridin-2-yl)piperidine-1-carboxylate (60 mg, 0.140 mmol) and t-butoxide (18.85 mg, 0.196 mmol) in xylene (3 mL) was sparged with N$_2$ and then 2-dicyclohexylphosphino-2',4',6'-tri-iso-propyl-1,1'-biphenyl (13.36 mg, 0.028 mmol) and tris(dibenzylideneacetone)dipalladium(0) (12.83 mg, 0.014 mmol) were added and the mixture was heated at 120° C. overnight. The reaction was cooled, concentrated, the residue treated with dichloromethane/TFA (1/1) and the solvent was removed in vacuo. The residue was dissolved with methanol and purified with preparative HPLC using a Sunfire Prep 5 μm C18, 75×30 mm column eluting with a gradient of 15-40% acetonitrile (containing 0.035% TFA) in water (containing 0.05% TFA) to give N-(2-(2-fluoro-5-methylphenyl)pyridin-4-yl)-2-(piperidin-4-yl)-2H-pyrazolo[4,3-b]pyridin-7-amine (49 mg, 87%)

Example 78 and 79

N-(2-(2-fluoro-5-methylphenyl)pyridin-4-yl)-1-(1-(methylsulfonyl)piperidin-4-yl)-1H-pyrazolo[4,3-b]pyridin-7-amine and N-(2-(2-fluoro-5-methylphenyl)pyridin-4-yl)-2-(1-(methylsulfonyl)piperidin-4-yl)-2H-pyrazolo[4,3-b]pyridin-7-amine

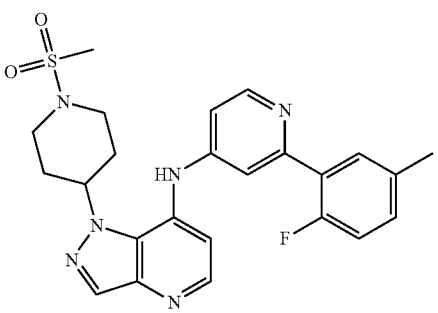

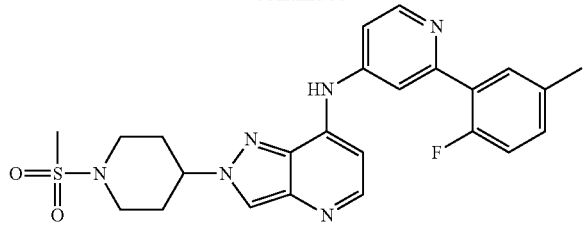

To a solution of N-(2-(2-fluoro-5-methylphenyl)pyridin-4-yl)-2-(piperidin-4-yl)-2H-pyrazolo[4,3-b]pyridin-7-amine (49 mg, 0.122 mmol) in dichloromethane (3 mL) at 0° C. was added triethylamine (0.051 ml, 0.365 mmol) and mesyl chloride (10.41 μl, 0.134 mmol). The reaction was removed from the ice bath and briefly stirred at room temperature. The reaction mixture was concentrated and subjected to silica column chromatography eluted with 0-5% methanol in dichloromethane using a step gradient (over 24 minutes) to give N-(2-(2-fluoro-5-methylphenyl)pyridin-4-yl)-2-(1-(methylsulfonyl)piperidin-4-yl)-2H-pyrazolo[4,3-b]pyridin-7-amine (12 mg, 21%). $^1$H NMR (400 MHz, CHLOROFORM-d) δ ppm 2.31-2.49 (m, 7H) 2.83-2.95 (m, 3H) 2.95-3.10 (m, 2H) 4.03 (d, J=12.63 Hz, 2H) 4.42-4.66 (m, 1H) 7.03-7.24 (m, 4H) 7.34 (s, 1H) 7.75 (s, 1H) 7.83 (dd, J=7.58, 2.02 Hz, 1H) 8.18 (s, 1H) 8.44 (d, J=4.80 Hz, 1H) 8.65 (d, J=5.56 Hz, 1H). MS [M+H] found 481.4.

N-(2-(2-Fluoro-5-methylphenyl)pyridin-4-yl)-1-(piperidin-4-yl)-1H-pyrazolo[4,3-b]pyridin-7-amine (17 mg, 0.042 mmol) and triethylamine (0.018 ml, 0.127 mmol) were combined in dichloromethane (3 mL) and cool in an ice bath. Mesyl chloride (3.61 μl, 0.046 mmol) was added and the reaction was briefly warmed to room temperature. The reaction mixture was concentrated and purified by silica column chromatography eluting with 0-5% methanol in dichloromethane to give to afford N-(2-(2-fluoro-5-methylphenyl)pyridin-4-yl)-1-(1-(methylsulfonyl)piperidin-4-yl)-1H-pyrazolo[4,3-b]pyridin-7-amine (4 mg, 20%). $^1$H NMR (400 MHz, CHLOROFORM-d) δ ppm 1.93 (d, J=10.61 Hz, 2H) 2.24-2.43 (m, 5H) 2.55-2.69 (m, 2H) 2.76 (s, 3H) 3.84 (d, J=12.63 Hz, 2H) 4.57 (t, J=10.74 Hz, 1H) 6.29 (br. s., 1H) 6.60 (dd, J=5.56, 2.02 Hz, 1H) 6.88-7.09 (m, 1H) 7.09-7.25 (m, 3H) 7.75 (dd, J=7.45, 2.15 Hz, 1H) 8.33 (s, 1H) 8.50 (d, J=5.56 Hz, 1H) 8.56 (d, J=4.55 Hz, 1H). MS [M+H] found 481.4.

Example 80

N-ethyl-7-(2-(2-fluoro-5-methylphenyl)pyridin-4-ylamino)-1H-pyrazolo[4,3-b]pyridine-1-carboxamide

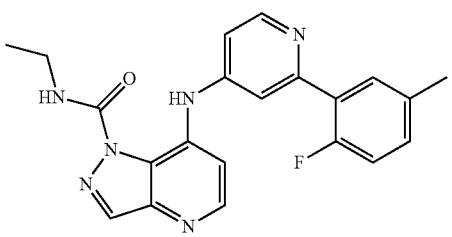 [SMILES: CCNC(=O)n1ncc2nccc(Nc3ccnc(-c4cc(C)ccc4F)c3)c21]

N-(2-(2-Fluoro-5-methylphenyl)pyridin-4-yl)-1H-pyrazolo[4,3-b]pyridin-7-amine (0.07 g, 0.219 mmol) and isocyanatoethane (0.017 ml, 0.219 mmol) were combined in acetonitrile (2.192 mL) and heated in an oil bath at 82° C. over night. The reaction mixture was then cooled and purified by preparative HPLC using a Sunfire Prep 5 μm C18, 30×75 mm column eluting with a gradient of 30-45% acetonitrile (containing 0.035% TFA) in water (containing 0.05% TFA) to give the title compound as a TFA salt. $^1$H NMR (400 MHz, METHANOL-d4) δ ppm 1.18-1.44 (m, 3H) 2.36-2.54 (m, 3H) 3.48-3.62 (m, 2H) 7.30 (dd, J=10.61, 8.59 Hz, 1H) 7.45-7.56 (m, 1H) 7.58-7.66 (m, 1H) 7.73 (dd, J=6.82, 2.53 Hz, 1H) 7.81 (d, J=2.78 Hz, 2H) 8.43-8.51 (m, 1H) 8.54 (d, J=6.82 Hz, 1H) 8.58-8.71 (m, 1H). MS [M+H] found 391.4.

Example 81

7-(5,6'-dimethyl-2,2'-bipyridin-4-ylamino)-N-methyl-1H-pyrazolo[4,3-b]pyridine-1-carboxamide

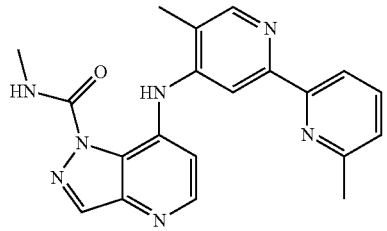 [SMILES: CNC(=O)n1ncc2nccc(Nc3cc(-c4cccc(C)n4)ncc3C)c21]

N-(5,6'-Dimethyl-2,2'-bipyridin-4-yl)-1H-pyrazolo[4,3-b]pyridin-7-amine (9 mg, 0.028 mmol) and pyridine (3.91 μl, 0.048 mmol) were combined in dichloroethylene (142 μl). Methylcarbamic chloride (2.92 mg, 0.028 mmol) was added and the reaction mixture was heated at 60° C. for 1 hour and then additional methylcarbamic chloride (2.92 mg, 0.028 mmol) was added and the reaction was stirred for 2 more hours. Methanol was added and the reaction mixture was concentrated to yellowish oil which was suspended in methanol and purified by preparative HPLC using a Sunfire Prep 5 μm C18, 30×75 mm column eluting with a gradient of 15-40% acetonitrile (containing 0.035% TFA) in water (containing 0.05% TFA) to afford the title compound as a TFA salt (7.3 mg). $^1$H NMR (400 MHz, METHANOL-$d_4$) δ ppm 2.63 (s, 3H) 2.70 (s, 3H) 3.06 (d, J=4.55 Hz, 3H) 7.53 (d, J=7.58 Hz, 1H) 7.83 (d, J=5.31 Hz, 1H) 7.96 (t, J=7.58 Hz, 1H) 8.06 (d, J=7.83 Hz, 1H) 8.38-8.54 (m, 3H) 8.59-8.71 (m, 1H) 8.87 (d, J=15.41 Hz, 1H). MS [M+H] found 373.0.

Example 82 and 83

1-(7-(2-(5-chloro-2-fluorophenyl)pyridin-4-ylamino)-1H-pyrazolo[4,3-b]pyridin-1-yl)-2-methylpropan-2-ol and 1-(7-(2-(5-chloro-2-fluorophenyl)pyridin-4-ylamino)-2H-pyrazolo[4,3-b]pyridin-2-yl)-2-methylpropan-2-ol

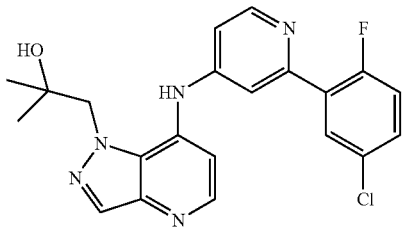

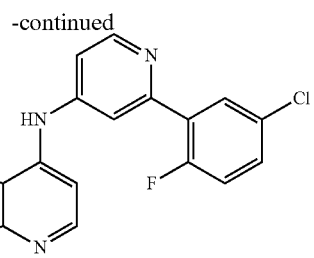

N-(2-(5-Chloro-2-fluorophenyl)pyridin-4-yl)-1H-pyrazolo[4,3-b]pyridin-7-amine (50 mg, 0.147 mmol), 2,2-dimethyloxirane (13.07 µl, 0.147 mmol) and K₂CO₃ (20.34 mg, 0.147 mmol) in were combined in DMA (775 µl) and heated at 80° C. over night. The reaction mixture was cooled and then purified by preparative HPLC using a Sunfire Prep 5 µm C18, 75×30 mm column eluting with a gradient of 15-18% acetonitrile (containing 0.035% TFA) in water (containing 0.05% TFA) to give the title compounds as TFA salts.

1-(7-(2-(5-chloro-2-fluorophenyl)pyridin-4-ylamino)-1H-pyrazolo[4,3-b]pyridin-1-yl)-2-methylpropan-2-ol ¹H NMR (400 MHz, DMSO-d6) δ ppm 1.15 (6H, s) 2.07 (1H, s) 4.47 (2H, s) 7.26 (1H, d, J=6.57 Hz) 7.46 (1H, dd, J=10.86, 8.84 Hz) 7.57-7.66 (2H, m) 7.98 (1H, s) 8.01 (1H, dd, J=6.82, 2.78 Hz) 8.56 (1H, d, J=6.57 Hz) 8.64 (1H, s) 8.77 (1H, d, J=5.56 Hz) 11.38 (1H, s). MS [M+H] found 412.3.

1-(7-(2-(5-chloro-2-fluorophenyl)pyridin-4-ylamino)-2H-pyrazolo[4,3-b]pyridin-2-yl)-2-methylpropan-2-ol 1-(7-(2-(5-chloro-2-fluorophenyl)pyridin-4-ylamino)-2H-pyrazolo[4,3-b]pyridin-2-yl)-2-methylpropan-2-ol. ¹H NMR (400 MHz, DMSO-d6) δ ppm 1.13-1.29 (4H, m) 4.45 (2H, d, J=7.58 Hz) 4.60 (2H, s) 7.26-7.47 (1H, m) 7.47-7.73 (2H, m) 7.93-8.09 (1H, m) 8.40 (1H, s) 8.52 (1H, br. s.) 8.63 (1H, d, J=5.05 Hz) 8.79 (1H, d, J=5.31 Hz) 8.95 (1H, s) 11.13 (1H, s). MS [M+H] found 412.3.

Examples 84 and 85

2-(7-(3'-fluoro-6'-methyl-2,2'-bipyridin-4-ylamino)-2H-pyrazolo[4,3-b]pyridin-2-yl)acetamide and 2-(7-(3'-fluoro-6'-methyl-2,2'-bipyridin-4-ylamino)-1H-pyrazolo[4,3-b]pyridin-1-yl)acetamide

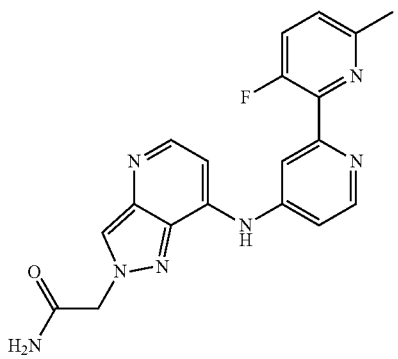

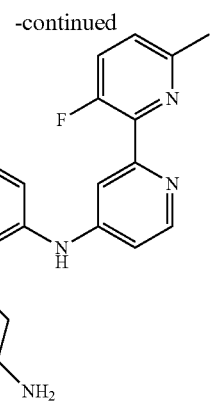

N-(3'-fluoro-6'-methyl-2,2'-bipyridin-4-yl)-1H-pyrazolo[4,3-b]pyridin-7-amine (140 mg, 0.437 mmol), DMF (2.2 mL), Cs₂CO₃ (142 mg, 0.437 mmol) and 2-chloroacetamide (41.7 mg, 0.437 mmol) were combined and heated in microwave at 80° C. for 15 minutes. The resulting crude material was purified via preparative HPLC using a gradient of 5-30% acetonitrile (containing 0.035% TFA) in water (containing 0.05% TFA) using a Sunfire Prep 5 µm C18, 75×30 mm column to 2-(7-(3'-fluoro-6'-methyl-2,2'-bipyridin-4-ylamino)-2H-pyrazolo[4,3-b]pyridin-2-yl)acetamide as a TFA salt: ¹H NMR (400 MHz, DMSO-d₆) δ ppm 2.63 (3H, s) 5.19 (2H, s) 7.10 (1H, d, J=4.80 Hz) 7.20 (1H, br. s.) 7.50 (1H, br. s.) 7.55-7.84 (3H, m) 7.96 (1H, dd, J=11.62, 8.59 Hz) 8.38-8.53 (2H, m) 8.62 (1H, br. s.) 10.97 (1H, br. s.). MS [M+H] found 378.3. Impure 2-(7-(3'-fluoro-6'-methyl-2,2'-bipyridin-4-ylamino)-1H-pyrazolo[4,3-b]pyridin-1-yl)acetamide was subjected to a second preparative HPLC using a gradient of 10-20% acetonitrile (containing 0.035% TFA) in water (containing 0.05% TFA) using a Sunfire Prep 5 µm C18, 75×30 mm column to give 2-(7-(3'-fluoro-6'-methyl-2,2'-bipyridin-4-ylamino)-1H-pyrazolo[4,3-b]pyridin-1-yl)acetamide as a TFA salt. ¹H NMR (400 MHz, DMSO-d₆) δ ppm 2.59 (3H, s) 5.27 (2H, s) 7.30 (1H, d, J=5.81 Hz) 7.46-7.57 (2H, m) 7.64 (1H, dd, J=6.06, 2.27 Hz) 7.76 (1H, s) 7.85 (1H, d, J=10.61 Hz) 8.16 (1H, s) 8.56 (1H, d, J=6.06 Hz) 8.67 (1H, br. s.) 8.78 (1H, s) 11.35 (1H, br. s.). MS [M+H] found 378.3.

Examples 86 and 87

2-(7-(2-(2,5-difluorophenyl)pyridin-4-ylamino)-1H-pyrazolo[4,3-b]pyridin-1-yl)acetamide and 2-(7-(2-(2,5-difluorophenyl)pyridin-4-ylamino)-2H-pyrazolo[4,3-b]pyridin-2-yl)acetamide

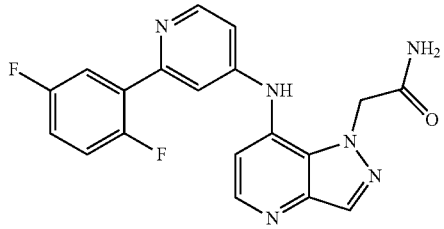

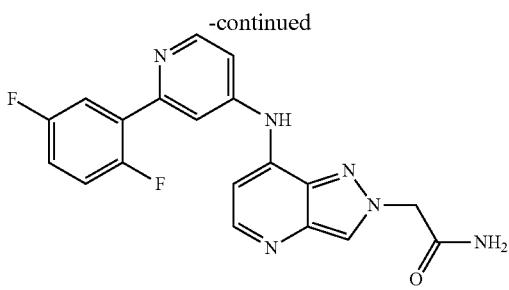

N-(2-(2,5-Difluorophenyl)pyridin-4-yl)-1H-pyrazolo[4,3-b]pyridin-7-amine (165 mg, 0.510 mmol), DMF (2.5 mL), Cs₂CO₃ (166 mg, 0.510 mmol) and 2-chloroacetamide (48.7 mg, 0.510 mmol) were combined and heated in a microwave at 80° C. for 15 minutes. The reaction mixture was then purified via preparative HPLC using a gradient of 10-20% acetonitrile (containing 0.035% TFA) in water (containing 0.05% TFA) using a Sunfire Prep 5 μm C18, 75×30 mm column to give 2-(7-(2-(2,5-difluorophenyl)pyridin-4-ylamino)-1H-pyrazolo[4,3-b]pyridin-1-yl)acetamide as a TFA salt, ¹H NMR (400 MHz, DMSO-d₆) δ ppm 5.67 (2H, s) 7.61 (1H, dd, J=6.69, 2.40 Hz) 7.72-7.81 (2H, m) 7.87-7.99 (3H, m) 8.10-8.21 (2H, m) 8.85 (1H, s) 8.94 (1H, d, J=6.57 Hz) 9.02 (1H, d, J=5.05 Hz) 11.35 (1H, br. s.). MS [M+H] found 381.3. Impure 2-(7-(2-(2,5-difluorophenyl)pyridin-4-ylamino)-2H-pyrazolo[4,3-b]pyridin-2-yl)acetamide was subjected to a second preparative HPLC using a gradient of 10-20% acetonitrile (containing 0.035% TFA) in water (containing 0.05% TFA) using a Sunfire Prep 5 μm C18, 75×30 mm column to provide the TFA salt of 2-(7-(2-(2,5-difluorophenyl)pyridin-4-ylamino)-2H-pyrazolo[4,3-b]pyridin-2-yl)acetamide. ¹H NMR (400 MHz, DMSO-d₆) δ ppm 5.23-5.42 (2H, m) 7.27 (1H, d, J=6.32 Hz) 7.36-7.52 (3H, m) 7.60 (1H, dd, J=5.43, 2.15 Hz) 7.71-7.83 (2H, m) 7.94-8.02 (1H, m) 8.55 (1H, d, J=6.82 Hz) 8.69-8.82 (2H, m) 11.32 (1H, s). MS [M+H] found 381.3.

Example 88

2-(6-fluoro-7-(3'-fluoro-5,6'-dimethyl-2,2'-bipyridin-4-ylamino)-2H-pyrazolo[4,3-b]pyridin-2-yl)acetamide

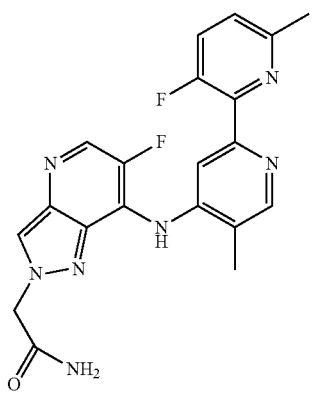 [SMILES: Cc1ccc(F)c(-c2cc(Nc3c(F)cnc4cn(CC(N)=O)nc34)c(C)cn2)n1]

To a solution of 6-fluoro-7-iodo-1H-pyrazolo[4,3-b]pyridine (150 mg, 0.570 mmol) in DMF (4 mL) was added Cs₂CO₃ (279 mg, 0.855 mmol) and tert-butyl 2-chloroacetylcarbamate (121 mg, 0.627 mmol). The mixture was heated at 110° C. for 2 hours. The mixture was then cooled and the reaction was concentrated under vacuum to give a residue. The residue was partitioned between saturated sodium bicarbonate solution and EtOAc (25 mL). The organic layer was separated and the aqueous layer was extracted with EtOAc (25 mL). The combined organic layers were, dried over Na₂SO₄ and evaporated to give tert-butyl 2-(6-fluoro-7-iodo-2H-pyrazolo[4,3-b]pyridin-2-yl)acetylcarbamate. MS [M+H] found 421.2.

To a solution of tert-butyl 2-(6-fluoro-7-iodo-2H-pyrazolo[4,3-b]pyridin-2-yl)acetylcarbamate (62 mg, 0.148 mmol) in dioxane (4 mL) was added (9,9-dimethyl-9H-xanthene-4,5-diyl)bis(diphenylphosphine) (21.34 mg, 0.037 mmol), Pd₂(dba)₃ (33.8 mg, 0.037 mmol), sodium tert-butoxide (42.5 mg, 0.443 mmol), and 3'-fluoro-5,6'-dimethyl-2,2'-bipyridin-4-amine (35.3 mg, 0.162 mmol) and the mixture was heated at 110° C. for 3 hours. The solution was then cooled, diluted with water and extracted with EtOAc (3×75 mL). The combined organics were dried over Na₂SO₄, filtered, and concentrated to give a residue which was suspended in DMSO and purified by preparative HPLC using a gradient of 20-65% acetonitrile (containing 0.035% TFA) in water (containing 0.05% TFA) using a Sunfire Prep 5 μm C18, 75×30 mm column to give the title compound. The title compound was combined with 1N HCl (4 mL) and lyophilized to give the title compound as a hydrochloride salt. ¹H NMR (400 MHz, DMSO-d6) δ ppm 2.52 (s, 3H), 2.60 (s, 3H) 3.43-3.58 (m, 1H) 3.61-3.79 (m, 1H) 7.29 (d, J=2.53 Hz, 1H) 7.35 (br. s., 1H) 7.53-7.65 (m, 1H) 7.71 (br. s., 1H) 7.82 (dd, J=11.12, 8.59 Hz, 1H) 8.52 (s, 1H) 8.76 (d, J=3.03 Hz, 1H) 8.87 (s, 1H) 10.14 (br. s., 1H). MS [M+H] found 410.4.

Example 89

1-(cyclopropylmethyl)-N-(3'-fluoro-6'-methyl-2,2'-bipyridin-4-yl)-1H-pyrazolo[4,3-b]pyridin-7-amine

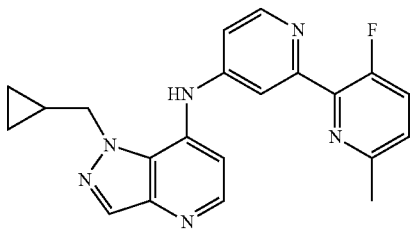 [SMILES: Cc1ccc(F)c(-c2cc(Nc3ccnc4cnn(CC5CC5)c34)ccn2)n1]

(9,9-Dimethyl-9H-xanthene-4,5-diyl)bis(diphenylphosphine) (4.45 mg, 7.69 μmol), 1-(cyclopropylmethyl)-7-iodo-1H-pyrazolo[4,3-b]pyridine (46 mg, 0.154 mmol), Pd₂(dba)₃ (7.04 mg, 7.69 μmol), 3'-fluoro-6'-methyl-2,2'-bipyridin-4-amine (31.3 mg, 0.154 mmol) and sodium 2-methylpropan-2-olate (44.3 mg, 0.461 mmol) were combined in dioxane (5 mL) and heated at 120° C. for 1 hour. The solution was cooled, concentrated, and purified by prep-HPLC using a Phenomenex Gemini C18, 5 μm, ID30×75 mm column eluting with a gradient of 5-40% acetonitrile (containing 0.035% TFA) in water (containing 0.05% TFA) to give the title compound as a TFA salt. ¹H NMR (400 MHz, METHANOL-d₄) δ ppm 0.24-0.32 (m, 2H) 0.39-0.46 (m, 2H) 1.06-1.24 (m, 1H) 2.65 (s, 3H) 4.43 (d, J=6.82 Hz, 2H) 7.30 (d, J=6.82, 2.53 Hz, 1H) 7.53-7.61 (m, 2H) 7.76 (dd, J=11.37, 8.59 Hz, 1H) 7.98 (d, J=2.53 Hz, 1H) 8.34 (s, 1H) 8.44 (d, J=7.07 Hz, 1H) 8.62 (d, J=5.30 Hz, 1H). MS [M+H] found 375.4.

Example 90

3-(7-(3'-fluoro-5,6'-dimethyl-2,2'-bipyridin-4-ylamino)-2H-pyrazolo[4,3-b]pyridin-2-yl)propan-1-ol

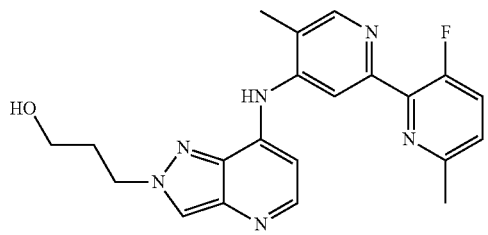 [SMILES: Cc1ccc(F)c(-c2cc(Nc3ccnc4cn(CCCO)nc34)c(C)cn2)n1]

7-Iodo-2H-pyrazolo[4,3-b]pyridine (200 mg, 0.816 mmol), 2-(3-bromopropoxy)tetrahydro-2H-pyran (182 mg, 0.816 mmol) and Cs$_2$CO$_3$ (532 mg, 1.633 mmol) were combined in DMF (5 mL) and the mixture was heated at 120° C. for 30 minutes in a microwave. The reaction mixture was then purified by preparative HPLC using a Sunfire Prep 5 μm C18, 75×30 mm column eluting with a gradient of 05-40% acetonitrile (containing 0.035% TFA) in water (containing 0.05% TFA) to give 7-iodo-2-(3-(tetrahydro-2H-pyran-2-yloxy)propyl)-2H-pyrazolo[4,3-b]pyridine and 7-iodo-1-(3-(tetrahydro-2H-pyran-2-yloxy)propyl)-1H-pyrazolo[4,3-b]pyridine. MS [M+H] found 388.0.

(9,9-Dimethyl-9H-xanthene-4,5-diyl)bis(diphenylphosphine) (3.74 mg, 6.46 μmol), 7-iodo-2-(3-(tetrahydro-2H-pyran-2-yloxy)propyl)-2H-pyrazolo[4,3-b]pyridine (100 mg, 0.258 mmol), Pd$_2$(dba)$_3$ (5.91 mg, 6.46 μmol), 3'-fluoro-5,6'-dimethyl-2,2'-bipyridin-4-amine (56.1 mg, 0.258 mmol) and sodium 2-methylpropan-2-olate (74.5 mg, 0.775 mmol) were combined in dioxane (5 mL) and heated at 120° C. for 1 hour. The reaction was then cooled, concentrated, and purified by prep-HPLC using a Sunfire Prep 5 μm C18, 75×30 mm column eluting with a gradient of 10-50% acetonitrile (containing 0.035% TFA) in water (containing 0.05% TFA) to give a residue which was combined with 1N HCl (4 mL) and stirred at room temperature for 1 hour before the solvent was removed to give the title compound as a hydrochloride salt. $^1$H NMR (400 MHz, METHANOL-d$_4$) δ ppm 2.14 (t, J=6.19 Hz, 2H) 2.68 (s, 3H) 2.71 (s, 3H) 3.52 (t, J=5.94 Hz, 2H) 4.68 (t, J=6.95 Hz, 2H) 7.54 (d, J=6.57 Hz, 1H) 7.64 (dd, J=8.59, 3.54 Hz, 1H) 7.82 (dd, J=11.37, 8.59 Hz, 1H) 8.53 (s, 1H) 8.71 (d, J=6.57 Hz, 1H) 8.86 (s, 1H) 8.90 (s, 1H). MS [M+H] found 393.4.

Example 91

2-(6-fluoro-7-(3'-fluoro-5,6'-dimethyl-2,2'-bipyridin-4-ylamino)-2H-pyrazolo[4,3-b]pyridin-2-yl)ethanol

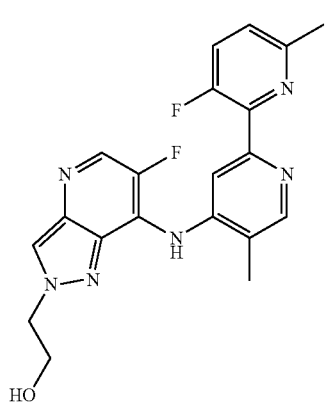 [SMILES: Cc1ccc(F)c(-c2cc(Nc3c(F)cnc4cn(CCO)nc34)c(C)cn2)n1]

A solution of 7-chloro-6-fluoro-1H-pyrazolo[4,3-b]pyridine (200 mg, 1.166 mmol) in DMF (5 mL), Cs$_2$CO$_3$ (570 mg, 1.749 mmol), and 2-(2-bromoethoxy)tetrahydro-2H-pyran (0.194 mL, 1.282 mmol) in a sealed pressure vessel was heated at 110° C. for 3 hours. The reaction mixture was then concentrated and partitioned between water (20 mL) and EtOAc (2×50 mL). The organics were dried over Na$_2$SO$_4$ and evaporated to give 7-chloro-6-fluoro-2-(2-(tetrahydro-2H-pyran-2-yloxy)ethyl)-2H-pyrazolo[4,3-b]pyridine and 7-chloro-6-fluoro-1-(2-(tetrahydro-2H-pyran-2-yloxy)ethyl)-1H-pyrazolo[4,3-b]pyridine which was used without further purification. MS [M+H] found 300.2.

To 7-chloro-6-fluoro-2-(2-(tetrahydro-2H-pyran-2-yloxy)ethyl)-2H-pyrazolo[4,3-b]pyridine (85 mg, 0.284 mmol) and 7-chloro-6-fluoro-1-(2-(tetrahydro-2H-pyran-2-yloxy)ethyl)-1H-pyrazolo[4,3-b]pyridine (85 mg, 0.284 mmol) in t-BuOH (4 mL) was added 3'-fluoro-5,6'-dimethyl-2,2'-bipyridin-4-amine (185 mg, 0.851 mmol), tri(dibenzylideneacetone)dipalladium(0) (26.0 mg, 0.028 mmol), dicyclohexyl(2',4',6'-triisopropylbiphenyl-2-yl)phosphine (27.0 mg, 0.057 mmol) and potassium carbonate (157 mg, 1.134 mmol) and the mixture was heated at 100° C. over night. The mixture was cooled and evaporated to give a residue which was partitioned between EtOAc (75 mL) and water. The layers were separated and the aqueous layer was extracted with EtOAc (75 mL). The combined organic layers were dried over Na$_2$SO$_4$, filtered, and concentrated to give a residue which was purified on HPLC using a gradient of 20-50% acetonitrile (containing 0.035% TFA) in water (containing 0.05% TFA) using a Sunfire Prep 5 μm C18, 75×30 mm column to give a residue. The residue was combined with 1N HCl (3 mL) and the solution was stirred for an hour, evaporated and lyophilized to give the title compound as a HCl salt. $^1$HNMR (400 MHz, DMSO-d6) δ ppm 2.52 (s, 3H) 2.58 (s, 3H) 3.80 (t, J=5.43 Hz, 2H) 4.47 (t, J=5.43 Hz, 2H) 7.28 (d, J=1.77 Hz, 1H) 7.57 (dd, J=8.59, 3.54 Hz, 1H) 7.82 (dd, J=11.37, 8.59 Hz, 1H) 8.52 (s, 1H) 8.74 (d, J=2.78 Hz, 1H) 8.87 (s, 1H) 10.16 (br. s., 1H). MS [M+H] found 397.4.

Example 92

7-(2-(2,5-difluorophenyl)-5,6-dimethylpyrimidin-4-ylamino)-N-ethyl-1H-pyrazolo[4,3-b]pyridine-1-carboxamide

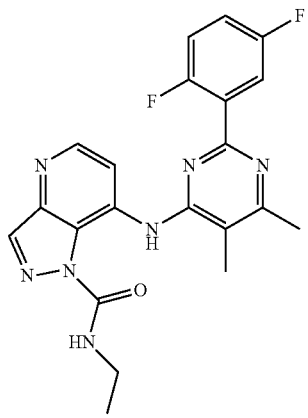 [SMILES: CCNC(=O)n1ncc2nccc(Nc3nc(-c4cc(F)ccc4F)nc(C)c3C)c21]

N-(2-(2,5-Difluorophenyl)-5,6-dimethylpyrimidin-4-yl)-1H-pyrazolo[4,3-b]pyridin-7-amine (0.081 g, 0.230 mmol) was suspended in acetonitrile (2.3 mL), isocyanatoethane (0.018 mL, 0.230 mmol) was added and the mixture was stirred at 70° C. for 2 hours. The reaction was filtered and purified on silica column chromatography using a step gradient of 0 to 5% MeOH in DCM to give the title compound. $^1$H NMR (400 MHz, DMSO-$d_6$) δ ppm 1.20-1.27 (3H, m) 2.40 (3H, s) 2.54 (3H, s) 3.37-3.48 (2H, m) 7.35-7.47 (2H, m) 7.76-7.87 (1H, m) 8.51 (1H, d, J=5.56 Hz) 8.64 (1H, s) 8.97 (1H, d, J=5.31 Hz) 9.11-9.19 (1H, m) 11.94 (1H, s). MS [M+H] found 424.4.

Example 93

7-(2-(2,5-difluorophenyl)pyridin-4-ylamino)-N-ethyl-1H-pyrazolo[4,3-b]pyridine-1-carboxamide

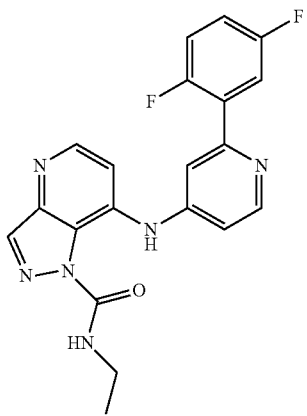 [SMILES: CCNC(=O)n1ncc2nccc(Nc3ccnc(-c4cc(F)ccc4F)c3)c21]

N-(2-(2,5-Difluorophenyl)pyridin-4-yl)-1H-pyrazolo[4,3-b]pyridin-7-amine (50.7 mg, 0.157 mmol) was suspended in acetonitrile (16 mL), isocyanatoethane (12.32 μl, 0.157 mmol) was added and the reaction was stirred at 70° C. for 2 hours, cooled to give a solid. The solid was collected by filtration, rinsed with acetonitrile (3×15 mL) and ether (3×5 mL) and dried under high vacuum to give the title compound. $^1$H NMR (400 MHz, DMSO-$d_6$) δ ppm 1.20 (3H, t, J=7.20 Hz) 3.36-3.46 (2H, m) 7.31-7.47 (3H, m) 7.52 (1H, d, J=5.31 Hz) 7.67 (1H, s) 7.77 (1H, ddd, J=9.47, 6.06, 3.16 Hz) 8.45 (1H, d, J=5.31 Hz) 8.58-8.63 (2H, m) 9.10 (1H, s) 11.43 (1H, s). MS [M+H] found 395.4.

Example 94

7-(2-(2,5-difluorophenyl)pyridin-4-ylamino)-N-methyl-1H-pyrazolo[4,3-b]pyridine-1-carboxamide

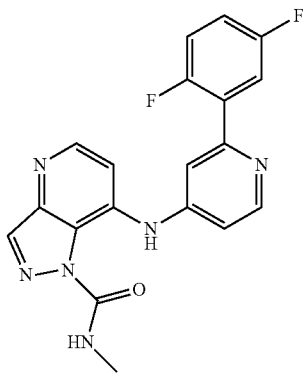 [SMILES: CNC(=O)n1ncc2nccc(Nc3ccnc(-c4cc(F)ccc4F)c3)c21]

To a suspension of N-(2-(2,5-difluorophenyl)pyridin-4-yl)-1H-pyrazolo[4,3-b]pyridin-7-amine (107 mg, 0.331 mmol) in dry dichloroethane (1.7 mL) containing pyridine (46 μL, 0.563 mmol) was added methylcarbamic chloride (30.9 mg, 0.331 mmol) and the mixture was heated at 70° C. for 2 hours. The reaction was then cooled to give a solid which was collected by filtration, rinsed with dichloromethane and purified by column chromatography eluted with step gradient of 0 to 5% MeOH in dichloromethane to give a residue which was dissolved in DMF (4 mL) and further purified with preparative HPLC using a gradient of 20-40% acetonitrile (containing 0.035% TFA) in water (containing 0.05% TFA) using a Sunfire Prep 5 μm C18, 75×30 mm column to give the title compound as a TFA salt. $^1$H NMR (400 MHz, DMSO-$d_6$) δ ppm 2.94 (d, J=4.55 Hz, 3H) 7.40-7.50 (m, 3H) 7.60 (d, J=5.56 Hz, 1H) 7.73 (s, 1H) 7.79 (ddd, J=9.28, 6.00, 3.16 Hz, 1H) 8.52 (d, J=5.56 Hz, 1H) 8.63 (d, J=5.81 Hz, 1H) 8.68 (s, 1H) 9.08 (d, J=4.80 Hz, 1H) 11.69 (br. s., 1H). MS [M+H] found 381.4.

Example 95

N-(6-(2,5-difluorophenyl)-2,3-dimethylpyridin-4-yl)-2H-pyrazolo[4,3-b]pyridin-7-amine

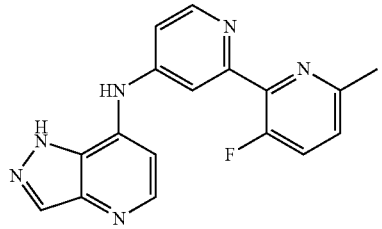 [SMILES: Cc1ccc(F)c(-c2cc(Nc3ccnc4cn[nH]c34)ccn2)n1]

7-Iodo-1H-pyrazolo[4,3-b]pyridine (500 mg, 2.041 mmol) and NaH (103 mg, 60% in oil, 4.08 mmol) were combined in DMF (10 mL) at 25° C. After 10 minutes, the mixture was cooled to 0° C. and 1-(chloromethyl)-4-methoxybenzene (0.297 mL, 2.143 mmol) was added and the mixture stirred for a further 15 minutes. The ice bath was removed and the mixture stirred for 1 hour then diluted with water (150 mL) and saturated ammonium chloride solution (50 mL). The product was extracted into EtOAc. The organic layers were combined, dried over magnesium sulfate, filtered and evaporated in vacuo onto silica and subjected to chromatography on silica eluted with EtOAc in hexanes (0-50%) to give 7-iodo-1-(4-methoxybenzyl)-1H-pyrazolo[4,3-b]pyridine and 7-iodo-2-(4-methoxybenzyl)-2H-pyrazolo[4,3-b]pyridine which was used without further purification.

Diacetoxypalladium (6.90 mg, 0.031 mmol) and 2,2'-bis(diphenylphosphino)-1,1'-binaphthyl (77 mg, 0.123 mmol) were combined in toluene (4 mL) and the solution was stirred at 40° C. for 10 minutes. A mixture of 7-iodo-1-(4-methoxybenzyl)-1H-pyrazolo[4,3-b]pyridine and 7-iodo-1-(4-methoxybenzyl)-2H-pyrazolo[4,3-b]pyridine (290 mg, 0.794 mmol) in toluene (4 mL), 6-(2,5-difluorophenyl)-2,3-dimethylpyridin-4-amine (72 mg, 0.307 mmol) and sodium 2-methylpropan-2-olate (29.5 mg, 0.307 mmol) were added. The reaction mixture was heated at 100° C. for 20 hours. A further 0.2 eq of diacetoxypalladium, 0.4 eq of 2,2'-bis(diphenylphosphino)-1,1'-binaphthyl and 2 eq of sodium 2-methylpropan-2-olate were added and the reaction heated at 100° C.

for 12 hours. The solvent was then evaporated in vacuo to give a residue which was purified via preparative HPLC using a gradient of 5-30% acetonitrile (containing 0.035% TFA) in water (containing 0.05% TFA) using a Sunfire Prep 5 μm C18, 75×30 mm column to give N-(6-(2,5-difluorophenyl)-2,3-dimethylpyridin-4-yl)-1-(4-methoxybenzyl)-2H-pyrazolo[4,3-b]pyridin-7-amine and N-(6-(2,5-difluorophenyl)-2,3-dimethylpyridin-4-yl)-2-(4-methoxybenzyl)-2H-pyrazol[4,3-b]pyridin-7-amine which was used without further purification.

N-(6-(2,5-Difluorophenyl)-2,3-dimethylpyridin-4-yl)-1-(4-methoxybenzyl)-2H-pyrazolo[4,3-b]pyridin-7-amine and N-(6-(2,5-difluorophenyl)-2,3-dimethylpyridin-4-yl)-2-(4-methoxybenzyl)-2H-pyrazolo[4,3-b]pyridin-7-amine was combined in TFA (5 mL) and heated at 70° C. for 12 hours. The reaction mixture was evaporated to give a residue which was purified via preparative HPLC using a gradient of 5-30% acetonitrile (containing 0.035% TFA) in water (containing 0.05% TFA) using a Sunfire Prep 5 μm C18, 75×30 mm column to give the title compound as a TFA salt. $^1$H NMR (400 MHz, METHANOL-d$_4$) δ ppm 1.93 (s, 1H) 2.24 (s, 1H) 2.42 (s, 3H) 2.75 (s, 3H) 6.96 (br. s., 1H) 7.23-7.33 (m, 2H) 7.60 (s, 1H) 7.61-7.68 (m, 1H) 8.44 (s, 2H). MS [M+H] found 352.1

Example 96

N-(2-(2,5-difluorophenyl)-5-methylpyrimidin-4-yl)-1H-pyrazolo[4,3-b]pyridin-7-amine

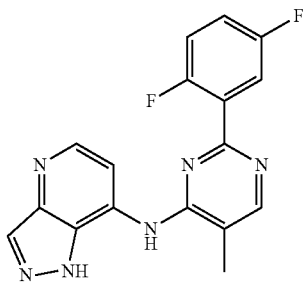 [SMILES: Cc1cnc(-c2cc(F)ccc2F)nc1Nc1ccnc2cn[nH]c12]

Bis(triphenylphosphine)palladium chloride (0.733 g, 1.045 mmol), 2-chloro-5-methylpyrimidin-4-amine (1.5 g, 10.45 mmol), Na$_2$CO$_3$ (5.22 mL, 10.45 mmol) and 2,5-difluorophenylboronic acid (2.145 g, 13.58 mmol) were combined and heated at 95° C. overnight. The reaction was filtered warm through a pad of Celite®, the solids rinsed with dioxane (3×25 mL) and the filtrate was concentrated directly onto a silica chromatography column which was then eluted with EtOAc (0-100%) in hexanes afforded 2-(2,5-difluorophenyl)-5-methylpyrimidin-4-amine. $^1$H NMR (400 MHz, DMSO-d$_6$) δ ppm 2.03 (d, J=0.76 Hz, 3H) 6.82 (br. s., 2H) 7.26-7.33 (m, 2H) 7.57-7.64 (m, 1H) 8.06 (d, J=0.76 Hz, 1H). MS [M+H] found 222.2.

(R)-BINAP (1.396 g, 2.243 mmol), diacetoxypalladium (0.117 g, 0.520 mmol) and toluene (8 mL) were combined and the solution was stirred at 40° C. for 10 minutes. 7-Iodo-2-(4-methoxybenzyl)-2H-pyrazolo[4,3-b]pyridine (1.9 g, 5.20 mmol) suspended in toluene (8 mL), 2-(2,5-difluorophenyl)-5-methylpyrimidin-4-amine (1.151 g, 5.20 mmol) and sodium 2-methylpropan-2-olate (0.750 g, 7.80 mmol) were added and the reaction was then heated at 100° C. overnight. The reaction mixture was cooled, concentrated to give N-(2-(2,5-difluorophenyl)-5-methylpyrimidin-4-yl)-2-(4-methoxybenzyl)-2H-pyrazolo[4,3-b]pyridin-7-amine and N-(2-(2,5-difluorophenyl)-5-methylpyrimidin-4-yl)-1-(4-methoxybenzyl)-1H-pyrazolo[4,3-b]pyridin-7-amine which was used without further purification. MS [M+H] found, 459.4.

N-(2-(2,5-Difluorophenyl)-5-methylpyrimidin-4-yl)-2-(4-methoxybenzyl)-2H-pyrazolo[4,3-b]pyridin-7-amine and N-(2-(2,5-difluorophenyl)-5-methylpyrimidin-4-yl)-1-(4-methoxybenzyl)-1H-pyrazolo[4,3-b]pyridin-7-amine and trifluoroacetic acid (48.0 mL) were combined and heated at 70° C. for 3 hours. The reaction mixture was then concentrated to dryness, suspended in DCM (50 mL) and then poured into a stirred saturated solution of sodium bicarbonate (50 mL). The mixture was sonicated and the solids were filtered and dried under vacuum. The dried solid was subsequently washed with EtOAc and dried under vacuum to give the title compound. $^1$H NMR (400 MHz, DMSO-d$_6$) δ ppm 2.54 (s, 3H) 7.39 (t, J=6.32 Hz, 2H) 7.70 (br. s., 1H) 8.16 (br. s., 1H) 8.41 (br. s., 1H) 8.64 (d, J=5.31 Hz, 1H) 8.71 (s, 1H) 10.24 (br. s., 1H) 14.48 (br. s., 1H). MS [M+H] found, 339.3.

Example 97

7-(2-(2,5-difluorophenyl)-5-methylpyrimidin-4-ylamino)-N-ethyl-1H-pyrazolo[4,3-b]pyridine-1-carboxamide

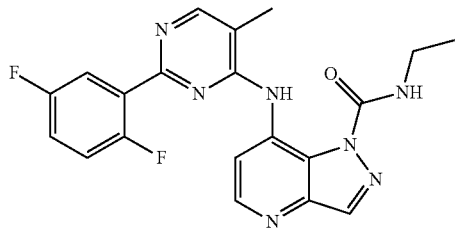 [SMILES: CCNC(=O)n1ncc2nccc(Nc3nc(-c4cc(F)ccc4F)ncc3C)c21]

To N-(2-(2,5-Difluorophenyl)-5-methylpyrimidin-4-yl)-1H-pyrazolo[4,3-b]pyridin-7-amine (108 mg, 0.319 mmol) suspended in acetonitrile (3.2 mL) was added isocyanatoethane (125.3 μl, 1.60 mmol), 15 drops of pyridine and the mixture was heated at 70° C. overnight. The reaction was cooled to give a solid which was collected by filtration, rinsed with a acetonitrile, and dried under high vacuum to give the title compound. $^1$H NMR (400 MHz, DMSO-d$_6$) δ ppm 1.22 (3H, t, J=7.20 Hz) 2.43 (3H, s) 3.37-3.48 (2H, m) 7.36-7.51 (2H, m) 7.85 (1H, ddd, J=9.22, 5.94, 3.03 Hz) 8.47-8.57 (1H, m) 8.65 (1H, s) 9.06 (1H, d, J=5.30 Hz) 9.13 (1H, t, J=5.94 Hz) 12.07 (1H, s). MS [M+H] found 410.4.

Example 98

(R)-1-(7-(3'-fluoro-6'-methyl-2,2'-bipyridin-4-ylamino)-1H-pyrazolo[4,3-b]pyridin-1-yl)propan-2-ol

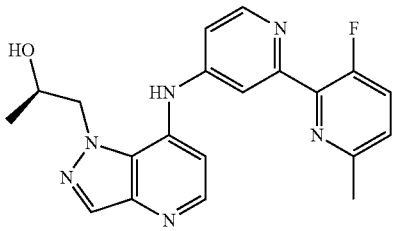 [SMILES: Cc1ccc(F)c(-c2cc(Nc3ccnc4cnn(C[C@@H](C)O)c34)ccn2)n1]

N-(3'-Fluoro-6'-methyl-2,2'-bipyridin-4-yl)-2H-pyrazolo[4,3-b]pyridin-7-amine (33 mg, 0.103 mmol), Cs₂CO₃ (67.1 mg, 0.206 mmol) and (R)-2-methyloxirane (5.98 mg, 0.103 mmol) were combined in DMF (5 mL). The mixture was heated at 120° C. for 30 minutes using a microwave and then purified by preparative HPLC using a Sunfire Prep 5 µm C18, 75×30 mm column eluting with a gradient of 0-40% acetonitrile (containing 0.035% TFA) in water (containing 0.05% TFA) to give the title compound as a TFA salt. ¹H NMR (400 MHz, METHANOL-d₄) δ ppm 1.30 (d, J=6.32 Hz, 3H) 2.72 (s, 3H) 4.25-4.38 (m, 1H) 4.64 (m, 1H) 4.75 (m, 1H) 7.52 (dd, J=6.95, 2.40 Hz, 1H) 7.64 (dd, J=8.59, 3.54 Hz, 1H) 7.69 (d, J=5.05 Hz, 1H) 7.84 (dd, J=11.49, 8.72 Hz, 1H) 8.11 (d, J=2.53 Hz, 1H) 8.36 (s, 1H) 8.53 (d, J=7.07 Hz, 1H) 8.62 (d, J=5.05 Hz, 1H). MS [M+H] found 379.4.

Example 99

1-(6-fluoro-7-(3'-fluoro-5,6'-dimethyl-2,2'-bipyridin-4-ylamino)-2H-pyrazolo[4,3-b]pyridin-2-yl)-2-methylpropan-2-ol

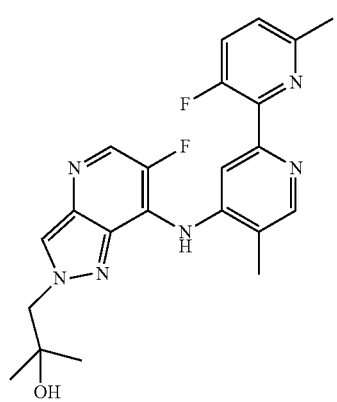 [SMILES: Cc1ccc(F)c(-c2cc(Nc3c(F)cnc4cn(CC(C)(C)O)nc34)c(C)cn2)n1]

To a solution of 7-chloro-6-fluoro-1H-pyrazolo[4,3-b]pyridine (300 mg, 1.749 mmol) in DMF (5 mL) was added Cs₂CO₃ (855 mg, 2.62 mmol) and 1-chloro-2-methylpropan-2-ol (209 mg, 1.924 mmol) and the mixture was heated at 110° C. for 2 hours. Water (20 mL) was then added and the mixture was extracted with EtOAc (2×50 mL). The combined organic layers were dried over Na₂SO₄, filtered, and evaporated to give 1-(7-chloro-6-fluoro-2H-pyrazolo[4,3-b]pyridin-2-yl)-2-methylpropan-2-ol and 1-(7-chloro-6-fluoro-1H-pyrazolo[4,3-b]pyridin-1-yl)-2-methylpropan-2-ol which were used i without further purification. MS [M+H] found 244.2.

To a solution of 1-(7-chloro-6-fluoro-2H-pyrazolo[4,3-b]pyridin-2-yl)-2-methylpropan-2-ol and 1-(7-chloro-6-fluoro-1H-pyrazolo[4,3-b]pyridin-1-yl)-2-methylpropan-2-ol (150 mg, 0.616 mmol), and 3'-fluoro-5,6'-dimethyl-2,2'-bipyridin-4-amine (134 mg, 0.616 mmol) in t-BuOH (15 mL) was added tri(dibenzylidene acetone)dipalladium(0) (56.4 mg, 0.062 mmol), dicyclohexyl(2',4',6'-triisopropylbiphenyl-2-yl)phosphine (58.7 mg, 0.123 mmol) and potassium carbonate (340 mg, 2.462 mmol) and the mixture was heated at 100° C. for 12 hours. The reaction was then cooled, concentrated, and extracted with ethyl acetate (2×75 mL). The combined organic layers were dried over Na₂SO₄, filtered, and concentrated to give a residue which was purified by prep-HPLC using a Sunfire Prep 5 µm C18, 75×30 mm column eluting with a gradient of 20-65% acetonitrile (containing 0.035% TFA) in water (containing 0.05% TFA) to give the title compound as a TFA salt. ¹H NMR (400 MHz, DMSO-d6) δ ppm 0.89 (s, 6H) 2.54 (s, 3H) 2.57 (s, 3H) 4.29 (s, 2H) 7.23 (s, 1H) 7.57 (dd, J=8.59, 3.54 Hz, 1H) 7.80 (dd, J=11.37, 8.59 Hz, 1H) 8.51 (s, 1H) 8.67-8.84 (m, 2H) 10.08 (br. s., 1H). MS [M+H] found 425.4.

Examples 100A and 100B (S)-1-(6-fluoro-7-(3'-fluoro-6'-methyl-2,2'-bipyridin-4-ylamino)-2H-pyrazolo[4,3-b]pyridin-2-yl)propan-2-ol and (S)-1-(6-fluoro-7-(3'-fluoro-6'-methyl-2,2'-bipyridin-4-ylamino)-1H-pyrazolo[4,3-b]pyridin-1-yl)propan-2-ol

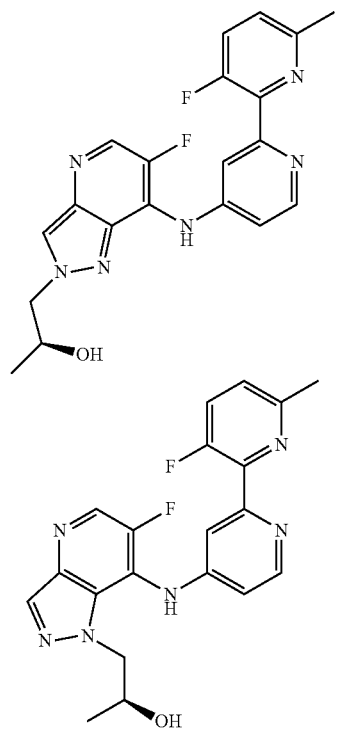

To a solution of 7-chloro-6-fluoro-1H-pyrazolo[4,3-b]pyridine (500 mg, 2.91 mmol) in DMF (5 mL) was added Cs₂CO₃ (1424 mg, 4.37 mmol) and (S)-2-methyloxirane (169 mg, 2.91 mmol) and the mixture was heated at 110° C. for 14 hours. Water (20 mL) was then added and the mixture was extracted with EtOAc (2×50 mL). The combined organic layers were dried over Na₂SO₄, filtered, and evaporated to give a mixture of (S)-1-(7-chloro-6-fluoro-2H-pyrazolo[4,3-b]pyridin-2-yl)propan-2-ol and (S)-1-(7-chloro-6-fluoro-1H-pyrazolo[4,3-b]pyridin-1-yl)propan-2-ol which was used without further purification. MS [M+H] found 230.1.

To a solution of (S)-1-(7-chloro-6-fluoro-2H-pyrazolo[4,3-b]pyridin-2-yl)propan-2-ol and (S)-1-(7-chloro-6-fluoro-1H-pyrazolo[4,3-b]pyridin-1-yl)propan-2-ol in THF (10 mL) was added 3,4-dihydro-2H-pyran (0.332 mL, 3.66 mmol) and p-TSA monohydrate (580 mg, 3.05 mmol) and the mixture was stirred at room temperature for 3 hours and then concentrated to give a residue which was purified on silica gel column chromatography eluted with dichloromethane/Methanol (0-10%) to give 7-chloro-6-fluoro-1-((2S)-2-(tetrahydro-2H-pyran-2-yloxy)propyl)-1H-pyrazolo[4,3-b]pyridine and 7-chloro-6-fluoro-2-((2S)-2-(tetrahydro-2H-pyran-2-yloxy) propyl)-2H-pyrazolo[4,3-b]pyridine which were used in next step. MS [M+H] found 314.3.

To a solution of 7-chloro-6-fluoro-2-((2S)-2-(tetrahydro-2H-pyran-2-yloxy)propyl)-2H-pyrazolo[4,3-b]pyridine and 7-chloro-6-fluoro-2-((2S)-2-(tetrahydro-2H-pyran-2-yloxy) propyl)-1H-pyrazolo[4,3-b]pyridine (155 mg, 0.494 mmol), 3'-fluoro-6'-methyl-2,2'-bipyridin-4-amine (100 mg, 0.494 mmol) in t-BuOH (15 mL) were added tri(dibenzylidene acetone)dipalladium(0) (45.2 mg, 0.049 mmol), dicyclohexyl (2',4',6'-triisopropylbiphenyl-2-yl)phosphine (47.1 mg, 0.099 mmol) and potassium carbonate (273 mg, 1.976 mmol) and the mixture was heated at 100° C. overnight. The reaction was cooled, concentrated, to give a residue which was extracted into ethyl acetate (2×75 mL). The combined organic layers were dried over Na₂SO₄, filtered, and concentrated to give a residue which was purified by preparative HPLC using a Sunfire Prep 5 µm C18, 75×30 mm column eluting with a gradient of 20-65% acetonitrile (containing 0.035% TFA) in water (containing 0.05% TFA) After evaporating to about 3 mL, 1N HCl (3 mL) was added and the mixture was stirred for 1 hour, evaporated, and lyophilized to the title compound as a hydrochloric acid salt. ¹H NMR (400 MHz, DMSO-d6) δ ppm 1.07 (d, J=6.32 Hz, 3H) 2.62 (s, 3H) 3.96-4.18 (m, 1H) 4.23-4.47 (m, 2H) 7.30 (d, J=6.82 Hz, 1H) 7.65 (dd, J=8.59, 3.54 Hz, 1H) 7.86-8.06 (m, 2H) 8.50 (d, J=6.82 Hz, 1H) 8.72 (d, J=3.03 Hz, 1H) 8.83 (s, 1H) 11.51 (br. s., 1H). MS [M+H] found 397.4.

Example 101 and 102

N-(3'-fluoro-6'-methyl-2,2'-bipyridin-4-yl)-1-(2-fluoroethyl)-1H-pyrazolo[4,3-b]pyridin-7-amine and N-(3'-fluoro-6'-methyl-2,2'-bipyridin-4-yl)-2-(2-fluoroethyl)-2H-pyrazolo[4,3-b]pyridin-7-amine

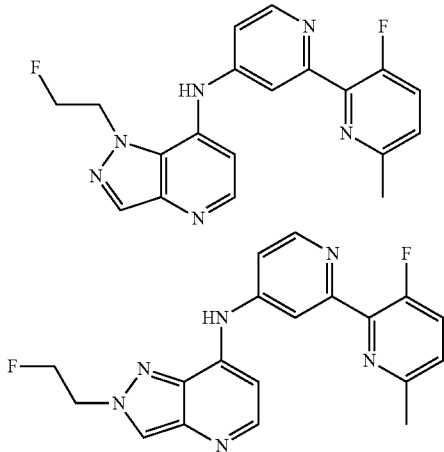

N-(3'-fluoro-6'-methyl-2,2'-bipyridin-4-yl)-1H-pyrazolo [4,3-b]pyridin-7-amine (75 mg, 0.234 mmol), Cs₂CO₃ (153 mg, 0.468 mmol) and 1-bromo-2-fluoroethane (0.017 mL, 0.234 mmol) were combined in anhydrous DMF (3 mL). The suspension was heated by microwave irradiation at 80° C. for 15 minutes. The reaction mixture was purified by preparative HPLC using a Sunfire Prep 5 µm C18, 75×30 mm column eluting with a gradient of 5-35% acetonitrile (containing 0.035% TFA) in water (containing 0.05% TFA) to give the title compounds as TFA salts: N-(3'-fluoro-6'-methyl-2,2'-bipyridin-4-yl)-1-(2-fluoroethyl)-1H-pyrazolo[4,3-b]pyridin-7-amine ¹H NMR (400 MHz, METHANOL-d₄) δ ppm 2.70 (s, 3H) 4.92 (d, J=3.03 Hz, 6H) 4.96-5.15 (m, 2H) 7.57-7.71 (m, 2H) 7.82 (dd, J=12, 8 Hz, 1H) 7.92-8.04 (m, 1H) 8.55 (s, 1H) 8.73 (dd, J=12, 4 Hz, 2H) 8.81 (s, 1H). MS [M+H] found 367.3; and N-(3'-fluoro-6'-methyl-2,2'-bipyridin-4-yl)-2-(2-fluoroethyl)-2H-pyrazolo[4,3-b]pyridin-7-amine ¹H NMR (400 MHz, METHANOL-d₄) δ ppm 2.68 (s, 3H) 4.65 (t, 1H) 4.72-4.79 (m, 1H) 4.79-4.82 (m, 1H) 4.87-4.96 (m, 1H) 7.17 (dd, J=8, 4 Hz, 1H) 7.52 (d, J=4 Hz, 1H) 7.59 (dd, J=12, 4 Hz, 1H) 7.78 (dd, J=8, 8 Hz, 1H) 7.89 (d, J=4 Hz, 1H) 8.33-8.47 (m, 2H) 8.63 (d, J=4 Hz, 1H). MS [M+H] found 367.3.

Example 103

N-(3'-fluoro-6'-methyl-2,2'-bipyridin-4-yl)-1H-pyrazolo[4,3-b]pyridin-7-amine

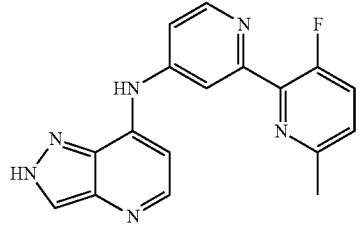 [SMILES: Cc1ccc(F)c(-c2cc(Nc3ccnc4c[nH]nc34)ccn2)n1]

To 7-iodo-1H-pyrazolo[4,3-b]pyridine (500 mg, 2.041 mmol) in DMF (10 mL) at 0° C. was added 1-(chloromethyl)-4-methoxybenzene (0.292 mL, 2.143 mmol) and the reaction was allowed to warm to room temperature over 1 hour. The reaction mixture was then quenched with saturated ammonium chloride solution and extracted with ethyl acetate (50 mL×2). The organic layers were dried over sodium sulfate and concentrated to give a residue which was loaded onto silica and purified using a 0-77% gradient of ethyl acetate in hexanes to give 7-iodo-1-(4-methoxybenzyl)-1H-pyrazolo [4,3-b]pyridine and 7-iodo-2-(4-methoxybenzyl)-2H-pyrazolo[4,3-b]pyridine which was used immediately. MS [M+H] found 366.2.

(9,9-Dimethyl-9H-xanthene-4,5-diyl)bis(diphenylphosphine) (60.0 mg, 0.104 mmol), 7-iodo-1-(4-methoxybenzyl)-1H-pyrazolo[4,3-b]pyridine (757 mg, 2.073 mmol), Pd₂(dba)₃ (95 mg, 0.104 mmol), 3'-fluoro-6'-methyl-2,2'-bipyridin-4-amine (421 mg, 2.073 mmol) and sodium 2-methylpropan-2-olate (598 mg, 6.22 mmol) were combined in dioxane (15 mL) and the mixture was heated at 110° C. for 10 minutes and then at 70° C. over night. The reaction was then cooled and concentrated to give a residue which was loaded onto silica and purified by column chromatography eluting with MeOH in CHCL₃ (0-15%) to give N-(3'-fluoro-6'-methyl-2,2'-bipyridin-4-yl)-1-(4-methoxybenzyl)-1H-pyrazolo[4,3-b]pyridin-7-amine and N-(3'-fluoro-6'-methyl-2,2'-bipyridin-4-yl)-2-(4-methoxybenzyl)-2H-pyrazolo[4,3-b]pyridin-7-amine as solid. MS [M+H] found 441.2.

N-(3'-Fluoro-6'-methyl-2,2'-bipyridin-4-yl)-1-(4-methoxybenzyl)-1H-pyrazolo[4,3-b]pyridin-7-amine and N-(3'-fluoro-6'-methyl-2,2'-bipyridin-4-yl)-2-(4-methoxybenzyl)-2H-pyrazolo[4,3-b]pyridin-7-amine and trifluoroacetic acid (20 mL) were combined and heated at 70° C. for 3 hours. The reaction mixture was then cooled, concentrated give a residue which was suspended in dichloromethane (50 mL) and added to a saturated solution of sodium bicarbonate (50 mL) with stirring. The mixture was sonicated and filtered. The solid was dried under vacuum and suspended in ethyl acetate. The solid again collected by filtration to give N-(3'-fluoro-6'-methyl-2,2'-bipyridin-4-yl)-1H-pyrazolo[4,3-b]pyridin-7-amine. MS [M+H] found 321.3.

Example 104 and 105

2-(2,2-difluoroethyl)-N-(3'-fluoro-6'-methyl-2,2'-bipyridin-4-yl)-2H-pyrazolo[4,3-b]pyridin-7-amine and 1-(2,2-difluoroethyl)-N-(3'-fluoro-6'-methyl-2,2'-bipyridin-4-yl)-1H-pyrazolo[4,3-b]pyridin-7-amine

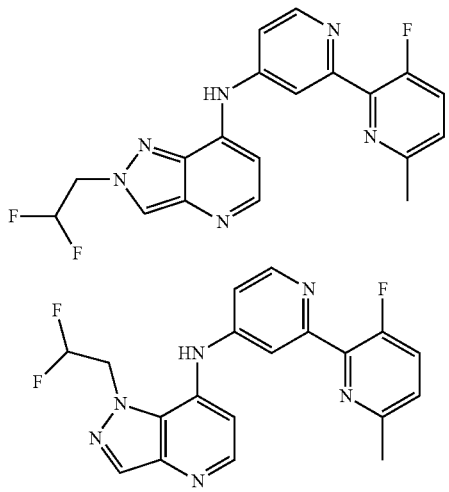

N-(3'-Fluoro-6'-methyl-2,2'-bipyridin-4-yl)-2H-pyrazolo[4,3-b]pyridin-7-amine (46 mg, 0.144 mmol) suspended in DMF (2 mL), was cooled to 0° C. and NaH (5.30 mg, 60% in oil, 0.144 mmol) was added and the mixture was stirred for 5 minutes. 1,1-Difluoro-2-iodoethane (0.016 mL, 0.151 mmol) was added, the mixture was warmed to room temperature and then heated at 65° C. for 15 minutes in a microwave. The reaction mixture was then cooled, concentrated in vacuo to give a residue which was dissolved in MeOH and filtered. The filtrate was purified by preparative HPLC using a using a Sunfire Prep 5 μm C18, 75×30 mm column eluting with a gradient of 15-30% acetonitrile (containing 0.035% TFA) in water (containing 0.05% TFA) to give the title compounds as TFA salts: 1-(2,2-difluoroethyl)-N-(3'-fluoro-6'-methyl-2,2'-bipyridin-4-yl)-1H-pyrazolo[4,3-b]pyridin-7-amine $^1$H NMR (400 MHz, METHANOL-d$_4$) δ ppm 2.68 (s, 3H) 4.98 (td, J=14.21, 3.66 Hz, 2H) 5.86-6.37 (m, 1H) 7.21 (dd, J=7.07, 2.53 Hz, 1H) 7.48-7.63 (m, 2H) 7.77 (dd, J=11.62, 8.59 Hz, 1H) 7.92 (d, J=2.27 Hz, 1H) 8.41 (t, J=3.54 Hz, 2H) 8.56-8.78 (m, 1H), MS [M+H] found 385.3; and 2-(2,2-difluoroethyl)-N-(3'-fluoro-6'-methyl-2,2'-bipyridin-4-yl)-2H-pyrazolo[4,3-b]pyridin-7-amine $^1$H NMR (400 MHz, METHANOL-d$_4$) δ ppm 2.70 (s, 3H) 5.11 (td, J=14.27, 3.54 Hz, 2H) 6.13-6.74 (m, 1H) 7.56-7.71 (m, 2H) 7.76-7.91 (m, 1H) 7.97 (d, J=6.06 Hz, 1H) 8.53 (br. s., 1H) 8.73 (d, J=4.04 Hz, 2H) 8.84 (s, 1H). MS [M+H] found 385.3.

Example 106 and 107

(S)-1-(7-(3'-fluoro-6'-methyl-2,2'-bipyridin-4-ylamino)-1H-pyrazolo[4,3-b]pyridin-1-yl)propan-2-ol and (S)-1-(7-(3'-fluoro-6'-methyl-2,2'-bipyridin-4-ylamino)-2H-pyrazolo[4,3-b]pyridin-2-yl)propan-2-ol

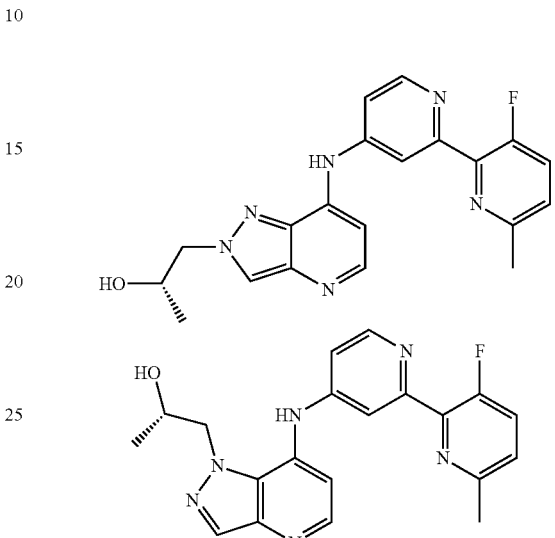

N-(3'-Fluoro-6'-methyl-2,2'-bipyridin-4-yl)-1H-pyrazolo[4,3-b]pyridin-7-amine (97 mg, 0.303 mmol) was dissolved in DMF (2 mL) and cooled to 0° C. Sodium hydride (11.18 mg, 60% in oil, 0.303 mmol) was added and the mixture stirred for 5 minutes. (S)-2-Methyloxirane (0.021 mL, 0.303 mmol) was added, the reaction vessel was sealed, and stirred for 5 minutes at room temperature and then heated in a microwave at 100° C. for 1.5 hours. The reaction mixture was cooled and purified by preparative HPLC using a Sunfire Prep 5 μm C18, 75×30 mm column eluting with a gradient of 5-25% acetonitrile (containing 0.035% TFA) in water (containing 0.05% TFA) to give a residue which was further purified by preparative HPLC using a Sunfire Prep 5 μm C18, 75×30 mm column eluting with a gradient of 20-35% acetonitrile (containing 10 mM NH$_4$HCO$_3$) in water (containing 10 mM NH$_4$HCO$_3$) to give the title compounds: (S)-1-(7-(3'-fluoro-6'-methyl-2,2'-bipyridin-4-ylamino)-1H-pyrazolo[4,3-b]pyridin-1-yl)propan-2-ol $^1$H NMR (400 MHz, METHANOL-d4) δ ppm 1.23 (d, J=4 Hz, 3H) 2.59 (s, 3H) 4.21-4.34 (m, 1H) 4.34-4.44 (m, 1H) 4.51 (dd, J=16, 4 Hz, 1H) 7.25 (d, J=4 Hz, 1H) 7.40 (br. s., 1H) 7.49 (br. s., 1H) 7.57-7.68 (m, 1H) 7.86 (br. s., 1H) 8.33 (d, J=4 Hz, 1H) 8.37 (s, 1H) 8.53 (br. s., 1H), MS [M+H] found 379.4; and (S)-1-(7-(3'-fluoro-6'-methyl-2,2'-bipyridin-4-ylamino)-2H-pyrazolo[4,3-b]pyridin-2-yl)propan-2-ol as a tan solid (12 mg). $^1$H NMR (400 MHz, METHANOL-d$_4$) δ ppm 1.27 (d, J=4 Hz, 3H) 2.68 (s, 3H) 4.20-4.36 (m, 1H) 4.63 (dd, J=12, 4 Hz, 1H) 4.69-4.78 (m, 1H) 7.53 (dd, J=4, 4 Hz, 1H) 7.60 (dd, J=8, 4 Hz, 1H) 7.70 (d, J=4 Hz, 1H) 7.80 (dd, J=12, 12 Hz, 1H) 8.10 (s, 1H) 8.34 (s, 1H) 8.52 (d, J=8 Hz, 1H) 8.56-8.66 (m, 1H). MS [M+H] found 379.4.

Example 108

N-(2-(2,5-difluorophenyl)-5-methylpyridin-4-yl)-1H-pyrazolo[4,3-b]pyridin-7-amine

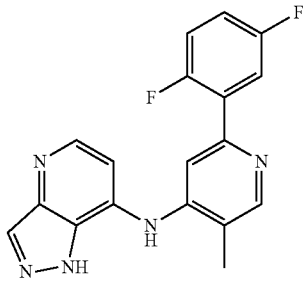 [SMILES: Cc1cnc(-c2cc(F)ccc2F)cc1Nc1ccnc2cn[nH]c12]

Bis(triphenylphosphine)palladium chloride (0.927 g, 1.321 mmol), 2-bromo-5-methylpyridin-4-amine (2.47 g, 13.21 mmol), Na$_2$CO$_3$ (6.60 mL, 13.21 mmol) and 2,5-difluorophenylboronic acid (2.71 g, 17.17 mmol) were combined and heated at 95° C. overnight. The reaction was cooled, filtered through a pad of Celite®, and concentrated directly onto silica gel and then purified by column chromatography (NH, silica) eluted with EtOAc/hexanes (0-100%) to give 2-(2,5-difluorophenyl)-5-methylpyridin-4-amine. $^1$H NMR (400 MHz, DMSO-d$_6$) δ ppm 2.05 (3H, s) 5.96 (2H, s) 7.04 (1H, d, J=2.02 Hz) 7.20-7.29 (1H, m) 7.29-7.38 (1H, m) 7.68 (1H, ddd, J=9.73, 6.19, 3.28 Hz) 8.02 (1H, s). MS [M+H] found 221.2.

(R)-BINAP (1.396 g, 2.243 mmol), diacetoxypalladium (0.117 g, 0.520 mmol) and toluene (15 mL) were combined and stirred at 40° C. for 10 minutes. 7-Iodo-2-(4-methoxybenzyl)-2H-pyrazolo[4,3-b]pyridine (1.9 g, 5.20 mmol) suspended in toluene (20 mL), 2-(2,5-difluorophenyl)-5-methylpyridin-4-amine (1.146 g, 5.20 mmol) and sodium 2-methylpropan-2-olate (0.750 g, 7.80 mmol) were added and the mixture was heated at 100° C. overnight. The reaction mixture was then cooled, diluted with MeOH (10 mL) and absorbed directly onto silica and purified by column chromatography (NH silica column), eluted with EtOAc/hexanes (50-100%) to give N-(2-(2,5-difluorophenyl)-5-methylpyridin-4-yl)-1-(4-methoxybenzyl)-1H-pyrazolo[4,3-b]pyridin-7-amine and N-(2-(2,5-difluorophenyl)-5-methylpyridin-4-yl)-2-(4-methoxybenzyl)-2H-pyrazolo[4,3-b]pyridin-7-amine.

N-(2-(2,5-Difluorophenyl)-5-methylpyridin-4-yl)-1-(4-methoxybenzyl)-1H-pyrazolo[4,3-b]pyridin-7-amine and N-(2-(2,5-difluorophenyl)-5-methylpyridin-4-yl)-2-(4-methoxybenzyl)-2H-pyrazolo[4,3-b]pyridin-7-amine and trifluoroacetic acid (35.0 mL) were combined and heated at 70° C. for 3 hours. The reaction was then cooled and concentrated to give a residue which was dissolved in dichloromethane (75 mL) and added with stirring to a saturated sodium bicarbonate solution (50 mL) to give a solid. The solid was collected by filtration and dissolved in ethyl acetate (500 mL) which was extracted with brine (50 mL), dried over magnesium sulfate, filtered, and concentrated to give title compound. $^1$H NMR (400 MHz, DMSO-d$_6$) δ ppm 2.37 (3H, s) 7.09 (1H, d, J=4.80 Hz) 7.26-7.36 (2H, m) 7.50 (1H, s) 7.75 (1H, ddd, J=9.54, 6.13, 3.28 Hz) 8.24 (1H, d, J=1.26 Hz) 8.35 (1H, d, J=5.05 Hz) 8.43 (1H, s) 8.50 (1H, s) 13.03 (1H, s). MS [M+H] found 338.3.

Example 109

7-(2-(2,5-difluorophenyl)-5-methylpyridin-4-ylamino)-N-ethyl-1H-pyrazolo[4,3-b]pyridine-1-carboxamide

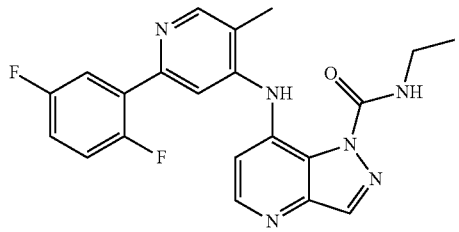 [SMILES: CCNC(=O)n1ncc2nccc(Nc3cc(-c4cc(F)ccc4F)ncc3C)c21]

Bis(triphenylphosphine)palladium chloride (0.927 g, 1.321 mmol), 2-bromo-5-methylpyridin-4-amine (2.47 g, 13.21 mmol), sodium carbonate (6.60 mL, 13.21 mmol) and 2,5-difluorophenylboronic acid (2.71 g, 17.17 mmol) were combined and heated at 95° C. overnight. The reaction was cooled and filtered through a pad of Celite®, rinsed with dioxane (3×50 mL) and the filtrate was concentrated directly onto silica gel and then purified by column chromatography on NH silica eluted with 0-100% ethyl acetate/hexanes to give 2-(2,5-difluorophenyl)-5-methylpyridin-4-amine. $^1$H NMR (400 MHz, DMSO-d6) δ ppm 2.05 (3H, s) 5.96 (2H, s) 7.04 (1H, d, J=2.02 Hz) 7.20-7.29 (1H, m) 7.29-7.38 (1H, m) 7.68 (1H, ddd, J=9.73, 6.19, 3.28 Hz) 8.02 (1H, s). MS [M+H] found 221.2

(R)-BINAP (1.396 g, 2.243 mmol), diacetoxypalladium (0.117 g, 0.520 mmol) and toluene (15 mL) were combined and stirred at 40° C. for 10 minutes. 7-Iodo-1-(4-methoxybenzyl)-1H-pyrazolo[4,3-b]pyridine and 7-iodo-2-(4-methoxybenzyl)-2H-pyrazolo[4,3-b]pyridine (1.9 g, 5.20 mmol) suspended in toluene (20 mL), 2-(2,5-difluorophenyl)-5-methylpyridin-4-amine (1.146 g, 5.20 mmol) and sodium 2-methylpropan-2-olate (0.750 g, 7.80 mmol) were added and reaction mixture was then heated at 100° C. The mixture was then cooled, diluted with MeOH (10 mL), and absorbed directly onto silica (about 8 g) and then purified by column chromatography on NH silica eluted with a gradient of 50-100% ethyl acetate/hexanes to give. MS [M+H] found 458.4

N-(2-(2,5-Difluorophenyl)-5-methylpyridin-4-yl)-1-(4-methoxybenzyl)-1H-pyrazolo[4,3-b]pyridin-7-amine and N-(2-(2,5-difluorophenyl)-5-methylpyridin-4-yl)-2-(4-methoxybenzyl)-2H-pyrazolo[4,3-b]pyridin-7-amine and trifluoroacetic acid (35 mL) were combined and heated at 70° C. for 3 hours, then cooled to room temperature and stirred overnight. The reaction mixture was then concentrated in vacuo to give a residue which was dissolved in dichloromethane (75 mL) and was poured into a saturated solution of sodium bicarbonate (50 mL) to give a solid which was collected by filtration and dissolved in ethyl acetate (500 mL), washed with brine (50 mL), dried over magnesium sulfate, filtered and concentrated to give N-(2-(2,5-difluorophenyl)-5-methylpyridin-4-yl)-1H-pyrazolo[4,3-b]pyridin-7-amine. $^1$H NMR (400 MHz, DMSO-d6) δ ppm 2.37 (3H, s) 7.09 (1H, d, J=4.80 Hz) 7.26-7.36 (2H, m) 7.50 (1H, s) 7.75 (1H, ddd, J=9.54, 6.13, 3.28 Hz) 8.24 (1H, d, J=1.26 Hz) 8.35 (1H, d, J=5.05 Hz) 8.43 (1H, s) 8.50 (1H, s) 13.03 (1H, s). MS [M+H] found 337.3.

N-(2-(2,5-Difluorophenyl)-5-methylpyridin-4-yl)-1H-pyrazolo[4,3-b]pyridin-7-amine (106 mg, 0.314 mmol) was suspended in acetonitrile (3.1 mL). Isocyanatoethane (30.8 μl, 0.393 mmol) and 1 drop of pyridine were added and the mixture was heated at 75° C. for 2 hours. The mixture was cooled to give a solid which was collected by filtration to give the title compound. $^1$H NMR (400 MHz, DMSO-$d_6$) δ ppm 1.20 (3H, t, J=7.07 Hz) 2.38 (3H, s) 3.34-3.45 (2H, m) 7.25-7.42 (3H, m) 7.76 (1H, ddd, J=9.47, 6.06, 3.16 Hz) 7.93 (1H, s) 8.41 (1H, d, J=5.30 Hz) 8.54 (1H, s) 8.60 (1H, s) 9.09 (1H, t, J=5.81 Hz) 11.05 (1H, s). MS [M+H] found 409.4.

Example 110

7-(2-(2,5-difluorophenyl)-5-methylpyridin-4-ylamino)-N-isopropyl-1H-pyrazolo[4,3-b]pyridine-1-carboxamide

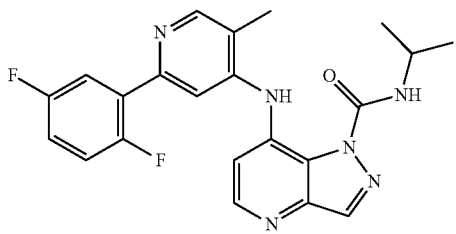 [SMILES: Cc1cnc(-c2cc(F)ccc2F)cc1Nc1ccnc2cnn(C(=O)NC(C)C)c12]

N-(2-(2,5-Difluorophenyl)-5-methylpyridin-4-yl)-1H-pyrazolo[4,3-b]pyridin-7-amine (100 mg, 0.296 mmol) was suspended in acetonitrile (3 mL). 2-Isocyanatopropane (29.1 μl, 0.296 mmol) was added and the reaction was stirred at 70° C. for 2 hours. The mixture was then cooled to give a solid which was collected by filtration to give the title compound. $^1$H NMR (400 MHz, DMSO-$d_6$) δ ppm 1.27 (6H, d, J=6.57 Hz) 2.38 (3H, s) 4.05-4.19 (1H, m) 7.26-7.45 (3H, m) 7.76 (1H, ddd, J=9.41, 6.13, 3.16 Hz) 7.93 (1H, s) 8.35-8.44 (1H, m) 8.54 (1H, s) 8.60 (1H, s) 8.82 (1H, d, J=8.34 Hz) 11.01 (1H, s). MS [M+H] found 423.5.

Example 111

2-(7-(3'-fluoro-6'-methyl-2,2'-bipyridin-4-ylamino)-2H-pyrazolo[4,3-b]pyridin-2-yl)-N-methylacetamide

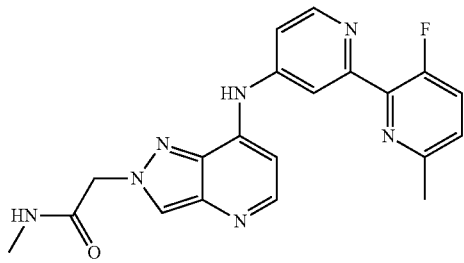 [SMILES: CNC(=O)Cn1cc2nccc(Nc3ccnc(-c4nc(C)ccc4F)c3)c2n1]

N-(3'-Fluoro-6'-methyl-2,2'-bipyridin-4-yl)-1H-pyrazolo[4,3-b]pyridin-7-amine (50 mg, 0.156 mmol) and NaH (3.75 mg, 60% in oil, 0.15 mmol) were combined in DMF (2 mL). 2-Bromo-N-methylacetamide (23.72 mg, 0.15 mmol) was added and the mixture heated in a microwave at 80° C. for 15 minutes and then at 100° C. for 30 minutes and finally at 110° C. for a further 45 minutes. The reaction mixture was cooled and purified by preparative HPLC using a Sunfire Prep 5 μm C18, 75×30 mm column eluting with a gradient of 20-25% acetonitrile (containing 10 mM NH$_4$HCO$_3$) in water (containing 10 mM NH$_4$HCO$_3$) to give the title compound. $^1$H NMR (400 MHz, METHANOL-$d_4$) δ ppm 2.60 (s, 3H) 2.81 (s, 3H) 5.11 (s, 2H) 7.08 (br. s., 1H) 7.41 (d, J=8 Hz, 1H) 7.50 (br. s., 1H) 7.65 (t, J=12 Hz, 1H) 7.92 (br. s., 1H) 8.08 (d, J=8 Hz, 1H) 8.28 (br. s., 1H) 8.68 (br. s., 1H) MS [M+H] found 392.1.

Examples 112 and 113

1,1,1-trifluoro-3-(7-(3'-fluoro-6'-methyl-2,2'-bipyridin-4-ylamino)-2H-pyrazolo[4,3-b]pyridin-2-yl)propan-2-ol and 1,1,1-trifluoro-3-(7-(3'-fluoro-6'-methyl-2,2'-bipyridin-4-ylamino)-1H-pyrazolo[4,3-b]pyridin-1-yl)propan-2-ol

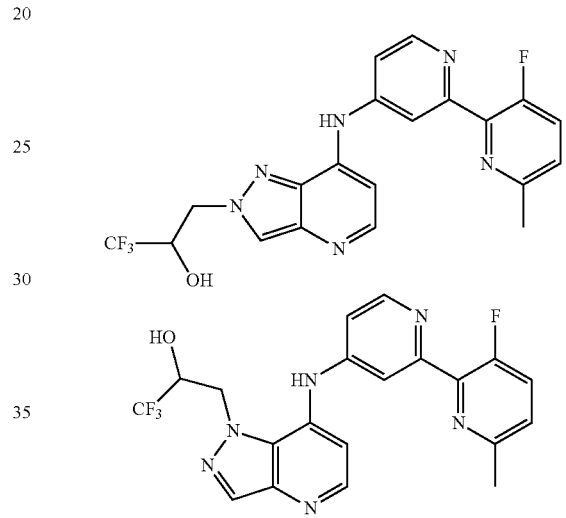

N-(3'-Fluoro-6'-methyl-2,2'-bipyridin-4-yl)-2H-pyrazolo[4,3-b]pyridin-7-amine (83 mg, 0.259 mmol) was dissolved in DMF (2 mL), cooled to 0° C. and NaH (9.57 mg, 60% in oil, 0.259 mmol) was added. The reaction mixture was stirred for 5 minutes and 2-(trifluoromethyl)oxirane (0.021 mL, 0.272 mmol) was added and the reaction was warmed to room temperature for 5 minutes then heated in a microwave at 65° C. for 15 minutes. The reaction mixture was cooled, concentrated in vacuo to give a residue which was combined in MeOH and filtered. The filtrate was purified by preparative HPLC using a Sunfire Prep 5 μm C18, 75×30 mm column 5 μm C18, 75×30 mm column eluting with a gradient of 5-30% 5-40% acetonitrile (containing 0.035% TFA) in water (containing 0.05% TFA) to give the title compounds as TFA salts:

1,1,1-trifluoro-3-(7-(3'-fluoro-6'-methyl-2,2'-bipyridin-4-ylamino)-1H-pyrazolo[4,3-b]pyridin-1-yl)propan-2-ol $^1$H NMR (400 MHz, METHANOL-$d_4$) δ ppm 2.68 (s, 3H) 4.44 (td, J=7.45, 4.04 Hz, 1H) 4.84-4.88 (m, 2H) 7.36 (dd, J=6.95, 2.40 Hz, 1H) 7.59 (dd, J=8.59, 3.54 Hz, 1H) 7.66 (d, J=5.05 Hz, 1H) 7.78 (dd, J=11.37, 8.59 Hz, 1H) 7.98 (d, J=2.02 Hz, 1H) 8.40 (s, 1H) 8.47 (d, J=6.82 Hz, 1H) 8.65 (d, J=4.80 Hz, 1H) and 1,1,1-trifluoro-3-(7-(3'-fluoro-6'-methyl-2,2'-bipyridin-4-ylamino)-2H-pyrazolo[4,3-b]pyridin-2-yl)propan-2-ol $^1$H NMR (400 MHz, METHANOL-$d_4$) δ ppm 2.70 (s, 3H) 4.52-4.73 (m, 1H) 4.81 (dd, J=13.77, 8.97 Hz, 1H) 4.96 (dd, J=13.64, 3.03 Hz, 1H) 7.55-7.72 (m, 2H) 7.83 (dd, J=11.24, 8.72 Hz, 1H) 7.99 (dd, J=6.69, 2.40 Hz, 1H) 8.57 (d, J=2.53

Hz, 1H) 8.75 (d, J=6.57 Hz, 1H) 8.72 (d, J=6.06 Hz, 1H) 8.83 (s, 1H), MS [M+H] found 433.4

Example 114

(R)-1-(7-(3'-fluoro-6'-methyl-2,2'-bipyridin-4-ylamino)-2H-pyrazolo[4,3-b]pyridin-2-yl)propan-2-ol

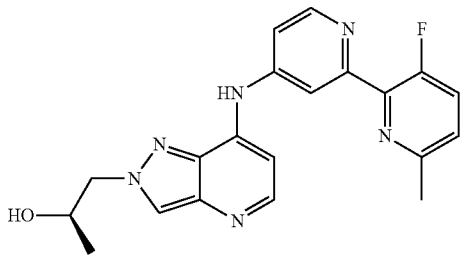 [SMILES: Cc1ccc(F)c(-c2cc(Nc3ccnc4cn(C[C@@H](C)O)nc34)ccn2)n1]

N-(3'-Fluoro-6'-methyl-2,2'-bipyridin-4-yl)-2H-pyrazolo[4,3-b]pyridin-7-amine (33 mg, 0.103 mmol), $Cs_2CO_3$ (67.1 mg, 0.206 mmol) and (R)-2-methyloxirane (5.98 mg, 0.103 mmol) were combined in DMF (5 mL). The mixture was heated in a microwave at 120° C. for 30 minutes. The reaction mixture was cooled and purified by preparative HPLC using a Sunfire Prep 5 μm C18, 75×30 mm column eluting with a gradient of 0-40% acetonitrile (containing 0.035% TFA) in water (containing 0.05% TFA) to give the title compound as a TFA salt. $^1$H NMR (400 MHz, METHANOL-$d_4$) δ ppm 1.30 (d, J=6.32 Hz, 3H) 2.72 (s, 3H) 4.28-4.44 (m, 1H) 4.51 (m, 1H) 4.67 (m, 1H) 7.55-7.65 (m, 2H) 7.80-7.90 (m, 2H) 8.44 (d, J=2.53 Hz, 1H) 8.66 (d, J=6.06 Hz, 1H) 8.70-8.74 (m, 2H), MS [M+H] found 379.4.

Example 115

N-ethyl-7-(3'-fluoro-5,6'-dimethyl-2,2'-bipyridin-4-ylamino)-1H-pyrazolo[4,3-b]pyridine-1-carboxamide

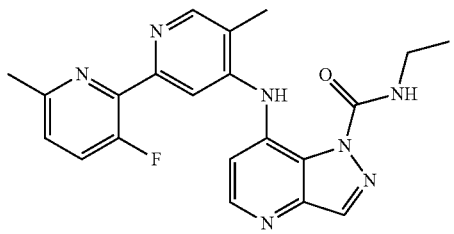 [SMILES: CCNC(=O)n1ncc2nccc(Nc3cc(-c4nc(C)ccc4F)ncc3C)c21]

N-(3'-Fluoro-5,6'-dimethyl-2,2'-bipyridin-4-yl)-1H-pyrazolo[4,3-b]pyridin-7-amine (81 mg, 0.242 mmol) was combined with acetonitrile (2.4 mL) and isocyanatoethane (23.78 μl, 0.303 mmol) along with 1 drop of pyridine. The mixture was heated at 75° C. The reaction was then cooled to give a solid which was collected by filtration, rinsed with acetonitrile to give the title compound. $^1$H NMR (400 MHz, CHLOROFORM-d) δ ppm 1.35 (3H, t, J=7.20 Hz) 2.47 (3H, s) 2.64 (3H, s) 3.51-3.63 (2H, m) 7.17-7.23 (1H, m) 7.33 (1H, d, J=4.55 Hz) 7.43 (1H, dd, J=10.48, 8.46 Hz) 7.51-7.59 (1H, m) 8.08 (1H, br. s.) 8.27 (1H, s) 8.41 (1H, d, J=5.31 Hz) 8.65 (1H, br. s.) 11.00 (1H, br. s.). MS [M+H] found 406.4.

Example 116

7-(2-(2,5-difluorophenyl)-5-methylpyridin-4-ylamino)-N-methyl-1H-pyrazolo[4,3-b]pyridine-1-carboxamide

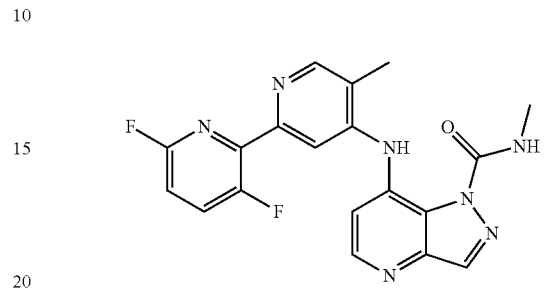

To N-(2-(2,5-difluorophenyl)-5-methylpyridin-4-yl)-1H-pyrazolo[4,3-b]pyridin-7-amine (100 mg, 0.296 mmol) in dry dichloroethane (1.5 mL) was added pyridine (81.6 μl, 1.01 mmol) and methylcarbamic chloride (55.4 mg, 0.592 mmol). The reaction mixture was heated at 70° C. for 1 day, cooled combined with DMSO (20 mL) and purified by preparative HPLC using a gradient of 25-40% acetonitrile (containing 0.035% TFA) in water (containing 0.05% TFA) using a Sunfire Prep 5 μm C18, 75×30 mm column to give the title compounds as a TFA salt. $^1$H NMR (400 MHz, DMSO-$d_6$) δ ppm 2.42 (3H, s) 2.93 (3H, d, J=4.80 Hz) 7.32-7.48 (3H, m) 7.78 (1H, ddd, J=9.41, 6.00, 3.03 Hz) 7.94 (1H, s) 8.46 (1H, d, J=5.31 Hz) 8.59 (1H, s) 8.65 (1H, s) 9.04 (1H, d, J=4.29 Hz) 11.28 (1H, br. s.). MS [M+H] found 395.4.

Examples 117 and 118

N-cyclopropyl-2-(7-(3'-fluoro-5,6'-dimethyl-2,2'-bipyridin-4-ylamino)-1H-pyrazolo[4,3-b]pyridin-1-yl)acetamide and N-cyclopropyl-2-(7-(3'-fluoro-5,6'-dimethyl-2,2'-bipyridin-4-ylamino)-2H-pyrazolo[4,3-b]pyridin-2-yl)acetamide

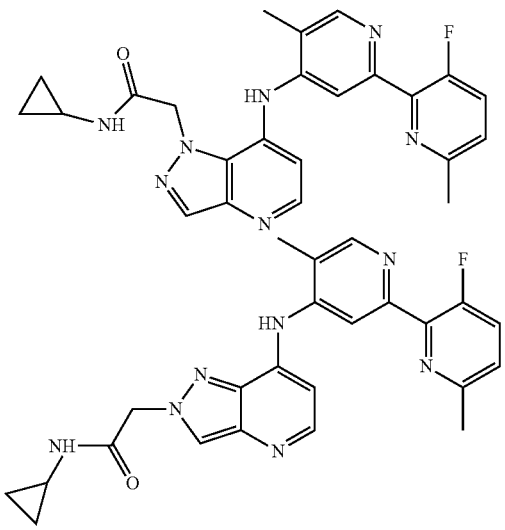

To a solution of 2-bromoacetyl chloride (0.529 mL, 6.35 mmol) in DCM (10 mL) at −78° C. was added triethyl amine (0.886 mL, 6.35 mmol) followed by cyclopropanamine (0.446 mL, 6.35 mmol) and the mixture was warmed to room temperature overnight. The crude reaction mixture was evaporated onto silica and purified using column chromatography eluted with 0-80% EtOAc in hexane to give 2-bromo-N-cyclopropylacetamide which was used without further purification.

To a solution of N-(3'-fluoro-5,6'-dimethyl-2,2'-bipyridin-4-yl)-1H-pyrazolo[4,3-b]pyridin-7-amine (50 mg, 0.150 mmol) in DMF (2 mL) was added NaH (5.98 mg, 60% in oil, 0.150 mmol). 2-Bromo-N-cyclopropylacetamide (26.6 mg, 0.150 mmol) was added, the vessel sealed and the reaction mixture was heated in a microwave at 100° C. for 15 minutes and then 80° C. for 10 minutes. The reaction mixture was then cooled and purified by preparative HPLC using a Sunfire Prep 5 μm C18, 75×30 mm column eluting with a isocratic gradient of 30-30% acetonitrile (containing 10 mM $NH_4HCO_3$) in water (containing 10 mM $NH_4HCO_3$) to give the title compounds: N-cyclopropyl-2-(7-(3'-fluoro-5,6'-dimethyl-2,2'-bipyridin-4-ylamino)-1H-pyrazolo[4,3-b]pyridin-1-yl)acetamide $^1$H NMR (400 MHz, MeOD) δ ppm 0.53-0.61 (m, 2H) 0.68-0.80 (m, 2H) 2.46 (s, 3H) 2.59 (s, 3H) 2.73 (m, 1H) 5.19 (s, 2H) 7.01 (d, J=4 Hz, 1H) 7.38 (dd, J=12, 4 Hz, 1H) 7.55-7.68 (m, 1H) 7.97 (s, 1H) 8.32 (d, J=8 Hz, 1H) 8.44 (s, 1H) 8.52 (s, 1H), MS [M+H] found 432.4; and N-cyclopropyl-2-(7-(3'-fluoro-5,6'-dimethyl-2,2'-bipyridin-4-ylamino)-2H-pyrazolo[4,3-b]pyridin-2-yl)acetamide $^1$H NMR (400 MHz, MeOD) δ ppm 0.36-0.48 (m, 2H) 0.61-0.73 (m, 2H) 2.52 (br. s., 3H) 2.59 (m, 1H) 2.64 (s, 3H) 5.26 (br. s., 2H) 7.52 (dd, J=8, 4 Hz, 1H) 7.59 (br. s., 1H) 7.69 (dd, J=12, 12 Hz, 1H) 7.92 (s, 1H) 8.28 (br. s., 1H) 8.41 (br. s., 1H) 8.58 (br. s., 1H), MS [M+H] found 432.4.

Example 119

4-(7-(3'-fluoro-6'-methyl-2,2'-bipyridin-4-ylamino)-2H-pyrazolo[4,3-b]pyridin-2-yl)-2-methylbutan-2-ol

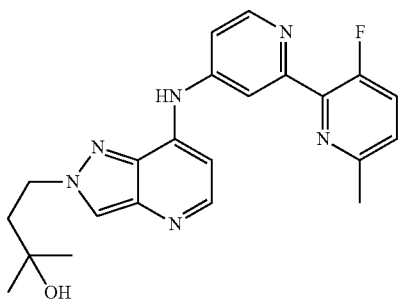 [SMILES: Cc1ccc(F)c(-c2cc(Nc3ccnc4cn(CCC(C)(C)O)nc34)ccn2)n1]

7-Iodo-2H-pyrazolo[4,3-b]pyridine (342 mg, 1.396 mmol), 4-bromo-2-methylbutan-2-ol (233 mg, 1.396 mmol) and $Cs_2CO_3$ (455 mg, 1.396 mmol) were combined in DMF (5 mL) and heated in a microwave at 120° C. for 60 minutes. The reaction was cooled, filtered, and concentrated to give a residue which purified on a silica column and eluted using a step gradient of EtOAc (0-90%) in hexanes to give 4-(7-iodo-2H-pyrazolo[4,3-b]pyridin-2-yl)-2-methylbutan-2-ol and 4-(7-iodo-1H-pyrazolo[4,3-b]pyridin-1-yl)-2-methylbutan-2-ol.

(9,9-Dimethyl-9H-xanthene-4,5-diyl)bis(diphenylphosphine) (11.01 mg, 0.019 mmol), 4-(7-iodo-2H-pyrazolo[4,3-b]pyridin-2-yl)-2-methylbutan-2-ol (126 mg, 0.380 mmol), $Pd_2(dba)_3$ (17.42 mg, 0.019 mmol), 3'-fluoro-6'-methyl-2,2'-bipyridin-4-amine (77 mg, 0.380 mmol) and sodium 2-methylpropan-2-olate (110 mg, 1.141 mmol) were combined in dioxane (15 mL) and heated at 110° C. for 45 minutes. The reaction mixture was then cooled, concentrated in vacuo to give a residue which was combined with MeOH and filtered. The filtrate was then purified by preparative HPLC using a Sunfire Prep 5 μm C18, 75×30 mm column eluting with a gradient of 15-40% acetonitrile (containing 0.035% TFA) in water (containing 0.05% TFA) to give the title compound as a TFA salt. $^1$H NMR (400 MHz, METHANOL-$d_4$) δ ppm 1.17 (s, 6H) 1.99-2.08 (m, 2H) 2.69 (s, 3H) 4.70-4.81 (m, 2H) 7.45 (dd, J=6.95, 2.40 Hz, 1H) 7.61 (dd, J=8.59, 3.54 Hz, 1H) 7.71 (d, J=5.31 Hz, 1H) 7.79 (dd, J=11.49, 8.72 Hz, 1H) 8.10 (d, J=2.27 Hz, 1H) 8.38 (s, 1H) 8.53 (d, J=7.07 Hz, 1H) 8.66 (d, J=5.56 Hz, 1H). MS [M+H] found 407.5.

Example 120

4-(7-(3'-fluoro-5,6'-dimethyl-2,2'-bipyridin-4-ylamino)-2H-pyrazolo[4,3-b]pyridin-2-yl)-2-methylbutan-2-ol

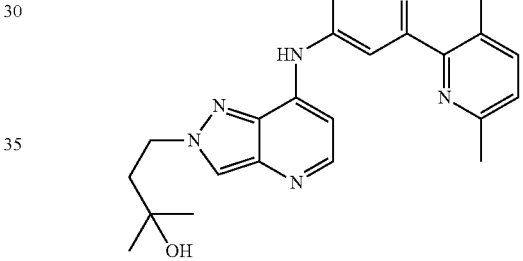

7-Iodo-2H-pyrazolo[4,3-b]pyridine (342 mg, 1.396 mmol), 4-bromo-2-methylbutan-2-ol (233 mg, 1.396 mmol) and $Cs_2CO_3$ (455 mg, 1.396 mmol) were combined in DMF (5 mL) and heated in a microwave at 120° C. for 60 minutes. The reaction was cooled, filtered, and concentrated to give a residue which was purified by silica column eluted using a step gradient of EtOAc (0-90%) in hexanes to give 4-(7-iodo-2H-pyrazolo[4,3-b]pyridin-2-yl)-2-methylbutan-2-ol.

(9,9-Dimethyl-9H-xanthene-4,5-diyl)bis(diphenylphosphine) (11.01 mg, 0.019 mmol), 4-(7-iodo-2H-pyrazolo[4,3-b]pyridin-2-yl)-2-methylbutan-2-ol (126 mg, 0.380 mmol), $Pd_2(dba)_3$ (17.42 mg, 0.019 mmol), 3'-fluoro-5,6'-dimethyl-2,2'-bipyridin-4-amine (83 mg, 0.380 mmol) and sodium 2-methylpropan-2-olate (110 mg, 1.141 mmol) were combined in dioxane (15 mL) and the mixture was heated at 110° C. for 45 minutes. The reaction mixture was cooled, concentrated in vacuo to give a residue which was combined with MeOH and filtered. The filtrate was purified by preparative HPLC using a Sunfire Prep 5 μm C18, 75×30 mm column eluting with a gradient of 15-40% acetonitrile (containing 0.035% TFA) in water (containing 0.05% TFA) to give the title compound as a TFA salt. $^1$H NMR (400 MHz, METHANOL-$d_4$) δ ppm 1.10 (s, 6H) 1.91-2.00 (m, 2H) 2.56 (s, 3H) 2.64 (s, 3H) 4.65-4.75 (m, 2H) 7.45 (d, J=5.31 Hz, 1H) 7.51 (dd, J=8.59, 3.54 Hz, 1H) 7.60-7.70 (m, 2H) 8.33 (s, 1H) 8.46 (s, 1H) 8.56 (d, J=5.31 Hz, 1H). MS [M+H] found 421.5.

Example 121

2-cyclopropyl-N-(3'-fluoro-6'-methyl-2,2'-bipyridin-4-yl)-2H-pyrazolo[4,3-b]pyridin-7-amine

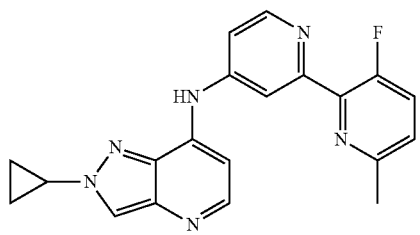 [SMILES: Cc1ccc(F)c(-c2cc(Nc3ccnc4cn(C5CC5)nc34)ccn2)n1]

(9,9-Dimethyl-9H-xanthene-4,5-diyl)bis(diphenylphosphine) (10.45 mg, 0.018 mmol), 2-cyclopropyl-7-iodo-2H-pyrazolo[4,3-b]pyridine (103 mg, 0.361 mmol), $Pd_2(dba)_3$ (16.54 mg, 0.018 mmol), 3'-fluoro-6'-methyl-2,2'-bipyridin-4-amine (73.4 mg, 0.361 mmol) and sodium 2-methylpropan-2-olate (69.4 mg, 0.723 mmol) were combined in dioxane (10 mL) and the mixture was heated at 110° C. for 30 minutes. The reaction mixture was then cooled, concentrated in vacuo to give a residue was combined with MeOH and filtered. The filtrate was purified by preparative HPLC using a Sunfire Prep 5 μm C18, 75×30 mm column eluting with a gradient of 15-40% acetonitrile (containing 0.035% TFA) in water (containing 0.05% TFA) to give the title compound as a TFA salt. $^1$H NMR (400 MHz, METHANOL-$d_4$) δ ppm 1.05-1.12 (m, 2H) 1.20-1.27 (m, 2H) 2.68 (s, 3H) 3.91 (tt, J=7.07, 3.54 Hz, 1H) 7.32 (dd, J=7.07, 2.53 Hz, 1H) 7.59 (dd, J=8.59, 3.54 Hz, 1H) 7.63 (d, J=5.05 Hz, 1H) 7.78 (dd, J=11.37, 8.59 Hz, 1H) 8.02 (d, J=2.53 Hz, 1H) 8.28 (s, 1H) 8.45 (d, J=7.07 Hz, 1H) 8.66 (d, J=5.05 Hz, 1H). MS [M+H] found 361.3.

Example 122

2-cyclopropyl-N-(3'-fluoro-5,6'-dimethyl-2,2'-bipyridin-4-yl)-2H-pyrazolo[4,3-b]pyridin-7-amine

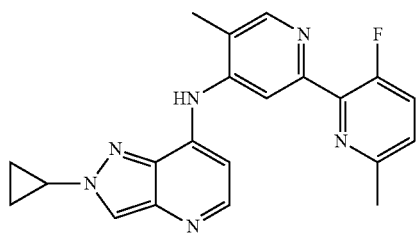 [SMILES: Cc1ccc(F)c(-c2cc(Nc3ccnc4cn(C5CC5)nc34)c(C)cn2)n1]

(9,9-Dimethyl-9H-xanthene-4,5-diyl)bis(diphenylphosphine) (10.45 mg, 0.018 mmol), 2-cyclopropyl-7-iodo-2H-pyrazolo[4,3-b]pyridine (103 mg, 0.361 mmol), 3'-fluoro-5,6'-dimethyl-2,2'-bipyridin-4-amine (78 mg, 0.361 mmol) and sodium 2-methylpropan-2-olate (69.4 mg, 0.723 mmol) were combined in dioxane (10 mL) and heated at 110° C. for 30 minutes. The reaction mixture was then cooled, concentrated in vacuo to give a residue which was combined with MeOH and filtered. The filtrate was purified by preparative HPLC using a Sunfire Prep 5 μm C18, 75×30 mm column eluting with a gradient of 15-40% acetonitrile (containing 0.035% TFA) in water (containing 0.05% TFA) to give the title compound as a TFA salt. $^1$H NMR (400 MHz, METHANOL-$d_4$) δ ppm 0.97-1.06 (m, 2H) 1.18-1.26 (m, 2H) 2.58 (s, 3H) 2.64 (s, 3H) 3.87 (tt, J=7.07, 3.66 Hz, 1H) 7.51 (dd, J=8.72, 3.66 Hz, 1H) 7.56 (d, J=5.05 Hz, 1H) 7.61 (s, 1H) 7.65 (dd, J=11.37, 8.59 Hz, 1H) 8.29 (s, 1H) 8.44-8.53 (m, 1H) 8.66 (d, J=5.30 Hz, 1H). MS [M+H] found 375.4.

Examples 123 and 124

N-(3'-fluoro-5,6'-dimethyl-2,2'-bipyridin-4-yl)-2-methyl-2H-pyrazolo[4,3-b]pyridin-7-amine and
N-(3'-fluoro-5,6'-dimethyl-2,2'-bipyridin-4-yl)-1-methyl-1H-pyrazolo[4,3-b]pyridin-7-amine

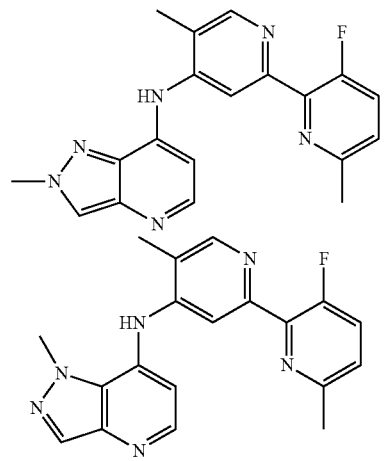

A mixture of 7-iodo-1-methyl-1H-pyrazolo[4,3-b]pyridine and 7-iodo-2-methyl-2H-pyrazolo[4,3-b]pyridine (162 mg, 0.625 mmol), 3'-fluoro-5,6'-dimethyl-2,2'-bipyridin-4-amine (136 mg, 0.625 mmol), tris(dibenzylideneacetone)dipalladium(0) (28.6 mg, 0.031 mmol), (9,9-dimethyl-9H-xanthene-4,5-diyl)bis(diphenylphosphine) (18.09 mg, 0.031 mmol) and sodium 2-methylpropan-2-olate (180 mg, 1.876 mmol) were combined in dioxane (15 mL) and heated at 110° C. for 15 minutes. The solvent was then removed in vacuo to give a residue which was purified by preparative HPLC using a Sunfire Prep 5 μm C18, 75×30 mm column eluting with a gradient of 30-35% acetonitrile (containing 10 mM $NH_4HCO_3$) in water (containing 10 mM $NH_4HCO_3$) to give N-(3'-fluoro-5,6'-dimethyl-2,2'-bipyridin-4-yl)-2-methyl-2H-pyrazolo[4,3-b]pyridin-7-amine: $^1$H NMR (400 MHz, METHANOL-$d_4$) δ ppm 0.84 (s, 3H) 0.91 (s, 3H) 1.72 (br. s., 1H) 2.54 (s, 3H) 5.58 (s, 1H) 5.62 (d, J=4 Hz, 1H) 5.72 (dd, J=12, 4 Hz, 1H) 5.94 (dd, J=12, 8 Hz, 1H) 6.58 (s, 1H) 6.80 (s, 1H) 6.83 (d, J=4 Hz, 1H). Melting point 102.9-103. Fractions were combined and further purified by a second preparative HPLC using a Sunfire Prep 5 μm C18, 75×30 mm column eluting with a gradient of 15-35% acetonitrile (containing 0.035% TFA) in water (containing 0.05% TFA) to give N-(3'-fluoro-5,6'-dimethyl-2,2'-bipyridin-4-yl)-1-methyl-1H-pyrazolo[4,3-b]pyridin-7-amine as a TFA salt. $^1$H NMR (400 MHz, METHANOL-$d_4$) δ ppm 0.90 (s, 3H) 0.98 (s, 3H) 1.54-1.64 (m, 1H) 2.63 (s, 3H) 5.59 (d, J=8 Hz, 1H) 5.87 (dd, J=12, 4 Hz, 1H) 6.06 (dd, J=12, 8 Hz, 1H) 6.69 (s, 1H) 6.90 (d, J=8 Hz, 1H) 7.00 (s, 1H) 7.09 (s, 1H).

Example 125

2-ethyl-N-(3'-fluoro-6'-methyl-2,2'-bipyridin-4-yl)-2H-pyrazolo[4,3-b]pyridin-7-amine

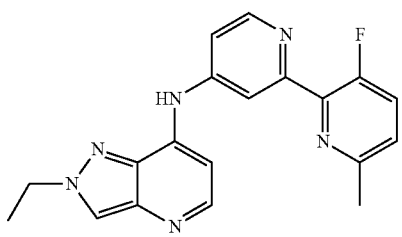 [SMILES: CCn1cc2nccc(Nc3ccnc(-c4nc(C)ccc4F)c3)c2n1]

(9,9-Dimethyl-9H-xanthene-4,5-diyl)bis(diphenylphosphine) (11.97 mg, 0.021 mmol), 2-ethyl-7-iodo-2H-pyrazolo[4,3-b]pyridine (113 mg, 0.414 mmol), Pd$_2$(dba)$_3$ (18.95 mg, 0.021 mmol), 3'-fluoro-6'-methyl-2,2'-bipyridin-4-amine (84 mg, 0.414 mmol) and sodium 2-methylpropan-2-olate (119 mg, 1.241 mmol) were combined in dioxane (15 mL) and heated at 110° C. for 45 minutes. The reaction mixture was then cooled, concentrated in vacuo to give a residue which was combined with MeOH and filtered. The filtrate was purified by preparative HPLC using a Sunfire Prep 5 μm C18, 75×30 mm column column eluting with a gradient of 15-40% acetonitrile (containing 0.035% TFA) in water (containing 0.05% TFA) to give the title compound as a TFA salt. The title compound as a TFA salt was suspended in EtOAc and extracted with saturated sodium bicarbonate. The organic layer was dried over Na$_2$SO$_4$, filtered, and evaporated to give the title compound as its free base. $^1$H NMR (400 MHz, CHLOROFORM-d) δ ppm 1.45 (t, J=7.33 Hz, 3H) 2.62 (s, 3H) 4.53 (q, J=7.16 Hz, 2H) 6.87 (dd, J=5.56, 2.27 Hz, 1H) 7.15-7.24 (m, 2H) 7.43 (dd, J=10.48, 8.46 Hz, 1H) 7.52 (s, 1H) 8.27 (s, 1H) 8.50 (d, J=4.80 Hz, 1H) 8.58 (d, J=5.56 Hz, 1H). MS [M+H] found 349.3

Example 126

2-ethyl-N-(3'-fluoro-5,6'-dimethyl-2,2'-bipyridin-4-yl)-2H-pyrazolo[4,3-b]pyridin-7-amine

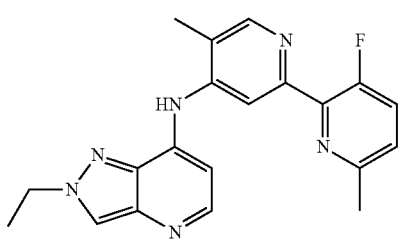 [SMILES: CCn1cc2nccc(Nc3cc(-c4nc(C)ccc4F)ncc3C)c2n1]

(9,9-Dimethyl-9H-xanthene-4,5-diyl)bis(diphenylphosphine) (11.97 mg, 0.021 mmol), 2-ethyl-7-iodo-2H-pyrazolo[4,3-b]pyridine (113 mg, 0.414 mmol), Pd$_2$(dba)$_3$ (18.95 mg, 0.021 mmol), 3'-fluoro-5,6'-dimethyl-2,2'-bipyridin-4-amine (90 mg, 0.414 mmol) and sodium 2-methylpropan-2-olate (119 mg, 1.241 mmol) were combined in dioxane (15 mL) and heated at 110° C. for 45 minutes. The reaction mixture was cooled, concentrated in vacuo to give a residue which was combined with MeOH and filtered. The filtrate was purified by preparative HPLC using a Sunfire Prep 5 μm C18, 75×30 mm column eluting with a gradient of 15-40% acetonitrile (containing 0.035% TFA) in water (containing 0.05% TFA) to give the title compound as a TFA salt. The title compound as a TFA salt was suspended in EtOAc and extracted with saturated sodium bicarbonate. The organic layer was dried over Na$_2$SO$_4$, filtered, and evaporated to give the title compound as its free base.

Example 127

1-ethyl-N-(3'-fluoro-6'-methyl-2,2'-bipyridin-4-yl)-1H-pyrazolo[4,3-b]pyridin-7-amine

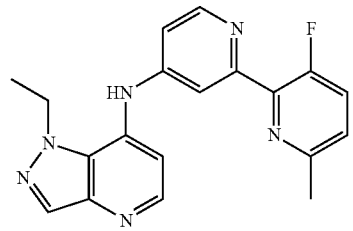 [SMILES: CCn1ncc2nccc(Nc3ccnc(-c4nc(C)ccc4F)c3)c21]

(9,9-Dimethyl-9H-xanthene-4,5-diyl)bis(diphenylphosphine) (11.34 mg, 0.020 mmol), 1-ethyl-7-iodo-1H-pyrazolo[4,3-b]pyridine (107 mg, 0.392 mmol), Pd$_2$(dba)$_3$ (17.94 mg, 0.020 mmol), 3'-fluoro-6'-methyl-2,2'-bipyridin-4-amine (80 mg, 0.392 mmol) and sodium 2-methylpropan-2-olate (113 mg, 1.176 mmol) were combined in dioxane (15 mL) and heated at 110° C. for 45 minutes. The reaction mixture was cooled, concentrated in vacuo to give a residue which was combined with MeOH and filtered. The filtrate was purified by preparative HPLC using a Sunfire Prep 5 μm C18, 75×30 mm column eluting with a gradient of 15-40% acetonitrile (containing 0.035% TFA) in water (containing 0.05% TFA) to give the title compound as a TFA salt. The title compound as a TFA salt was suspended in EtOAc and extracted with saturated sodium bicarbonate. The organic layer was dried over Na$_2$SO$_4$, filtered, and evaporated to give the title compound as its free base.

Example 128

N-(2-(5-chloro-2-fluorophenyl)-5-methylpyridin-4-yl)-2-methyl-2H-pyrazolo[4,3-b]pyridin-7-amine

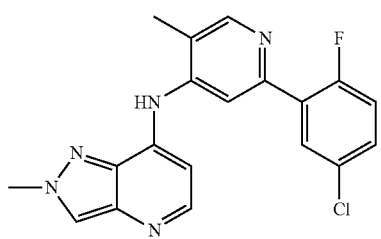 [SMILES: Cc1cnc(-c2cc(Cl)ccc2F)cc1Nc1ccnc2cn(C)nc12]

A mixture of 7-iodo-2-methyl-2H-pyrazolo[4,3-b]pyridine and 7-iodo-1-methyl-1H-pyrazolo[4,3-b]pyridine (110 mg, 0.425 mmol), 2-(5-chloro-2-fluorophenyl)-5-methylpyridin-4-amine (100 mg, 0.425 mmol), tris(dibenzylideneacetone)dipalladium(0) (19.44 mg, 0.021 mmol), (9,9-dimethyl-9H-xanthene-4,5-diyl)bis(diphenylphosphine) (12.29 mg, 0.021 mmol) and sodium 2-methylpropan-2-olate (122 mg, 1.274 mmol) were combined in dioxane (15 mL) and heated at 110° C. for 1 hour. The reaction was then cooled and purified by preparative HPLC using a Sunfire Prep 5 μm C18, 75×30 mm column eluting with a gradient of 15-35% acetonitrile (containing 0.035% TFA) in water (containing 0.05% TFA) to give the title compound as a TFA salt. ¹H NMR (400 MHz, METHANOL-d₄) δ ppm 2.52 (s, 3H) 4.28 (s, 3H) 7.28-7.35 (m, 2H) 7.40 (d, J=4 Hz, 1H) 7.59 (m, 1H) 7.74 (dd, J=8, 4 Hz, 1H) 8.28 (s, 1H) 8.52 (s, 1H) 8.58 (br. s., 1H). MS [M+H] found 368.8.

Examples 129 and 130

N-(3'-fluoro-5,6'-dimethyl-2,2'-bipyridin-4-yl)-2-(2-fluoroethyl)-2H-pyrazolo[4,3-b]pyridin-7-amine and N-(3'-fluoro-5,6'-dimethyl-2,2'-bipyridin-4-yl)-1-(2-fluoroethyl)-1H-pyrazolo[4,3-b]pyridin-7-amine

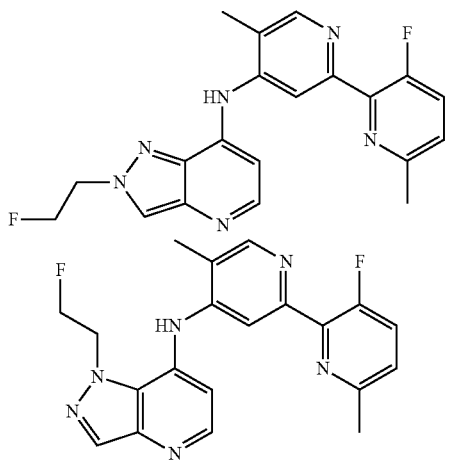

A mixture of N-(3'-fluoro-5,6'-dimethyl-2,2'-bipyridin-4-yl)-1H-pyrazolo[4,3-b]pyridin-7-amine and N-(3'-fluoro-5,6'-dimethyl-2,2'-bipyridin-4-yl)-2H-pyrazolo[4,3-b]pyridin-7-amine (100 mg, 0.299 mmol) was dissolved in DMF (2 mL) and cooled to 0° C. NaH (11.96 mg, 60% in oil, 0.299 mmol) was added and the mixture stirred for 10 minutes, 1-bromo-2-fluoroethane (0.022 mL, 0.299 mmol) was added and the vessel was sealed and heated in a microwave at 80° C. for 15 minutes. The solvent was then removed in vacuo to give a residue which was purified by preparative HPLC using a Sunfire Prep 5 μm C18, 75×30 mm column eluting with a gradient of 15-35% acetonitrile (containing 0.035% TFA) in water (containing 0.05% TFA) to give the title compounds as TFA salts: N-(3'-fluoro-5,6'-dimethyl-2,2'-bipyridin-4-yl)-2-(2-fluoroethyl)-2H-pyrazolo[4,3-b]pyridin-7-amine ¹H NMR (400 MHz, METHANOL-d₄) δ ppm 2.60 (s, 3H) 2.67 (s, 3H) 4.84 (dd, J=8, 4 Hz, 2H) 4.93 (s, 2H) 7.29 (d, J=8 Hz, 1H) 7.57 (dd, J=8, 4 Hz, 1H) 7.64-7.82 (m, 1H) 8.37 (s, 1H) 8.62 (d, J=8 Hz, 1H) 8.79 (d, J=4 Hz, 2H), MS [M+H] found 381.4; and N-(3'-fluoro-5,6'-dimethyl-2,2'-bipyridin-4-yl)-1-(2-fluoroethyl)-1H-pyrazolo[4,3-b]pyridin-7-amine ¹H NMR (400 MHz, METHANOL-d₄) δ ppm 2.52 (s, 3H) 2.63 (s, 3H) 4.58-4.70 (m, 2H) 4.75-4.80 (m, 2H) 7.38 (br. s., 1H) 7.50 (dd, J=8, 4 Hz, 2H) 7.65 (dd, J=12, 8 Hz, 1H) 8.34 (br. s., 1H) 8.40 (s, 1H) 8.50 (br. s., 1H), MS [M+H] found 381.4.

Examples 131 and 132

6-fluoro-N-(3'-fluoro-5,6'-dimethyl-2,2'-bipyridin-4-yl)-2-methyl-2H-pyrazolo[4,3-b]pyridin-7-amine and 6-fluoro-N-(3'-fluoro-5,6'-dimethyl-2,2'-bipyridin-4-yl)-1-methyl-1H-pyrazolo[4,3-b]pyridin-7-amine

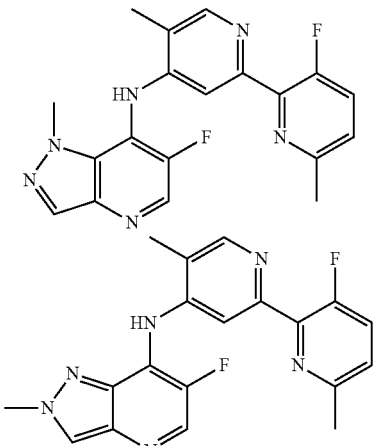

A mixture of 7-chloro-6-fluoro-1-methyl-1H-pyrazolo[4,3-b]pyridine and 7-chloro-6-fluoro-2-methyl-2H-pyrazolo[4,3-b]pyridine (60.0 mg, 0.323 mmol), 3'-fluoro-5,6'-dimethyl-2,2'-bipyridin-4-amine (70.2 mg, 0.323 mmol), tris(dibenzylideneacetone)-dipalladium(0) (14.80 mg, 0.016 mmol), (9,9-dimethyl-9H-xanthene-4,5-diyl)bis(diphenylphosphine) (9.35 mg, 0.016 mmol) and sodium 2-methylpropan-2-olate (93 mg, 0.970 mmol) were combined in dioxane (15 mL), heated at 110° C. for 2 hours. The reaction mixture was then cooled and concentrated to give a residue which was dissolved in MeOH and purified by preparative HPLC using a Sunfire Prep 5 μm C18, 75×30 mm column eluting with a gradient of 20-35% acetonitrile (containing 0.035% TFA) in water (containing 0.05% TFA) to give the title compounds as TFA salts: 6-fluoro-N-(3'-fluoro-5,6'-dimethyl-2,2'-bipyridin-4-yl)-2-methyl-2H-pyrazolo[4,3-b]pyridin-7-amine ¹H NMR (400 MHz, METHANOL-d₄) δ ppm 2.58 (s, 3H) 2.63 (s, 3H) 4.23 (s, 3H) 7.47 (d, J=4 Hz, 1H) 7.51 (dd, J=8, 4 Hz, 1H) 7.64 (dd, J=12, 12 Hz, 1H) 8.43 (s, 1H) 8.65 (s, 1H) 8.66 (d, J=4 Hz, 1H), MS [M+H] found 367.3; and 6-fluoro-N-(3'-fluoro-5,6'-dimethyl-2,2'-bipyridin-4-yl)-1-methyl-1H-pyrazolo[4,3-b]pyridin-7-amine ¹H NMR (400 MHz, METHANOL-d₄) δ ppm 2.59 (s, 3H) 2.63 (s, 3H) 4.13 (s, 3H) 7.29 (d, J=4 Hz, 1H) 7.51 (dd, J=12, 4 Hz, 1H) 7.64 (dd, J=12, 8 Hz, 1H) 8.30 (s, 1H) 8.47 (s, 1H) 8.68 (d, J=4 Hz, 1H), MS [M+H] found 367.3.

Example 133

1-cyclopropyl-N-(3'-fluoro-6'-methyl-2,2'-bipyridin-4-yl)-1H-pyrazolo[4,3-b]pyridin-7-amine

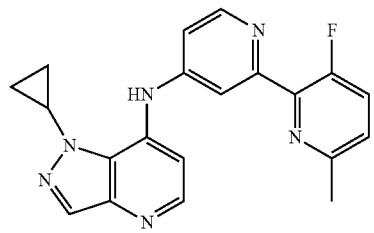 [SMILES: Cc1ccc(F)c(-c2cc(Nc3ccnc4cnn(C5CC5)c34)ccn2)n1]

N-Sodiohexamethyldisilazane (3.40 mL, 2.041 mmol), N,N-dimethylpyridin-4-amine (748 mg, 6.12 mmol), 7-iodo-2H-pyrazolo[4,3-b]pyridine (500 mg, 2.041 mmol), diacetoxycopper (371 mg, 2.041 mmol) and cyclopropylboronic acid (351 mg, 4.08 mmol) were combined in toluene (15 mL) and sparged with air. The mixture was heated at 95° C. overnight. The mixture was then cooled and poured into saturated NH₄Cl solution and extracted with EtOAc (2×). The combined organic layers were dried over Na₂SO₄ and concentrated to give a residue which was purified on silica column chromatography eluted with EtOAc/hexanes (0-97%) using a step gradient and then to 98% EtOAc to give 2-cyclopropyl-7-iodo-2H-pyrazolo[4,3-b]pyridine. Other fractions were combined and purified on a second silica column chromatography eluted with EtOAc/hexanes (0-50%) using a step gradient and then to 90% EtOAc to give 1-cyclopropyl-7-iodo-1H-pyrazolo[4,3-b]pyridine. MS [M+H] found 286.1.

(9,9-Dimethyl-9H-xanthene-4,5-diyl)bis(diphenylphosphine) (1.015 mg, 1.754 μmol), 1-cyclopropyl-7-iodo-1H-pyrazolo[4,3-b]pyridine (10 mg, 0.035 mmol), Pd2(dba)3 (1.606 mg, 1.754 μmol), 3'-fluoro-6'-methyl-2,2'-bipyridin-4-amine (7.13 mg, 0.035 mmol) and sodium 2-methylpropan-2-olate (6.74 mg, 0.070 mmol) were combined in dioxane (4 mL) and the mixture was heated at 110° C. for 30 minutes. The reaction mixture was cooled, concentrated in vacuo to give a residue which was combined with MeOH and filtered. The filtrate was purified by preparative HPLC using a Sunfire Prep 5 μm C18, 75×30 mm column eluting with a gradient of 15-40% acetonitrile (containing 0.035% TFA) in water (containing 0.05% TFA) to give the title compound as a TFA salt. The title compound as a TFA salt was suspended in EtOAc and extracted with saturated sodium bicarbonate. The organic layer was dried over Na₂SO₄, filtered, and evaporated to give the title compound as its free base. ¹H NMR (400 MHz, METHANOL-d₄) δ ppm 1.17-1.22 (m, 2H) 1.38-1.44 (m, 2H) 2.60 (s, 3H) 4.15 (dt, J=7.52, 3.69 Hz, 1H) 7.25 (d, J=5.31 Hz, 1H) 7.41 (dd, J=8.59, 3.54 Hz, 1H) 7.49 (dd, J=5.81, 2.27 Hz, 1H) 7.63-7.66 (m, 1H) 7.88 (s, 1H) 8.33 (d, J=5.31 Hz, 1H) 8.46 (s, 1H) 8.53 (d, J=5.81 Hz, 1H). MS [M+H] found 361.3.

Example 134

1-ethyl-N-(3'-fluoro-5,6'-dimethyl-2,2'-bipyridin-4-yl)-1H-pyrazolo[4,3-b]pyridin-7-amine

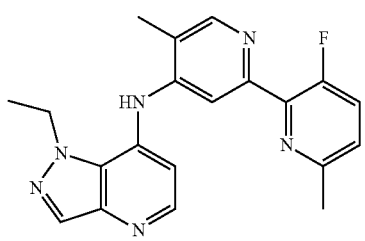 [SMILES: CCn1ncc2nccc(Nc3cc(-c4nc(C)ccc4F)ncc3C)c21]

(9,9-Dimethyl-9H-xanthene-4,5-diyl)bis(diphenylphosphine) (11.34 mg, 0.020 mmol), 1-ethyl-7-iodo-1H-pyrazolo[4,3-b]pyridine (107 mg, 0.392 mmol), Pd₂(dba)₃ (17.94 mg, 0.020 mmol), 3'-fluoro-5,6'-dimethyl-2,2'-bipyridin-4-amine (85 mg, 0.392 mmol) and sodium 2-methylpropan-2-olate (113 mg, 1.176 mmol) were combined in dioxane (15 mL) and heated at 110° C. for 45 minutes. The reaction mixture was cooled, concentrated in vacuo to give a residue which was combined with MeOH and filtered. The filtrate was purified by preparative HPLC using a Sunfire Prep 5 μm C18, 75×30 mm column eluting with a gradient of 15-40% acetonitrile (containing 0.035% TFA) in water (containing 0.05% TFA) to give the title compound as a TFA salt. The title compound as a TFA salt was suspended in EtOAc and extracted with saturated sodium bicarbonate. The organic layer was dried over Na₂SO₄, filtered, and evaporated to give the title compound as its free base. ¹H NMR (400 MHz, DMSO-d₆) δ ppm 1.50 (t, J=7.33 Hz, 3H) 2.33 (s, 3H) 2.47 (s, 3H) 4.47 (q, J=7.33 Hz, 2H) 6.61 (d, J=4.80 Hz, 1H) 7.35 (dd, J=8.59, 3.28 Hz, 1H) 7.69 (dd, J=10.86, 8.34 Hz, 1H) 7.81 (s, 1H) 8.22 (d, J=4.80 Hz, 1H) 8.49 (s, 1H) 8.57 (s, 1H) 8.68 (s, 1H). MS [M+H] found 363.3.

Example 135

4-(7-(3'-fluoro-6'-methyl-2,2'-bipyridin-4-ylamino)-1H-pyrazolo[4,3-b]pyridin-1-yl)-2-methylbutan-2-ol

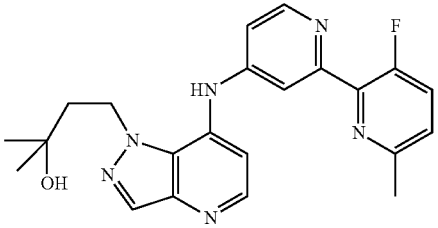 [SMILES: Cc1ccc(F)c(-c2cc(Nc3ccnc4cnn(CCC(C)(C)O)c34)ccn2)n1]

7-Iodo-2H-pyrazolo[4,3-b]pyridine (357 mg, 1.457 mmol), 4-bromo-2-methylbutan-2-ol (243 mg, 1.457 mmol) and Cs₂CO₃ (475 mg, 1.457 mmol) were combined in DMF (5 mL) and heated in a microwave at 120° C. for 40 minutes. The reaction was then cooled, filtered, and concentrated to give a residue which was purified by silica chromatography eluted with a step gradient of EtOAc in hexanes to give 4-(7-iodo-1H-pyrazolo[4,3-b]pyridin-1-yl)-2-methylbutan-2-ol which was dried and used immediately.

(9,9-Dimethyl-9H-xanthene-4,5-diyl)bis(diphenylphosphine) (11.36 mg, 0.020 mmol), 4-(7-iodo-1H-pyrazolo[4,3-b]pyridin-1-yl)-2-methylbutan-2-ol (130 mg, 0.393 mmol), Pd₂(dba)₃ (17.97 mg, 0.020 mmol), 3'-fluoro-6'-methyl-2,2'-bipyridin-4-amine (80 mg, 0.393 mmol) and sodium 2-methylpropan-2-olate (75 mg, 0.785 mmol) were combined in dioxane (15 mL) and the mixture was heated at 110° C. for 45 minutes. The reaction mixture was cooled, concentrated in vacuo to give a residue which was combined with MeOH and filtered. The filtrate was purified by preparative HPLC using a Sunfire Prep 5 μm C18, 75×30 mm column eluting with a gradient of 5-30% acetonitrile (containing 0.035% TFA) in water (containing 0.05% TFA) to give the title compound as a TFA salt. The title compound as a TFA salt was suspended in EtOAc and extracted with saturated sodium bicarbonate. The organic layer was dried over Na₂SO₄, filtered, and evaporated to give the title compound as its free base. ¹H NMR (400 MHz, DMSO-d6) δ ppm 1.17 (s, 6H) 2.00-2.14 (m, 2H) 2.53 (s, 3H) 4.33 (t, J=5.05 Hz, 1H) 4.52-4.59 (m, 2H) 7.10 (d, J=5.05 Hz, 1H) 7.32-7.46 (m, 2H) 7.72 (dd, J=10.86, 8.59 Hz, 1H) 7.94 (d, J=2.27 Hz, 1H) 8.30 (d, J=4.80 Hz, 1H) 8.48 (d, J=5.56 Hz, 1H) 8.61 (s, 1H) 9.61 (s, 1H). MS [M+H] found 407.4.

Examples 136 and 137

(R)—N-(3'-fluoro-5,6'-dimethyl-2,2'-bipyridin-4-yl)-2-(tetrahydrofuran-3-yl)-2H-pyrazolo[4,3-b]pyridin-7-amine and (R)—N-(3'-fluoro-5,6'-dimethyl-2,2'-bipyridin-4-yl)-1-(tetrahydrofuran-3-yl)-1H-pyrazolo[4,3-b]pyridin-7-amine

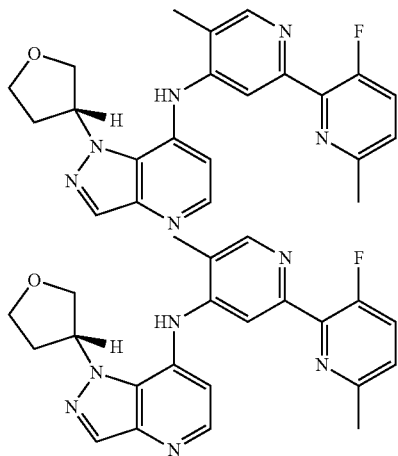

To a solution of (R)-tetrahydrofuran-3-ol (644 mg, 7.31 mmol) in DCM (50 mL) was added sequentially phosphorus triphenyl (3.6 g, 13.89 mmol), glyoxaline (945 mg, 13.89 mmol), and iodine (3.5 g, 13.89 mmol) and the reaction mixture was refluxed overnight. The reaction was then cooled and quenched with a saturated solution of sodium thiosulfate. The organic layers were separated, dried over $Na_2SO_4$, filtered and evaporated to give a yellow solid which was then triturated with hexanes for 2 hours at room temperature. The mixture was filtered and the filtrate was concentrated to a thin yellow oil which was purified with silica column chromatography eluting with EtOAc/hexanes 0-5% over 30 minutes to give (S)-3-iodotetrahydrofuran as clear oil (824 mg, 57%).

A solution of N-(3'-fluoro-5,6'-dimethyl-2,2'-bipyridin-4-yl)-2H-pyrazolo[4,3-b]pyridin-7-amine (65 mg, 0.194 mmol) in DMF (2 mL) was cooled to 0° C. and NaH (7.18 mg, 60% in oil, 0.194 mmol) was added and the mixture was stirred for 5 minutes. (S)-3-iodotetrahydrofuran (38.5 mg, 0.194 mmol) was added and the reaction was brought to room temperature for 5 minutes and then heated at 65° C. for 40 minutes in a microwave. The reaction mixture was cooled, concentrated in vacuo to give a residue which was combined with MeOH and filtered. The filtrate was purified by preparative HPLC using a Sunfire Prep 5 μm C18, 75×30 mm column eluting with a gradient of 5-30% acetonitrile (containing 0.035% TFA) in water (containing 0.05% TFA) to give the title compounds as TFA salts: (R)—N-(3'-fluoro-5,6'-dimethyl-2,2'-bipyridin-4-yl)-2-(tetrahydrofuran-3-yl)-2H-pyrazolo[4,3-b]pyridin-7-amine $^1$H NMR (400 MHz, METHANOL-$d_4$) δ ppm 2.40 (br. s., 1H) 2.50-2.71 (m, 7H) 3.88 (d, J=5.81 Hz, 1H) 3.97-4.22 (m, 3H) 5.46 (br. s., 1H) 7.22 (br. s., 1H) 7.54 (br. s., 1H) 7.72 (d, J=9.09 Hz, 1H) 8.30 (br. s., 1H) 8.56 (br. s., 1H) 8.64-8.81 (m, 2H), MS [M+H] found 405.4; and (R)—N-(3'-fluoro-5,6'-dimethyl-2,2'-bipyridin-4-yl)-1-(tetrahydrofuran-3-yl)-1H-pyrazolo[4,3-b]pyridin-7-amine $^1$H NMR (400 MHz, METHANOL-$d_4$) δ ppm 2.22-2.42 (m, 1H) 2.51 (s, 4H) 2.64 (s, 3H) 3.82-3.96 (m, 1H) 3.96-4.07 (m, 2H) 4.14 (q, J=7.66 Hz, 1H) 5.74 (s, 1H) 7.26 (br. s., 1H) 7.52 (dd, J=8.72, 3.66 Hz, 2H) 7.67 (dd, J=11.37, 8.59 Hz, 1H) 8.26 (br. s., 1H) 8.40 (s, 2H), MS [M+H] found 405.4.

Examples 138 and 139

2-ethyl-6-fluoro-N-(3'-fluoro-5,6'-dimethyl-2,2'-bipyridin-4-yl)-2H-pyrazolo[4,3-b]pyridin-7-amine and 1-ethyl-6-fluoro-N-(3'-fluoro-5,6'-dimethyl-2,2'-bipyridin-4-yl)-1H-pyrazolo[4,3-b]pyridin-7-amine

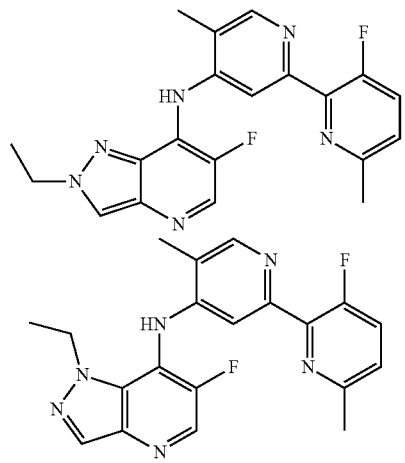

7-Chloro-1-ethyl-6-fluoro-1H-pyrazolo[4,3-b]pyridine and 7-chloro-2-ethyl-6-fluoro-2H-pyrazolo[4,3-b]pyridine (116 mg, 0.581 mmol), 3'-fluoro-5,6'-dimethyl-2,2'-bipyridin-4-amine (126 mg, 0.581 mmol), tris(dibenzylideneacetone)dipalladium(0) (26.6 mg, 0.029 mmol), (9,9-dimethyl-9H-xanthene-4,5-diyl)bis(diphenylphosphine) (16.81 mg, 0.029 mmol) and sodium 2-methylpropan-2-olate (168 mg, 1.743 mmol) were combined in dioxane (15 mL) and heated at 110° C. for 20 minutes. The reaction was cooled, the solvent was removed in vacuo to give a residue which was dissolved in MeOH. This solution was purified by preparative HPLC using a Sunfire Prep 5 μm C18, 75×30 mm column eluting with a gradient of 20-25% acetonitrile (containing 0.035% TFA) in water (containing 0.05% TFA) to give the title compounds as TFA salts: 2-ethyl-6-fluoro-N-(3'-fluoro-5,6'-dimethyl-2,2'-bipyridin-4-yl)-2H-pyrazolo[4,3-b]pyridin-7-amine $^1$H NMR (400 MHz, METHANOL-$d_4$) δ ppm 1.53 (t, 3H) 2.60 (s, 3H) 2.64 (s, 3H) 4.51 (m, 2H) 7.46-7.54 (m, 2H) 7.63 (dd, J=12, 8 Hz, 1H) 8.44 (s, 1H) 8.66 (d, J=4 Hz, 1H) 8.69 (s, 1H), MS [M+H] found 381.3; and 1-ethyl-6-fluoro-N-(3'-fluoro-5,6'-dimethyl-2,2'-bipyridin-4-yl)-1H-pyrazolo[4,3-b]pyridin-7-amine $^1$H NMR (400 MHz, METHANOL-$d_4$) δ ppm 1.35 (t, 3H) 2.60 (s, 3H) 2.63 (s, 3H) 4.40-4.55 (m, 2H) 7.25 (d, J=4 Hz, 1H) 7.51 (dd, J=8, 4 Hz, 1H) 7.64 (dd, J=12, 8 Hz, 1H) 8.34 (s, 1H) 8.49 (s, 1H) 8.63-8.73 (d, J=4 Hz, 1H), MS [M+H] found 381.3.

Examples 140 and 141

(S)—N-(3'-fluoro-5,6'-dimethyl-2,2'-bipyridin-4-yl)-2-(tetrahydrofuran-3-yl)-2H-pyrazolo[4,3-b]pyridin-7-amine and (S)—N-(3'-fluoro-5,6'-dimethyl-2,2'-bipyridin-4-yl)-1-(tetrahydrofuran-3-yl)-1H-pyrazolo[4,3-b]pyridin-7-amine

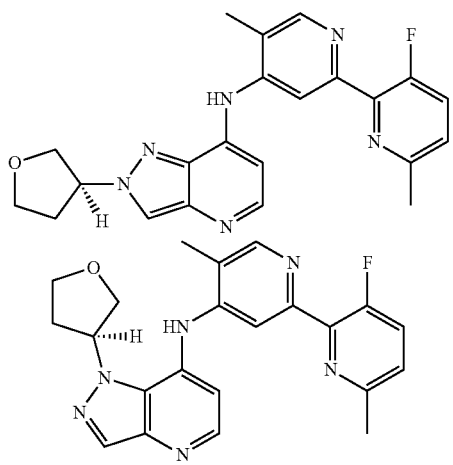

To a solution of (S)-tetrahydrofuran-3-ol (983 mg, 11.16 mmol) in dichloromethane (50 mL) was added phosphorus triphenyl (5. g, 21.20 mmol), glyoxaline (1.4 g, 21.20 mmol), and Iodine (5. g, 21.20 mmol) sequentially. The mixture was refluxed overnight, cooled and quenched with a saturated sodium thiosulfate solution. The organic layers were separated and dried over Na₂SO₄, filtered and evaporated to give a yellow solid which was triturated with hexanes for 2 hours at room temperature. The mixture was filtered, concentrated and purified by silica chromatography eluted with EtOAc/Hexanes 0-5% over 20 minutes to give (R)-3-iodotetrahydrofuran as clear oil (1. g, 52%).

N-(3'-Fluoro-5,6'-dimethyl-2,2'-bipyridin-4-yl)-2H-pyrazolo[4,3-b]pyridin-7-amine (43 mg, 0.129 mmol) was dissolved in DMF (2 mL), cooled to 0° C. and sodium hydride (4.75 mg, 60%, 0.129 mmol) was added. The reaction mixture was stirred for 5 minutes and (R)-3-iodotetrahydrofuran (25.5 mg, 0.129 mmol) was added and further stirred for 5 minutes at room temperature and then heated in a microwave at 65° C. for 40 minutes. The reaction mixture was then cooled, concentrated in vacuo to give a residue which was combined with MeOH and filtered. The filtrate was purified by preparative HPLC using a Sunfire Prep 5 µm C18, 75×30 mm column eluting with a gradient of 5-30% acetonitrile (containing 0.035% TFA) in water (containing 0.05% TFA) to give the title compounds as TFA salts: (S)—N-(3'-fluoro-5,6'-dimethyl-2,2'-bipyridin-4-yl)-1-(tetrahydrofuran-3-yl)-1H-pyrazolo[4,3-b]pyridin-7-amine ¹H NMR (400 MHz, CHLOROFORM-d) δ ppm 1.27-1.42 (m, 1H) 2.36-2.39 (m, 4H) 2.39-2.51 (m, 2H) 2.55 (s, 3H) 3.80-3.89 (m, 1H) 4.01 (dd, J=9.85, 7.33 Hz, 1H) 4.11-4.22 (m, 2H) 7.01 (d, J=3.54 Hz, 1H) 7.14 (dd, J=8.46, 3.41 Hz, 1H) 7.31-7.44 (m, 2H) 8.25 (s, 1H) 8.41 (br. s., 1H), MS [M+H] found 405.4; and (S)—N-(3'-fluoro-5,6'-dimethyl-2,2'-bipyridin-4-yl)-1-(tetrahydrofuran-3-yl)-1H-pyrazolo[4,3-b]pyridin-7-amine ¹H NMR (400 MHz, CHLOROFORM-d) δ ppm 2.44 (s, 3H) 2.46-2.56 (m, 1H) 2.57-2.70 (m, 4H) 4.04 (td, J=8.59, 5.56 Hz, 1H) 4.18-4.31 (m, 3H) 5.22-5.33 (m, 1H) 7.02 (d, J=5.05 Hz, 1H) 7.13-7.23 (m, 2H) 7.43 (dd, J=10.48, 8.46 Hz, 1H) 8.13 (d, J=1.26 Hz, 1H) 8.26 (s, 1H) 8.41 (d, J=5.05 Hz, 1H) 8.62 (s, 1H), MS [M+H] found 405.4.

Example 142

4-(7-(2-(2,5-difluorophenyl)-5-methylpyridin-4-ylamino)-2H-pyrazolo[4,3-b]pyridin-2-yl)-2-methylbutan-2-ol

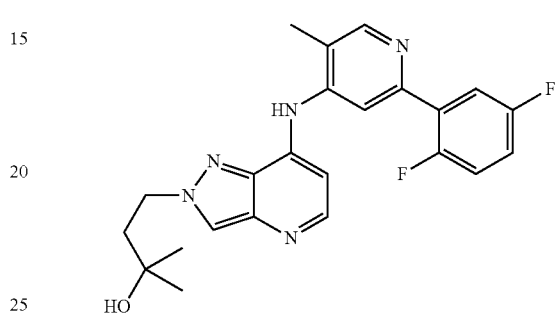

N-(2-(2,5-Difluorophenyl)-5-methylpyridin-4-yl)-2H-pyrazolo[4,3-b]pyridin-7-amine (163 mg, 0.483 mmol), 4-bromo-2-methylbutan-2-ol (81 mg, 0.483 mmol) and Cs₂CO₃ (157 mg, 0.483 mmol) were combined in DMF (5 mL) and heated at 120° C. for 40 minutes in a microwave. The reaction mixture was cooled, concentrated in vacuo to give a residue which was combined with MeOH and filtered. The filtrate was purified by preparative HPLC using a Sunfire Prep 5 µm C18, 75×30 mm column eluting with a gradient of 10-30% acetonitrile (containing 0.035% TFA) in water (containing 0.05% TFA) to give the title compound as a TFA salt. ¹H NMR (400 MHz, CHLOROFORM-d) δ ppm 1.26 (br. s., 1H) 1.34 (br. s., 6H) 2.23 (br. s., 2H) 2.42 (br. s., 3H) 4.62 (br. s., 2H) 7.05 (br. s., 3H) 7.77 (br. s., 1H) 8.02 (br. s., 1H) 8.18 (br. s., 1H) 8.41 (br. s., 1H) 8.52 (br. s., 1H). MS [M+H] found 424.5.

Examples 143 and 144

1-(7-(2-(2,5-difluorophenyl)-5-methylpyridin-4-ylamino)-2H-pyrazolo[4,3-b]pyridin-2-yl)propan-2-ol and 1-(7-(2-(2,5-difluorophenyl)-5-methylpyridin-4-ylamino)-1H-pyrazolo[4,3-b]pyridin-1-yl)propan-2-ol

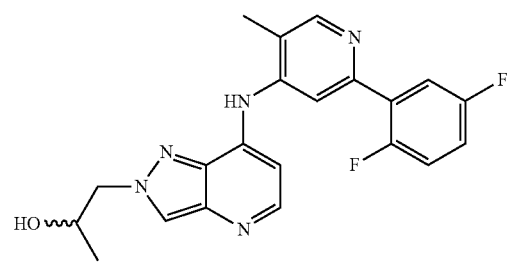

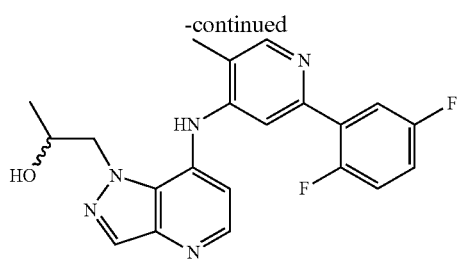
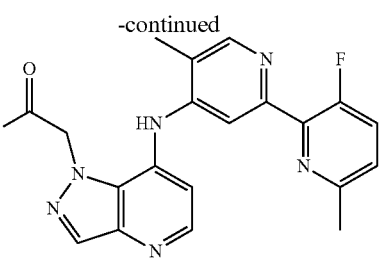

N-(2-(2,5-Difluorophenyl)-5-methylpyridin-4-yl)-1H-pyrazolo[4,3-b]pyridin-7-amine (460 mg, 1.364 mmol) and Cs$_2$CO$_3$ (444 mg, 1.364 mmol) were combined in DMF (6 mL) for 10 minutes. 2-Methyloxirane (0.096 mL, 1.364 mmol) was added, the vessel sealed and the mixture was heated in a microwave at 120° C. for 30 minutes. The reaction mixture was cooled and concentrated in vacuo to give a residue which was combined with MeOH and filtered. The filtrate was purified with 2D preparative HPLC using first a Phenomenex Gemini 5u C18 30×75 mm column eluting with a gradient of 15-40% acetonitrile (containing 0.035% TFA) in water (containing 0.05% TFA) and then a Waters XBridge 5u C18 30×75 mm column eluting with a gradient of 40-40% acetonitrile (containing 10 mM NH$_4$HCO$_3$ in water) in water (containing 10 mM NH$_4$HCO$_3$ in 20/80 water/Acetonitrile) to give the title compounds. The title compounds were separately taken up in EtOAc and washed with water. The organic layers were dried over Na$_2$SO$_4$ and concentrated to give 1-(7-(2-(2,5-difluorophenyl)-5-methylpyridin-4-ylamino)-2H-pyrazolo[4,3-b]pyridin-2-yl)propan-2-ol: $^1$H NMR (400 MHz, METHANOL-d4) δ ppm 1.22 (d, J=6.32 Hz, 3H) 2.42 (s, 3H) 4.22-4.32 (m, 1H) 4.38 (dd, J=13.64, 7.58 Hz, 1H) 4.50 (dd, J=13.52, 3.92 Hz, 1H) 6.95 (d, J=5.31 Hz, 1H) 7.12-7.28 (m, 2H) 7.59 (ddd, J=9.22, 5.94, 3.03 Hz, 1H) 7.83 (s, 1H) 8.28 (d, J=4.55 Hz, 1H) 8.38 (s, 1H) 8.47 (s, 1H), MS [M+H] found 396.4; and 1-(7-(2-(2-(2,5 difluorophenyl)-5-methylpyridin-4-ylamino)-1H-pyrazolo[4,3-b]pyridin-1-yl)propan-2-ol: $^1$H NMR (400 MHz, METHANOL-d$_4$) δ ppm 1.27-1.29 (m, 3H) 2.40 (s, 3H) 4.24 (quind, J=6.47, 6.47, 6.47, 6.47, 3.16 Hz, 1H) 4.56-4.71 (m, 2H) 7.11-7.26 (m, 2H) 7.29 (d, J=5.31 Hz, 1H) 7.55 (ddd, J=9.09, 6.06, 3.03 Hz, 1H) 7.68 (d, J=1.77 Hz, 1H) 8.16 (s, 1H) 8.32 (d, J=5.05 Hz, 1H) 8.40 (s, 1H), MS [M+H] found 396.4.

Examples 145 and 146

2-(7-(3'-fluoro-5,6'-dimethyl-2,2'-bipyridin-4-ylamino)-1H-pyrazolo[4,3-b]pyridin-1-yl)-N-methylacetamide and 2-(7-(3'-fluoro-5,6'-dimethyl-2,2'-bipyridin-4-ylamino)-2H-pyrazolo[4,3-b]pyridin-2-yl)-N-methylacetamide

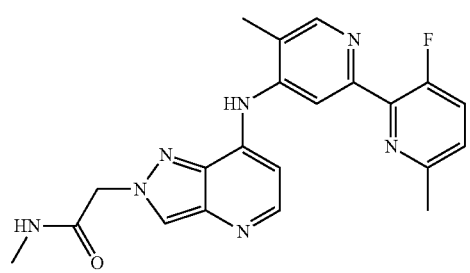

A mixture N-(3'-fluoro-5,6'-dimethyl-2,2'-bipyridin-4-yl)-1H-pyrazolo[4,3-b]pyridin-7-amine and N-(3'-fluoro-5,6'-dimethyl-2,2'-bipyridin-4-yl)-2H-pyrazolo[4,3-b]pyridin-7-amine (54 mg, 0.162 mmol) and Cs$_2$CO$_3$ (52.6 mg, 0.162 mmol) were stirred in DMF (2 mL) for 5 minutes. 2-Bromo-N-methylacetamide (24.55 mg, 0.162 mmol) was added; the vessel was sealed and heated in a microwave at 85° C. for 35 minutes. The reaction mixture was cooled and purified by preparative HPLC using a Sunfire Prep 5 μm C18, 75×30 mm column eluting with a gradient of 20-30% acetonitrile (containing 10 mM NH$_4$HCO$_3$) in water (containing 10 mM NH$_4$HCO$_3$) to give 2-(7-(3'-fluoro-5,6'-dimethyl-2,2'-bipyridin-4-ylamino)-1H-pyrazolo[4,3-b]pyridin-1-yl)-N-methylacetamide: $^1$H NMR (400 MHz, METHANOL-d$_4$) δ ppm 2.46 (s, 3H) 2.58 (s, 3H) 2.78 (s, 3H) 5.23 (s, 2H) 7.01 (d, J=4 Hz, 1H) 7.30-7.42 (m, 1H) 7.56-7.67 (m, 1H) 7.96 (s, 1H) 8.32 (d, J=4 Hz, 1H) 8.45 (s, 1H) 8.52 (s, 1H); MS [M+H] found 406.4; and 2-(7-(3'-fluoro-5,6'-dimethyl-2,2'-bipyridin-4-ylamino)-2H-pyrazolo[4,3-b]pyridin-2-yl)-N-methylacetamide; $^1$H NMR (400 MHz, METHANOL-d$_4$) δ ppm 2.42 (s, 3H) 2.54 (s, 3H) 2.75 (s, 3H) 5.24 (s, 2H) 7.29-7.41 (m, 2H) 7.52-7.59 (m, 1H) 7.61 (d, J=4 Hz, 1H) 8.18 (s, 1H) 8.40 (s, 2H); MS [M+H] found 406.4.

Examples 147 and 148

2-(6-fluoro-7-(3'-fluoro-5,6'-dimethyl-2,2'-bipyridin-4-ylamino)-2H-pyrazolo[4,3-b]pyridin-2-yl)-N-methylacetamide and 2-(6-fluoro-7-(3'-fluoro-5,6'-dimethyl-2,2'-bipyridin-4-ylamino)-1H-pyrazolo[4,3-b]pyridin-1-yl)-N-methylacetamide

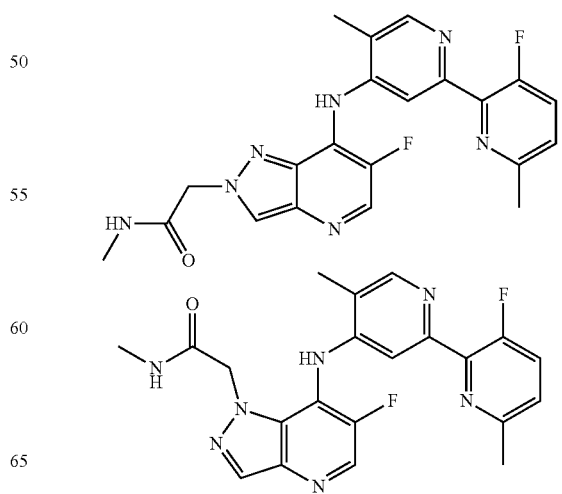

7-Chloro-6-fluoro-1H-pyrazolo[4,3-b]pyridine (100 mg, 0.583 mmol) and NaH (28.0 mg, 60% in oil, 0.699 mmol) in THF (2.0 mL) was stirred at 0° C. for 15 minutes. 2-Bromo-N-methylacetamide (89 mg, 0.583 mmol) was added and the reaction was allowed to warm to room temperature for 12 hours. The reaction mixture was then concentrated in vacuo to give 2-(7-chloro-6-fluoro-1H-pyrazolo[4,3-b]pyridin-1-yl)-N-methylacetamide and 2-(7-chloro-6-fluoro-2H-pyrazolo[4,3-b]pyridin-2-yl)-N-methylacetamide which were used without further purification.

The mixture of 2-(7-chloro-6-fluoro-1H-pyrazolo[4,3-b]pyridin-1-yl)-N-methylacetamide and 2-(7-chloro-6-fluoro-2H-pyrazolo[4,3-b]pyridin-2-yl)-N-methylacetamide (140 mg, 0.577 mmol), 3'-fluoro-5,6'-dimethyl-2,2'-bipyridin-4-amine (125 mg, 0.577 mmol), tris(dibenzylideneacetone)dipalladium(0) (26.4 mg, 0.029 mmol), (9,9-dimethyl-9H-xanthene-4,5-diyl)bis(diphenylphosphine) (16.69 mg, 0.029 mmol) and sodium 2-methylpropan-2-olate (166 mg, 1.731 mmol) were combined in dioxane (15 mL) and heated at 110° C. for 20 minutes. The reaction mixture was cooled and concentrated to give a residue which was taken up in methanol and purified by preparative HPLC using a Sunfire Prep 5 µm C18, 75×30 mm column eluting with a gradient of 20-30% acetonitrile (containing 10 mM $NH_4HCO_3$) in water (containing 10 mM $NH_4HCO_3$) to title compounds: 2-(6-fluoro-7-(3'-fluoro-5,6'-dimethyl-2,2'-bipyridin-4-ylamino)-2H-pyrazolo[4,3-b]pyridin-2-yl)-N-methylacetamide $^1$H NMR (400 MHz, METHANOL-$d_4$) δ ppm 2.42 (s, 3H) 2.49 (s, 3H) 2.57 (s, 3H) 5.16 (s, 2H) 6.90 (d, J=4 Hz, 1H) 7.30 (dd, J=8, 4 Hz, 1H) 7.53 (dd, J=12, 8 Hz, 1H) 8.24 (s, 1H) 8.29 (br. s., 1H) 8.54 (d, J=4 Hz, 1H).), MS [M+H] found 424.4; and 2-(6-fluoro-7-(3'-fluoro-5,6'-dimethyl-2,2'-bipyridin-4-ylamino)-1H-pyrazolo[4,3-b]pyridin-1-yl)-N-methylacetamide $^1$H NMR (400 MHz, METHANOL-$d_4$) δ ppm 2.44 (s, 3H) 2.51 (s, 3H) 2.70 (s, 3H) 5.14 (s, 2H) 7.26 (d, J=4 Hz, 1H) 7.30 (dd, J=8, 4 Hz, 1H) 7.54 (dd, J=12, 8 Hz, 1H) 8.38 (s, 1H) 8.46 (d, J=4 Hz, 1H) 8.52 (s, 1H), MS [M+H] found 424.4.

Examples 149 and 150 and 151 and 152

(S)-1-(7-(3'-fluoro-5,6'-dimethyl-2,2'-bipyridin-4-ylamino)-2H-pyrazolo[4,3-b]pyridin-2-yl)propan-2-ol and (R)-1-(7-(3'-fluoro-5,6'-dimethyl-2,2'-bipyridin-4-ylamino)-2H-pyrazolo[4,3-b]pyridin-2-yl)propan-2-ol and (R)-1-(7-(3'-fluoro-5,6'-dimethyl-2,2'-bipyridin-4-ylamino)-1H-pyrazolo[4,3-b]pyridin-1-yl)propan-2-ol and (S)-1-(7-(3'-fluoro-5,6'-dimethyl-2,2'-bipyridin-4-ylamino)-1H-pyrazolo[4,3-b]pyridin-1-yl)propan-2-ol

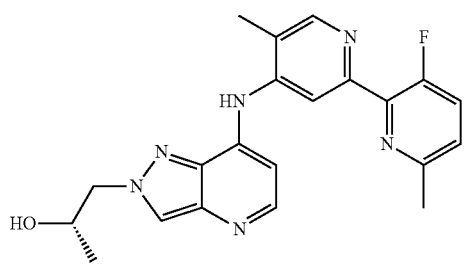

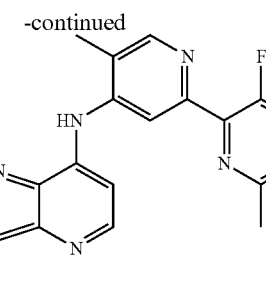

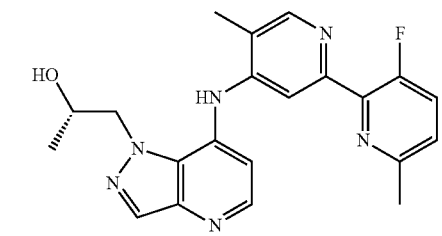

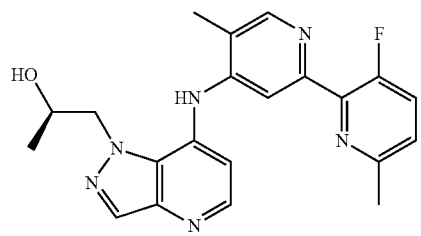

N-(3'-Fluoro-5,6'-dimethyl-2,2'-bipyridin-4-yl)-1H-pyrazolo[4,3-b]pyridin-7-amine (374 mg, 1.119 mmol) and $Cs_2CO_3$ (364 mg, 1.119 mmol) were stirred in DMF (6 mL) for 10 minutes. 2-Methyloxirane (0.079 mL, 1.119 mmol) was added, the vessel sealed and the mixture was heated in a microwave at 120° C. for 30 minutes. The reaction mixture was cooled and purified by preparative HPLC using a Sunfire Prep 5 µm C18, 75×30 mm column eluting with a gradient of 10-25% acetonitrile (containing 0.035% TFA) in water (containing 0.05% TFA) to separate the regioisomers which in turn were further purified using a Chiralcel AD-H (5 um, 20×150 mm) column eluting with $CO_2$: 15% EtOH+0.1% DEA at 50 mL/min to give (S)-1-(7-(3'-fluoro-5,6'-dimethyl-2,2'-bipyridin-4-ylamino)-2H-pyrazolo[4,3-b]pyridin-2-yl)propan-2-ol $^1$H NMR (400 MHz, METHANOL-$d_4$) δ ppm 1.21 (d, J=4 Hz, 3H) 2.44 (s, 3H) 2.56 (s, 3H) 4.20-4.33 (m, 1H) 4.37 (dd, J=12, 8 Hz, 1H) 4.49 (dd, J=16, 4 Hz, 1H) 6.99 (d, J=4 Hz, 1H) 7.35 (dd, J=8, 4 Hz, 1H) 7.60 (dd, J=12, 8 Hz, 1H) 7.92 (s, 1H) 8.28 (d, J=4 Hz, 1H) 8.37 (s, 1H) 8.49 (s, 1H), MS [M+H] found 393.4; (R)-1-(7-(3'-fluoro-5,6'-dimethyl-2,2'-bipyridin-4-ylamino)-2H-pyrazolo[4,3-b]pyridin-2-yl)propan-2-ol $^1$H NMR (400 MHz, METHANOL-$d_4$) δ ppm 1.22 (d, J=4 Hz, 3H) 2.46 (s, 3H) 2.57 (s, 3H) 4.21-4.34 (m, 1H) 4.39 (dd, J=12, 8 Hz, 1H) 4.51 (dd, J=12, 4 Hz, 1H) 7.01 (d, J=4 Hz, 1H) 7.36 (dd, J=8, 4 Hz, 1H) 7.61 (dd, J=8, 4 Hz, 1H) 7.93 (s, 1H) 8.29 (d, J=4 Hz, 1H) 8.38 (s, 1H) 8.50 (s, 1H), MS [M+H] found 393.4; (R)-1-(7-(3'-fluoro-5,6'-dimethyl-2,2'-bipyridin-4-ylamino)-1H-pyrazolo[4,3-b]pyridin-1-yl)propan-2-ol $^1$H NMR (400 MHz, METHANOL-$d_4$) δ ppm 1.22 (d, J=8 Hz, 3H) 2.46 (s, 3H) 2.58 (s, 3H) 4.14-4.34 (m, 1H) 4.34-4.43 (m, 1H) 4.51 (m, 1H) 7.01 (d, J=4 Hz, 1H) 7.37 (dd, J=8, 4 Hz, 1H) 7.61 (dd, J=12, 12 Hz, 1H) 7.94 (s, 1H) 8.29 (d, J=4 Hz, 1H) 8.39 (s, 1H) 8.50 (s, 1H), MS [M+H] found 393.4; and (S)-1-(7-(3'-fluoro-5,6'-dimethyl-2,2'-bipyridin-4-ylamino)-1H-pyrazolo[4,3-b]pyridin-1-yl)propan-2-ol $^1$H NMR (400 MHz, METHANOL-d$_4$) δ ppm 1.21 (d, J=8 Hz, 3H) 2.46 (s, 3H) 2.57 (s, 3H) 4.19-4.34 (m, 1H) 4.38 (m, 1H) 4.50 (m, 1H) 7.00 (d, J=4 Hz, 1H) 7.36 (dd, J=8, 4 Hz, 1H) 7.61 (dd, J=8, 8 Hz, 1H) 7.93 (s, 1H) 8.29 (d, J=4 Hz, 1H) 8.38 (s, 1H) 8.50 (s, 1H), MS [M+H] found 393.4.

Examples 153 and 154

N-ethyl-2-(7-(3'-fluoro-5,6'-dimethyl-2,2'-bipyridin-4-ylamino)-1H-pyrazolo[4,3-b]pyridin-1-yl)acetamide and N-ethyl-2-(7-(3'-fluoro-5,6'-dimethyl-2,2'-bipyridin-4-ylamino)-2H-pyrazolo[4,3-b]pyridin-2-yl)acetamide

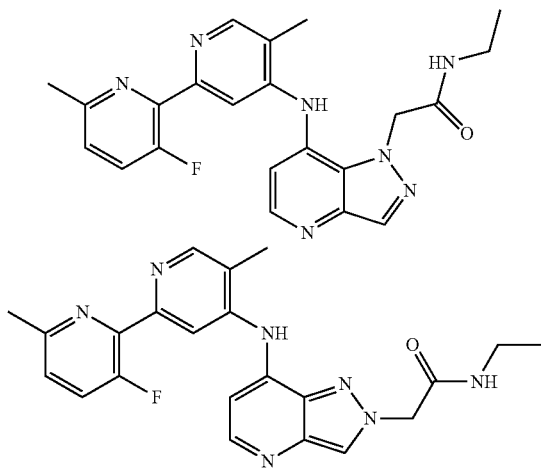

N-(3'-Fluoro-5,6'-dimethyl-2,2'-bipyridin-4-yl)-1H-pyrazolo-4,3-b]pyridin-7-amine (114 mg, 0.341 mmol) and Cs$_2$CO$_3$ (111 mg, 0.341 mmol) were stirred in DMF (2 mL) for 5 minutes. 2-Bromo-N-ethylacetamide (56.6 mg, 0.341 mmol) was added and the vessel was sealed and heated in a microwave at 85° C. for 20 minutes. The reaction mixture was then cooled an purified by preparative HPLC using a Sunfire Prep 5 μm C18, 75×30 mm column eluting with a gradient of 20-30% acetonitrile (containing 10 mM NH$_4$HCO$_3$) in water (containing 10 mM NH$_4$HCO$_3$) to give the title compounds: N-ethyl-2-(7-(3'-fluoro-5,6'-dimethyl-2,2'-bipyridin-4-ylamino)-1H-pyrazolo[4,3-b]pyridin-1-yl)acetamide $^1$H NMR (400 MHz, METHANOL-d$_4$) δ ppm 1.14 (t, J=8 Hz, 3H) 2.44 (s, 3H) 2.57 (s, 3H) 3.19-3.28 (m, 2H) 5.21 (s, 2H) 7.00 (d, J=4 Hz, 1H) 7.36 (dd, J=8, 4 Hz, 1H) 7.61 (dd, J=8, 8 Hz, 1H) 7.95 (s, 1H) 8.30 (d, J=4 Hz, 1H) 8.43 (s, 1H) 8.50 (s, 1H), MS [M+H] found 420.4; and N-ethyl-2-(7-(3'-fluoro-5,6'-dimethyl-2,2'-bipyridin-4-ylamino)-2H-pyrazolo[4,3-b]pyridin-2-yl)acetamide: $^1$H NMR (400 MHz, METHANOL-d$_4$) δ ppm 1.12 (t, J=8 Hz, 3H) 2.42 (s, 3H) 2.54 (s, 3H) 3.24 (m, 2H) 5.24 (s, 2H) 7.31-7.40 (m, 2H) 7.58 (dd, J=8, 8 Hz, 1H) 7.64 (s, 1H) 8.18 (s, 1H) 8.32-8.47 (m, 2H), MS [M+H] found 420.4.

Examples 155 and 156

2-(7-(2-(2,5-difluorophenyl)-5-methylpyridin-4-ylamino)-1H-pyrazolo[4,3-b]pyridin-1-yl)-N-ethylacetamide and 2-(7-(2-(2,5-difluorophenyl)-5-methylpyridin-4-ylamino)-2H-pyrazolo[4,3-b]pyridin-2-yl)-N-ethylacetamide

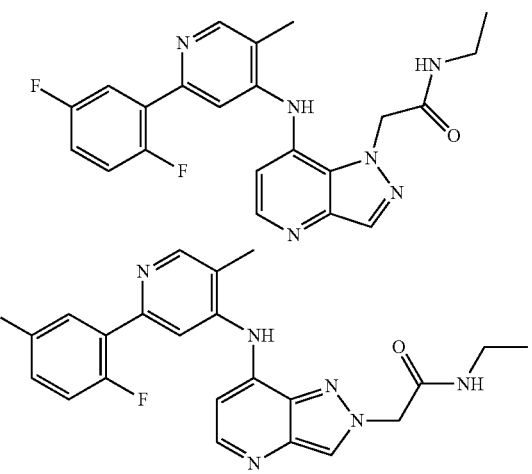

A mixture of N-(2-(2,5-difluorophenyl)-5-methylpyridin-4-yl)-1H-pyrazolo[4,3-b]pyridin-7-amine (100 mg, 0.296 mmol), 2-bromo-N-ethylacetamide (49.2 mg, 0.296 mmol) and Cs$_2$CO$_3$ (97 mg, 0.296 mmol) in DMF (1.5 mL) was heated in a microwave at 80° C. for 15 minutes. The reaction mixture was filtered and purified via preparative HPLC using a gradient of 17-22% acetonitrile (containing 0.035% TFA) in water (containing 0.05% TFA) using a Sunfire Prep 5 μm C18, 75×30 mm column to give the title compounds as TFA salts: 2-(7-(2-(2,5-difluorophenyl)-5-methylpyridin-4-ylamino)-1H-pyrazolo[4,3-b]pyridin-1-yl)-N-ethylacetamide $^1$H NMR (400 MHz, DMSO-d$_6$) δ ppm 0.89 (5H, t, J=7.20 Hz) 2.39 (3H, br. s.) 2.76-2.98 (2H, m) 5.28 (2H, br. s.) 7.21-7.56 (3H, m) 7.65 (1H, br. s.) 8.41 (1H, s) 8.46-8.69 (2H, m) 10.14 (1H, br. s.), MS [M+H] found 423.4; and 2-(7-(2-(2,5-difluorophenyl)-5-methylpyridin-4-ylamino)-2H-pyrazolo[4,3-b]pyridin-2-yl)-N-ethylacetamide $^1$H NMR (400 MHz, DMSO-d$_6$) δ ppm 1.03-1.14 (m, 3H) 2.30-2.36 (m, 4H) 2.65-2.73 (m, 1H) 3.15 (dd, J=7.33, 5.56 Hz, 2H) 5.29 (s, 2H) 6.53 (d, J=6.57 Hz, 1H) 7.41 (td, J=9.73, 4.55 Hz, 2H) 7.74-7.86 (m, 1H) 7.86 (s, 1H) 8.37-8.46 (m, 1H) 8.75 (s, 1H) 8.79 (s, 1H), MS [M+H] found 423.4.

Example 157

N-[1-(1,1-dioxidotetrahydrothiophen-3-yl)-1H-pyrazolo[4,3-b]pyridin-7-yl]-3'-fluoro-5,6'-dimethyl-2,2'-bipyridin-4-amine

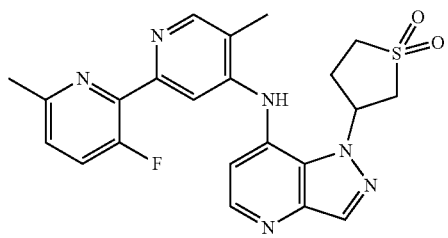 [SMILES: Cc1ccc(F)c(-c2cc(Nc3ccnc4cnn(C5CCS(=O)(=O)C5)c34)c(C)cn2)n1]

N-(3'-Fluoro-5,6'-dimethyl-2,2'-bipyridin-4-yl)-1H-pyrazolo[4,3-b]pyridin-7-amine (56 mg, 0.167 mmol), 3-bromosulfolane (50.0 mg, 0.251 mmol), copper(I)oxide (1.198 mg, 8.37 µmol), $Cs_2CO_3$ (109 mg, 0.335 mmol) and (Z)-6-((hydroxyamino)methylene)cyclohexa-2,4-dienone (4.59 mg, 0.033 mmol) were dissolved in acetonitrile (1.6 mL) and heated at 80° C. for 15 minutes. The reaction was further heated at 85° C. for 1 hour and then cooled and stirred overnight at room temperature. The reaction mixture was then purified via preparative HPLC using a gradient of 15-30% acetonitrile (containing 0.035% TFA) in water (containing 0.05% TFA) using a Sunfire Prep 5 µm C18, 75×30 mm column to give the title compound as a TFA salt. $^1$H NMR (400 MHz, CHLOROFORM-d) δ ppm 1.24-1.28 (6H, m) 2.70 (7H, d, J=7.83 Hz) 2.77 (2H, d, J=4.29 Hz) 3.71 (2H, d, J=5.81 Hz) 8.26 (1H, s) 8.52 (1H, s) 8.79 (1H, s) 9.17 (1H, s). MS [M+H] found 453.4.

Examples 158 and 159

2-(7-(2-(2,5-difluorophenyl)-5-methylpyridin-4-ylamino)-2H-pyrazolo[4,3-b]pyridin-2-yl)-N-methylacetamide and 2-(7-(2-(2,5-difluorophenyl)-5-methylpyridin-4-ylamino)-1H-pyrazolo[4,3-b]pyridin-1-yl)-N-methylacetamide

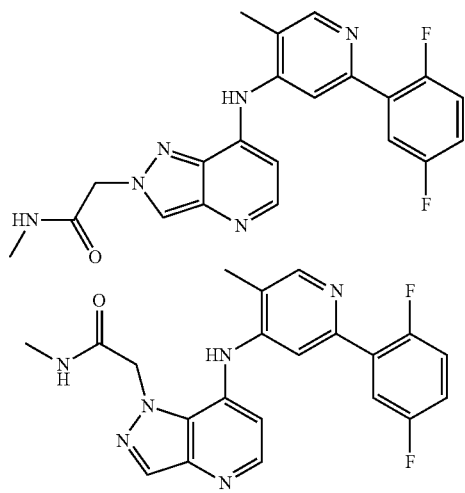

A mixture of N-(2-(2,5-difluorophenyl)-5-methylpyridin-4-yl)-1H-pyrazolo[4,3-b]pyridin-7-amine (76 mg, 0.225 mmol), 2-bromo-N-methylacetamide (34.2 mg, 0.225 mmol) and $Cs_2CO_3$ (73.4 mg, 0.225 mmol) in DMF (1127 µl) was heated in a microwave for 15 minutes at 80° C. The reaction was then cooled and concentrated in vacuo to give a residue which was combined with MeOH and filtered. The filtrate was purified by HPLC using a Phenomenex Gemini 5u C18 30×75 mm column eluting with a gradient of 15-40% acetonitrile (containing 0.035% TFA) in water (containing 0.05% TFA) and then 2D LC method using a Waters XBridge 5u C18 30×75 mm column (2DLC-2D_Basic_40_40_8 min) (containing 10 mM $NH_4HCO_3$) in water (containing 10 mM $NH_4HCO_3$) in 20/80 water/acetonitrile to give the title compounds: 2-(7-(2-(2,5-difluorophenyl)-5-methylpyridin-4-ylamino)-2H-pyrazolo[4,3-b]pyridin-2-yl)-N-methylacetamide $^1$H NMR (400 MHz, METHANOL-d4) δ ppm 2.41 (s, 3H) 2.69-2.89 (m, 3H) 5.31 (s, 2H) 6.68 (d, J=6.57 Hz, 1H) 7.20-7.31 (m, 2H) 7.71 (ddd, J=8.91, 6.00, 3.03 Hz, 1H) 7.83-7.96 (m, 1H) 8.34 (d, J=6.57 Hz, 1H) 8.60 (s, 1H) 8.74 (s, 1H), MS [M+H] found 409.4; and 2-(7-(2-(2,5-difluorophenyl)-5-methylpyridin-4-ylamino)-1H-pyrazolo[4,3-b]pyridin-1-yl)-N-methylacetamide MS [M+H] found 409.5.

The compounds of the invention can be administered alone or in the form of a pharmaceutical composition. In practice, the compounds of the invention are usually administered in the form of pharmaceutical compositions, that is, in admixture with at least one pharmaceutically acceptable excipient, the proportion and nature of which are determined by the properties of the selected compound of the invention, the chosen route of administration, and standard pharmaceutical practice.

In another embodiment, the present invention provides pharmaceutical compositions comprising: a compound of invention and at least one pharmaceutically acceptable excipient.

In effecting treatment of a patient in need of such treatment, a compound of the invention can be administered in any form and route which makes the compound bioavailable. The compounds of the invention can be administered by a variety of routes, including oral and parenteral routes, more particularly by inhalation, subcutaneously, intraperitoneally, intramuscularly, intravenously, intraarterially, transdermally, intranasally, rectally, vaginally, occularly, topically, sublingually, buccally, transbuccally, intraadiposally, intrathecally, and via local delivery for example by catheter.

The pharmaceutical compositions of the invention may be administered to the patient, for example, in the form of tablets, capsules, cachets, papers, lozenges, wafers, elixirs, ointments, transdermal patches, aerosols, inhalants, suppositories, solutions, and suspensions. One skilled in the art can readily select a form and route of administration depending upon the particular characteristics of the compound selected, the disorder or condition to be treated, the stage of the disorder or condition, and other relevant circumstances.

The present pharmaceutical compositions are preferably formulated in a unit dosage form, each dosage typically containing from about 0.5 mg to about 200 mg of the selected compound(s) of the invention, typically, comprising between 1% to about 70% of the total weight of the unit dosage form. The term "unit dosage form" refers to a physically discrete unit. Each unit containing a predetermined quantity of active ingredient with at least one pharmaceutical excipient, by which one or more is used throughout the dosing regimen to produce the desired therapeutic effect.

The pharmaceutical compositions of the present invention are prepared in a manner well known in the pharmaceutical art. The term "pharmaceutically acceptable excipient" refers to those typically used in preparing pharmaceutical compositions and should be pharmaceutically pure and non-toxic in the amounts used. They generally are a solid, semi-solid, or liquid material which can serve as a vehicle or medium for the active ingredient. Some of pharmaceutically acceptable excipients are found in Remington's Pharmaceutical Sciences and the Handbook of Pharmaceutical Excipients and include diluents, vehicles, carriers, ointment bases, binders, disintegrates, lubricants, glidants, sweetening agents, flavoring agents, gel bases, sustained release matrices, stabilizing agents, preservatives, solvents, suspending agents, buffers, emulsifiers, dyes, propellants, coating agents, and others.

In one particular variation, the composition is a pharmaceutical composition adapted for oral administration, such as a tablet or a capsule or a liquid formulation, for example, a solution or suspension adapted for oral administration. In still another particular variation, the pharmaceutical composition is a liquid formulation adapted for parenteral administration.

In another embodiment, the invention provides methods of treating conditions associated with ALK5, comprising: administering to a patient in need thereof an effective amount of a compound of the invention. In a particular embodiment the present invention provides a method for treating cancer, comprising: administering to a patient in need thereof an effective amount of a compound of invention. In a further embodiment, the invention provides a method of inhibiting ALK5: comprising, administering a first compound to a subject that is converted in vivo to a compound of the invention. In another embodiment, compounds of the invention, particularly including the compound of formula I, are provided for use as a medicament. The invention also provides the use of compounds of the invention, including the use for the manufacture of a medicament, to treat the conditions associated with ALK5 described herein. The compounds of the present invention are stable and are relatively safe in their end use. The compounds of the present invention are useful as ALK5 inhibitors for a variety of subjects (e.g., humans, non-human mammals and non-mammals).

The terms "treat," "treats," "treatment," and "treating" include improvement of the conditions described herein. Also, it is also recognized that one skilled in the art may affect the conditions by treating a patient presently afflicted with the disorders or by prophylactically treating a patient believed to be susceptible to such conditions with an effective amount of a compound of invention. Thus, the terms "treat," "treats," "treatment," and "treating" include all processes providing slowing, interrupting, arresting, controlling, or stopping of the conditions described herein or the progression of the conditions described herein, but does not necessarily indicate a total elimination of all symptoms or a cure of the condition, and is intended to include prophylactic and therapeutic treatment of such disorders. A particular embodiment relates to therapeutic treatment of such disorders.

As used herein the terms "patient" and "subject" includes humans and non-human animals, for example, mammals, such as mice, rats, guinea pigs, dogs, cats, rabbits, cows, horses, sheep, goats, and pigs. The term also includes birds, fish, reptiles, amphibians, and the like. A particular patient is a human. Also, particular patients and subjects are non-human mammals, such as mice, rats, and dogs.

As used herein, the term "effective amount" refers to the amount of compound of the invention which treats, upon single or multiple dose administration, a patient suffering from the mentioned condition. An effective amount can be readily determined by the attending diagnostician, as one skilled in the art, by the use of known techniques and by observing results obtained under analogous circumstances. In determining the effective amount, the dose, a number of factors are considered by the attending diagnostician, including, but not limited to: the species of patient; its size, age, and general health; the specific condition, disorder, or disease involved; the degree of or involvement or the severity of the condition, disorder, or disease, the response of the individual patient; the particular compound administered; the mode of administration; the bioavailability characteristics of the preparation administered; the dose regimen selected; the use of concomitant medication; and other relevant circumstances. An effective amount of the present use invention, including a compound of the invention, is expected to vary from about 0.1 milligram per kilogram of body weight per day (mg/kg/day) to about 20 mg/kg/day. Specific amounts can be determined by the skilled person.

As used herein terms "condition," "disorder," and "disease" relate to any unhealthy or abnormal state. The term "conditions associated with ALK5" includes conditions, disorders, and diseases in which the inhibition of ALK5 provides a therapeutic benefit, such as cancer, fibrotic disorders, cardiovascular diseases, pulmonary diseases, liver disease, kidney disease, allergy/asthma, diseases and conditions of the immune system, inflammation, disease and conditions of the central nervous system, viral infections, dermatological disease, and diseases and conditions related to uncontrolled angiogenesis, wound healing and scarring, and the like.

Where general terms are used herein to describe conditions associated with ALK5 it is understood by the skilled person that the more specifically described conditions mentioned in the various diagnostic manuals and other materials are included within the scope of this invention.

For example, it is understood that the treatment of cancer includes treatment of all neoplasia, regardless of their histopathological appearance. Particularly, the cancers that can be treated include, but are not limited to, cancer of blood, including leukemia (including acute myelogenous leukemia, chronic myelogenous leukemia, acute lymphocytic leukemia, chronic lymphocytic leukemia), cancer of the skin (including melanoma, basal cell carcinoma, squamous cell carcinoma of both ulcerating and papillary type), bone, liver, lung (including small-cell lung tumor, non small-cell lung cancer and bronchioalveolar cancer), brain, breast, prostate, larynx, gall bladder, pancreas, rectum, bile duct, parathyroid, thyroid, adrenal, neural tissue, bladder, spleen, head and neck, included the jaw, mouth, and nose, colon, stomach, testes, esophagus, uterus, ovary, cervix and vulva, colorectal, bronchi, bile duct, bladder, kidney, pancreas, multiple myeloma, lymphomas, osteo sarcoma, Ewing's sarcoma, veticulum cell sarcoma, myeloma, giant cell tumor, islet cell tumor, acute and chronic lymphocytic and granulocytic tumors, hairy-cell tumor, adenoma, hyperplasia, medullary carcinoma, pheochromocytoma, mucosal neuronms, intestinal ganglioneuromas, hyperplastic corneal nerve tumor, marfanoid habitus tumor, Wilm's tumor, seminoma, ovarian tumor, leiomymater tumor, cervical dysplasia and in situ carcinoma, neuroblastoma, retinoblastoma, myelodysplastic syndrome, mycosis fungicide, rhabdomyosarcoma, astrocytoma, non-Hodgkin's lymphoma, Kaposi's sarcoma, osteogenic and other sarcoma, malignant hypercalcemia, polycythermia vera, adenocarcinoma, glioblastoma multiforma, glioma, lymphomas, epidermoid carcinomas, and other carcinomas and sarcomas.

Benign tumors may also be treated by the ALK5 inhibitors of the present invention and include, but not limited to, hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas, pyogenic granulomas, and the like, and hamartoma conditions such as Peutz-Jeghers Syndrome (PJS), Cowden disease, Bannayan-Riley-Ruvalcaba Syndrome (BRRS), Proteus syndrome, Lhermitte-Duclos disease and Tuberous Sclerosis (TSC).

It is understood that fibrotic disorders include disorders and diseases in which fibrosis is part of the pathology, such as fibrosis of the kidney, liver, lung, heart, and skin.

It is understood that cardiovascular disease includes myocardial infarction, stroke, thrombosis, hypertension, heart failure, cardiomyopathy, myocarditis, vascular stenosis, restenosis, atherosclerosis and arterial hyperplasia.

It is understand that pulmonary disease includes pulmonary hypertension, chronic obstructive pulmonary diseases, acute lung injury, adult respiratory distress syndrome and idiopathic pulmonary fibrosis.

It is understood that liver disease includes liver fibrosis, hepatic dysfunction, alcohol-induced hepatitis and non-alcohol-induced hepatitis.

It is understood that kidney disease includes glomerulonephritis, diabetic nephropathy and nephritis.

The term "conditions associated with ALK5" also includes inflammation, Crohn's disease, ulcerative colitis, inflammatory bowel disease, neurological conditions characterized by TGF-β production or enhanced sensitivity to TGF-β, including states post-traumatic or hypoxic injury, osteoporosis, Alzheimer's disease, and Parkinson's disease. The term "conditions associated with ALK5" also includes the treatment of wounds and the scarring, including adhesion formation as a result of trauma or surgical wounds, polyposis or states post polyp surgery; chronic scarring of the peritoneum associated with endometriosis, ovarian disease, peritoneal dialysis, or surgical wounds; diseases of the joints involving scarring, such as states post-mechanical or surgical trauma, osteoarthritis and rheumatoid arthritis, muscular diseases, fibrosclerosis, sclerodema, and dermal scarring.

A wide variety of therapeutic agents may have a therapeutic additive or synergistic effect with ALK5 inhibitors according to the present invention. Combination therapies that comprise one or more compounds of the present invention with one or more other therapeutic agents can be used, for example, to: 1) enhance the therapeutic effect(s) of the one or more compounds of the present invention and/or the one or more other therapeutic agents; 2) reduce the side effects exhibited by the one or more compounds of the present invention and/or the one or more other therapeutic agents; and/or 3) reduce the effective dose of the one or more compounds of the present invention and/or the one or more other therapeutic agents. For example, such therapeutic agents may additively or synergistically combine with the inhibitors of the present invention to inhibit undesirable cell growth, such as inappropriate cell growth resulting in undesirable benign conditions or tumor growth. It is understood that combination therapy includes administering a compound according to the present invention before, at the same time, and/or after the subject is treated with another anti-proliferative agent.

In one embodiment, a method is provided for treating cancer comprising treating cells with a compound according to the present invention in combination with an anti-proliferative agent Examples of therapeutic agents that may be used in combination with the inhibitors of the present invention include, but are not limited to, anticancer agents, antibiotic agents, antimetabolic agents, hormonal agents, plant-derived agents, and biologic agents.

Alkylating agents are an example of anti-proliferative agents. Examples of alkylating agents include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), non-classic alkylating agents (altretamine, dacarbazine, and procarbazine), platinum compounds (carboplastin and cisplatin). Combination therapy including an inhibitor of the present invention and an alkylating agent may have therapeutic synergistic effects on cancer and reduce sides affects associated with these chemotherapeutic agents.

Antibiotic agents are a group of drugs that produced in a manner similar to antibiotics as a modification of natural products. Examples of antibiotic agents include, but are not limited to, anthracyclines (e.g. doxorubicin, daunorubicin, epirubicin, idarubicin and anthracenedione), mitomycin C, bleomycin, dactinomycin, plicatomycin. These antibiotic agents interfere with cell growth by targeting different cellular components. For example, anthracyclines are generally believed to interfere with the action of DNA topoisomerase II in the regions of transcriptionally active DNA, which leads to DNA strand scissions. Bleomycin is generally believed to chelate iron and forms an activated complex, which then binds to bases of DNA, causing strand scissions and cell death. Combination therapy including an inhibitor of the present invention and an antibiotic agent may have therapeutic synergistic effects on cancer and reduce sides affects associated with these chemotherapeutic agents.

Antimetabolic agents are a group of drugs that interfere with metabolic processes vital to the physiology and proliferation of cancer cells. Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, and gemcitabine. Combination therapy including an inhibitor of the present invention and a antimetabolic agent may have therapeutic synergistic effects on cancer and reduce sides affects associated with these chemotherapeutic agents.

Hormonal agents are a group of drug that regulate the growth and development of their target organs. Most of the hormonal agents are sex steroids and derivatives and analogs thereof, such as estrogens, androgens, and progestins, or functional equivalents Examples of such hormonal agents are synthetic estrogens (e.g. diethylstibestrol), antiestrogens (e.g. tamoxifen, toremifene, fluoxymesterol and raloxifene), antiandrogens (bicalutamide, nilutamide, and flutamide), aromatase inhibitors (e.g., aminoglutethimide, anastrozole and tetrazole), ketoconazole, goserelin acetate, leuprolide, megestrol acetate and mifepristone. Combination therapy including an inhibitor of the present invention and a hormonal agent may have therapeutic synergistic effects on cancer and reduce sides affects associated with these chemotherapeutic agents.

Plant-derived agents are a group of anti-proliferative agents that are derived from plants or modified based on the molecular structure of the agents. Examples of plant-derived agents include, but are not limited to, vinca alkaloids (e.g., vincristine, vinblastine, vindesine, vinzolidine and vinorelbine), podophyllotoxins (e.g., etoposide (VP-16) and teniposide (VM-26)), and taxanes (e.g., paclitaxel and docetaxel). These plant-derived agents generally act as antimitotic agents that bind to tubulin and inhibit mitosis. Podophyllotoxins such as etoposide are believed to interfere with DNA synthesis by interacting with topoisomerase II, leading to DNA strand scission. Combination therapy including an inhibitor of the present invention and a plant-derived agent may have therapeutic synergistic effects on cancer and reduce sides affects associated with these chemotherapeutic agents.

Biologic agents are a group of biomolecules that elicit cancer/tumor regression when used alone or in combination with chemotherapy and/or radiotherapy. Examples of biologic agents include, but are not limited to, immuno-modulating proteins such as cytokines, monoclonal antibodies against tumor antigens, tumor suppressor genes, and cancer vaccines. Combination therapy including an inhibitor of the present invention and a biologic agent may have therapeutic synergistic effects on cancer, enhance the patient's immune responses to tumorigenic signals, and reduce potential sides affects associated with this chemotherapeutic agent.

The activity of compounds as ALK5 inhibitors may be determined by a variety of methods, including in vitro and in vivo methods.

Example: A

In Vitro Inhibition of ALK5

Test compounds were screened for TGF-β R1 ALK5 inhibition by use of a LanthaScreen™ activity assay (PV5837 Invitrogen, Invitrogen Corp. Madison, Wis.).

In brief, the assay procedure was as follows:

Solutions of test compounds were prepared in DMSO and diluted two-fold serially.

Assays were conducted at 15 μL volumes consisting of 50 mM HEPES pH 7.4, 10 mM NaCl, 10 mM MgCl2, 0.01% Brij® 35, 1 mM DTT, 2 μM ATP, 1.2 μM of Fluorescein-SMAD3 Peptide FAM-NH2-KVLTQMGSPSIRCSS[PO4]VS (M4337 Invitrogen), 15 nM ALK5 and test compounds at 1% final DMSO concentration.

Assays were incubated for 90 minutes at room temperature and then quenched by the addition of 60 mM EDTA and 8 nM Terbium labeled anti-pSMAD3 Antibody (M4337 from Invitrogen) giving a final concentration of 15 mM EDTA and 2 nM Terbium labeled anti-pSMAD3 Antibody. Phosphorylated peptide product was quantified by measuring an increase in TR-FRET on a BMG LABTECH PHERA star plus. Response is defined as the ratio of Channel A/Channel B. The response of a blank (uninhibited) using vehicle alone is also determined. Enzyme activity was defined as the response of uninhibited enzyme activity minus the response of assays containing no enzyme. The percent inhibition of ALK5 at a given compound concentration is defined as: $100\% \times [1-(\text{response compound/response blank})]$ where response compound is defined as the enzyme activity in the presence of test compound and response blank is defined as the uninhibited enzyme activity. The $pIC_{50}$ value (negative log of the molar concentration of the compound that produces 50% inhibition) of a test compound is calculated by non-linear least squares curve fitting of the equation: Percent Inhibition=$100\%/(1+(10-pIC_{50}/10 \log [I]))$.

The exemplified compounds measured in vitro inhibition of ALK5 in the assay of Example A with a $pIC_{50}$ as given below in Table 1. Where inhibition was measured in multiple experiments the value in Table 1 is an average. N.T. means not tested.

TABLE 1

| Example | pIC$_{50}$ | Example | pIC$_{50}$ | Example | pIC$_{50}$ |
|---|---|---|---|---|---|
| 1 | 8.0 | 2 | 8.2 | 3 | 8.2 |
| 4 | 8.2 | 5 | 7.4 | 6 | 8.3 |
| 7 | 7.8 | 8 | 6.6 | 9 | 8.1 |
| 10 | 8.0 | 11 | 8.6 | 12 | 7.5 |
| 13 | 8.6 | 14 | 8.0 | 15 | 8.1 |
| 16 | 7.5 | 17 | 8.3 | 18 | 7.3 |
| 19 | 7.3 | 20 | 7.4 | 21 | 7.0 |
| 23 | 6.5 | 24 | 5.8 | 25 | 5.6 |
| 26 | 5.6 | 27 | 7.2 | 28 | 5.6 |
| 29 | 7.0 | 30 | 7.3 | 31 | 6.7 |
| 32 | 7.3 | 33 | 6.7 | 34 | 6.4 |
| 35 | 6.6 | 36 | 6.2 | 37 | 7.2 |
| 38 | 6.6 | 39 | 7.0 | 41 | 6.5 |
| 42 | 6.5 | 43 | 8.1 | 44 | 7.5 |
| 45 | 7.3 | 46 | 7.2 | 48 | 6.7 |
| 49 | 7.5 | 50 | 7.8 | 51 | 7.9 |
| 52 | 7.5 | 53 | 7.5 | 54 | 7.2 |
| 55 | 7.1 | 56 | 7.9 | 57 | 7.4 |
| 58 | 7.1 | 59 | 6.5 | 56 | 7.9 |
| 60A | 7.5 | 61 | 6.6 | 62 | 7.9 |
| 63 | 7.5 | 64 | 6.9 | 65 | 7.0 |
| 66 | 7.4 | 67 | 6.9 | 68 | 5.9 |
| 69 | 5.3 | 70 | 7.8 | 71 | 7.3 |
| 72 | 6.8 | 73 | 7.8 | 74 | 7.4 |
| 75 | 7.6 | 78 | 6.2 | 80 | 7.5 |
| 81 | 7.2 | 82 | N.T. | 83 | N.T. |
| 84 | 7.5 | 85 | 7.6 | 86 | 7.3 |
| 87 | 7.6 | 88 | 8.0 | 89 | 7.6 |
| 90 | 8.1 | 91 | 7.7 | 92 | 7.1 |
| 93 | 8.3 | 94 | 8.7 | 95 | 7.7 |
| 96 | 7.7 | 97 | 7.8 | 98 | 8.2 |
| 99 | 6.3 | 100A | 6.4 | 100B | 7.2 |
| 101 | 7.6 | 102 | 7.8 | 103 | N.T. |
| 104 | 7.1 | 105 | 7.7 | 106 | 6.9 |
| 107 | 8.2 | 108 | 9.0 | 109 | 8.8 |
| 110 | 8.3 | 111 | 6.3 | 112 | 7.2 |
| 113 | 7.3 | 114 | 6.8 | 115 | >9 |
| 116 | 9.0 | 117 | 8.0 | 118 | 7.0 |
| 119 | 7.7 | 120 | 7.7 | 121 | 8.5 |
| 122 | 8.7 | 123 | 7.6 | 124 | 8.4 |
| 125 | 7.8 | 126 | 8.0 | 127 | 8.1 |
| 128 | 8.2 | 129 | 8.2 | 130 | 8.4 |
| 131 | 8.5 | 132 | 7.2 | 133 | 8.3 |
| 134 | 8.7 | 135 | 7.8 | 136 | 8.2 |
| 137 | 7.7 | 138 | 8.1 | 139 | 7.6 |
| 140 | 8.1 | 141 | 7.6 | 142 | 7.6 |
| 143 | 7.7 | 144 | 8.6 | 145 | 7.8 |
| 146 | 7.5 | 147 | 7.5 | 148 | 6.7 |
| 149 | 8.2 | 150 | 8.1 | 151 | 8.2 |
| 152 | 8.1 | 153 | 8.1 | 154 | 7.5 |
| 155 | 7.6 | 156 | 8.5 | 157 | 7.6 |
| 158 | 8.2 | 159 | 7.4 | | |

Example: B

Cellular Inhibition of ALK5

Test compounds were screened for cellular TGF-β R1 ALK5 inhibition by use of a CellSensor® SBE-bla HEK 293T (K1550, Invitrogen Corp. Madison, Wis.) cell line. The CellSensor® SBE-bla HEK 293T cell line contains a beta-lactamase reporter gene under control of the SBE response element stably integrated into HEK 293T cells. The SBE response element is a DNA region that binds activated SMADs which results from the binding of TGF-β to, and subsequent activation of ALK5.

The assay procedure was as follows:

CellSensor® SBE-bla HEK 293T cell line were plated at 12,000 cells/well in 40 ul DMEM plus 5 ug/ml blasticidin into 384-well, black-wall, clear-bottom assay plate and incubated overnight.

The following day 5 uL of 10×, 2.5-fold serially diluted test compounds in DMSO were added into cells to a final compound concentration of 1× and DMSO concentration of 0.5%. Assay was incubated for 1 hour at 37° C., 5% CO$_2$, 5 uL of 100 ng/mL TGFb-1 was then added to activate ALK5 and incubated for 5 hours at 37° C., 5% CO$_2$, 10 uL of detector, LiveBLAzer FRET B/G substrate (CCF4-AM, Invitrogen Corp. Madison, Wis.) was added to cells and incubated for 2 hours at RT. Assay was measured using Spectramax, a bottom-read fluorescence plate reader, at excitation setting of 405 nm and emission settings of 460 nm and 530 nm.

Response is defined as the ratio of background corrected 460 nM emission values/background corrected 530 nM emission values. Cellular activity was defined as percent inhibition of uninhibited ALK5 activity (wells treated with DMSO+TGF-β). The percent inhibition of cellular ALK5 at a given compound concentration is defined as: $100\% \times [1-(\text{response compound+TGF-β/response DMSO+TGF-β})]$ where response compound+TGF-β is defined as the activity in the presence of test compound and response DMSO+TGF-β is defined as the uninhibited cellular ALK5 activity. The $pIC_{50}$ value (negative log of the molar concentration of the compound that produces 50% inhibition) of a test compound is calculated by non-linear least squares curve fitting. $pIC_{50}$ values, the negative of the log of the IC$_{50}$, are calculated by non-linear curve fitting of the compound concentrations and percent of inhibition to the standard $pIC_{50}$ equation.

The exemplified compounds measured cellular inhibition of ALK5 in the assay of Example B with a $pIC_{50}$ as given below in Table 2. Where inhibition was measured in multiple experiments the value in Table 2 is an average. N.T. means not tested.

TABLE 2

| Example | $pIC_{50}$ | Example | $pIC_{50}$ | Example | $pIC_{50}$ |
|---|---|---|---|---|---|
| 1 | 7.3 | 2 | 7.1 | 3 | N.T. |
| 4 | N.T. | 5 | 6.7 | 6 | 7.6 |
| 7 | 6.7 | 8 | N.T. | 9 | N.T. |
| 10 | 7.7 | 11 | N.T. | 12 | N.T. |
| 13 | N.T. | 14 | N.T. | 15 | 7.4 |
| 16 | 6.3 | 17 | 7.3 | 18 | 6.2 |
| 19 | 6.4 | 20 | 7.0 | 21 | 6.1 |
| 27 | 6.0 | 28 | 5.6 | 29 | 7.0 |
| 31 | 6.7 | 32 | 7.3 | 33 | 6.7 |
| 34 | 6.4 | 35 | 6.6 | 36 | 6.2 |
| 37 | 6.4 | 39 | 6.5 | 43 | 7.0 |
| 46 | 6.5 | 47 | 6.4 | 48 | 6.7 |
| 49 | 7.5 | 50 | 7.9 | 51 | 7.7 |
| 52 | 7.5 | 53 | 7.3 | 54 | 7.0 |
| 55 | 6.2 | 58 | 6.9 | 60A | 6.3 |
| 63 | 6.4 | 65 | 6.9 | 66 | 7.4 |
| 67 | 6.9 | 68 | 5.9 | 69 | 5.3 |
| 70 | 7.5 | 71 | 7.2 | 73 | 7.2 |
| 81 | 6.9 | 82 | N.T. | 83 | N.T. |
| 84 | N.T. | 85 | N.T. | 86 | 6.8 |
| 87 | 6.6 | 88 | 6.8 | 89 | 6.7 |
| 90 | 7.2 | 91 | 6.8 | 92 | 6.3 |
| 93 | 7.6 | 94 | 7.7 | 95 | 6.8 |
| 96 | 7.2 | 97 | 6.4 | 98 | 7.6 |
| 99 | 5.9 | 100A | 5.9 | 100B | 6.6 |
| 101 | 7.0 | 102 | 7.3 | 103 | N.T. |
| 104 | 6.5 | 105 | 7.4 | 106 | 5.9 |
| 107 | 7.4 | 108 | 8.1 | 109 | 7.7 |
| 110 | 6.8 | 111 | 4.9 | 112 | 6.3 |
| 113 | 5.8 | 114 | 5.9 | 115 | 8.2 |
| 116 | 7.6 | 117 | 6.9 | 118 | 6.1 |
| 119 | 7.1 | 120 | 6.7 | 121 | 7.9 |
| 122 | 8.0 | 123 | 7.1 | 124 | 8.2 |
| 125 | 7.4 | 126 | 7.8 | 127 | 7.5 |
| 128 | 7.6 | 129 | 7.8 | 130 | 7.7 |
| 131 | 8.0 | 132 | 6.9 | 133 | 7.5 |
| 134 | 7.3 | 135 | 7.3 | 136 | 7.1 |
| 137 | 7.1 | 138 | 7.8 | 139 | 6.9 |
| 140 | 7.3 | 141 | 6.8 | 142 | 6.8 |
| 143 | 6.9 | 144 | 7.7 | 145 | 6.9 |
| 146 | 6.3 | 147 | 6.7 | 148 | 6.0 |
| 149 | 7.1 | 150 | 6.8 | 151 | 7.2 |
| 152 | 7.0 | 153 | 7.1 | 154 | 5.8 |
| 155 | 6.1 | 156 | 6.9 | 157 | 6.4 |
| 158 | 6.9 | 159 | N.T. | | |

What is claimed is:

1. A compound of the formula

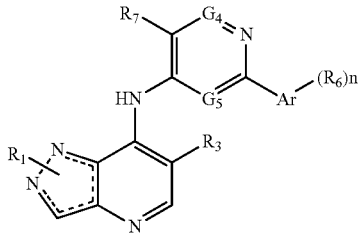

Wherein

Ar is selected from the group consisting of phenyl, pyridine, and pyrimidine;

$R_1$ is selected from the group consisting of hydrogen, optionally substituted $C_{1-6}$ alkyl, $C_{1-6}$ alkyl substituted with a $C_{3-6}$ heterocycloalkylamide, optionally substituted $C_{1-8}$ sulfonyl, optionally substituted $C_{5-14}$ aryl, optionally substituted $C_{3-8}$ cycloalkyl, optionally substituted $C_{3-6}$ heterocycloalkyl, optionally substituted $C_{1-10}$ heteroaryl, —C(O)NR$_8$R$_9$, —C(S)NR$_8$R$_9$, —C(O)OR$_{10}$, and —C(O)R$_{11}$;

$R_3$ is selected from the group consisting of hydrogen, halo, and $C_{1-3}$ alkyl;

$G_4$ is selected from the group consisting of N and CR$_4$;

$R_4$ is selected from the group consisting of hydrogen, halo, and $C_{1-3}$ alkyl;

$G_5$ is selected from the group consisting of N and CR$_5$;

$R_5$ is selected from the group consisting of hydrogen, halo, and $C_{1-3}$ alkyl;

each $R_6$ is independently selected from the group consisting of halo, cyano, optionally substituted $C_{1-4}$ alkyl, optionally substituted $C_{2-4}$ alkenyl, optionally substituted $C_{2-4}$ alkynyl, and optionally substituted $C_{1-4}$ alkoxy;

n is 0, 1, 2, or 3;

$R_7$ is selected from the group consisting of hydrogen, halo, cyano, optionally substituted $C_{1-4}$ alkyl, optionally substituted $C_{2-4}$ alkenyl, optionally substituted $C_{2-4}$ alkynyl, and optionally substituted $C_{1-4}$ alkoxy;

$R_8$ is selected from the group consisting of hydrogen, optionally substituted $C_{1-6}$ alkyl, optionally substituted $C_{3-8}$ cycloalkyl, optionally substituted $C_{5-14}$ aryl, optionally substituted $C_{3-6}$ heterocycloalkyl, and optionally substituted $C_{1-10}$ heteroaryl;

SEQUENCE LISTING

<160> NUMBER OF SEQ ID NOS: 1

<210> SEQ ID NO 1
<211> LENGTH: 17
<212> TYPE: PRT
<213> ORGANISM: Artificial Sequence
<220> FEATURE:
<223> OTHER INFORMATION: Kinase Assay

<400> SEQUENCE: 1

Lys Val Leu Thr Gln Met Gly Ser Pro Ser Ile Arg Cys Ser Ser Val
1               5                   10                  15

Ser

R$_9$ is selected from the group consisting of hydrogen and C$_{1-6}$ alkyl;

or R$_8$ and R$_9$ together with the nitrogen to which they are attached form an optionally substituted C$_{3-6}$ heterocycloalkyl;

R$_{10}$ is selected from the group consisting of optionally substituted C$_{1-6}$ alkyl and optionally substituted C$_{3-8}$ cycloalkyl;

R$_{11}$ is selected from the group consisting of hydrogen, optionally substituted C$_{1-6}$ alkyl, optionally substituted C$_{3-8}$ cycloalkyl, optionally substituted C$_{5-14}$ aryl, optionally substituted C$_{3-6}$ heterocycloalkyl, and optionally substituted C$_{1-10}$ heteroaryl;

⎓ is a bond that can be depicted as a single or a double bond;

or a pharmaceutically acceptable salt thereof.

2. A compound of claim 1 wherein G$_4$ is CR$_4$ and G$_5$ is CR$_5$ and R$_4$ is hydrogen and R$_5$ is hydrogen or a pharmaceutically acceptable salt thereof.

3. A compound of claim 2 wherein Ar is phenyl or a pharmaceutically acceptable salt thereof.

4. A compound of claim 3 wherein R$_1$ is selected from the group consisting of hydrogen and C$_{1-6}$ alkyl or a pharmaceutically acceptable salt thereof.

5. A compound of claim 3 wherein R$_1$ is C$_{1-6}$ alkyl optionally substituted with 1 or 2 substituents selected from the group consisting of C$_{1-4}$ alkoxy, C$_{1-9}$ amide, C$_{3-8}$ cycloalkyl, hydroxy, and C$_{3-6}$ heterocycloalkyl or a pharmaceutically acceptable salt thereof.

6. A compound of claim 3 wherein R$_1$ is C$_{3-6}$ heterocycloalkyl or a pharmaceutically acceptable salt thereof.

7. A compound of claim 3 wherein R$_1$ is —C(O)NR$_8$R$_9$ or a pharmaceutically acceptable salt thereof.

8. A compound of claim 3 wherein R$_1$ is —C(O)NR$_8$R$_9$ and R$_8$ is selected from the group consisting of hydrogen and C$_{1-6}$ alkyl and R$_9$ is selected from the group consisting of hydrogen and C$_{1-6}$ alkyl or a pharmaceutically acceptable salt thereof.

9. A compound of claim 3 wherein R$_1$ is —C(O)NR$_8$R$_9$ wherein R$_8$ is C$_{1-6}$ alkyl and R$_9$ is hydrogen or a pharmaceutically acceptable salt thereof.

10. A compound of any one of claims 1 to 9 wherein R$_3$ is hydrogen or a pharmaceutically acceptable salt thereof.

11. A compound of claim 10 wherein R$_7$ is selected from the group consisting of hydrogen, halogen, and methyl or a pharmaceutically acceptable salt thereof.

12. A compound of claim 1 selected from the group consisting of
N-(2-(5-chloro-2-fluorophenyl)-5-methylpyridin-4-yl)-6-fluoro-2-(2-methoxyethyl)-2H-pyrazolo[4,3-b]pyridin-7-amine;
N-(2-(5-chloro-2-fluorophenyl)pyridin-4-yl)-1H-pyrazolo[4,3-b]pyridin-7-amine;
N-(2-(5-chloro-2-fluorophenyl)pyridin-4-yl)-1-propyl-1H-pyrazolo[4,3-b]pyridin-7-amine;
N-(2-(5-chloro-2-fluorophenyl)pyridin-4-yl)-2-propyl-2H-pyrazolo[4,3-b]pyridin-7-amine;
N-(2-(5-chloro-2-fluorophenyl)pyridin-4-yl)-1-isopropyl-1H-pyrazolo[4,3-b]pyridin-7-amine;
N-(2-(5-chloro-2-fluorophenyl)pyridin-4-yl)-1-(tetrahydro-2H-pyran-4-yl)-1H-pyrazolo[4,3-b]pyridin-7-amine;
N-(2-(5-chloro-2-fluorophenyl)pyridin-4-yl)-1-(4-methoxybenzyl)-1H-pyrazolo[4,3-b]pyridin-7-amine;
N-(2-(5-chloro-2-fluorophenyl)pyridin-4-yl)-2-(4-methoxybenzyl)-2H-pyrazolo[4,3-b]pyridin-7-amine;
N-(2-(5-chloro-2-fluorophenyl)pyridin-4-yl)-2-((tetrahydro-2H-pyran-4-yl)methyl)-2H-pyrazolo[4,3-b]pyridin-7-amine;
N-(2-(5-chloro-2-fluorophenyl)pyridin-4-yl)-1-((tetrahydro-2H-pyran-4-yl)methyl)-1H-pyrazolo[4,3-b]pyridin-7-amine;
N-(2-(5-chloro-2-fluorophenyl)pyridin-4-yl)-2-((tetrahydrofuran-2-yl)methyl)-2H-pyrazolo[4,3-b]pyridin-7-amine;
N-(2-(5-chloro-2-fluorophenyl)pyridin-4-yl)-1-(piperidin-4-ylmethyl)-1H-pyrazolo[4,3-b]pyridin-7-amine;
N-(2-(5-chloro-2-fluorophenyl)pyridin-4-yl)-2-(piperidin-4-ylmethyl)-2H-pyrazolo[4,3-b]pyridin-7-amine;
4-((7-(2-(5-chloro-2-fluorophenyl)pyridin-4-ylamino)-2H-pyrazolo[4,3-b]pyridin-2-yl)methyl)-N-ethylpiperidine-1-carboxamide;
7-(2-(5-chloro-2-fluorophenyl)pyridin-4-ylamino)-N-ethyl-1H-pyrazolo[4,3-b]pyridine-1-carboxamide;
7-(2-(5-chloro-2-fluorophenyl)pyridin-4-ylamino)-1H-pyrazolo[4,3-b]pyridine-1-carboxamide;
2-(7-(2-(5-chloro-2-fluorophenyl)pyridin-4-ylamino)-1H-pyrazolo[4,3-b]pyridin-1-yl)-N-methylacetamide;
7-(2-(5-chloro-2-fluorophenyl)pyridin-4-ylamino)-N-methyl-1H-pyrazolo[4,3-b]pyridine-1-carboxamide;
N-(2-(5-chloro-2-fluorophenyl)pyridin-4-yl)-1-(3-methoxypropyl)-1H-pyrazolo[4,3-b]pyridin-7-amine;
N-(2-(5-chloro-2-fluorophenyl)pyridin-4-yl)-2-(3-methoxypropyl)-2H-pyrazolo[4,3-b]pyridin-7-amine;
N-(2-(5-chloro-2-fluorophenyl)pyridin-4-yl)-2-(2-methoxyethyl)-2H-pyrazolo[4,3-b]pyridin-7-amine;
N-(2-(5-chloro-2-fluorophenyl)pyridin-4-yl)-1-(2-methoxyethyl)-2H-pyrazolo[4,3-b]pyridin-7-amine;
N-(2-(5-chloro-2-fluorophenyl)pyridin-4-yl)-1-(cyclopropylmethyl)-1H-pyrazolo[4,3-b]pyridin-7-amine;
N-(2-(5-chloro-2-fluorophenyl)pyridin-4-yl)-2-(cyclopropylmethyl)-2H-pyrazolo[4,3-b]pyridin-7-amine;
2-(7-(2-(5-chloro-2-fluorophenyl)pyridin-4-ylamino)-1H-pyrazolo[4,3-b]pyridin-1-yl)-N,N-dimethylacetamide;
7-(2-(5-chloro-2-fluorophenyl)pyridin-4-ylamino)-N,N-dimethyl-1H-pyrazolo[4,3-b]pyridine-1-carboxamide;
1-(2-(7-(2-(5-chloro-2-fluorophenyl)pyridin-4-ylamino)-2H-pyrazolo[4,3-b]pyridin-2-yl)ethyl)imidazolidin-2-one;
1-(2-(7-(2-(5-chloro-2-fluorophenyl)pyridin-4-ylamino)-1H-pyrazolo[4,3-b]pyridin-1-yl)ethyl)imidazolidin-2-one;
2-(7-(2-(5-chloro-2-fluorophenyl)pyridin-4-ylamino)-1H-pyrazolo[4,3-b]pyridin-1-yl)-1-morpholinoethanone;
2-(7-(2-(5-chloro-2-fluorophenyl)pyridin-4-ylamino)-2H-pyrazolo[4,3-b]pyridin-2-yl)acetamide;
2-(7-(2-(5-chloro-2-fluorophenyl)pyridin-4-ylamino)-1H-pyrazolo[4,3-b]pyridin-1-yl)acetamide;
2-(7-(2-(5-chloro-2-fluorophenyl)pyridin-4-ylamino)-2H-pyrazolo[4,3-b]pyridin-2-yl)propanamide;
(R)-3-(7-(2-(5-chloro-2-fluorophenyl)pyridin-4-ylamino)-2H-pyrazolo[4,3-b]pyridin-2-yl)propane-1,2-diol;
(S)-3-(7-(2-(5-chloro-2-fluorophenyl)pyridin-4-ylamino)-2H-pyrazolo[4,3-b]pyridin-2-yl)propane-1,2-diol;
1-(7-(2-(5-chloro-2-fluorophenyl)pyridin-4-ylamino)-1H-pyrazolo[4,3-b]pyridin-1-yl)-2-methylpropan-2-ol;
1-(7-(2-(5-chloro-2-fluorophenyl)pyridin-4-ylamino)-2H-pyrazolo[4,3-b]pyridin-2-yl)-2-methylpropan-2-ol;

N-(2-(3-chlorophenyl)pyridin-4-yl)-2-methyl-2H-pyrazolo[4,3-b]pyridin-7-amine;
N-(2-(5-chloro-2-fluorophenyl)-5-methylpyridin-4-yl)-1H-pyrazolo[4,3-b]pyridin-7-amine;
2-(7-(2-(5-chloro-2-fluorophenyl)-5-methylpyridin-4-ylamino)-2H-pyrazolo[4,3-b]pyridin-2-yl)acetamide;
2-(7-(2-(5-chloro-2-fluorophenyl)-5-methylpyridin-4-ylamino)-1H-pyrazolo[4,3-b]pyridin-1-yl)acetamide;
7-(2-(5-chloro-2-fluorophenyl)-5-methylpyridin-4-ylamino)-N-methyl-1H-pyrazolo[4,3-b]pyridine-1-carboxamide;
7-(2-(5-chloro-2-fluorophenyl)-5-methylpyridin-4-ylamino)-N-ethyl-1H-pyrazolo[4,3-b]pyridine-1-carboxamide;
7-(2-(5-chloro-2-fluorophenyl)-5-methylpyridin-4-ylamino)-N-isopropyl-1H-pyrazolo[4,3-b]pyridine-1-carboxamide;
2-(7-(2-(5-chloro-2-fluorophenyl)-5-methylpyridin-4-ylamino)-2H-pyrazolo[4,3-b]pyridin-2-yl)-2-methylpropanamide;
N-(2-(5-chloro-2-fluorophenyl)-5-methylpyridin-4-yl)-2-(ethylsulfonyl)-2H-pyrazolo[4,3-b]pyridin-7-amine;
N-(2-(5-chloro-2-fluorophenyl)-6-methylpyridin-4-yl)-1H-pyrazolo[4,3-b]pyridin-7-amine;
7-(2-(5-chloro-2-fluorophenyl)-6-methylpyridin-4-ylamino)-N-methyl-1H-pyrazolo[4,3-b]pyridine-1-carboxamide;
7-(2-(5-chloro-2-fluorophenyl)-6-methylpyridin-4-ylamino)-N-ethyl-1H-pyrazolo[4,3-b]pyridine-1-carboxamide;
2-(7-(2-(5-chloro-2-fluorophenyl)-6-methylpyridin-4-ylamino)-1H-pyrazolo[4,3-b]pyridin-1-yl)acetamide;
2-(7-(2-(5-chloro-2-fluorophenyl)-6-methylpyridin-4-ylamino)-2H-pyrazolo[4,3-b]pyridin-2-yl)acetamide;
N-(2-(5-chloro-2-fluorophenyl)-6-methylpyridin-4-yl)-2-(ethylsulfonyl)-2H-pyrazolo[4,3-b]pyridin-7-amine;
7-(2-(5-chloro-2,4-difluorophenyl)pyridin-4-ylamino)-N-ethyl-1H-pyrazolo[4,3-b]pyridine-1-carboxamide;
7-(2-(5-chloro-2,4-difluorophenyl)pyridin-4-ylamino)-N-methyl-1H-pyrazolo[4,3-b]pyridine-1-carboxamide;
N-(3'-fluoro-6'-methyl-2,2'-bipyridin-4-yl)-2H-pyrazolo[4,3-b]pyridin-7-amine;
N-(3'-fluoro-6'-methyl-2,2'-bipyridin-4-yl)-1-methyl-1H-pyrazolo[4,3-b]pyridin-7-amine;
N-(3'-fluoro-6'-methyl-2,2'-bipyridin-4-yl)-2-methyl-2H-pyrazolo[4,3-b]pyridin-7-amine;
N-(3'-fluoro-6'-methyl-2,2'-bipyridin-4-yl)-1-isopropyl-1H-pyrazolo[4,3-b]pyridin-7-amine;
N-(3'-fluoro-6'-methyl-2,2'-bipyridin-4-yl)-2-isopropyl-2H-pyrazolo[4,3-b]pyridin-7-amine;
(S)-3-(7-(3'-fluoro-6'-methyl-2,2'-bipyridin-4-ylamino)-2H-pyrazolo[4,3-b]pyridin-2-yl)propane-1,2-diol;
1-(7-(3'-fluoro-6'-methyl-2,2'-bipyridin-4-ylamino)-1H-pyrazolo[4,3-b]pyridin-1-yl)-2-methylpropan-2-ol;
2-(7-(3'-fluoro-6'-methyl-2,2'-bipyridin-4-ylamino)-1H-pyrazolo[4,3-b]pyridin-1-yl)ethanol;
2-(7-(3'-fluoro-6'-methyl-2,2'-bipyridin-4-ylamino)-2H-pyrazolo[4,3-b]pyridin-2-yl)ethanol;
N-(3'-fluoro-6'-methyl-2,2'-bipyridin-4-yl)-1-(2-methoxyethyl)-1H-pyrazolo[4,3-b]pyridin-7-amine;
7-(3'-fluoro-6'-methyl-2,2'-bipyridin-4-ylamino)-N-methyl-1H-pyrazolo[4,3-b]pyridine-1-carboxamide;
7-(2-(2-fluoro-5-methylphenyl)pyridin-4-ylamino)-N-methyl-1H-pyrazolo[4,3-b]pyridine-1-carboxamide;
N-(2-(2-fluoro-5-methylphenyl)pyridin-4-yl)-1-(piperidin-4-yl)-1H-pyrazolo[4,3-b]pyridin-7-amine;
N-(2-(2-fluoro-5-methylphenyl)pyridin-4-yl)-2-(piperidin-4-yl)-2H-pyrazolo[4,3-b]pyridin-7-amine;
N-(2-(2-fluoro-5-methylphenyl)pyridin-4-yl)-1-(1-(methylsulfonyl)piperidin-4-yl)-1H-pyrazolo[4,3-b]pyridin-7-amine;
N-(2-(2-fluoro-5-methylphenyl)pyridin-4-yl)-2-(1-(methylsulfonyl)piperidin-4-yl)-2H-pyrazolo[4,3-b]pyridin-7-amine;
N-ethyl-7-(2-(2-fluoro-5-methylphenyl)pyridin-4-ylamino)-1H-pyrazolo[4,3-b]pyridine-1-carboxamide;
7-(5,6'-dimethyl-2,2'-bipyridin-4-ylamino)-N-methyl-1H-pyrazolo[4,3-b]pyridine-1-carboxamide;
N-(2-(5-chloro-2-fluorophenyl)-5-methylpyridin-4-yl)-6-fluoro-1-(2-methoxyethyl)-1H-pyrazolo[4,3-b]pyridin-7-amine;
N-(2-(5-chloro-2-fluorophenyl)-5-methylpyrimidin-4-yl)-1H-pyrazolo[4,3-b]pyridin-7-amine;
7-(2-(5-chloro-2-fluorophenyl)-5-methylpyrimidin-4-ylamino)-N-methyl-1H-pyrazolo[4,3-b]pyridine-1-carboxamide;
2-(7-(2-(5-chloro-2-fluorophenyl)-5-methylpyrimidin-4-ylamino)-1H-pyrazolo[4,3-b]pyridin-1-yl)acetamide;
2-(7-(2-(5-chloro-2-fluorophenyl)-5-methylpyrimidin-4-ylamino)-2H-pyrazolo[4,3-b]pyridin-2-yl)acetamide;
N-(3'-fluoro-5,6'-dimethyl-2,2'-bipyridin-4-yl)-1-isopropyl-1H-pyrazolo[4,3-b]pyridin-7-amine;
N-(5,6'-dimethyl-2,2'-bipyridin-4-yl)-1H-pyrazolo[4,3-b]pyridin-7-amine;
(S)-3-(7-(3'-fluoro-5,6'-dimethyl-2,2'-bipyridin-4-ylamino)-2H-pyrazolo[4,3-b]pyridin-2-yl)propane-1,2-diol;
1-(7-(3'-fluoro-5,6'-dimethyl-2,2'-bipyridin-4-ylamino)-2H-pyrazolo[4,3-b]pyridin-2-yl)-2-methylpropan-2-ol;
2-(7-(3'-fluoro-5,6'-dimethyl-2,2'-bipyridin-4-ylamino)-2H-pyrazolo[4,3-b]pyridin-2-yl)ethanol;
2-(7-(3'-fluoro-5,6'-dimethyl-2,2'-bipyridin-4-ylamino)-1H-pyrazolo[4,3-b]pyridin-1-yl)ethanol;
N-(3'-fluoro-5,6'-dimethyl-2,2'-bipyridin-4-yl)-1H-pyrazolo[4,3-b]pyridin-7-amine;
2-(7-(5,6'-dimethyl-2,2'-bipyridin-4-ylamino)-2H-pyrazolo[4,3-b]pyridin-2-yl)acetamide;
2-(7-(3'-fluoro-5,6'-dimethyl-2,2'-bipyridin-4-ylamino)-1H-pyrazolo[4,3-b]pyridin-1-yl)acetamide;
2-(7-(3'-fluoro-5,6'-dimethyl-2,2'-bipyridin-4-ylamino)-2H-pyrazolo[4,3-b]pyridin-2-yl)acetamide;
2-(7-(3'-fluoro-6'-methyl-2,2'-bipyridin-4-ylamino)-2H-pyrazolo[4,3-b]pyridin-2-yl)acetamide;
2-(7-(3'-fluoro-6'-methyl-2,2'-bipyridin-4-ylamino)-1H-pyrazolo[4,3-b]pyridin-1-yl)acetamide;
N-(2-(2,5-difluorophenyl)pyridin-4-yl)-1H-pyrazolo[4,3-b]pyridin-7-amine;
2-(7-(2-(2,5-difluorophenyl)pyridin-4-ylamino)-1H-pyrazolo[4,3-b]pyridin-1-yl)acetamide;
2-(7-(2-(2,5-difluorophenyl)pyridin-4-ylamino)-2H-pyrazolo[4,3-b]pyridin-2-yl)acetamide;
2-(6-fluoro-7-(3'-fluoro-5,6'-dimethyl-2,2'-bipyridin-4-ylamino)-2H-pyrazolo[4,3-b]pyridin-2-yl)acetamide;
1-(cyclopropylmethyl)-N-(3'-fluoro-6'-methyl-2,2'-bipyridin-4-yl)-1H-pyrazolo[4,3-b]pyridin-7-amine;
3-(7-(3'-fluoro-5,6'-dimethyl-2,2'-bipyridin-4-ylamino)-2H-pyrazolo[4,3-b]pyridin-2-yl)propan-1-ol;
2-(6-fluoro-7-(3'-fluoro-5,6'-dimethyl-2,2'-bipyridin-4-ylamino)-2H-pyrazolo[4,3-b]pyridin-2-yl)ethanol;
7-(2-(2,5-difluorophenyl)-5,6-dimethylpyrimidin-4-ylamino)-N-ethyl-1H-pyrazolo[4,3-b]pyridine-1-carboxamide;

7-(2-(2,5-difluorophenyl)pyridin-4-ylamino)-N-ethyl-1H-pyrazolo[4,3-b]pyridine-1-carboxamide;
7-(2-(2,5-difluorophenyl)pyridin-4-ylamino)-N-methyl-1H-pyrazolo[4,3-b]pyridine-1-carboxamide;
N-(6-(2,5-difluorophenyl)-2,3-dimethylpyridin-4-yl)-2H-pyrazolo[4,3-b]pyridin-7-amine;
N-(2-(2,5-difluorophenyl)-5-methylpyrimidin-4-yl)-1H-pyrazolo[4,3-b]pyridin-7-amine;
7-(2-(2,5-difluorophenyl)-5-methylpyrimidin-4-ylamino)-N-ethyl-1H-pyrazolo[4,3-b]pyridine-1-carboxamide;
(R)-1-(7-(3'-fluoro-6'-methyl-2,2'-bipyridin-4-ylamino)-1H-pyrazolo[4,3-b]pyridin-1-yl)propan-2-ol;
1-(6-fluoro-7-(3'-fluoro-5',6'-dimethyl-2,2'-bipyridin-4-ylamino)-2H-pyrazolo[4,3-b]pyridin-2-yl)-2-methylpropan-2-ol;
(S)-1-(6-fluoro-7-(3'-fluoro-6'-methyl-2,2'-bipyridin-4-ylamino)-2H-pyrazolo[4,3-b]pyridin-2-yl)propan-2-ol;
(S)-1-(6-fluoro-7-(3'-fluoro-6'-methyl-2,2'-bipyridin-4-ylamino)-1H-pyrazolo[4,3-b]pyridin-1-yl)propan-2-ol;
N-(3'-fluoro-6'-methyl-2,2'-bipyridin-4-yl)-1-(2-fluoroethyl)-1H-pyrazolo[4,3-b]pyridin-7-amine;
N-(3'-fluoro-6'-methyl-2,2'-bipyridin-4-yl)-2-(2-fluoroethyl)-2H-pyrazolo[4,3-b]pyridin-7-amine;
N-(3'-fluoro-6'-methyl-2,2'-bipyridin-4-yl)-1H-pyrazolo[4,3-b]pyridin-7-amine;
2-(2,2-difluoroethyl)-N-(3'-fluoro-6'-methyl-2,2'-bipyridin-4-yl)-2H-pyrazolo[4,3-b]pyridin-7-amine;
1-(2,2-difluoroethyl)-N-(3'-fluoro-6'-methyl-2,2'-bipyridin-4-yl)-1H-pyrazolo[4,3-b]pyridin-7-amine;
(S)-1-(7-(3'-fluoro-6'-methyl-2,2'-bipyridin-4-ylamino)-1H-pyrazolo[4,3-b]pyridin-1-yl)propan-2-ol;
(S)-1-(7-(3'-fluoro-6'-methyl-2,2'-bipyridin-4-ylamino)-2H-pyrazolo[4,3-b]pyridin-2-yl)propan-2-ol;
N-(2-(2,5-difluorophenyl)-5-methylpyridin-4-yl)-1H-pyrazolo[4,3-b]pyridin-7-amine;
7-(2-(2,5-difluorophenyl)-5-methylpyridin-4-ylamino)-N-ethyl-1H-pyrazolo[4,3-b]pyridine-1-carboxamide;
7-(2-(2,5-difluorophenyl)-5-methylpyridin-4-ylamino)-N-isopropyl-1H-pyrazolo[4,3-b]pyridine-1-carboxamide;
2-(7-(3'-fluoro-6'-methyl-2,2'-bipyridin-4-ylamino)-2H-pyrazolo[4,3-b]pyridin-2-yl)-N-methylacetamide;
1,1,1-trifluoro-3-(7-(3'-fluoro-6'-methyl-2,2'-bipyridin-4-ylamino)-2H-pyrazolo[4,3-b]pyridin-2-yl)propan-2-ol;
1,1,1-trifluoro-3-(7-(3'-fluoro-6'-methyl-2,2'-bipyridin-4-ylamino)-1H-pyrazolo[4,3-b]pyridin-1-yl)propan-2-ol;
(R)-1-(7-(3'-fluoro-6'-methyl-2,2'-bipyridin-4-ylamino)-2H-pyrazolo[4,3-b]pyridin-2-yl)propan-2-ol;
N-ethyl-7-(3'-fluoro-5',6'-dimethyl-2,2'-bipyridin-4-ylamino)-1H-pyrazolo[4,3-b]pyridine-1-carboxamide;
7-(2-(2,5-difluorophenyl)-5-methylpyridin-4-ylamino)-N-methyl-1H-pyrazolo[4,3-b]pyridine-1-carboxamide;
N-cyclopropyl-2-(7-(3'-fluoro-5',6'-dimethyl-2,2'-bipyridin-4-ylamino)-1H-pyrazolo[4,3-b]pyridin-1-yl)acetamide;
N-cyclopropyl-2-(7-(3'-fluoro-5',6'-dimethyl-2,2'-bipyridin-4-ylamino)-2H-pyrazolo[4,3-b]pyridin-2-yl)acetamide;
4-(7-(3'-fluoro-6'-methyl-2,2'-bipyridin-4-ylamino)-2H-pyrazolo[4,3-b]pyridin-2-yl)-2-methylbutan-2-ol;
4-(7-(3'-fluoro-5',6'-dimethyl-2,2'-bipyridin-4-ylamino)-2H-pyrazolo[4,3-b]pyridin-2-yl)-2-methylbutan-2-ol;
2-cyclopropyl-N-(3'-fluoro-6'-methyl-2,2'-bipyridin-4-yl)-2H-pyrazolo[4,3-b]pyridin-7-amine;
2-cyclopropyl-N-(3'-fluoro-5',6'-dimethyl-2,2'-bipyridin-4-yl)-2H-pyrazolo[4,3-b]pyridin-7-amine;
N-(3'-fluoro-5',6'-dimethyl-2,2'-bipyridin-4-yl)-2-methyl-2H-pyrazolo[4,3-b]pyridin-7-amine;
N-(3'-fluoro-5',6'-dimethyl-2,2'-bipyridin-4-yl)-1-methyl-1H-pyrazolo[4,3-b]pyridin-7-amine;
2-ethyl-N-(3'-fluoro-6'-methyl-2,2'-bipyridin-4-yl)-2H-pyrazolo[4,3-b]pyridin-7-amine;
2-ethyl-N-(3'-fluoro-5',6'-dimethyl-2,2'-bipyridin-4-yl)-2H-pyrazolo[4,3-b]pyridin-7-amine;
1-ethyl-N-(3'-fluoro-6'-methyl-2,2'-bipyridin-4-yl)-1H-pyrazolo[4,3-b]pyridin-7-amine;
N-(2-(5-chloro-2-fluorophenyl)-5-methylpyridin-4-yl)-2-methyl-2H-pyrazolo[4,3-b]pyridin-7-amine;
N-(3'-fluoro-5',6'-dimethyl-2,2'-bipyridin-4-yl)-2-(2-fluoroethyl)-2H-pyrazolo[4,3-b]pyridin-7-amine;
N-(3'-fluoro-5',6'-dimethyl-2,2'-bipyridin-4-yl)-1-(2-fluoroethyl)-1H-pyrazolo[4,3-b]pyridin-7-amine;
6-fluoro-N-(3'-fluoro-5',6'-dimethyl-2,2'-bipyridin-4-yl)-2-methyl-2H-pyrazolo[4,3-b]pyridin-7-amine;
6-fluoro-N-(3'-fluoro-5',6'-dimethyl-2,2'-bipyridin-4-yl)-1-methyl-1H-pyrazolo[4,3-b]pyridin-7-amine;
1-cyclopropyl-N-(3'-fluoro-6'-methyl-2,2'-bipyridin-4-yl)-1H-pyrazolo[4,3-b]pyridin-7-amine;
1-ethyl-N-(3'-fluoro-5',6'-dimethyl-2,2'-bipyridin-4-yl)-1H-pyrazolo[4,3-b]pyridin-7-amine;
4-(7-(3'-fluoro-6'-methyl-2,2'-bipyridin-4-ylamino)-1H-pyrazolo[4,3-b]pyridin-1-yl)-2-methylbutan-2-ol;
(R)—N-(3'-fluoro-5',6'-dimethyl-2,2'-bipyridin-4-yl)-2-(tetrahydrofuran-3-yl)-2H-pyrazolo[4,3-b]pyridin-7-amine;
(R)—N-(3'-fluoro-5',6'-dimethyl-2,2'-bipyridin-4-yl)-1-(tetrahydrofuran-3-yl)-1H-pyrazolo[4,3-b]pyridin-7-amine;
2-ethyl-6-fluoro-N-(3'-fluoro-5',6'-dimethyl-2,2'-bipyridin-4-yl)-2H-pyrazolo[4,3-b]pyridin-7-amine;
1-ethyl-6-fluoro-N-(3'-fluoro-5',6'-dimethyl-2,2'-bipyridin-4-yl)-1H-pyrazolo[4,3-b]pyridin-7-amine;
(S)—N-(3'-fluoro-5',6'-dimethyl-2,2'-bipyridin-4-yl)-2-(tetrahydrofuran-3-yl)-2H-pyrazolo[4,3-b]pyridin-7-amine;
(S)—N-(3'-fluoro-5',6'-dimethyl-2,2'-bipyridin-4-yl)-1-(tetrahydrofuran-3-yl)-1H-pyrazolo[4,3-b]pyridin-7-amine;
4-(7-(2-(2,5-difluorophenyl)-5-methylpyridin-4-ylamino)-2H-pyrazolo[4,3-b]pyridin-2-yl)-2-methylbutan-2-ol;
1-(7-(2-(2,5-difluorophenyl)-5-methylpyridin-4-ylamino)-2H-pyrazolo[4,3-b]pyridin-2-yl)propan-2-ol;
1-(7-(2-(2,5-difluorophenyl)-5-methylpyridin-4-ylamino)-1H-pyrazolo[4,3-b]pyridin-1-yl)propan-2-ol;
2-(7-(3'-fluoro-5',6'-dimethyl-2,2'-bipyridin-4-ylamino)-1H-pyrazolo[4,3-b]pyridin-1-yl)-N-methylacetamide;
2-(7-(3'-fluoro-5',6'-dimethyl-2,2'-bipyridin-4-ylamino)-2H-pyrazolo[4,3-b]pyridin-2-yl)-N-methylacetamide;
2-(6-fluoro-7-(3'-fluoro-5',6'-dimethyl-2,2'-bipyridin-4-ylamino)-2H-pyrazolo[4,3-b]pyridin-2-yl)-N-methylacetamide;
2-(6-fluoro-7-(3'-fluoro-5',6'-dimethyl-2,2'-bipyridin-4-ylamino)-1H-pyrazolo[4,3-b]pyridin-1-yl)-N-methylacetamide;
(S)-1-(7-(3'-fluoro-5',6'-dimethyl-2,2'-bipyridin-4-ylamino)-2H-pyrazolo[4,3-b]pyridin-2-yl)propan-2-ol;
(R)-1-(7-(3'-fluoro-5',6'-dimethyl-2,2'-bipyridin-4-ylamino)-2H-pyrazolo[4,3-b]pyridin-2-yl)propan-2-ol;
(R)-1-(7-(3'-fluoro-5',6'-dimethyl-2,2'-bipyridin-4-ylamino)-1H-pyrazolo[4,3-b]pyridin-1-yl)propan-2-ol;
(S)-1-(7-(3'-fluoro-5',6'-dimethyl-2,2'-bipyridin-4-ylamino)-1H-pyrazolo[4,3-b]pyridin-1-yl)propan-2-ol;

N-ethyl-2-(7-(3'-fluoro-5,6'-dimethyl-2,2'-bipyridin-4-ylamino)-1H-pyrazolo[4,3-b]pyridin-1-yl)acetamide;

N-ethyl-2-(7-(3'-fluoro-5,6'-dimethyl-2,2'-bipyridin-4-ylamino)-2H-pyrazolo[4,3-b]pyridin-2-yl)acetamide;

2-(7-(2-(2,5-difluorophenyl)-5-methylpyridin-4-ylamino)-1H-pyrazolo[4,3-b]pyridin-1-yl)-N-ethylacetamide;

2-(7-(2-(2,5-difluorophenyl)-5-methylpyridin-4-ylamino)-2H-pyrazolo[4,3-b]pyridin-2-yl)-N-ethylacetamide;

N-[1-(1,1-dioxidotetrahydrothiophen-3-yl)-1H-pyrazolo[4,3-b]pyridin-7-yl]-3'-fluoro-5,6'-dimethyl-2,2'-bipyridin-4-amine;

2-(7-(2-(2,5-difluorophenyl)-5-methylpyridin-4-ylamino)-2H-pyrazolo[4,3-b]pyridin-2-yl)-N-methylacetamide; and 2-(7-(2-(2,5-difluorophenyl)-5-methylpyridin-4-ylamino)-1H-pyrazolo[4,3-b]pyridin-1-yl)-N-methylacetamide;

or a pharmaceutically acceptable salt of the afore-mentioned compounds.

13. A pharmaceutical composition, comprising: a compound of claim 1 and at least one pharmaceutically acceptable excipient.

* * * * *